US010562962B2

(12) United States Patent
Pedersen et al.

(10) Patent No.: US 10,562,962 B2
(45) Date of Patent: *Feb. 18, 2020

(54) ANTIBODIES SPECIFIC FOR HYPERPHOSPHORYLATED TAU AND METHODS OF USE THEREOF

(71) Applicant: H. Lundbeck A/S, Valby (DK)

(72) Inventors: Jan Torleif Pedersen, Valby (DK); Lars Østergaard Pedersen, Valby (DK); Justus Claus Daechsel, Valby (DK); Ayodeji Abdur-rasheed Asuni, Valby (DK); Nina Helen Rosenqvist, Valby (DK); Christiane Volbracht, Valby (DK); Lone Helboe, Valby (DK); Anders Brandt Elvang, Valby (DK); Florence Sotty, Valby (DK); Søren Christensen, Valby (DK); Jeffrey B. Stavenhagen, Valby (DK)

(73) Assignee: H. Lundbeck A/S, Valby (DK)

( * ) Notice: Subject to any disclaimer, the term of this patent is extended or adjusted under 35 U.S.C. 154(b) by 0 days.

This patent is subject to a terminal disclaimer.

(21) Appl. No.: 16/188,489

(22) Filed: Nov. 13, 2018

(65) Prior Publication Data

US 2019/0177401 A1 Jun. 13, 2019

Related U.S. Application Data

(63) Continuation of application No. 15/207,836, filed on Jul. 12, 2016, now Pat. No. 10,196,439.

(30) Foreign Application Priority Data

Jul. 13, 2015 (GB) .................................. 1512211.2
Oct. 16, 2015 (GB) .................................. 1518375.9

(51) Int. Cl.
*C07K 16/18* (2006.01)
*A61K 39/395* (2006.01)
*G01N 33/68* (2006.01)
*A61K 49/00* (2006.01)
*A61K 39/00* (2006.01)

(52) U.S. Cl.
CPC ............ *C07K 16/18* (2013.01); *A61K 39/395* (2013.01); *A61K 49/00* (2013.01); *G01N 33/6896* (2013.01); *A61K 2039/505* (2013.01); *C07K 2317/24* (2013.01); *C07K 2317/30* (2013.01); *C07K 2317/33* (2013.01); *C07K 2317/34* (2013.01); *C07K 2317/565* (2013.01); *C07K 2317/76* (2013.01); *C07K 2317/92* (2013.01); *C07K 2317/94* (2013.01); *G01N 2333/4709* (2013.01); *G01N 2800/2821* (2013.01)

(58) Field of Classification Search
None
See application file for complete search history.

(56) References Cited

U.S. PATENT DOCUMENTS

| | | |
|---|---|---|
| 4,179,337 A | 12/1979 | Davis et al. |
| 4,495,285 A | 1/1985 | Shimizu et al. |
| 4,609,546 A | 9/1986 | Hiratani |
| 4,735,210 A | 4/1988 | Goldenberg |
| 4,766,106 A | 8/1988 | Katre et al. |
| 4,861,581 A | 8/1989 | Epstein et al. |
| 4,946,778 A | 8/1990 | Ladner et al. |
| 5,101,827 A | 4/1992 | Goldenberg |
| 5,102,990 A | 4/1992 | Rhodes |
| 5,225,539 A | 7/1993 | Winter |
| 5,530,101 A | 6/1996 | Queen et al. |
| 5,545,806 A | 8/1996 | Lonberg et al. |
| 5,545,807 A | 8/1996 | Surani et al. |
| 5,569,825 A | 10/1996 | Lonberg et al. |
| 5,585,089 A | 12/1996 | Queen et al. |
| 5,589,466 A | 12/1996 | Felgner et al. |
| 5,625,126 A | 4/1997 | Lonberg et al. |
| RE35,500 E | 5/1997 | Rhodes |
| 5,633,425 A | 5/1997 | Lonberg et al. |
| 5,648,471 A | 7/1997 | Buttram et al. |
| 5,661,016 A | 8/1997 | Lonberg et al. |
| 5,697,902 A | 12/1997 | Goldenberg |
| 5,741,957 A | 4/1998 | Deboer et al. |
| 5,750,172 A | 5/1998 | Meade et al. |
| 5,756,687 A | 5/1998 | Denman et al. |
| 5,770,429 A | 6/1998 | Lonberg et al. |
| 5,789,650 A | 8/1998 | Lonberg et al. |
| 5,814,318 A | 9/1998 | Lonberg et al. |
| 5,827,690 A | 10/1998 | Meade et al. |
| 5,859,205 A | 1/1999 | Adair et al. |

(Continued)

FOREIGN PATENT DOCUMENTS

WO WO 1992/003918 3/1992
WO WO 1992/022645 12/1992

(Continued)

OTHER PUBLICATIONS

International Search Report and Written Opinion for Application No. PCT/EP2016/066470 dated Mar. 6, 2017.
International Search Report and Written Opinion for Application No. PCT/EP2017/067067 dated Oct. 18, 2017.
Ahmed Z. et al., A Novel in Vivo Model of Tau Propagation With Rapid and Progressive Neurofibrillary Tangle Pathology: The Pattern of Spread Is Determined by Connectivity, Not Proximity, Acta Neuropathol. 2014;127:667-683.
Allen, B. et al. (2002) "Abundant Tau Filaments and Nonapoptotic Neurodegeneration in Transgenic Mice Expressing Human P301S Tau Protein," J. Neurosci. 22(21): 9340-9351.

(Continued)

*Primary Examiner* — Adam Weidner
(74) *Attorney, Agent, or Firm* — Wolf, Greenfield & Sacks, P.C.

(57) ABSTRACT

The present invention relates to a novel class of monoclonal antibody that specifically binds the phosphorylated serine 396 residue on pathological hyperphosphorylated (PHF) tau (pS396), as well as to methods of using these molecules and their tau binding fragments in the treatment of Alzheimer's disease and tauopathies.

11 Claims, 52 Drawing Sheets

Specification includes a Sequence Listing.

(56) References Cited

U.S. PATENT DOCUMENTS

| | | | |
|---|---|---|---|
| 5,874,299 | A | 2/1999 | Lonberg et al. |
| 5,877,397 | A | 3/1999 | Lonberg et al. |
| 5,973,972 | A | 10/1999 | Kwon et al. |
| 6,077,835 | A | 6/2000 | Hanson et al. |
| 6,407,213 | B1 | 6/2002 | Carter et al. |
| 6,881,557 | B2 | 4/2005 | Foote |
| 8,609,097 | B2 | 12/2013 | Bormann et al. |
| 8,926,974 | B2 | 1/2015 | Griswold-Prenner et al. |
| 8,940,272 | B2 | 1/2015 | Nitsch et al. |
| 8,940,727 | B2 | 1/2015 | Nitsch et al. |
| 10,196,439 | B2 | 2/2019 | Pedersen et al. |
| 2012/0087861 | A1 | 4/2012 | Nitsch et al. |
| 2014/0086921 | A1 | 3/2014 | Griswold-Prenner et al. |
| 2014/0248666 | A1 | 9/2014 | Paszty et al. |
| 2014/0302046 | A1 | 10/2014 | Sigurdsson |
| 2017/0015738 | A1 | 1/2017 | Pedersen et al. |
| 2018/0016330 | A1 | 1/2018 | Pedersen et al. |

FOREIGN PATENT DOCUMENTS

| | | |
|---|---|---|
| WO | WO 1993/001227 | 1/1993 |
| WO | WO 1993/012227 | 6/1993 |
| WO | WO 1994/025585 | 11/1994 |
| WO | WO 1998/024884 | 6/1998 |
| WO | WO 2000/046147 | 8/2000 |
| WO | WO 2000/070087 | 11/2000 |
| WO | WO 2001/009187 | 2/2001 |
| WO | WO 2001/014424 | 3/2001 |
| WO | WO 2002/027017 | 4/2002 |
| WO | WO 2002/043478 | 6/2002 |
| WO | WO 2007/059782 | 5/2007 |
| WO | WO 2009/033743 | 3/2009 |
| WO | WO 2009/097006 | 8/2009 |
| WO | WO 2012/045882 | 4/2012 |
| WO | WO 2012/049570 | 4/2012 |
| WO | WO 2013/050567 | 4/2013 |
| WO | WO 2013/151762 | 10/2013 |
| WO | WO 2014/008404 | 1/2014 |
| WO | WO 2014/028777 | 2/2014 |
| WO | WO 2014/165271 | 10/2014 |
| WO | WO 2014/170549 | 10/2014 |
| WO | WO 2016/007414 | 1/2016 |
| WO | WO 2017/009308 | 1/2017 |
| WO | WO 2018/011073 | 1/2018 |

OTHER PUBLICATIONS

Altschul S.F., Amino Acid Substitution Matrices From an Information Theoretic Perspective. J. Mol. Biol. 1991;219:555-565.
Anonymous (2006) Anti-phospho-Tau (pSer199/202), Data sheet; Sigma Aldrich, Cat. No. T6819 (2 pages).
Anonymous (2008) "Mouse anti-Phospho-Tau 396," Invitrogen Catalogue, Catalog No. 35-5300 (2 pages).
Anonymous (2010) "Tau Phosphorylation Site-Specific Antibody Sampler (Containing Tau pS199, pT205, pT231, pS262, pS356, pS396, pS404, pS409, pS422 Rabbit Polyclonal & tau [TAU-5] Monoclonal Antibodies, Unconjugated)," Product Analysis Sheet INVITROGEN (2 pages).
Anonymous (2011) "Tau [pS199] Abfinity TM Recombinant Rabbit Monoclonal Antibody—Purified; Cat. No. 701054," Product Analysis Sheet, NOVEX (2 pages).
Anonymous (2014) "Anti-Tau (phospho S199) antibody [EPR2401Y] (ab81268)," Product Datasheet; retrieved on Feb. 3, 2017; ABCAM (4 pages).
Anonymous (2014) "Anti-Tau (Phospho S396) Antibody [EPR2731] ab109390," Product Data Sheet, ABCAM Product Catalogue (6 pages).
Barderas R., et al. (2008) "Affinity Maturation of Antibodies Assisted by in Silica Modeling," Proc. Natl. Acad. Sci. (USA) 105(26):9029-9034.
Benvenisty N., et al. (1986) "Direct Introduction of Genes Into Rats and Expression of the Genes," Proc. Natl. Acad. Sci. U.S.A. 83: 9551-9555.
Bird R.E., et al. (1988) "Single-Chain Antigen-Binding Proteins," Science 242: 423-426.
Bitter G.A. et al. (1987) "Expression and Secretion Vectors for Yeast," Methods Enzymol. 153: 516-544.
Boer E. et al. (2007) "Yeast Expression Platforms," Appl. Microbial. Biotechnol. 77(3): 513-523.
Bondareff et al. (1990) "Molecular Analysis of Neurofibrillary Degeneration in Alzheimer's Disease: An Immunohistochemical Study," Am. J. Pathol. 137(3): 711-723.
Bostrom J., et al. (2009) "Improving Antibody Binding Affinity and Specificity for Therapeutic Development," Methods Mol. Biol. 525: 353-376.
Boutajangout, A. et al. (2011) "Passive Immunization Targeting Pathological Phospho-tau Protein in a Mouse Model Reduces Functional Decline and Cleans Tau Aggregates from the Brain," J. Neurochem. 118:658-667.
Boutajangout, A. et al. (2011) "Targeting Hypeiphosphorylated Tau Protein with a Monoclonal Antibody at an Advances Stage of Tau Pathology Improves Cognition in a Mouse Model," AAIC 7(4) Suppl. Ed.: s480-s48 1.
Braak, E. et al. (1999) "Neuropathology of Alzheimer's Disease: What is New Since A. Alzheimer?" Eur. Arch. Psychiatry. Clin. Neurosci. 249(Suppl. 3): III/14-III/22.
Braak, H. et al. (1996) "Evolution of the Neuropathology of Alzheimer's Disease," Acta Neurol. Scand. Suppl. 165:3-12.
Breteler M.M. et al. (1992) "A Community-Based Study of Dementia: The Rotterdam Elderly Study," Neuroepidemiology 11 (Suppl 1): 23-28.
Bright, J. et al. (2015) "Human Secreted Tau Increases Amyloid-Beta Production," Neurobiol. Aging, 36: 693-709.
Brister M.A. et al. (2014) "OGlcNAcylation and Phosphorylation Have Opposing Structural Effects in Tau: Phosphothreonine Induces Particular Conformational Order," J. Am. Chem. Soc. 136:3803-3816.
Brister, M.A. et al. (2014) "OGlcNAcylation and Phosphorylation Have Opposing Structural Effects in Tau: Phosphothreonine nduces Particular Conformational Order," J. Am. Chem. Soc. 136:3803-3816.
Carter P. et al. (1992) "Humanization of an Anti-p185her2 Antibody for Human Cancer Therapy," Proc. Natl. Acad. Sci. (U.S.A.) 89:4285-4289.
Celik E. et al. (2012) "Production of Recombinant Proteins by Yeast Cells," Biotechnol. Adv. 30(5): 1108-1118.
Chai, X. et al. (2011) "Passive Immunization with Anti-Tau Antibodies in Two Transgenic Models," J. Biol. Chem. 286(39):34457-34467.
Chen J. et al. (1993) "Immunoglobulin Gene Rearrangement in B Cell Deficient Mice Generated by Targeted Deletion of the JH Locus," Int. Immunol. 5( 6) :647-656.
Chothia C. et al. (1987) "Canonical Structures for the Hypervariable Regions of Immunoglobulins," J. Mol. Biol. 196:901-917.
Clackson T. et al. (1991) "Making Antibody Fragments Using Phage Display Libraries," Nature 352:624-628.
Clavaguera F. et al. (2014) "Peripheral Administration of Tau Aggregates Triggers Intracerebral Tauopathv in Transgenic Mice," Acta Neuropathol. 127: 299-301.
Clavaguera, F. et al. (2009) "Transmission and Spreading of Tauopathy in Transgenic Mouse Brain," Nat. Cell Biol. 11(7):909-913.
Clavaguera, F. et al. (2013) "Brain Homogenates from Human Tauopathies Induce Tau Inclusions in Mouse Brain," PNAS 110(23):9535-9540.
Co M.S. et al. (1991) "Humanized Antibodies for Antiviral Therapy," Proc. Natl. Acad. Sci. U.S.A. 88:2869-2873.
Co M.S. et al. (1992) "Chimeric and Humanized Antibodies With Specificity for the CD33 Antigen," J. Immunol. 148:1149-1154.
Cohen T.J. et al. (2011) "The Acetylation of Tau Inhibits Its Function and Promotes Pathological Tau Aggregation," Nat. Commun. 2:252 (9 pages).
Congdon, E.E. et al. (2013) "Antibody Uptake into Neurons Occurs Primarily via Cathrin-dependent Fey Receptor Endocytosis and is a Prerequisite for Acute Tau Protein Clearance," J. Biol. Chem. 288(49):35452-35465.

(56) References Cited

OTHER PUBLICATIONS

Corsaro C.M. et al. (1981) "Enhancing the Efficiency of DNA-Mediated Gene Transfer in Mammalian Cells," Somatic Cell Genetics (2):603-616.
Crary J.F. et al. (2014) "Primary Age-Related Tauopahty (PART): A Common Pathology Associated with Human Aging," Acta Neuropathol. 128:755-766.
D'Abramo, C. et al. (2013) "Tau Passive Immunotherapy in Mutant P301L Mice: Antibody Affinity versus Specificitv," PLoS One 8(4): e62402:1-10.
De Calignon A. et al. (2010) "Caspase Activation Precedes and Leads to Tangles," Nature 464: 1201-1204.
Delobel P. et al. (2008) "Analysis of Tau Phosphrylation and Truncation in a Mouse Model of Human Tauopathy," Am. J. Pathol. 172:123-131.
Eddy S.R. (2004) "Where Did the BLOSUM62 Alignment Score Matrix Come From?," Nature Biotech. 22(8): 1035-1036.
Evans M.J. et al. (1995) "Rapid Expression of an Anti-Human C5 Chimeric Fab Utilizing a Vector That Replicates in COS and 293 Cells," J. Immunol. Meth. 184: 123-138.
Ferreira A. et al. (2011) "Calpain-Mediated Tau Cleavage: A Mechanism Leading to Neurodegeneration Shared by Multiple Tauopathies," Mol. Med. 17:676-685.
Finlay W.J. et al. (2009) "Affinity Maturation of a Humanized Rat Antibody for Anti-RAGE Therapy: Comprehensive Mutagenesis Reveals a High Level of Mutational Plasticity Both Inside and Outside the Complementarity-Determining Regions," J. Mol. Biol. 388(3):541-558.
Fishwild D.M. et al. (1996) "High Avidity Human IgGkMonoclonal Antibodies From a Novel Strain of Minilocus Transgenic Mice," Nat. Biotechnol. 14:845-851.
Gamblin T.C. et al. (2003) "Caspase Cleavage of Tau: Linking Amyloid and Neurofibrillary Tangles in Alzheimer's Disease," Proc. Natl. Acad. Sci. U.S.A. 100:10032-10037.
Glaser S.M. et al. (1992) "Antibody Engineering by Codon-Based Mutagenesis in a Filamentous Phage Vector System," J. Immunol. 149:3903-3913.
Goedert M. et al. (2010) "The Propagation of Prion-Like Protein Inclusions in Neurodegenerative Diseases," Trends Neurosci. 33:317-325.
Gonzales N.R. et al. (2004) "SDR Grafting of a Murine Antibody Using Multiple Human Germline Templates to Minimize Its Immunogenicity," Mol. Immunol. 41:863-872.
Gorman S.D. et al. (1991) "Reshaping a Therapeutic CD4 Antibody," Proc. Natl. Acad. Sci. U.S.A. 88:4181-4185.
Greenberg, S.G. et al. (1990) "A Preparation of Alzheimer Paired Helical Filaments That Displays Distinct T Proteins by Polyacrylamide Gel Electrophoresis," PNAS USA 87:5827-5831.
Gu, J. et al. (2013) "Two Novel Tau Antibodies Targeting the 396/404 Region are Primarily Taken Up by Neurons and Reduce Tau Protein Pathology," J. Biol. Chem. 288(46):33081-33095.
Gunasekaran K. et al. (2010) "Enhancing Antibody Fc Heterodimer Formation Through Electrostatic Steering Effects," J. Biol. Chem. 285:19637-19646.
Gustchina E. et al. (2009) "Affinity maturation by targeted diversification of the CDR-H2 loop of a monoclonal Fab derived from a synthetic naïve human antibody library and directed against the internal trimeric coiled-coil of gp41 yields a set of Fabs with improved HIV-1 neutralization potency and breadth," Virology 393(1):112-119.
Hackel B.J. et al. (2010) "Stability and CDR Composition Biases Enrich Binder Functionality Landscapes," J. Mol. Biol. 401(1)84-96.
Hanger D.P. et al. (2009) "Tau Phosphorylation: The Therapeutic Challenge for Neurodegenerative Disease," Trends Mol. Med. 15(3):112-119.
Harding F.A. et al. (1995) "Class Switching in Human Immunoglobulin Transgenic Mice," Ann. N. Y. Acad. Sci. 764:536-546.
Hasegawa M. et al. (1992) "Protein Sequence and Mass Spectrometric Analyses of Tau in the Alzheimer's Disease Brain," J. Biol. Chem. 267:17047-17054.
Henikoff J.G. (1992) "Amino Acid Substitution Matrices From Protein Blocks," Proc. Natl. Acad. Sci. U.S.A. 89:10915-10919.
Hoffmann, R. et al. (1997) "Unique Alzheimer's Disease Paired Helical Filament Specific Epitopes Involve Double Phosphorylation at Specific Sites," Biochemistry 36:8114-8124.
Holliger P. et al. (1993) "'Diabodies': Small Bivalent and Bispecific Antibody Fragments," Proc. Natl. Acad. Sci. U.S.A. 90(14):6444-6448.
Holliger, P. (2002) "Expression of Antibody Fragments in Pichia Pastoris," Methods Mol. Biol. 178, 349-357.
Holt L.J. et al. (2003) "Domain Antibodies: Proteins for Therapy," Trends Biotechnol. 21(11):484-90.
Hu et al., Levels of nonphosphorylated and phosphorylated tau in cerebrospinal fluid of Alzheimer's disease patients : an ultrasensitive bienzyme-substrate-recycle enzyme-linked immunosorbent assay. Am J Pathol. Apr. 2002;160(4):1269-78.
Huston et al. (1988) "Protein Engineering of Antibody Binding Sites: Recovery of Specific Activity in an Anti-Digoxin Single-Chain Fv Analogue Produced in *Escherichia coli*," Proc. Natl. Acad. Sci. (U.S.A.) 85:5879-5883.
Jack, C.R. et al. (2013) "Update on Hypothetical Model of Alzheimer's Disease Biomarkers," Lancet Neurol. 12(2):207-216.
Jackson, J.R. et al. (1994) "In Vitro Antibody Maturation," J Immunol. Apr. 1, 1995;154(7):3310-9.
Jicha, G.A. et al. (1997) "Alz-50 and MC-1, A New Monoclonal Antibody Raised to Paired Helical Filaments, Recognize Conformational Epitopes on Recombinant Tau," J. Neurosci. Res. 48, 128-132.
Karlin, S. et al. (1990) "Methods for Assessing the Statistical Significance of Molecular Sequence Features by Using General Scoring Schemes," Proc. Natl. Acad. Sci. (USA) 87:2264-2268.
Kettleborough, C. A. et al. (1991) "Humanization of a Mouse Monoclonal Antibody by CDR-Grafting: The Importance of Framework Residues on Loop Conformation," Protein Engineering 4:773-783.
Kfoury, N. et al. (2012) "Trans-cellular Propagation of Tau Aggregation by Fibrillar Species," J. Biol. Chem. 287(23):19440-19451.
Kohler G. et al., (1975) "Continuous Cultures of Fused Cells Secreting Antibody of Predefined Specificity," Nature 256, 495-497 (1975).
Kolarova, M. et al. (2012) "Structure and Pathology of Tau Protein in Alzheimer Disease," Int. J. Alzheimers. Dis. 2012, 731526 (13 pages).
Kosik K.S. et. al. (1986) "Microtubule-Associated Protein Tau(t) Is a Major Antigenic Component of Paired Helical Filaments in Alzheimer Disease," Proc. Natl. Acad. Sci. U.S.A. 86, 4044-4048.
Krause, J.C. et al. (2011) "An Insertion Mutation That Distorts Antibody Binding Site Architecture Enhances Function of a Human Antibody," MBio. 2(1): e00345-10. (8 pages).
Kuan, C.T. et al. (2011) "Affinity-Matured Anti-Glycoprotein NMB Recombinant Immunotoxins Targeting Malignant Gliomas and Melanomas," Int. J. Cancer 129:111-121.
Kurth, M. et al. (1993) "Site-specific conjugation of a radioiodinated phenethylamine derivative to a monoclonal antibody results in increased radioactivity localization in tumor," J. Med. Chem. 36(9):1255-1261.
Labrijn A.F. et al. (2013) "Efficient Generation of Stable Bispecific IgG1 by Controlled Fab-Arm Exchange," Proc. Natl. Acad. Sc. U.S.A. 100(113):5145-5150.
Lambert J.C. et al. (2013) "Meta-Analysis of 74,046 Individuals Identifies 11 New Susceptibility Loci for Alzheimer's Disease," Nat. Genet. 45:1452-1460.
Launer L.J. (1992) "Overview of Incidence Studies of Dementia Conducted in Europe," Neuroepidemiology 11 (Suppl 1):2-13.
Li P. et al. (2007) "Expression of Recombinant Proteins in Pichia Pastoris," Appl. Biochem. Biotechnol. 142(2):105-124.
Lindegren, S. et al. (1998) "Chloramine-T in High-Specific-Activity Radioiodination of Antibodies Using N-Succinimidyl-3-(Trimethylstannyl)Benzoate As an Intermediate," Nucl. Med. Biol. 25(7):659-665.

(56) References Cited

OTHER PUBLICATIONS

LoBuglio, A.F. et al. (1989) "Mouse/Human Chimeric Monoclonal Antibody in Man: Kinetics and Immune Response," Proc. Natl. Acad. Sci. (U.S.A.) 86:4220-4224.
Lonberg N. et al. (1994) "Antigen-specific human antibodies from mice comprising four distinct genetic modifications," Nature 368:856-859.
Lonberg N. et al. (1995) "Human Antibodies From Transgenic Mice," Intern. Rev. Immunol. 13:65-93.
Mabry R. et al. (2010) "Engineering of Stable Bispecific Antibodies Targeting IL-17A and IL-23," Protein Eng. Des. Sel. 23(3):115-127.
Maeda, H. et al. (1991) "Construction of Reshaped Human Antibodies With HIV-Neutralizing Activity," Human Antibodies Hybridoma 2:124-134.
Marks et al. (1991) "By-Passing Immunization—Human Antibodies From V-Gene Libraries Displayed on Page," J. Mol. Biol. 222, 581-597.
McCafferty J. et al. (1990) "Phage Antibodies: Filamentous Phage Displaying Antibody Variable Domains," Nature 348, 552-554.
Metz S. et al. (2012) "Bispecific Antibody Derivatives With Restricted Binding Functionalities That Are Activated by Proteolytic Processing," Protein Eng. Des. Sel. 25(10):571-580.
Min S.W. et al. (2010) "Acetylation of Tau Inhibits Its Degradation and Contributes to Tauopathy," Neuron 67:953-966.
Montgomery, D.L. et al. (2009) "Affinity Maturation and Characterization of a Human Monoclonal Antibody Against HIV-1 gp41," MAbs 1(5):462-474.
Moore G.L. et al. (2011) "A Novel Bispecific Antibody Format Enables Simultaneous Bivalent and Monovalent Co-Engagement of Distinct Target Antigens," MAbs 3(6):546-557.
Mukrasch, M.D. et al. (2009) "Structural Polymorphism of 441-Residue Tau at Single Residue Resolution," PLoS Biol. 7(2): e1000034: 0399-0414.
Nelson, P.T. et al. (2012) "Correlation of Alzheimer Disease Neuropathologic Changes with Cognitive Status: A Review of the Literature," J. Neuropathol. Exp. Neurol. 71(5):362-381.
Ohgushi M. et al. (1983) "'Molten-Globule State': A Compact Form of Globular Proteins With Mobile Side Chains," FEBS Lett. 164:21-24.
Paul, Chapter 9: Structure and Function of Immunoglobulins. Fundamental Immunology, 3rd Edition. 1993:292-295.
Probst, A. et al. (2000) "Axonopathy and Amyotrophy in Mice Transgenic for Human Four-Repeat Tau Protein," Acta Neuropathol. 99:469-481.
Rafii et al., Recent developments in Alzheimer's disease therapeutics. BMC Med. Feb. 19, 2009;7:7. doi: 10.1186/1741-7015-7-7.
Rea, D.W. et al. (1990) "Site-specifically radioiodinated antibody for targeting tumors," Cancer Res. 50(3 Suppl):857s-861s.
Reinecke, J.B. et al. (2011) "Implicating Calpain in Tau-Mediated Toxicity In Vivo," PLoS One. 6:e23865 (9 pages).
Revets H. et al. (2005) "Nanobodies As Novel Agents for Cancer Therapy," Expert Opin. Biol. Ther. 5(1):111-124.
Ridgway J.B.B. et al. (1996) "'Knobs-Into-holes' Engineering of Antibody CH3 Domains for Heavy Chain Heterodimerization," Protein Eng 9(7):617-621.
Riechmann, L. et al. (1988) "Reshaping Human Antibodies for Therapy," Nature 332:323-327.
Rosseels, J. et al. (2015) "Tau Monoclonal Antibody Generation Based on Humanized Yeast Models," J. Biol. Chem. 290(7):4059-4074.
Rudikoff, S. et al. (1982) "Single Amino Acid Substitution Altering Antigen-Binding Specificity," Proc. Nat'l. Acad. Sci. USA 79:1979-1983.
Sahara, N. et al. (2013) "Characteristics of TBS-extractable Hyperphosphorylated Tau Species: Aggregation Intermediates in rTg4510 Mouse Brain," J. Alzheimer's Dis. 33:249-263.
Sanders, D.W. et al. (2014) "Distinct Tau Prion Strains Propagate in Cells and Mice and Define Different Tauopathies," Neuron 82:1271-1288.
Sankaranarayanan, S. et al. (2015) "Passive Immunization with Phospho-Tau Antibodies Reduces Tau Pathology and Functional Deficits in Two Distinct Mouse Tauopathy Models," PLoS One 10(5): e0125614:1-28.
Sato K. et al. (1993) "Reshaping a Human Antibody to Inhibit the Interleukin 6-Dependent Tumor Cell Growth," Cancer Res 53:851-856.
Schakowski F. et al. (2001) "A Novel Minimal-Size Vector (MIDGE) Improves Transgene Expression in Colon Carcinoma Cells and Avoids Transfection of Undesired DNA," Mol. Ther. 3:793-800.
Schier R. et al. (1996) "Isolation of picomolar affinity anti-c-erbB-2 single-chain Fv by molecular evolution of the complementarity determining regions in the center of the antibody binding site," J. Mol. Biol. 263:551-567.
Schraen-Maschke et al., Tau as a biomarker of neurodegenerative diseases. Biomark Med. Aug. 2008;2(4):363-84. doi: 10.2217/17520363.2.4.363.
Sigurdsson E.M. et al. (2002) "Infectivity of Amyloid Diseases," Trends Mol. Med. 8:411-413.
Singer, D. et al. (2005) "Characterization of Phosphorylation Dependent Antibodies to Study the Phosphorylation Status of the Tau Protein," nt'l J. Peptide Res. and Therapeutics 11(4):279-289.
Steidl, S. et al. (2008) "In Vitro Affinity Maturation of Human GM-CSF Antibodies by Targeted CDR-Diversification," Mol. Immunol. 46(1):135-144.
Strop P. et al. (2012) Generating Bispecific Human IgG1 and IgG2 Antibodies From Any Antibody Pair, J. Mol. Biol. 420:204-219.
Sykes K.F. et al. (1997) "Linear Expression Elements: A Rapid, in Vivo, Method to Screen for Gene Functions," Nat Biotech 12:355-359.
Taylor L. D. et al. (1992) "A Transgenic Mouse That Expresses a Diversity of Human Sequence Heavy and Light Chain Immunoglobulins," Nucleic Acids Res. 20:6287-6295.
Taylor L. D. et al. (1994) "Human Immunoglobulin Transgenes Undergo Rearrangement, Somatic Mutation and Class Switching in Mice That Lack Endogenous IgM," Int Immunol 6(4):579-591.
Tempest, P.R. et al. (1991) "Reshaping a Human Monoclonal Antibody to Inhibit Human Respiratory Syncytial Virus Infection in vivo," Bio/Technology 9:266-271.
Tuaillon N. et al. (1994) "Biased Utilization of DHQ52 and JH4 Gene Segments in a Human Ig Transgenic Minilocus Is Independent of Antigenic Selection," J. Immunol. 152:2912-2920.
Van der Vaart J.M. (2002) "Expression of VHH antibody fragments in *Saccharomyces cerevisiae*," Methods Mol. Biol. 178:359-366.
Van Heeke G. et al. (1989) "Expression of Human Asparagine Synthetase in *Escherichia coli*," J. Biol. Chem. 264:5503-5509.
Verhoeyen, M. et al. (1988) "Reshaping Human Antibodies: Grafting an Antilysozyme Activity," Science 239:1534-1536.
Von Kreudenstein T.S. et al. (2013) "Improving Biophysical Properties of a Biospecific Antibody Scaffold to Aid Developability," MAbs 5(5):646-654.
Walker, L.C. et al. (2013) "Mechanism of Protein Seeding in Neurodegenerative Diseases," JAMA Neurol. 70:304-310.
Ward E.S. et al. (1989) "Binding Activities of a Repertoire of Single Immunoglobulin Variable Domains Secreted From *Escherichia coli*," Nature 341:544-546.
Weiner, M.W. et al. (2015) "Impact of the Alzheimer's Disease neuroimaging Initiative, 2004-2014," Alzheimers Dement. 11(7):865-884.
Wigler M. et al. (1978) "Biochemical Transfer of Single-Copy Eucaryotic Genes Using Total Cellular DNA As Donor," Cell 14:725-731.
Wong, Y.W. et al. (1998) "Structural Requirements for a Specificity Switch and for Maintenance of Affinity Using Mutational Analysis of a Phage-Displayed Anti-Arsonate Antibody of Fab Heavy Chain First Complementarity-Determining Region," J. Immunol. 160:5990-5997.
Wu H. et al. (1998) "Stepwise in Vitro Affinity Maturation of Vitaxin, An avb3-Specific Humanized mAb," Proc. Natl. Acad. Sci. U.S.A. 95:6037-6042.
Yanamandra et al., Anti-tau antibodies that block tau aggregate seeding in vitro markedly decrease pathology and improve cogni-

(56) References Cited

OTHER PUBLICATIONS tion in vivo. Neuron. Oct. 16, 2013;80(2):402-414. doi: 10.1016/j.neuron.2013.07.046. Epub Sep. 26, 2013.

Yelton D.E. et al. (1995) "Affinity Maturation of the BR96 Anti-Carcinoma Antibody by Codon-Based Mutagenesis," J. Immunol. 155:1994-2004.

Zhu Y. et al. (2014) "The Emerging Link Between O-GlcNAc and Alzheimer Disease," J. Biol. Chem. 289:50:34472-34481.

Zou Y.R. et al. (1993) "Gene Targeting in the IgK Locus: Efficient Generation of ? Chain-Expressing B Cells, Independent of Gene Rearrangement in IgK," EMBO J. 12(3):811-820.

International Search Report and Written Opinion for Application No. PCT/EP2018/050149 dated May 4, 2018. 20 pages.

Aboelnour et al., Amyloid beta deposition and phosphorylated tau accumulation are key features in aged choroidal vessels in the complement factor H knock out model of retinal degeneration. Exp Eye Res. Jun. 2016;147:138-143. doi: 10.1016/j.exer.2016.05.015. Epub May 12, 2016.

Chiasseu et al., Tau Accumulation, Altered Phosphorylation, and Missorting Promote Neurodegeneration in Glaucoma. J Neurosci. May 25, 2016;36(21):5785-98. doi: 10.1523/JNEUROSCI.3986-15.2016.

Gupta et al., Retinal tau pathology in human glaucomas. Can J Ophthalmol. Feb. 2008;43(1):53-60. doi: 10.3129/i07-185.

Wostyn et al., Alzheimer's disease: cerebral glaucoma? Med Hypotheses. Jun. 2010;74(6):973-7. doi: 10.1016/j.mehy.2009.12.019. Epub Jan. 6, 2010.

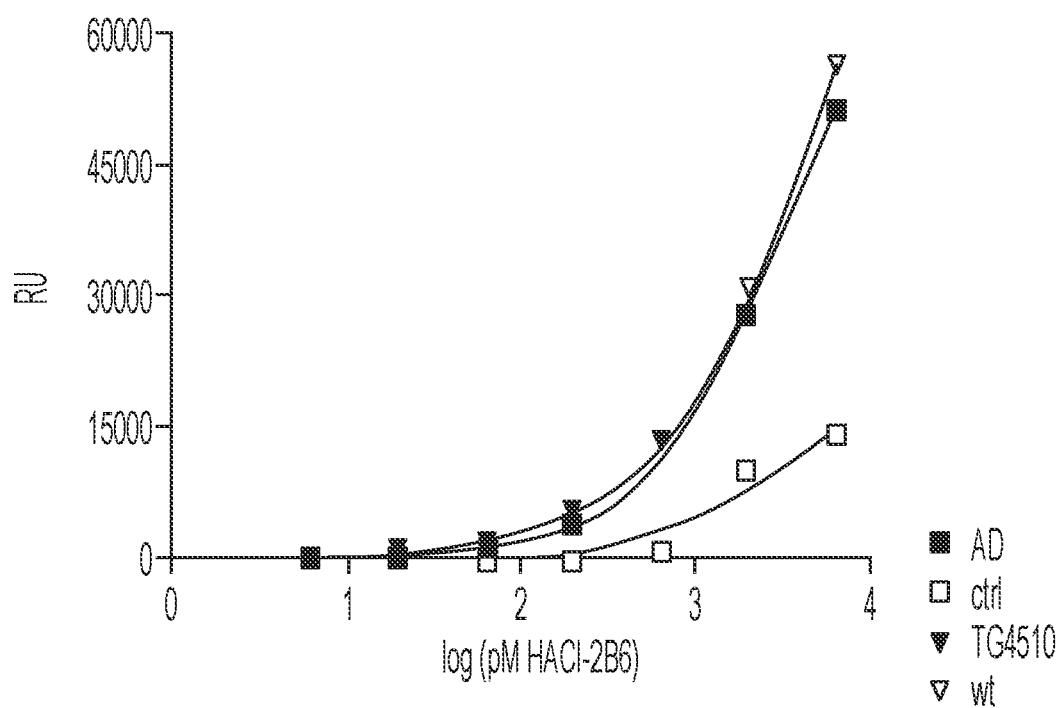

|   | A  | R  | N  | D  | C  | Q  | E  | G  | H  | I  | L  | K  | M  | F  | P  | S  | T  | W  | Y  | V  |
|---|----|----|----|----|----|----|----|----|----|----|----|----|----|----|----|----|----|----|----|----|
| A | +4 | -1 | -2 | -2 | 0  | -1 | -1 | 0  | -2 | -1 | -1 | -1 | -1 | -2 | -1 | +1 | 0  | -3 | -2 | 0  |
| R | -1 | +5 | 0  | -2 | -3 | +1 | 0  | -2 | 0  | -3 | -2 | +2 | -1 | -3 | -2 | -1 | -1 | -3 | -2 | -3 |
| N | -2 | 0  | +6 | +1 | -3 | 0  | 0  | 0  | +1 | -3 | -3 | 0  | -2 | -3 | -2 | +1 | 0  | -4 | -2 | -3 |
| D | -2 | -2 | +1 | +6 | -3 | 0  | +2 | -1 | -1 | -3 | -4 | -1 | -3 | -3 | -1 | 0  | -1 | -4 | -3 | -3 |
| C | 0  | -3 | -3 | -3 | +9 | -3 | -4 | -3 | -3 | -1 | -1 | -3 | -1 | -2 | -3 | -1 | -1 | -2 | -2 | -1 |
| Q | -1 | +1 | 0  | 0  | -3 | +5 | +2 | -2 | 0  | -3 | -2 | +1 | 0  | -3 | -1 | 0  | -1 | -2 | -1 | -2 |
| E | -1 | 0  | 0  | +2 | -4 | +2 | +5 | -2 | 0  | -3 | -3 | +1 | -2 | -3 | -1 | 0  | -1 | -3 | -2 | -2 |
| G | 0  | -2 | 0  | -1 | -3 | -2 | -2 | +6 | -2 | -4 | -4 | -2 | -3 | -3 | -2 | 0  | -2 | -2 | -3 | -3 |
| H | -2 | 0  | +1 | -1 | -3 | 0  | 0  | -2 | +8 | -3 | -3 | -1 | -2 | -1 | -2 | -1 | -2 | -2 | +2 | -3 |
| I | -1 | -3 | -3 | -3 | -1 | -3 | -3 | -4 | -3 | +4 | +2 | -3 | +1 | 0  | -3 | -2 | -1 | -3 | -1 | +3 |
| L | -1 | -2 | -3 | -4 | -1 | -2 | -3 | -4 | -3 | +2 | +4 | -2 | +2 | 0  | -3 | -2 | -1 | -2 | -1 | +1 |
| K | -1 | +2 | 0  | -1 | -3 | +1 | +1 | -2 | -1 | -3 | -2 | +5 | -1 | -3 | -1 | 0  | -1 | -3 | -2 | -2 |
| M | -1 | -1 | -2 | -3 | -1 | 0  | -2 | -3 | -2 | +1 | +2 | -1 | +5 | 0  | -2 | -1 | -1 | -1 | -1 | +1 |
| F | -2 | -3 | -3 | -3 | -2 | -3 | -3 | -3 | -1 | 0  | 0  | -3 | 0  | +6 | -4 | -2 | -2 | +1 | +3 | -1 |
| P | -1 | -2 | -2 | -1 | -3 | -1 | -1 | -2 | -2 | -3 | -3 | -1 | -2 | -4 | +7 | -1 | -1 | -4 | -3 | -2 |
| S | +1 | -1 | +1 | 0  | -1 | 0  | 0  | 0  | -1 | -2 | -2 | 0  | -1 | -2 | -1 | +4 | +1 | -3 | -2 | -2 |
| T | 0  | -1 | 0  | -1 | -1 | -1 | -1 | -2 | -2 | -1 | -1 | -1 | -1 | -2 | -1 | +1 | +5 | -2 | -2 | 0  |
| W | -3 | -3 | -4 | -4 | -2 | -2 | -3 | -2 | -2 | -3 | -2 | -3 | -1 | +1 | -4 | -3 | -2 | +11| +2 | -3 |
| Y | -2 | -2 | -2 | -3 | -2 | -1 | -2 | -3 | +2 | -1 | -1 | -2 | -1 | +3 | -3 | -2 | -2 | +2 | +7 | -1 |
| V | 0  | -3 | -3 | -3 | -1 | -2 | -2 | -3 | -3 | +3 | +1 | -2 | +1 | -1 | -2 | -2 | 0  | -3 | -1 | +4 |

FIG. 35

ANTIBODIES SPECIFIC FOR HYPERPHOSPHORYLATED TAU AND METHODS OF USE THEREOF

RELATED APPLICATIONS

This application is a Continuation of U.S. application Ser. No. 15/207,836, filed Jul. 12, 2016, and claims priority to Great Britain Application No. 1518375.9, filed Oct. 16, 2015, and Great Britain Application No. 1512211.2, filed Jul. 13, 2015. The entire contents of these applications are incorporated herein by reference in their entirety.

FIELD OF THE INVENTION

The present invention relates to a novel class of monoclonal antibody that specifically binds the phosphorylated serine 396 residue on pathological hyperphosphorylated (PHF) tau (pS396), as well as to methods of using these molecules and their tau binding fragments in the treatment of Alzheimer's disease and tauopathies.

REFERENCE TO SEQUENCE LISTING

This application includes one or more Sequence Listings pursuant to 37 C.F.R. 1.821 et seq., which are disclosed in computer-readable media (file name: 0995.txt, created on 23 Jun. 2016, and having a size of 40 kB), which file is herein incorporated by reference in its entirety.

BACKGROUND OF THE INVENTION

Age-related neurodegenerative diseases such as Alzheimer's disease (AD) and dementia are one of the largest societal challenges today. The World Health Organization estimates that costs for care of the elderly will continue to increase and that the number of diagnosed dementia cases will triple by 2050 (World Health Organization and Alzheimer's Disease International—Status Report (2012) DEMENTIA: A public health priority, WHO). The first treatments for AD were neurotransmitter modulators such as acetylcholine esterase inhibitors and NMDA modulators. These therapies became available at the turn of the millennium and still form the cornerstone for symptomatic relief of memory deficits related to dementia and AD. However, these drugs do not target the underlying causes of AD, accumulation of amyloid-β (Aβ) peptide and tau protein aggregates and associated loss of neuronal synapses and eventually neurons.

Longitudinal, community-wide studies of the elderly (Weiner, M. W. et al. (2014) ADNI online: http://www.adni-info.org/; Breteler, M. M. et al. (1992) Neuroepidemiology 11 Suppl 1, 23-28; Launer, L. J. (1992) Neuroepidemiology 11 Suppl 1, 2-13) together with large genome-wide association studies (Lambert, J. C. et al. (2013) Nat. Genet. 45, 1452-1458) have shown that AD is a heterogeneous mix of dementias where up to 10 percent of the advanced AD patients lack amyloid pathology (Crary, J. F. et al. (2014) Acta Neuropathol. 128, 755-766). Furthermore, seminal pathological studies by Braak & Braak (Braak, H. and Braak, E. (1996) Acta Neurol. Scand. Suppl 165, 3-12) demonstrated a clear correlation between the degree of neurofibrillary tangle pathology and cognitive state prior to autopsy. These observations have been reinforced by several investigators (Nelson, P. T. et al. (2012) J. Neuropathol. Exp. Neurol. 71, 362-381), and in recent longitudinal biomarker studies, which indicate that cerebrospinal fluid (CSF) levels of tau and phospho-tau increase throughout early and late stages of the disease (Jack, C. R., Jr. et al. (2013) Lancet Neurol. 12, 207-216).

As indicated above, the microtubule-associated protein, tau, and its hyper-phosphorylated version, form the main constituent of intracellular neurofibrillary tangles, which are one of the main hallmarks of AD. Furthermore, specific genetic variants of tau are associated with familial forms of fronto-temporal dementia (FTD). Appearance of tau pathology in AD occurs in a distinct spatial pattern, starting in the entorhinal cortex, followed by hippocampal and cortical areas (Braak, H. and Braak, E. (1996) Acta Neurol. Scand. Suppl 165, 3-12). The specific stage of tau pathology also correlates well with cognitive abilities (Nelson, P. T. et al. (2012) J. Neuropathol. Exp. Neurol. 71, 362-381; Braak, E. et al. (1999) Eur. Arch. Psychiatry Clin. Neurosci. 249 Suppl 3, 14-22). Taken together, this evidence forms the basis of a tau-based hypothesis for AD. It entails that the intracellular accumulation of tau leads to microtubule degeneration and spinal collapse. As a result, communication between neurons malfunctions and cell death follows. Recently, it has also been shown that tau itself may form an endo-pathogenic species that can transmit neurodegeneration from one cell to the next (Clavaguera, F. et al. (2009) Nat. Cell Biol. 11, 909-913).

I. Tau as an Endo-Pathogen

Clavaguera and colleagues have demonstrated that tau itself may act as an endo-pathogen (Clavaguera, F. et al. (2009) Nat. Cell Biol. 11, 909-913). Low spin brain extracts were isolated from P301S tau transgenic mice (Allen, B. et al. (2002) J. Neurosci. 22, 9340-9351), diluted and injected into the hippocampus and cortical areas of young ALZ17 mice. The ALZ17 mouse is a tau transgenic mouse line which only develops late pathology (Probst, A. et al. (2000) Acta Neuropathol. 99, 469-481). The injected ALZ17 mice quickly developed solid filamentous pathology, and administration of immuno-depleted brain extracts from P301S mice or extracts from wild type mice did not induce tau pathology. Fractionation of the brain extracts in soluble (S1) and sarcosyl-insoluble tau (P3) (Sahara, N. et al. (2013) J. Alzheimer's. Dis. 33, 249-263) and injection of these into ALZ17 mice demonstrated that the P3 fraction is most competent in inducing pathology. It contains most of the intracellular hyper-phosphorylated filamentous tau. The majority of pathology could also be induced when injecting P301S extracts into the brains of wild type mice, but no NFTs were formed. In subsequent studies, Clavaguera et al. have shown that human tau extracted from post-mortem brain tissue of other tauopathies (Argyrophilic Grain Disease (AGD), Progressive Supranuclear Palsy (PSP), and Corticobasal Degeneration (CBD)) may also induce tau pathology in the ALZ17 model (Clavaguera, F. et al. (2013) Proc. Natl. Acad. Sci. U.S.A. 110, 9535-9540). Since the presentation of these data, several other tau seeding and spreading models have been reported (Ahmed, Z. et al. (2014) Acta Neuropathol. 127, 667-683; Walker, L. C. et al. (2013) JAMA Neurol. 70, 304-310). The main conclusion from these studies indicates a mechanism by which pathogenic tau in intracellular inclusions is secreted from the cell into the periplasmic space. The pathological tau material is then transported along the vesicular sheath in both anterograde and retrograde direction and subsequently taken up by neighboring cells by means of bulk endocytosis. This mechanism explains why the spread of pathology observed in human disease follows a distinct anatomical pattern. Intriguingly, peripheral administration of pathological tau may accelerate the formation of tau pathology in ALZ17 mice (Clavaguera, F. et al. (2014) Acta Neuropathol. 127, 299-301). This spreading mechanism may explain disease propagation in other proteinopathies (Goedert, M. et al. (2010) Trends Neurosci. 33, 317-325; Sigurdsson, E. M. et al. (2002) Trends Mol. Med. 8, 411-413).

II. Tau Species

The discovery that the tau protein may act as an endopathogen has spawned a search for "The Pathogenic Species" that could be targeted in potential interventive therapies.

The microtubule-associated protein tau gene (MAPT) is located on chromosome 17 of the human genome and expresses six isoforms of the tau protein in adult human brain. These isoforms arise from the alternative splicing of exons 2, 3 and 10 of the 16 exons within the MAPT gene. Exons 2 and 3 express a 29 amino acid repeat and exon 10 expresses an additional microtubule binding domain. As a result, tau isoforms will contain 0, 1 or 2 N-terminal repeats and 3 or 4 C-terminal microtubule binding domains (3R or 4R tau). Commonly six isoforms of tau are expressed. The longest (2N4R) and shortest (ON3R) isoforms consist of 441 and 352 amino acids, respectively (Kolarova, M. et al. (2012) Int. J. Alzheimers. Dis. 2012, 731526). The N-terminal projection domain of tau (2N4R) consists of a 44 amino acid glycine-rich tail and residues 45-102 encompass two highly acidic regions (N1, N2-domains). Two proline-rich regions are found at residues 151-243 (P1, P2 domains). The remainder of the protein is constituted by four microtubule binding domains (R1-R4), followed by a short C-terminal region.

Tau is very soluble and highly phosphorylation-labile protein. Approximately 20 percent or 85 of the amino acid residues in the longest isoform of tau are potential (Ser, Thr or Tyr) phosphorylation sites. Roughly half of these have been observed experimentally (Hanger, D. P. et al. (2009) Trends Mol. Med. 15, 112-119; Hasegawa, M. et al. (1992) J. Biol. Chem. 267, 17047-17054), and are clustered around the terminal residues of the microtubule binding domains. Tau is dynamically phosphorylated and de-phosphorylated during the cell cycle. It must dissociate from microtubules to allow for meiosis to occur. Its main role in post mitotic cells (the differentiated neuron) is to act as a microtubule stabilizer, allowing for optimal axonal transport. It can only associate with microtubules in its mostly de-phosphorylated form, thus phosphorylation acts as a direct microtubule association/dissociation switch within the neuron. Under normal conditions, cytosolic tau contains on average two phosphorylated sites. In paired helical filamentous material, at least 7-8 sites are phosphorylated (Hanger, D. P. et al. (2009) Trends Mol. Med. 15, 112-119; Hasegawa, M. et al. (1992) J. Biol. Chem. 267, 17047-17054). Hyperphosphorylated, paired helical filamentous tau is a key hallmark of Alzheimer's disease (Kosik et. al. (1986) PNAS, 86, 4044-4048), a distinct mobility shift of hyperphosphorylated tau is observed in immune-cytochemical analysis of human AD brain material.

It has been difficult to study the tau protein with traditional structural techniques like x-ray crystallography or NMR spectroscopy, reflecting its meta-stable nature. Such studies have mainly been conducted on domain fragments of the un-phosphorylated protein. The only structural study to date on full-length tau (2N4R), using NMR spectroscopy, reveals that the protein contains only sparse stretches of stable secondary structure (Mukrasch, M. D. et al. (2009) PLoS. Biol. 7, e34). This analysis indicates that the secondary structure of the peptide backbone has a large propensity for adapting a β-sheet structure. The backbone's first 200 residues are considerably more ordered than the C-terminus encompassing the microtubule binding domains. The presence of many specific long-range interactions within the protein in solution indicates that it exists in a largely disordered molten globular state (Ohgushi, M. and Wada, A. (1983) FEBS Lett. 164, 21-24).

Protease products of tau generated in particular by caspase and calpain (Asp13, Glu391 and Asp421) have been identified in tangle material (Gamblin, T. C. et al. (2003) Proc. Natl. Acad. Sci. U.S.A. 100, 10032-10037). In particular, the truncation at Asp421 has been studied in detail using the tau C3 antibody, which binds to the free Asp421 terminus. This truncation has been postulated as an early event in AD pathogenesis associated with induction of apoptosis (deCalignon A. et al. (2010) Nature 464, 1201-1204). The N-terminal cleavage at Asp13 and the C-terminal cleavage at Glu391 are considered late events in the pathogenesis (deCalignon A. et al. (2010) Nature 464, 1201-1204; Delobel, P. et al. (2008) Am. J. Pathol. 172, 123-131). Recently, an additional N-terminal fragment (residues 1-224) was identified in CSF from AD and PSP patients, and has been hypothesized to be an early marker of disease and particularly pathogenic (U.S. Ser. No. 14/092,539; Bright, J. et al. (2014) Neurobiol. Ageing, 1-17). A similar calpain cleaved fragment was reported by other groups (Ferreira, A. and Bigio, E. H. (2011) Mol. Med. 17, 676-685; Reinecke, J. B. et al. (2011) PLoS. One. 6, e23865).

Apart from hyper-phosphorylation and tau fragmentation, post-translational acetylation (Cohen, T. J. et al. (2011) Nat. Commun. 2, 252; Min, S. W. et al. (2010) Neuron 67, 953-966) and O-GlcNAcylation (Zhu, Y. et al. (2014) J. Biol. Chem.) have been proposed to be pathology defining processes in the formation of tangle pathology associated with AD.

III. Tau Immunotherapies

Immunotherapies are traditionally separated into passive and active vaccine approaches. In an active vaccine approach, a pathogenic agent is injected into the patient and the innate immune system elicits an immune response. This triggers the maturation of B-cells generating high affinity antibodies against the administered antigen. In a passive vaccine approach, the triggering of the innate immune system is circumvented by infusing a specific antibody against the antigen. The inherent clearance system then removes antibody bound ligand.

AC Immune is pursuing a mouse monoclonal antibody against phospho-serine 409 of tau. Antibodies were profiled against human AD and control brain tissue and were selected based on their ability to recognize tangle pathology. The humanized version of two antibodies, hACI-36-2B6-Ab1 and hACI-36-3A8-Ab1, both bind to a tau epitope within amino acids 401-418 (WO 2013/151762).

The group of Roger Nitsch have isolated tau auto-antibodies from elderly healthy individuals with no sign of degenerative tauopathy. A number of antibodies have been isolated using full length recombinant human tau (2N4R) to find tau specific antibodies. These were then screened for their ability to discriminate tau isolates from diseases and healthy individuals. Three lead antibodies, 4E4, 4A3 and 24B2, have been described in the patent literature (WO2012049570; US2012087861). Their epitope mapping indicates that all recognize amino acids within and C-terminal to the microtubule binding region, from position V339 to K369. These antibodies do not exhibit any phospho-specificity.

C2N Diagnostics focus mainly on developing diagnostic tools for early detection of neurodegenerative disease. Antibodies were generated against full length human and mouse tau protein. Eight and five antibodies were identified, recognizing human and mouse tau, respectively (Yanamandra, K. et al. (2013) Neuron 80, 402-414). Three antibodies with different binding kinetics were selected for in vivo evaluation. Namely, HJ9.3, HJ9.4 and HJ8.5, recognizing tau residues 306-320, 7-13 and 25-30, respectively, with the last one being specific for human tau. The antibodies were also selected based on their ability to prevent transfer of pathology in an ingenious mechanistic reporter assay of transcellular propagation of tau (Sanders, D. W. et al. (2014) Neuron 82, 1271-1288; Kfoury, N. et al. (2012) J. Biol. Chem. 287, 19440-19451). Their evaluation in chronic i.c.v. injection studies in P301S transgenic mice demonstrated their ability to reduce levels of hyper-phosphorylated tau protein as determined by AT8 staining in immuno-histochemical analysis of the treated mice.

The antibodies of Peter Davies were developed originally as diagnostic tools that could differentiate between pathological and normal tau in AD and control brain material (Greenberg, S. G. and Davies, P. (1990) Proc. Natl. Acad. Sci. U.S.A. 87, 5827-5831). Evaluation of the therapeutic utility of the PHF1 and MC1 antibodies was demonstrated in P301S and JPNL3 (P301L) (Boutajangout, A. et al. (2011) J. Neurochem. 118, 658-667; Chai, X. et al. (2011) J. Biol. Chem. 286, 34457-34467; D'Abramo, C. et al. (2013) PLoS. One. 8, e62402 mice). PHF1 recognizes a linear phospho-tau epitope (pS396, pS404) whereas MC1 is a conformation-dependent antibody that recognizes a structural tau epitope requiring two distinct parts of the linear sequence, an epitope within residues 46-202 and a C-terminal epitope between residues 312-342 (Jicha, G. A. et al. (1997) J. Neurosci. Res. 48, 128-132). Injection of these two antibodies in chronic 12-13 week immunization studies resulted in substantial reduction of spinal cord and brainstem pathology among other brain regions, which translated to an attenuation of the motor deficit observed in these mice. (D'Abramo, C. et al. (2013) PLoS. One. 8, e62402).

iPerian/Bristol Meyers Squibb has developed tau antibodies against a postulated pathological tau species, composed of an N-terminal fragment of tau (etau: residues 1-224), which promoted hyperactivity in induced pluripotent stem cell based neuronal cultures. A portfolio of antibodies has been developed, but characterization has focused on antibodies IPN001 and IPN002 that recognize an N-terminal epitope within residues 9-18. Accordingly, these antibodies detect elevated tau levels in CSF from staged AD and PSP patients that may be an early sign of disease. In vivo injections of the antibodies in JPNL3 (P301L) mice led to partial reversal of progressive motor deficits (U.S. Ser. No. 14/092,539).

Einar Sigurdsson were the first program to demonstrate the efficacy of tau based immunotherapy. An active vaccine consisting of tau peptide 379-408[pS396, pS404] together with Adju-Phos adjuvant was used to immunize JPNL3 (P301L) mice. In this study a prominent reduction of tau pathology was observed in the vaccine treated mice when compared to control animals. An attenuation of tauopathy-related motor phenotype was detected as well. Its efficacy was confirmed in a different mouse model (htau/PS1) not driven by mutant tau (Boutajangout, A. et al. (2011) AAIC 2011 (7, issue 4, Supplement edn) p. s480-s431; Congdon, E. E. et al. (2013) J. Biol. Chem. 288, 35452-35465; Gu, J. et al. (2013) J. Biol. Chem. 288, 33081-33095).

Prothena has evaluated three tau antibodies in the K369I (K3) transgenic tau mouse and in a P301L mouse model. Antibodies with varying properties were selected for in-vivo evaluation. Two pS404 antibodies with different isotype (IgG1/k and IgG2a/k) or a total (pan) anti-tau antibody (IgG1/k) were injected in a chronic paradigm. K369I mice were treated with weekly injections for 21 weeks starting at 3 weeks of age, and P301L mice were treated for 7 months with weekly injections starting at 4 months of age. A reduction in tau positive neurofibrillary inclusions was observed in the K3 mice with the IgG2a/k pS404 antibody. Both of the pS404 antibodies were able to reduce the levels of pS422 positive tau, whereas no reduction was observed in the pan-anti-tau antibody treated mice. These studies suggest that: 1) tau clearance may be isotype-dependent, and; 2) It may be important to target a tau species that is relevant to disease, as the total-anti-tau antibody was unable to reduce hyper-phosphorylated tau (PCT/US2014/025044).

The inventors of the present invention have surprisingly found antibodies specific for the phosphorylated tau serine residue 396 (pS396); this is in contrast to the prior art antibodies which recognize primarily the tau proteins phosphorylated at both 396 and 404 residues, phosphorylated at the 404 residue only or at other residues on tau.

The inventors have developed antibodies which furthermore have a remarkable specificity and selectivity towards human pathological tau. There is a need for antibodies which are highly selective and specific for pathogenic tau protein. The antibodies of the present invention show a much higher degree of specificity and selectivity towards human pathological tau over non-pathological tau compared to the antibodies of WO2013/050567 (see FIG. 1 of WO2013/050567). The antibodies of WO2012/045882 reported to have a specific binding, were elicited from 6 to 9 residue amino acid sequences of Tau amino acids 393-401, 396-401, 394-400 and 393-400. This contrasts from the antibodies of the present invention which were elicited against pathogenic hyperphosphorylated tau comprising a longer amino acid sequence as described herein.

As shown in the Examples, comparison to five published tau antibodies: hACI-2B6 (described WO2013151762); IPN002 (described in WO 2014028777); HJ8.5 (described in WO 2014008404); the anti-Tau pS422 monoclonal antibody 2.10.3 (described in U.S. Pat. No. 8,609,097); PHF13 (a commercially available antibody (e.g. SigmaAldrich) recommended for detection of Tau phosphorylated at Ser 396 of mouse, rat and human origin and discussed by Sankaranarayanan (PLOSONE, DOI:10.1371/journal-.pone.0125614 May 1, 2015 and Otvos (Biochemistry 1997, 36, 8114-8124); and the 4E4 antibody, (described as binding to V339, E342, D387, E391 and K395 in U.S. Pat. No. 8,940,272), showed that the antibodies, and epitope-binding fragments thereof, of the present invention exhibit a higher degree of specificity and selectivity towards human pathological tau than any of the comparator antibodies.

Further, the antibodies, and epitope-binding fragments thereof, of the present invention show many advantageous features such as the ability to discriminate between pathological and non-pathological human tau protein, and in particular to bind tau associated with Alzheimer's (AD) pathology. In electrophysiological studies, the antibodies, and epitope-binding fragments thereof, of the invention were additionally able to reverse reduced paired pulse facilitation and spontaneous miniature excitatory synaptic current (mEPSC).

SUMMARY OF THE INVENTION

The present invention relates to monoclonal antibodies, and epitope-binding fragments thereof, capable of specifically binding to the phosphorylated residue serine 396 of human (2N4R isoform) tau (SEQ ID NO:33) and to such antibodies that have been produced using a new method that allows such specific isolation and recovery. The antibodies are further characterized by their ability to discriminate between phosphorylated residues 396 and 404 such that they substantially do not bind the phosphorylated 404 residue.

Without being bound by a particular theory, evidence from the inventors demonstrates that the discrimination and selectivity of the antibodies of the present invention for human tau protein phosphorylated at residue 396 in the presence of tau protein phosphorylated at residue 404 but not at 396 is significant from a pathological and therapeutic perspective. The antibodies of the present invention are selective for pathological tau in the presence of non-pathological—yet phosphorylated—tau. The antibodies of the present invention are able to deplete tau tangles of pathological tau in the presence of normal tau. Without being bound to a particular theory, it is believed that depleting tangles of tau comprising tau protein that has been phosphorylated at tau position 396 prevents seeding of pathological tau into tau tangles. Accordingly, one aspect of the invention relates to an antibody that is capable of selectively binding to 396-phosphorylated tau even when such molecules are in the presence of tau protein that has been phosphorylated at tau position 404. A related aspect of the invention relates to an antibody that is capable of selectively binding to 396-phosphorylated tau even when such molecules are in the presence of non-pathogenic tau. Further defined, the invention relates to an antibody selective for pathological tau said pathological tau being hyperphosphorylated tau appearing as 64 kDa band (by Western Blot analysis) in transgenic mice overexpressing the human 2N4R isoform of tau.

One aspect of the invention is directed to an anti-tau antibody meeting the following test criteria: i) the antibody does not bind to non-phosphorylated tau; ii) the antibody does not bind to tau phosphorylated at 404 and not phosphorylated at 396; iii) the antibody does bind to tau phosphorylated at 396; and iv) the antibody does bind to tau phosphorylated at both 396 and 404. The inventors have found that the binding under test criteria iii) and iv) are in the same order of magnitude and postulate that phosphorylation at position 404 does not interfere nor enhance the binding process. The inventors have further found that, contrarily to test criteria ii), binding to a tau protein which is not phosphorylated at 396 but is phosphorylated at 404, does not deplete tangles or clear pathological tau in test models.

One aspect of the invention is directed to an anti-tau antibody that, when used with immune-depleted rTg4510 extracts from transgenic mice, specifically reduces the hyperphosphorylated tau 64 and 70 kDa bands by at least 90%, while reducing the 55 kDa tau band by not more than 10%. A further aspect of the invention is directed to an anti-tau antibody that specifically reduces the hyperphosphorylated tau 64 and 70 kDa bands by at least 90%, while reducing the 55 kDa tau band by not more than 10%; or the capability, when used as described herein with extracts from human AD post-mortem brains, to specifically reduce the phosphorylated S396 hyperphosphorylated tau bands by at least 90%, while not reducing the non-hyperphosphorylated tau bands by more than 10%.

Another aspect of the invention is directed to a method of treating a patient with a taupathy, such as Alzheimer's Disease, comprising depleting a tangle or attenuating the progression of said tangle, said tangle comprising hyperphosphorylated Tau, said method comprising contacting hyperphosphorylated Tau with an antibody of the invention such that the tangle is depleted, reduced in its content of hyperphosphorylated tau or progression of tangle formation is attenuated.

Alternatively defined, the invention relates to a method of treating a patient with a taupathy, such as Alzheimer's Disease, said method comprising contacting tangles with an antibody selective for tau having residue 396 phosphorylated such that the tangle is depleted of hyperphosphorylated Tau.

More specifically the invention relates to any one of four monoclonal antibodies selected from the group comprising:
Antibody C5.2
wherein Antibody C5.2 comprises:
(a) a Light Chain CDR1 having the amino acid sequence of SEQ ID NO:17;
(b) a Light Chain CDR2 having the amino acid sequence of SEQ ID NO:18;
(c) a Light Chain CDR3 having the amino acid sequence of SEQ ID NO:19;
(d) a Heavy Chain CDR1 having the amino acid sequence of SEQ ID NO:20;
(e) a Heavy Chain CDR2 having the amino acid sequence of SEQ ID NO:21; and
(f) a Heavy Chain CDR3 having the amino acid sequence of SEQ ID NO:22;
Antibody C8.3
wherein Antibody C8.3 comprises:
(a) a Light Chain CDR1 having the amino acid sequence of SEQ ID NO:25;
(b) a Light Chain CDR2 having the amino acid sequence of SEQ ID NO:26;
(c) a Light Chain CDR3 having the amino acid sequence of SEQ ID NO:27;
(d) a Heavy Chain CDR1 having the amino acid sequence of SEQ ID NO:28;
(e) a Heavy Chain CDR2 having the amino acid sequence of SEQ ID NO:29; and
(f) a Heavy Chain CDR3 having the amino acid sequence of SEQ ID NO:30;
Antibody C10-2
wherein Antibody C10-2 comprises:
(a) a Light Chain CDR1 having the amino acid sequence of SEQ ID NO:9;
(b) a Light Chain CDR2 having the amino acid sequence of SEQ ID NO:10;
(c) a Light Chain CDR3 having the amino acid sequence of SEQ ID NO:11;
(d) a Heavy Chain CDR1 having the amino acid sequence of SEQ ID NO:12;
(e) a Heavy Chain CDR2 having the amino acid sequence of SEQ ID NO:13; and
(f) a Heavy Chain CDR3 having the amino acid sequence of SEQ ID NO:14;
and
Antibody D1.2
wherein Antibody D1.2 comprises:
(a) a Light Chain CDR1 having the amino acid sequence of SEQ ID NO:1;
(b) a Light Chain CDR2 having the amino acid sequence of SEQ ID NO:2;
(c) a Light Chain CDR3 having the amino acid sequence of SEQ ID NO:3;
(d) a Heavy Chain CDR1 having the amino acid sequence of SEQ ID NO:4;
(e) a Heavy Chain CDR2 having the amino acid sequence of SEQ ID NO:5; and (f) a Heavy Chain CDR3 having the amino acid sequence of SEQ ID NO:6.

The amino acid sequences of the full light and heavy chains of an exemplary antibody C5.2, including the constant domains therein, are shown in SEQ ID NO:23 and SEQ ID NO:24, respectively (as used in the Examples).

The amino acid sequences of the full light and heavy chains of an exemplary antibody C8.3, including the constant domains therein, are shown in SEQ ID NO:31 and SEQ ID NO:32, respectively (as used in the Examples).

The amino acid sequences of the full light and heavy chains of an interesting antibody C10-2, including the constant domains therein, are shown in SEQ ID NO:15 and SEQ ID NO:16, respectively (as used in the Examples). The amino acid sequence of the heavy chain of humanized C10-2 antibody is shown in SEQ ID NO:35. The amino acid sequence of the light chain of humanized C10-2 antibody is shown in SEQ ID NO:36. One aspect of the invention relates to an antibody of the invention comprising SEQ ID NO:35 or SEQ ID NO:36, or both.

The amino acid sequences of the full light and heavy chains of an exemplary antibody D1.2, including the constant domains therein, are shown in SEQ ID NO:7 and SEQ ID NO:8, respectively (as used in the Examples).

In an alternative embodiment, the antibody D1.2 comprises a light chain having the amino acid sequence of SEQ ID NO:34, wherein the amino acid at position 3 is valine (whereas in the exemplary light chain of SEQ ID NO:7, this amino acid is a methionine). This light chain may be paired with a heavy chain as described above, i.e. having CDRs of SEQ ID NOs:4, 5 and 6. For example, the antibody may comprise a light chain having the amino acid sequence of SEQ ID NO:34 together with a heavy chain having the amino acid sequence of SEQ ID NO:8 (antibody "D1.2*").

One aspect of the invention is directed to an antibody comprising:
(a) a Light Chain CDR1 having the amino acid sequence of SEQ ID NO:9;
(b) a Light Chain CDR2 having the amino acid sequence of SEQ ID NO:10; and/or
(c) a Light Chain CDR3 having the amino acid sequence of SEQ ID NO:11.

A further aspect of the invention is directed to an antibody comprising, or additionally comprising:
(a) a Heavy Chain CDR1 having the amino acid sequence of SEQ ID NO:12;
(b) a Heavy Chain CDR2 having the amino acid sequence of SEQ ID NO:13; and/or
(c) a Heavy Chain CDR3 having the amino acid sequence of SEQ ID NO:14.

The antibodies, and epitope-binding fragments thereof, of the invention can be used in treating tauopathies such as Alzheimer's disease (AD), Argyrophilic Grain Disease (AGD), Progressive Supranuclear Palsy (PSP), Corticobasal Degeneration (CBD), TBI (traumatic brain injury, mild, acute or chronic), and chronic traumatic encephalopathy (CTE).

The antibodies, and epitope-binding fragments thereof, of the invention are furthermore intended for use in treating Psychosis, particularly Psychosis due to AD or Psychosis in patients with AD.

BRIEF DESCRIPTION OF THE FIGURES

FIGS. 1A-1B present the results of a dot blot analysis displaying 500 ng S1 and P3 fractions (generation of the S1 and P3 fractions are disclosed in Example 3) derived from brains of AD patients (AD) and aged healthy individuals (con) or from 32 weeks old rTg4510 and non-transgenic (wt) littermates probed with 1 µg/ml D1.2 or C10-2 to assess detection of pathological tau (Example 3). The dot plot shows that D1.2 (FIG. 1A) or C10-2 (FIG. 1B) specifically reacts on disease material from AD patients or human (P301L) tau as expressed in transgenic mice (Tg4510).

FIGS. 2A-2B present the results of a Western blot analysis displaying 2 µg S1 and P3 fractions derived from brains of 32 week old rTg4510 and non-transgenic (wt) littermates or 20 µg S1 and P3 fractions derived from brains from AD patients (AD) and aged healthy individuals (con) probed with 1 µg/ml D1.2 (FIG. 2A) or C10-2 (FIG. 2B). S1 and P3 fractions were loaded at a ratio of 1:50 (based on tissue weight) which was derived from 0.01 mg tissue. In Western blot, normal P301L mutant human 4RON tau is displayed at 55 kDa, while hyper-phosphorylated P301L mutant human 4RON tau species is displayed at 64 and 70 kDa. In P3 fractions from AD hyper-phosphorylated tau is displayed at 54, 64, 69 and 74 kDa (Example 3). The figure illustrates that the antibodies specifically bind to hyper-phosphorylated, mobility shifted tau protein.

FIGS. 3A-3D present the results of Meso Scale Discovery (MSD) ELISA binding of D1.2 (FIG. 3A), C5-2 (FIG. 3B), C10-2 (FIG. 3C) and C8-3 (FIG. 3D) to tau isolated from human AD and non-diseased control brains (Example 4). Similar to demonstrated in FIGS. 1A-1B, immobilisation of tau isolated from disease (AD) and healthy control brains on ELISA plates can be used to demonstrate that the antibodies in this invention specifically bind pathological tau species. Increasing concentrations of antibody lead to saturation binding. The quantity of bound antibody is detected with secondary anti-mouse antibody.

FIGS. 4A-4D present the results of an analysis of the specific binding of C10-2 (FIG. 4A) and D1.2 (FIG. 4B) to tau (386-409) peptides with all combinations of phosphorylation at positions S396 and S404 (Example 5). Specific affinity towards human pathological material is difficult to assess, for this reason we use specific peptide binding to determine the exact epitope affinity, using specific phosphorylated and un-phosphorylated peptides. Specific, dose response curves are shown for binding of antibodies C10-2 (FIG. 4C) and D1.2 (FIG. 4D) to the peptide: TDHGAEIVYK$^{\{p\}}$SPVVSGDT$^{\{p\}}$SPRHL (SEQ ID NO:37) (pS396/pS404), phosphorylated at residues Ser396 and Ser404. Competition binding was conducted with un-phosphorylated peptide (NP) and mono-phosphorylated peptides (pS396 and pS404). Additionally, a control peptide corresponding to phosphorylated serine 262 was included. The competition binding demonstrates that all binding is obtained through the phosphorylated 396 serine residue. Additionally, the data demonstrates that phosphorylation at residue 404 does not interfere with the binding of antibodies at phosphor-serine 396.

FIG. 5A shows that C10-2 (left column) and D1.2 (right column) antibodies bind to p-tau species in Tg4510 (top row) cell bodies and neuropil. No immunoreactivity is detected in non-Tg brain sections (bottom row). FIG. 5B shows that C10-2 (left column) and D1.2 (right column) antibodies bind to p-tau species in cell bodies and neuropil threads in AD donor (AD) (top row). Control donor brains are devoid of immunoreactivity (bottom row) (Example 6).

FIGS. 6A-6E: Binding to pathological and non-pathological P3 for C10-2 and reference antibodies FIGS. 6A-6E present results demonstrating the superiority of the antibody C10-2 (FIG. 6C) of the present invention in recognizing pathological material compared to prior art antibodies 2-10-3 (FIG. 6A), HACI-2B6 (FIG. 6B), IPN 002 (FIG. 6D), and HJ8.5 (FIG. 6E). The Figure shows the specific binding of C10-2 to tau from healthy (as a control) and disease (AD) human brains, together with the binding to tau from 10 month old Tg4510 mice expressing P301L mutant human tau. Increasing concentrations of antibody are added to P3 tau material immobilized on ELISA plates. Ratio of selectivity towards pathological tau is determined at full saturation with active species. The fold selectivity for each of the prior art antibodies is shown in the figure (Example 7).

FIGS. 7A-7C present a quantification of tau aggregation by Cisbio assay. Seeded pcDNA HEK293 cells showed no signal, confirming the absence of detection for input seeding material. Wt (wild type) seeding material (WW) showed no seeding, but in contrast rTg4510 homogenates (CC) seeded efficiently, compared to unseeded. This seeding effect was not affected by treatment with HEL, but was partially reversed by treatment with tau antibodies (C10-2>D1.2>hACI36-2B6-Ab1). Graphs (FIGS. 7A-7C) represent three independent sets of samples and are plotted as relative tau aggregation (fold signal over background normalized to total protein) (Example 8).

FIGS. 8A-8D show antibody reversal of paired pulse facilitation (FIGS. 86 and 8D) and basal synaptic transmission (FIGS. 8A and 8C) deficits in CA1 evoked field potentials (C10-2, FIG. 8A; D1.2, FIG. 8B), illustrating the evoked filed potentials in CA1 subchronic treatment with C10-2 in Tg4510 mice with and tTa mice as a control. Animals were treated twice-weekly with a 15 mg/kg dose of antibody for two weeks (see Example 9). In FIG. 8A (for C10-2) and FIG. 8C (for D1.2), the Field potentials (fEPSP) slope is plotted against stimulation intensity. FIGS. 8A and 8C illustrate that in in vivo electrophysiological assessment of synaptic transmission and plasticity in the CA1 area of the hippocampus in 4.5 to 5.5 months old rTg4510 (lower 2 curves) and tTA (upper 2 curves) control mice i) basal synaptic transmission is significantly impaired in rTg4510 compared to tTA mice, and ii) paired-pulse facilitation is significantly reduced rTg4510 compared to tTA mice.

Figure 8A:
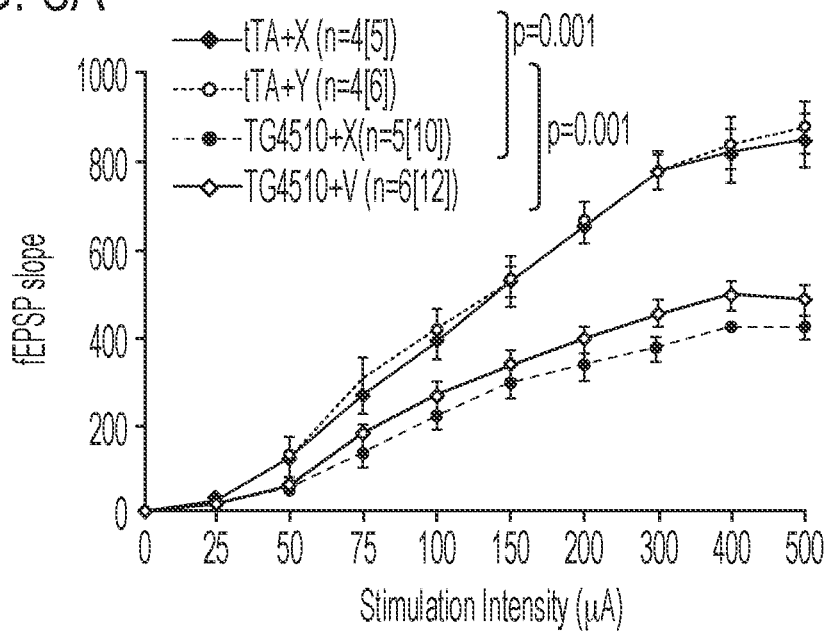
FIGS. 8A-8D: Reversal of electrophysiological deficit
Figure 8B:
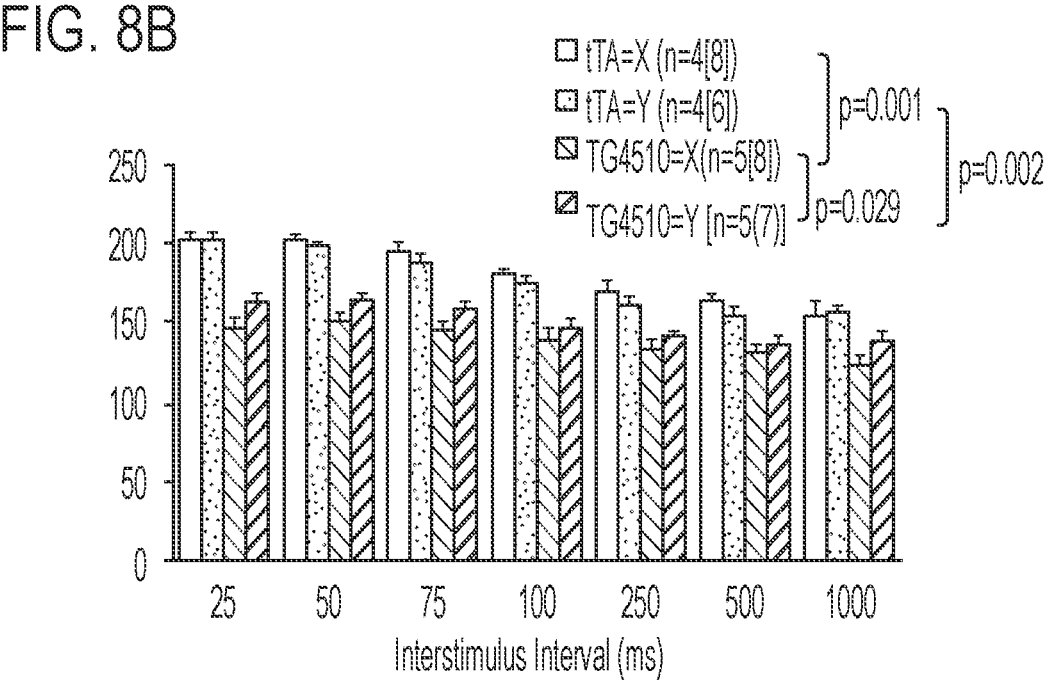
Figure 8C:
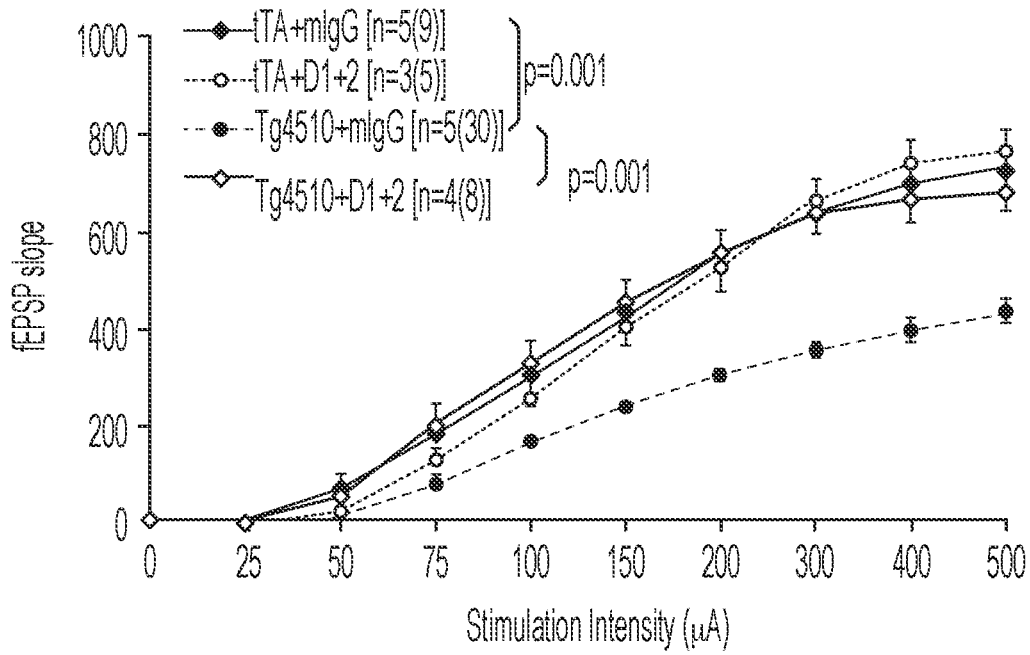
Figure 8D:
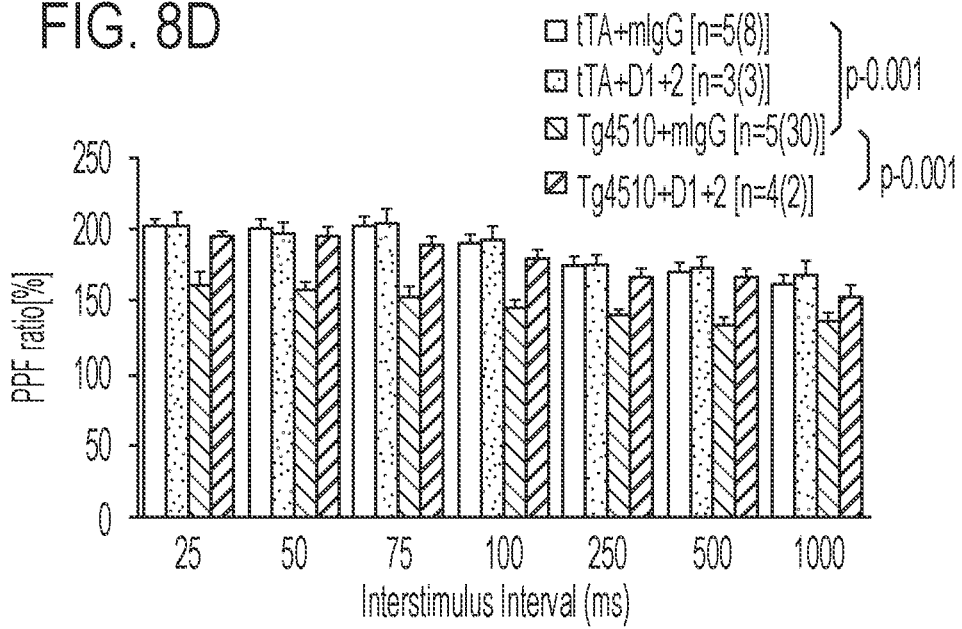

Paired-pulse facilitation, a short-term synaptic plasticity believed to rely on presynaptic mechanisms, was further measured in rTg4510 and tTA mice (FIG. 8B for C10-2 and FIG. 8D for D1.2). Briefly, a pair of stimuli with an inter-stimulus interval (ISI) varying from 25 to 1000 ms was applied to the Schaffer collateral, and the slope of the second fEPSP was compared to the slope of the first fEPSP. Facilitation was observed at all ISIs, with a maximum facilitation at ISIs of 50 and 75 ms. Interestingly, a significantly lower PPF was observed in rTg4510 mice (second 2 bars) when compared to tTA mice (first 2 bars).

Figure 9:
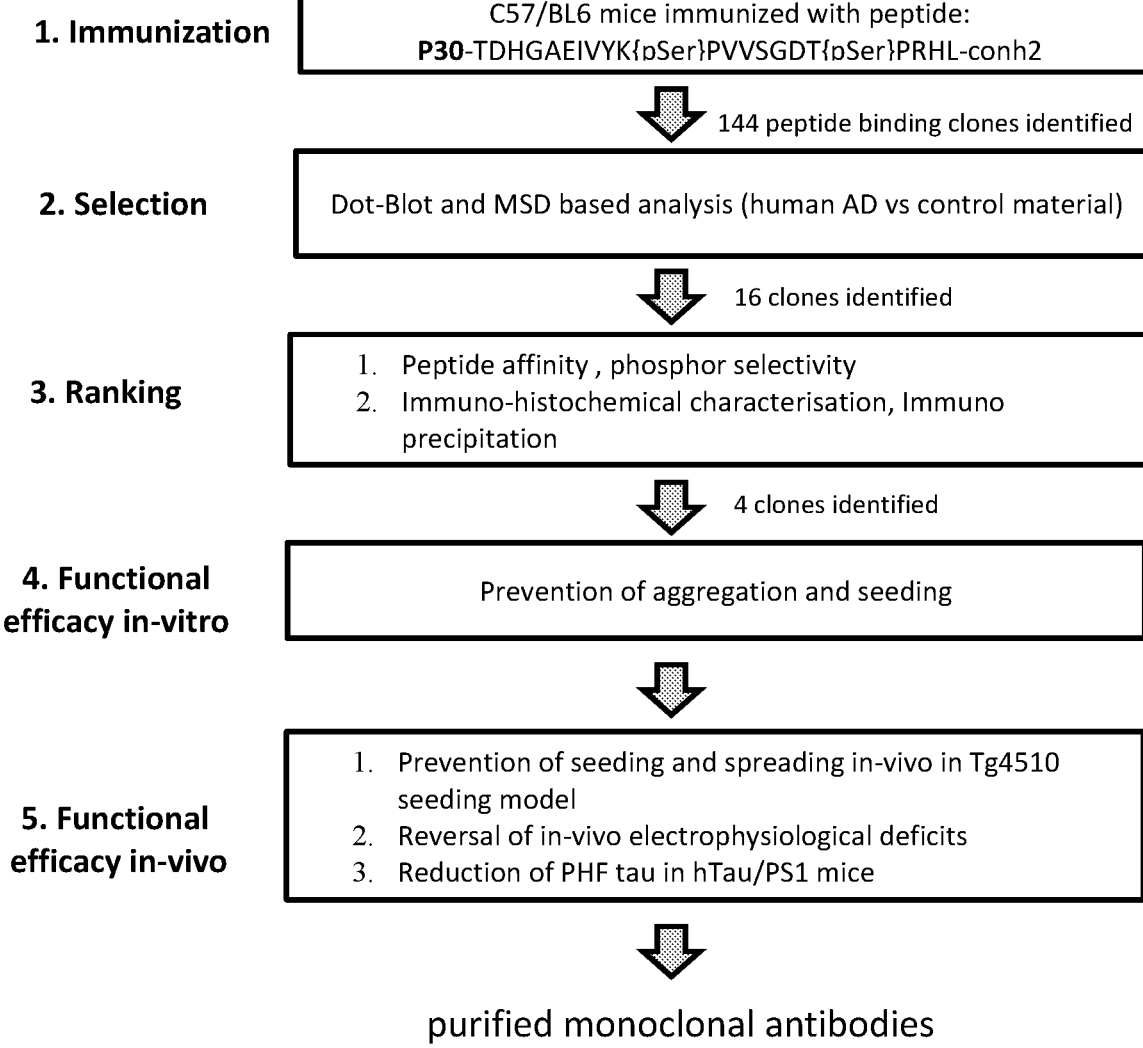

FIG. 9: Overview of screening as outlined in FIGS. 1-8

Antibodies were raised against the bi-phosphorylated peptide: TDHGAEIVYK$^{\{p\}}$SPVVSGDT$^{\{p\}}$SPRHL (SEQ ID NO:37) covering residues 386-410 of 2N4R tau. Hybridomas are screened using dot-blot and MSD ELISA with immobilized human pathological and non-pathological tau (Example 4) to isolate clones that were highly specific towards the either of the phospho-epitopes S396 and/or S404 and at the same time specifically recognize hyperphosphorylated tau from human Alzheimer's disease brains. The ability to discriminate between pathological and non-pathological human tau protein in dot-blot and Western blot is used for selection of hybridomas. 16 clones were selected of which four clones (D1.2, C10-2, C5.2 and C8.3) exhibit extraordinary capabilities for binding to human pathological material. Use of the specific immunization and screening protocol produces highly phospho-serine-396 (pS396) specific antibodies.

Figure 10:
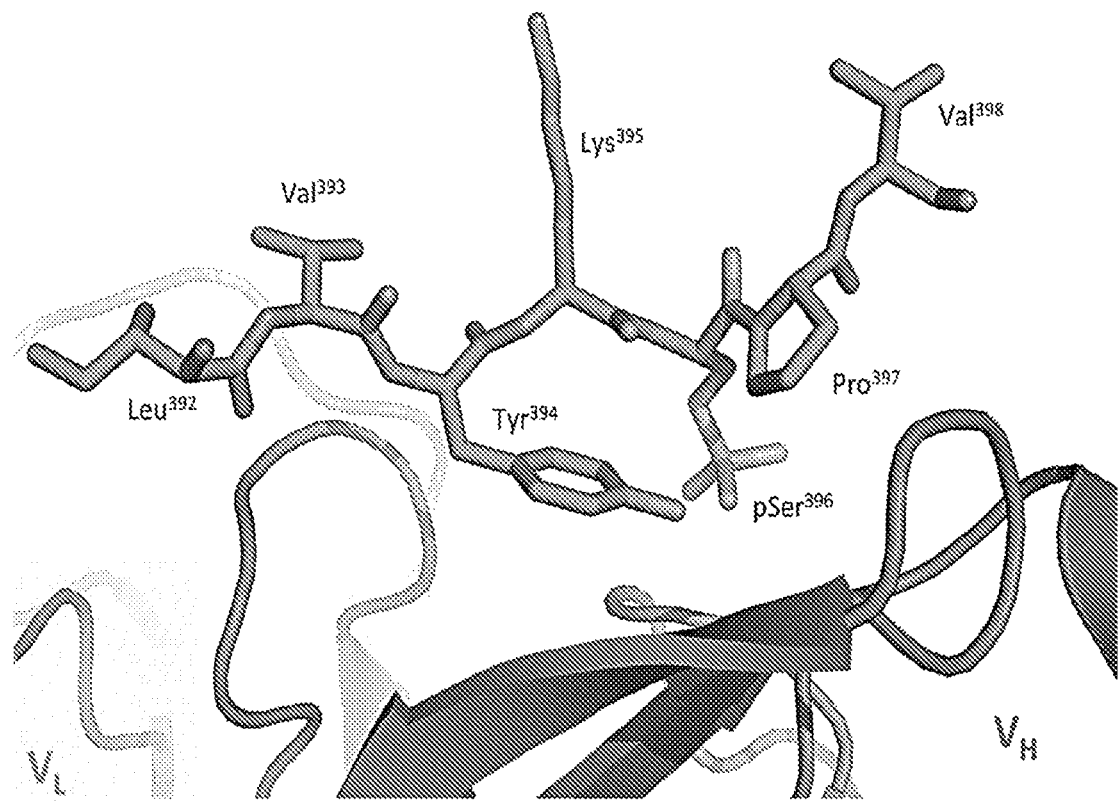

FIG. 10: Residue pSer396 is bound at the center of the antigen binding site of mAb C5.2

The crystal structure of mAb C5.2 in a complex with phospho-peptide 386-410 at 1.9 Å resolution. In this structure the electron density of residues 392-398 are resolved. Residue $^{\{p\}}$Ser396 is bound at the center of the antigen binding site of mAb C5.2 In this structural study of anti-Tau mAbs, the epitope is bound across the heavy chain (bottom right) and light (bottom left) chains.

Figure 11:
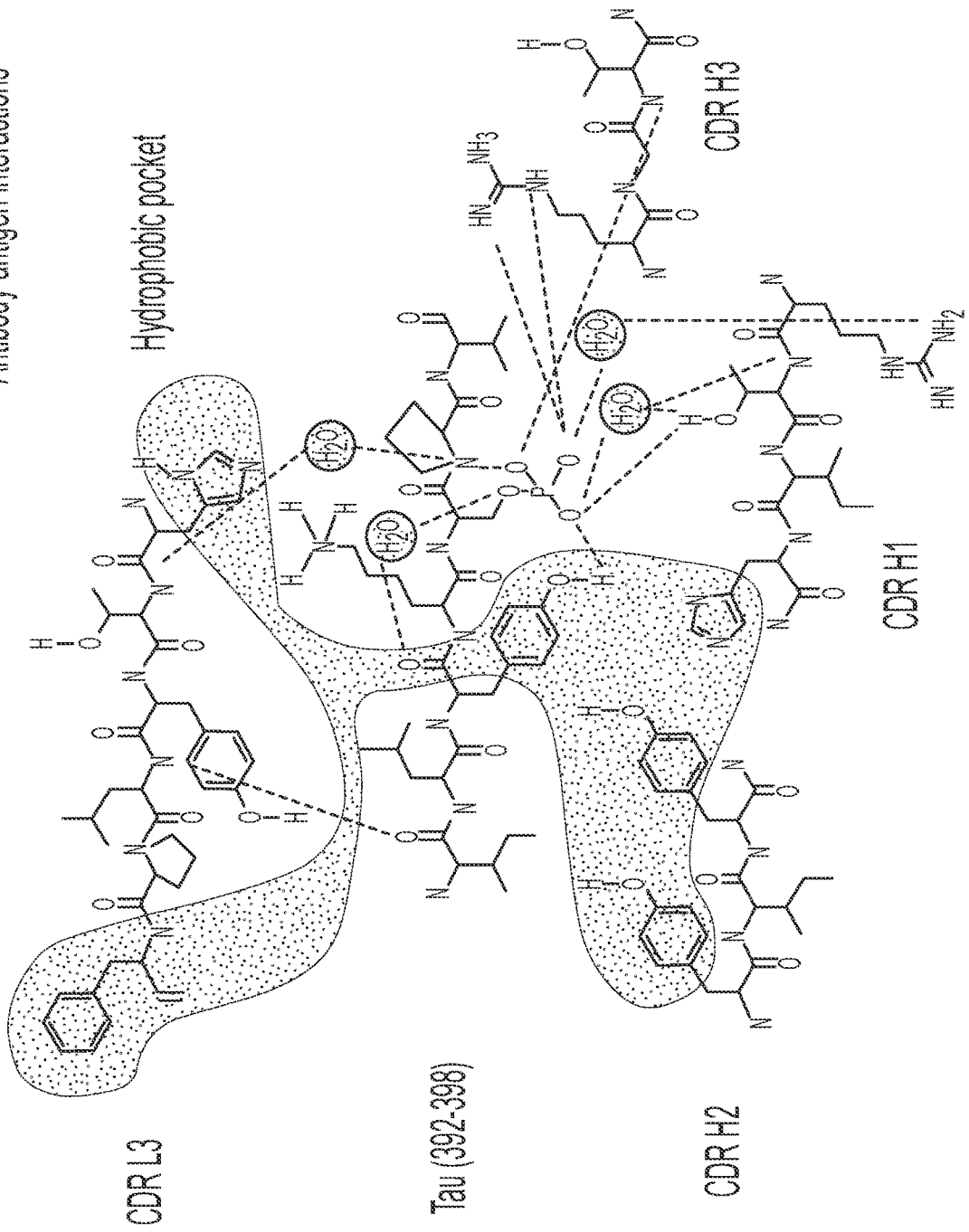

FIG. 11: Antibody C5.2 interaction with phosphoserine tau (292-298) peptide

FIG. 11 represents the interaction between antibody C5.2 with phosphoserine tau (292-298) peptide. The structure of Ile(392)-VAL(393)-Tyr(394)-Lys(395)-P-Ser(396)-Pro (397)-Val(398) is shown. The main interaction involves the hydrophobic pocket formed by L3:H3, L3:F8*, H1:H13, H2:Y1, H2:Y3 and Y(394) of tau peptide. There is an extensive hydrogen bonding network formed between solvated $^{\{p\}}$S(396) and L3:T4, H1:R10, H1:T11, H3:R1, H3:T3. In the employed nomenclature, the first letter (e.g., "L" of L3:H3) denotes whether the involved CDR residue is a light chain CDR or a heavy chain CDR, the first number denotes which CDR of such chain is involved (e.g., "L3" denotes CDR3 of the light chain), the remaining terms (e.g., "H3" of L3:H3) denote the name and position of the involved amino acid (e.g., "H3" denotes a histidine at the third residue position of the CDR); thus "L3:H3" denotes the histidine residue at the third position of the of light chain CDR3. There are strong hydrogen bonding and charge/polar interactions between the Y(394) sidechain and the backbone with phosphonate of $^{\{p\}}$S396 forms turn in peptide backbone. (*) L3:F8 is the C-terminal flanking framework residue of CDR L3.

The CDR sequences of C5.2 are:

```
CDR L1:
                                        (SEQ ID NO: 17)
QASQDTSINLN

CDR L2:
                                        (SEQ ID NO: 18)
GASNLED

CDR L3:
                                        (SEQ ID NO: 19)
LQHTYLP

CDR H1:
                                        (SEQ ID NO: 20)
KASGYTFTDRTIH

CDR H2:
                                        (SEQ ID NO: 21)
YIYPGDDSTKYNDNFKG

CDR H3:
                                        (SEQ ID NO: 22)
RGTMDY
```

Figure 12A:
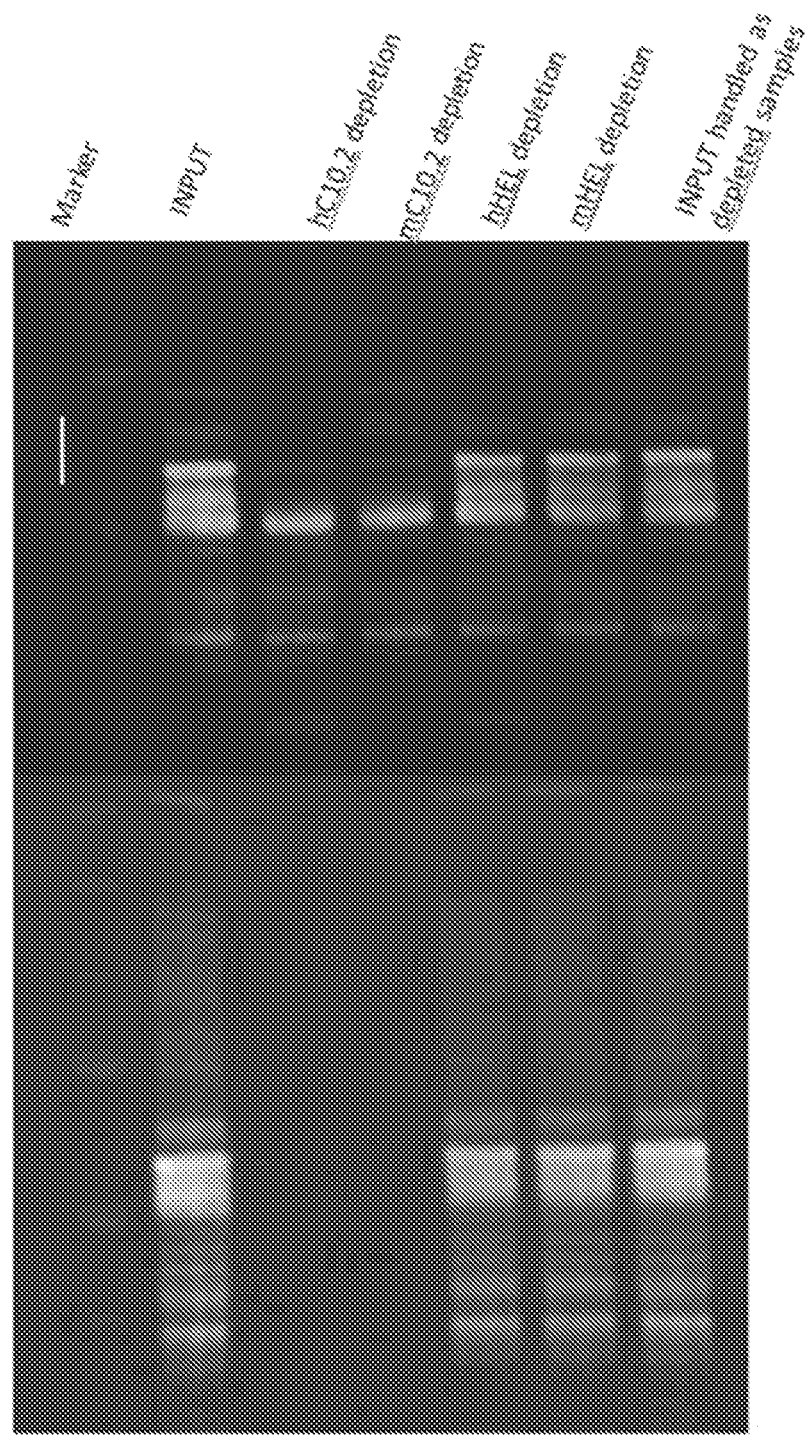
Figure 12B:
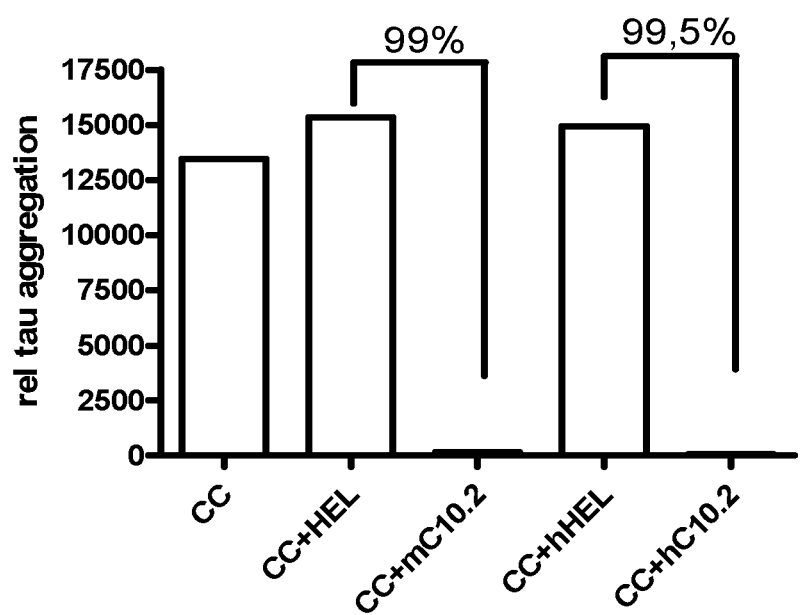

FIGS. 12A-12B: Depletion of Tau for seeding assay (HEK293)

FIGS. 12A-12B show immuno-depletion of rTg4510 brain homogenates using murine C10-2 (mC10-2) and humanized C10-2 (hC10-2). Western blots of depleted homogenates were detected with E1 (total tau; FIG. 12A; Lower)) and C10-2 (pS396 tau; FIG. 12A; Upper) and both mC10-2 and hC10-2 efficiently depleted hyperphosphorylated tau (upper bands on E1 blot and all bands on C10-2 blot). Depleted homogenates were also analyzed for the depletion of aggregated tau using the Cisbio assay. FIG. 12B shows the change in aggregated Tau in samples. Depletion studies with mC10-2 and hC10-2 removed tau aggregates by 99 and 99.5% respectively (FIG. 12B).

Figure 13A:
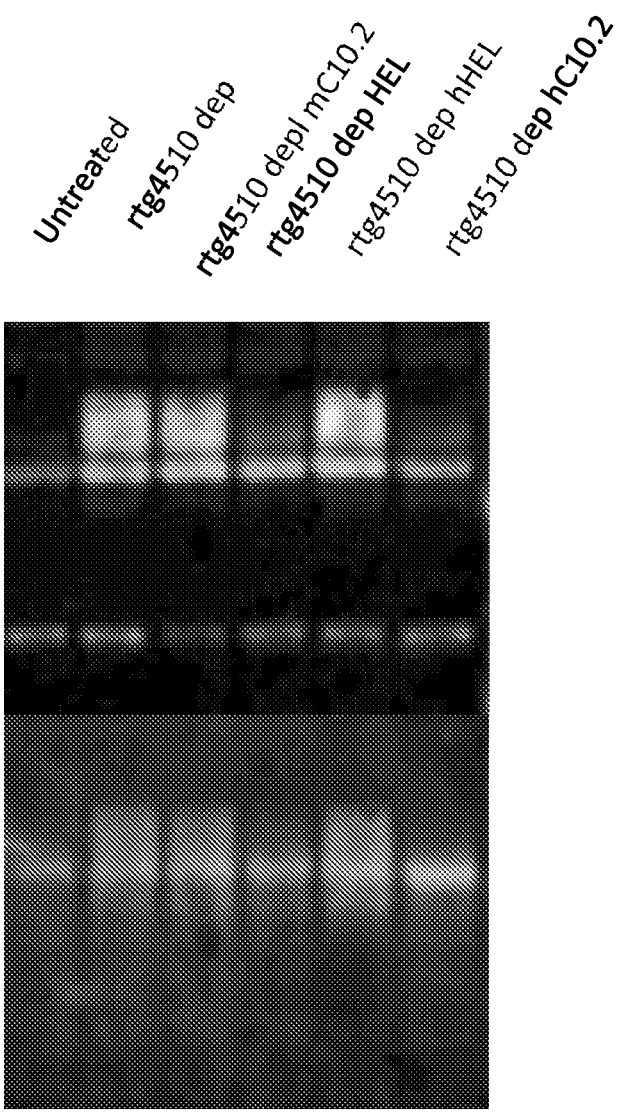
Figure 13B:
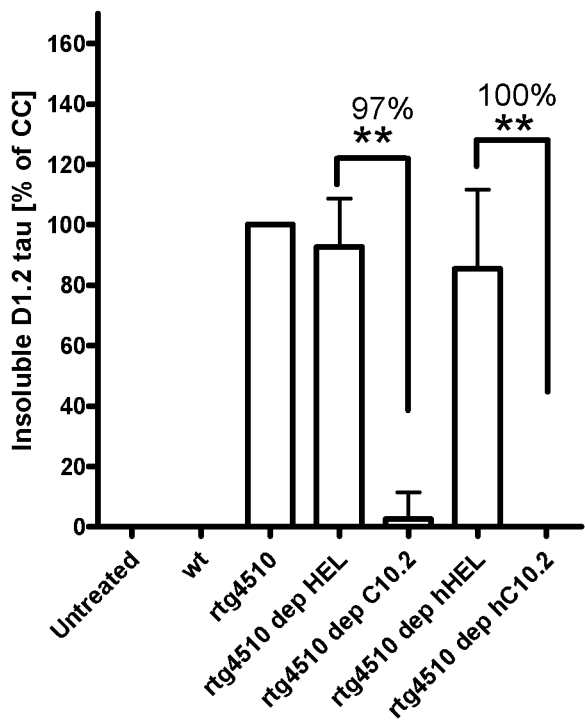
Figure 13C:
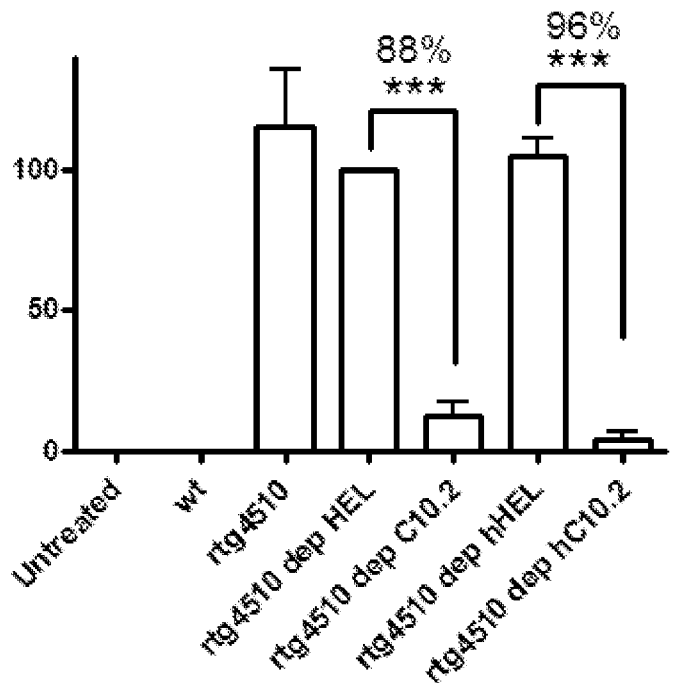

FIGS. 13A-13C: Seeding assay (HEK293) with depleted material

FIGS. 13A-13C show depleted homogenates used to seed P301L-hTau in HEK293 cells. Homogenates from control animals (WW) did not seed, whereas rTg4510 homogenates (CC) seeded efficiently, as measured by the Cisbio aggregation assay on total cell lysates or by fractionation of HEK293 cells in 1% triton-X (quantification of insoluble hyperphosphorylated D1.2 and tau (FIG. 13A, Upper and Lower)). Depletion with HEL and hHEL antibodies did not affect seeding, whereas depletion with mC10-2 and hC10-2 prevented tau aggregation 88% and 96% (FIG. 13C) and insoluble tau 97% and 100% (FIG. 13B) respectively.

Figure 14A:
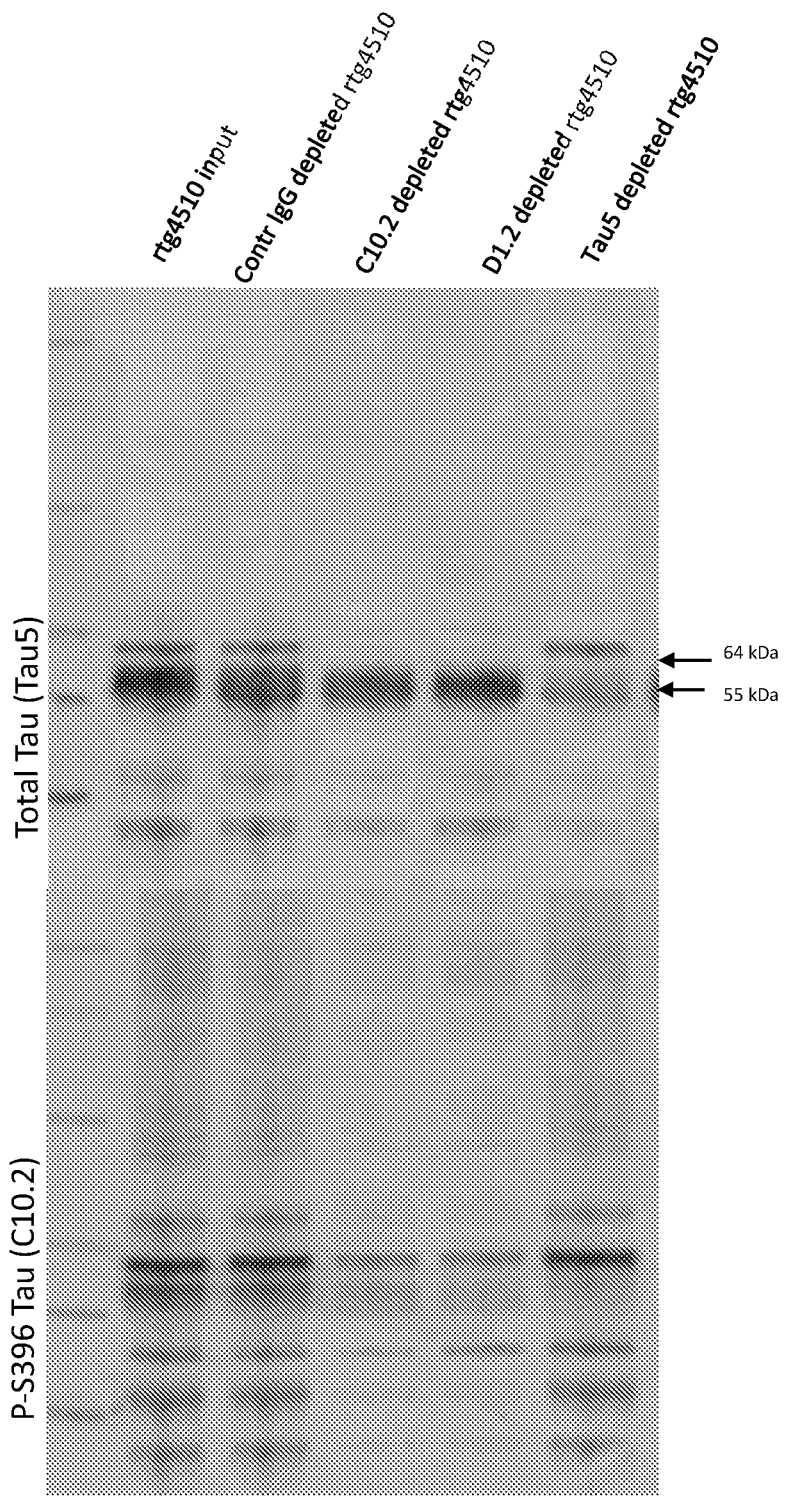
Figure 14B:
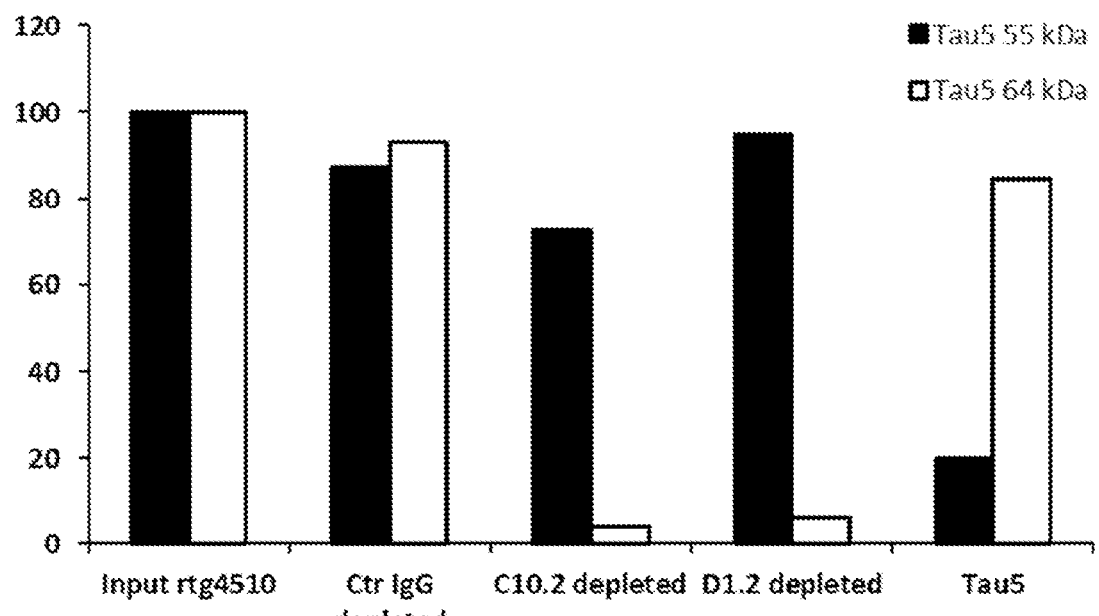
Figure 14C:
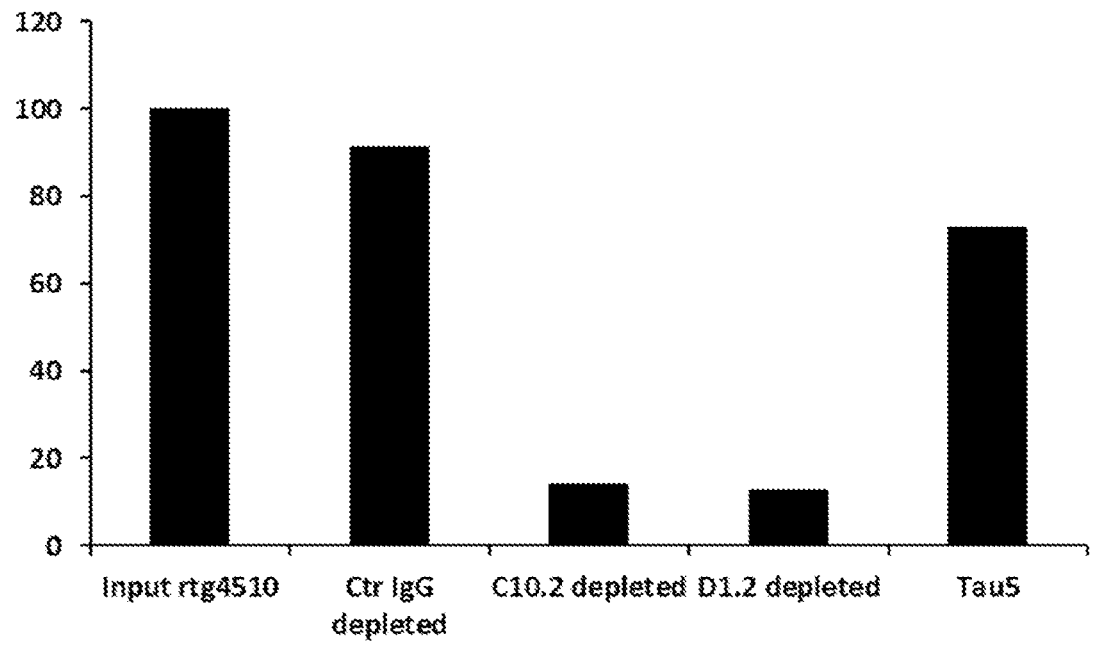

FIGS. 14A-14C: Immuno depletion rTg4510 material (used for in vivo seeding studies)

FIGS. 14A-14C demonstrate Western blot (FIG. 14A; Upper, Lower) analysis of immuno-depleted rTg4510 brain extracts. C10-2 and D1.2 specifically reduce the human hyperphosphorylated 64 kDa band by 90% and has no effect on the 55 kDa Tau Tau5, a commercial total Tau antibody does in contrast reduce normal 55 kDa Tau by 74% and no effect on the human 64 kDa Tau (FIGS. 14B-14C).

FIGS. 14A-15C: Immuno depletion AD material (used for in vivo seeding studies)

Figure 15A:
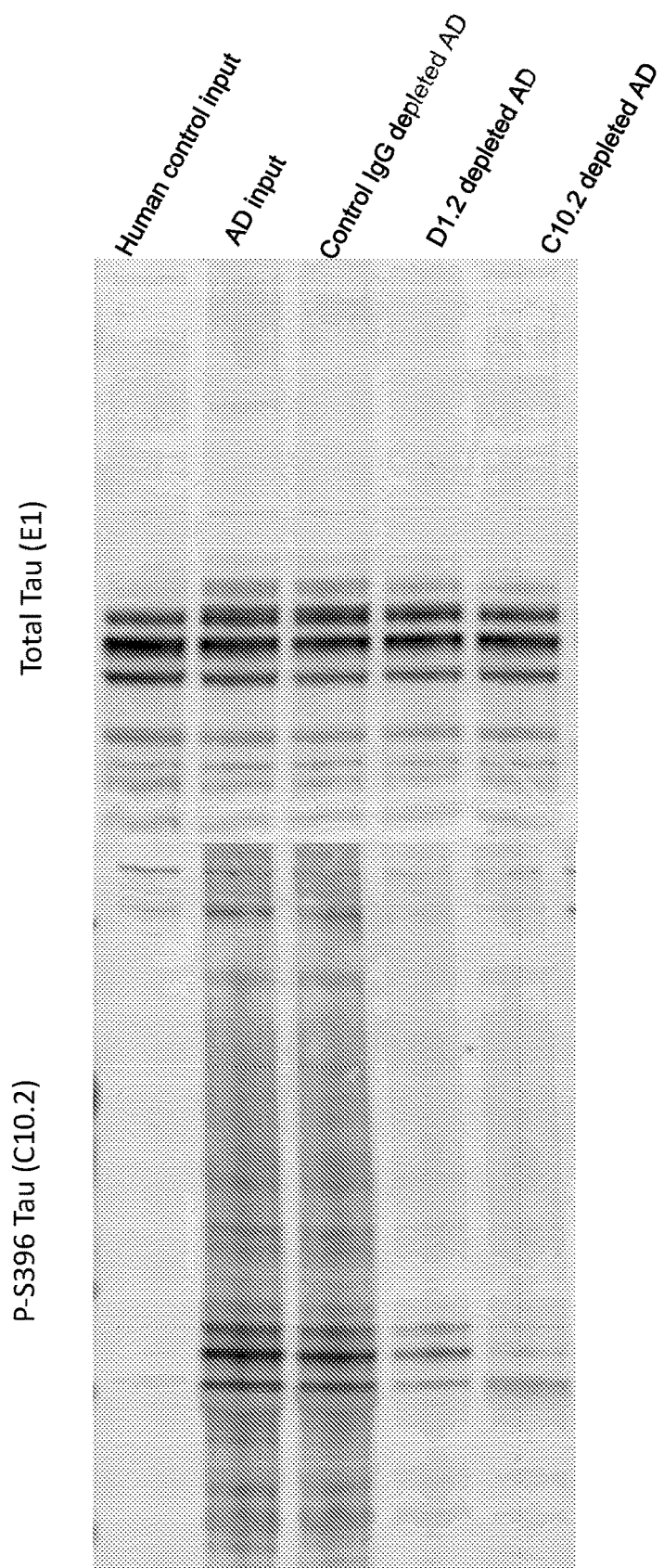
Figure 15B:
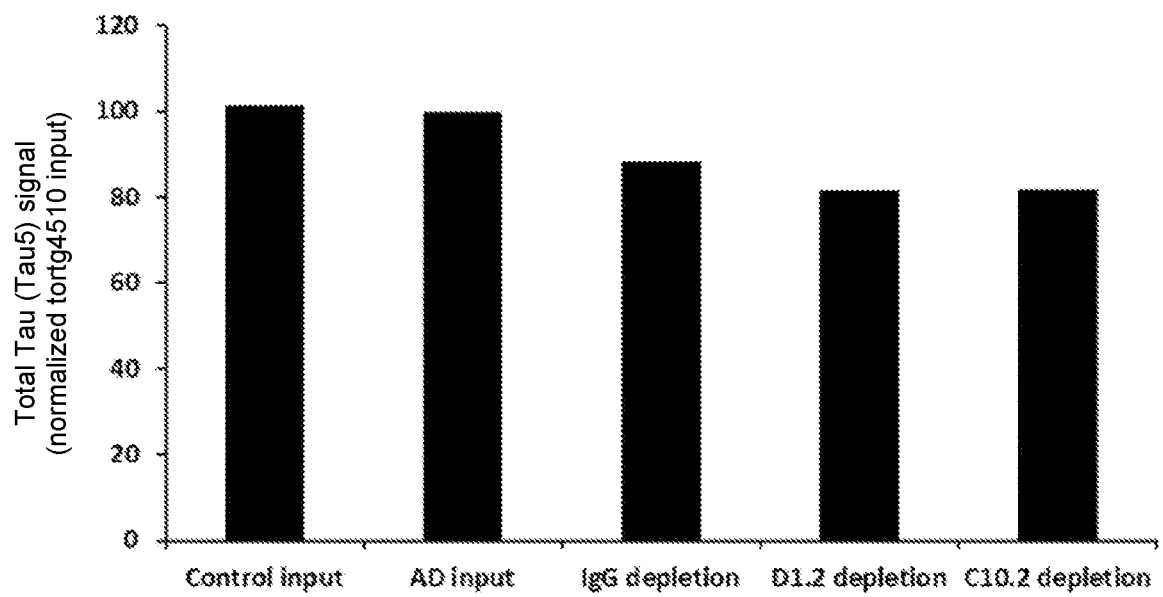
Figure 15C:
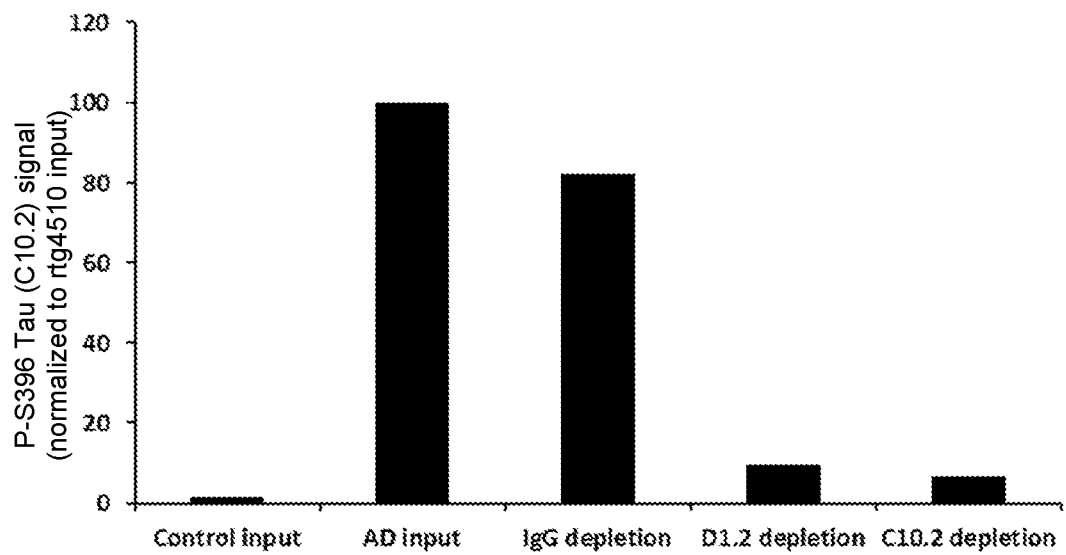

FIGS. 15A-15C depict Western blot (FIG. 15A) analysis of immuno-depleted Alzheimer brain extracts. Immuno-depletion using C10-2 and D1.2 does not reduce the total Tau levels by more than 10%, but specifically lower hyperphosphorylated Tau (90% reduction) (FIGS. 15-15C).

Figure 16A:
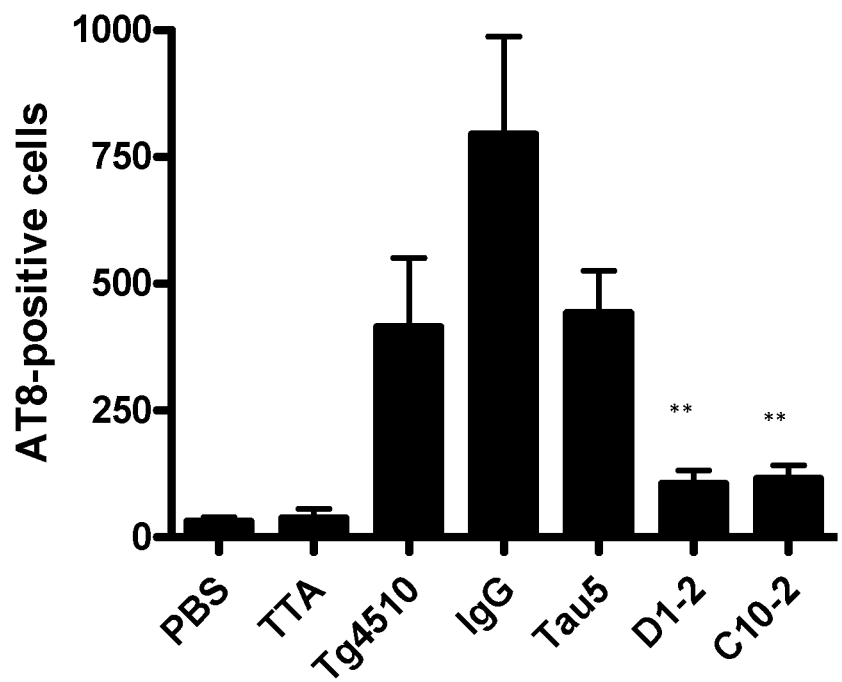

FIG. 16A: Hippocampal Tau pathology in rTg4510 mice seeded with immuno depleted rTg4510 material FIG. 16A illustrates the quantification of Tau pathology in rTg4510 brains seeded with rTg4510 or AD brain homogenates. Prior to seeding the hyperphosphorylated Tau, but not normal Tau, had been reduced in the homogenates by 90-95% by using C10-2 or D1.2. By removing hyperphosphorylated tau from the homogenates, the homogenates do no longer induce seeding of Tau pathology.

Figure 16B:
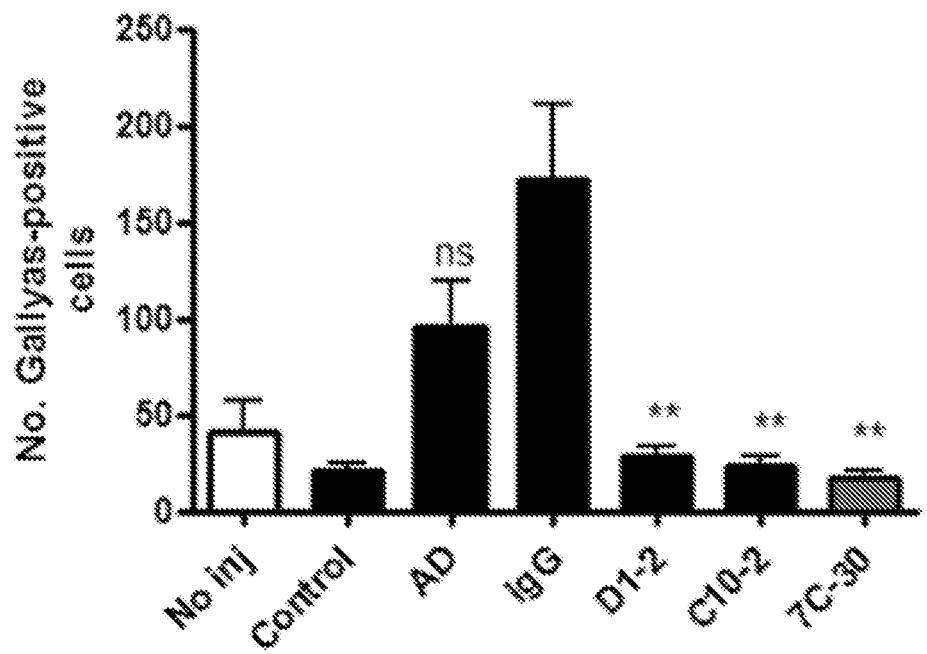

FIG. 16B Hippocampal tangle pathology in rTg4510 mice seeded with immuno depleted AD material FIG. 16B illustrates the quantification of Tau pathology in rTg4510 brains seeded with rTg4510 (A) or AD (B) brain homogenates. Prior to seeding the hyperphosphorylated Tau, but not normal Tau, had been reduced in the homogenates by 90-95% by using C10-2 or D1.2. By removing hyperphosphorylated tau from the homogenates, the homogenates do no longer induce seeding of Tau pathology.

Figure 17:
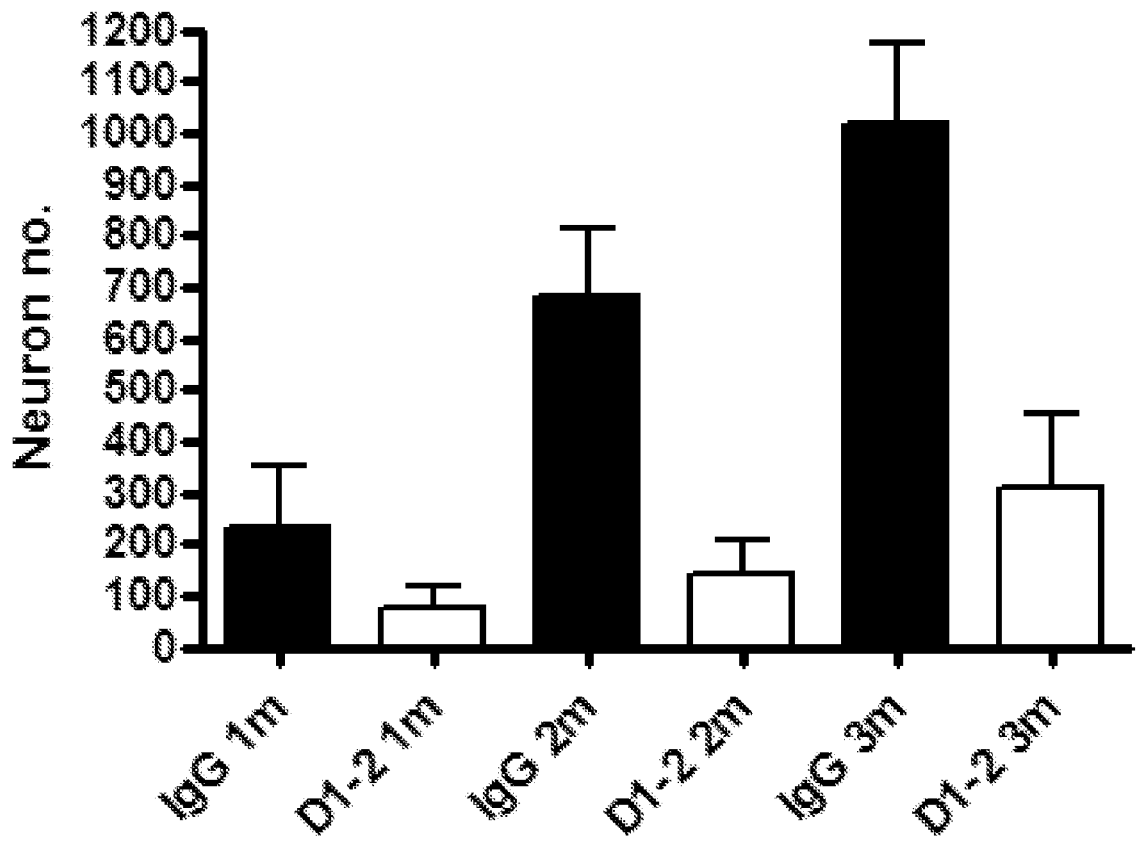

FIG. 17: Hippocampal tangle pathology in seeded rTg4510 mice treated with D1.2

FIG. 17 depicts the quantification of tangle bearing neurons in hippocampus of seeded rTg4510 mice. The pathology increases with time (Ig G, 1 month; IgG 2 months; IgG 3 months). However, treating the mice with D1.2, the pathology is significantly lowered 1, 2 and 3 months after seeding. (D1.2 1 month; D1.2 2 months; D1.2 3 months).

Figure 18A:
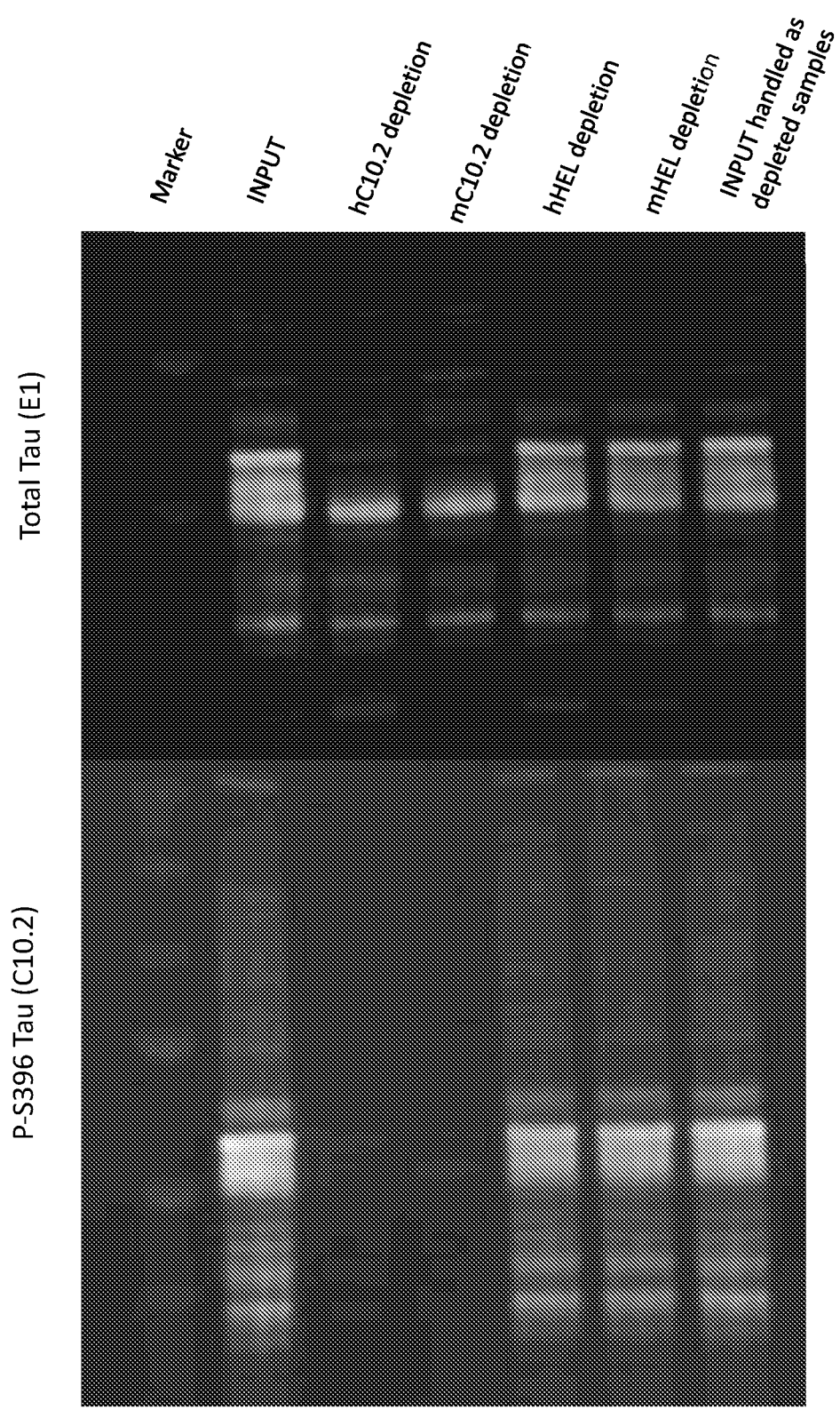
Figure 18B:
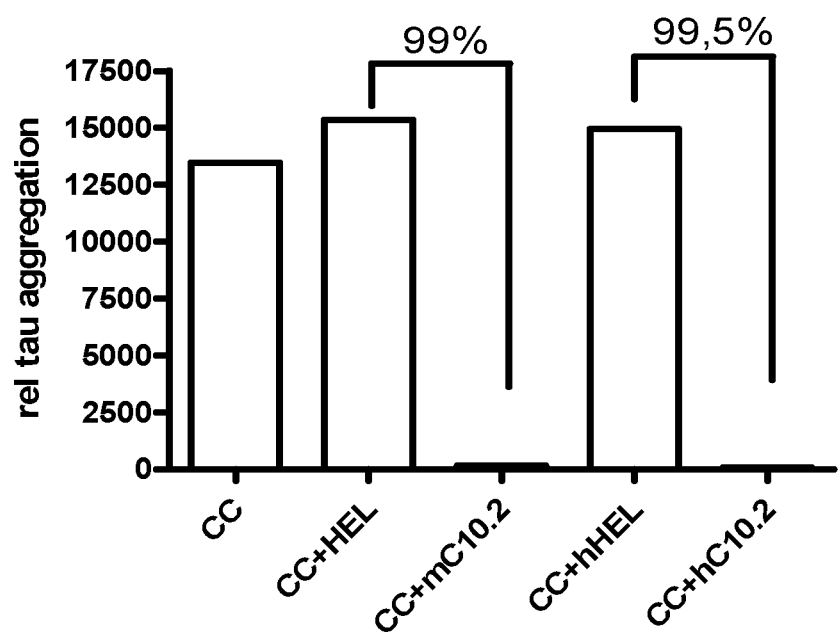

FIGS. 18A-18B: Depletion of Tau for seeding assay (HEK293)

FIG. 18A shows immuno-depletion of rTg4510 brain homogenates using murine C10-2 (mC10-2) and humanized C10-2 (hC10-2). Western blots of depleted homogenates were detected with E1 (total tau) and C10-2 (pS396 tau) and both mC10-2 and hC10-2 efficiently depleted hyperphosphorylated tau (upper bands on E1 blot and all bands on C10-2 blot). Depleted homogenates were analyzed for the depletion of aggregated tau using the Cisbio assay. FIG. 18B shows depletion with mC10-2 and hC10-2 removed tau aggregates 99 and 99.5% respectively.

Figure 19A:
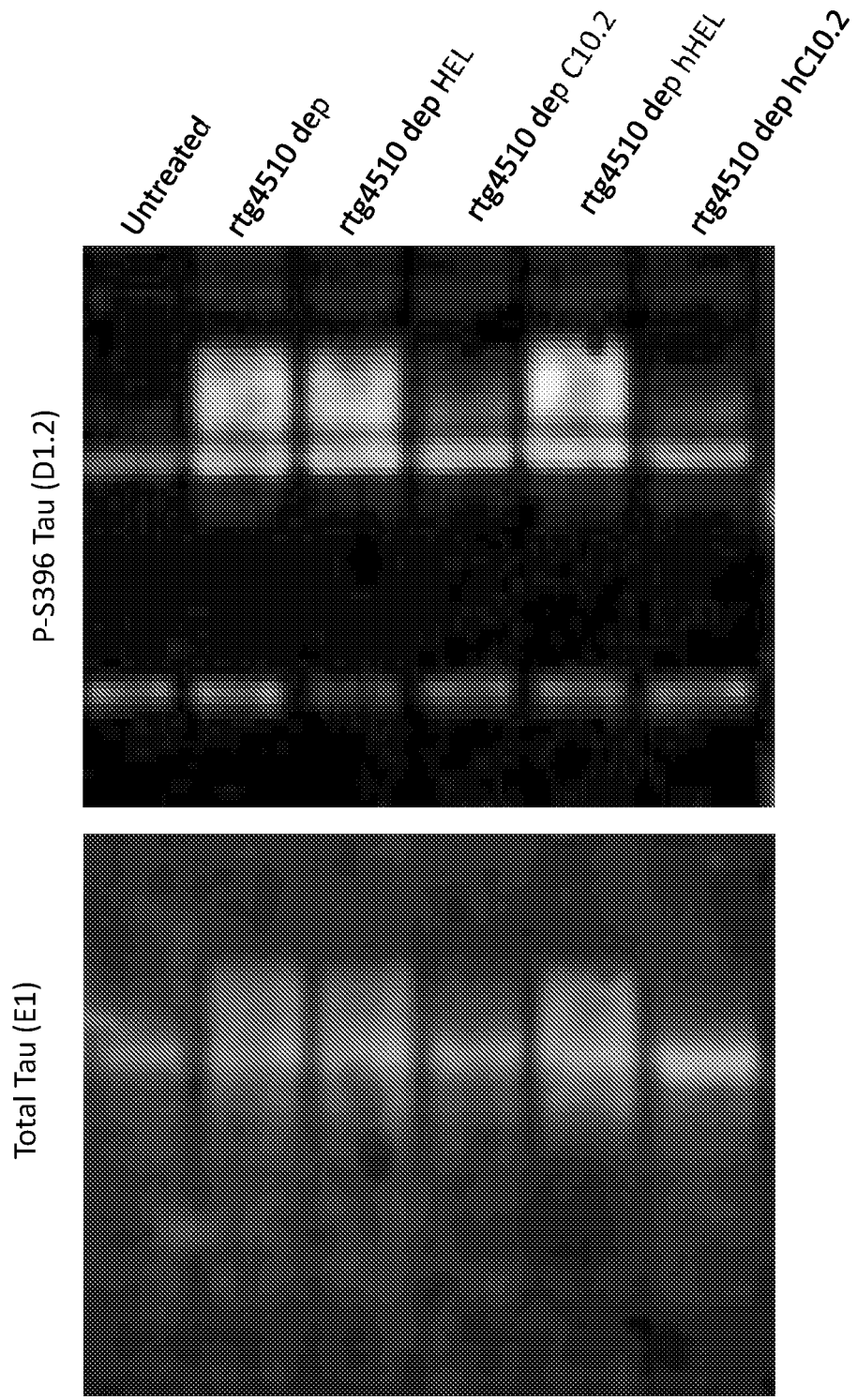
Figure 19B:
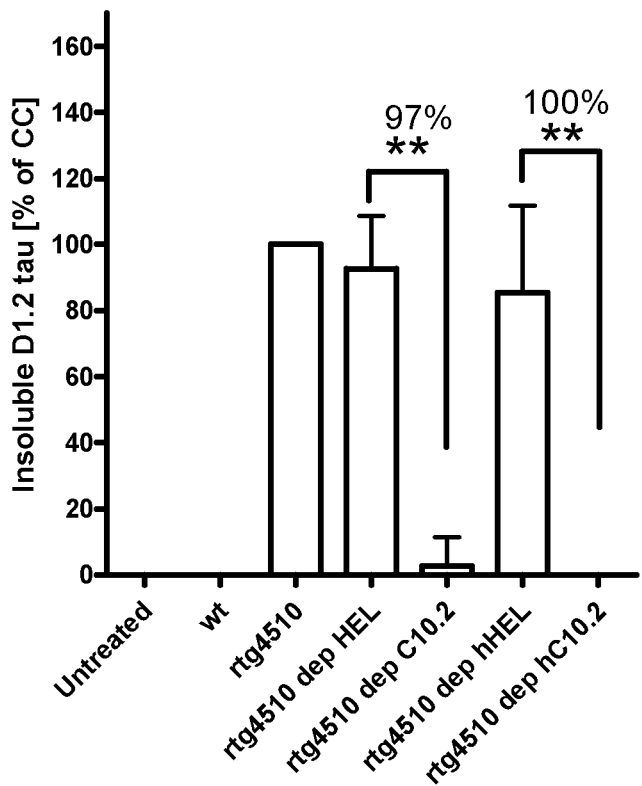
Figure 19C:
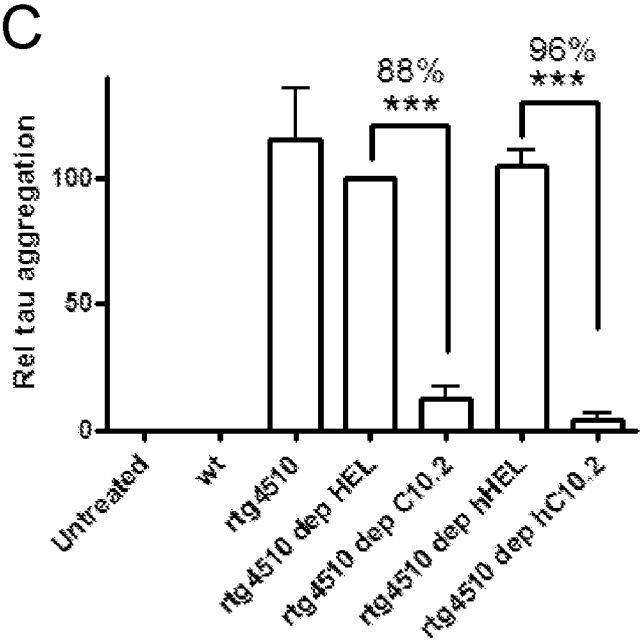

FIGS. 19A-19C: Seeding assay (HEK293) with depleted material

FIG. 19A shows Tau fractionation (western on insoluble fraction. FIG. 19B shows Western blow quantification. FIG. 19C shows aggregated Tau in cell lysates. Depleted homogenates were used to seed P301L-hTau in HEK293 cells. Homogenates from control animals (WW) did not seed, whereas rTg4510 homogenates (CC) seeded efficiently, as measured by the Cisbio aggregation assay on total cell lysates or by fractionation of HEK293 cells in 1% triton-X (quantification of insoluble hyperphosphorylated $D1.2_+$ tau). Depletion with HEL and hHEL antibodies did not affect seeding, whereas depletion with mC10-2 and hC10-2 (FIG. 19C) prevented tau aggregation by 88% and 96% and insoluble tau by 97% and 100% respectively (FIG. 19B).

Figure 20A:
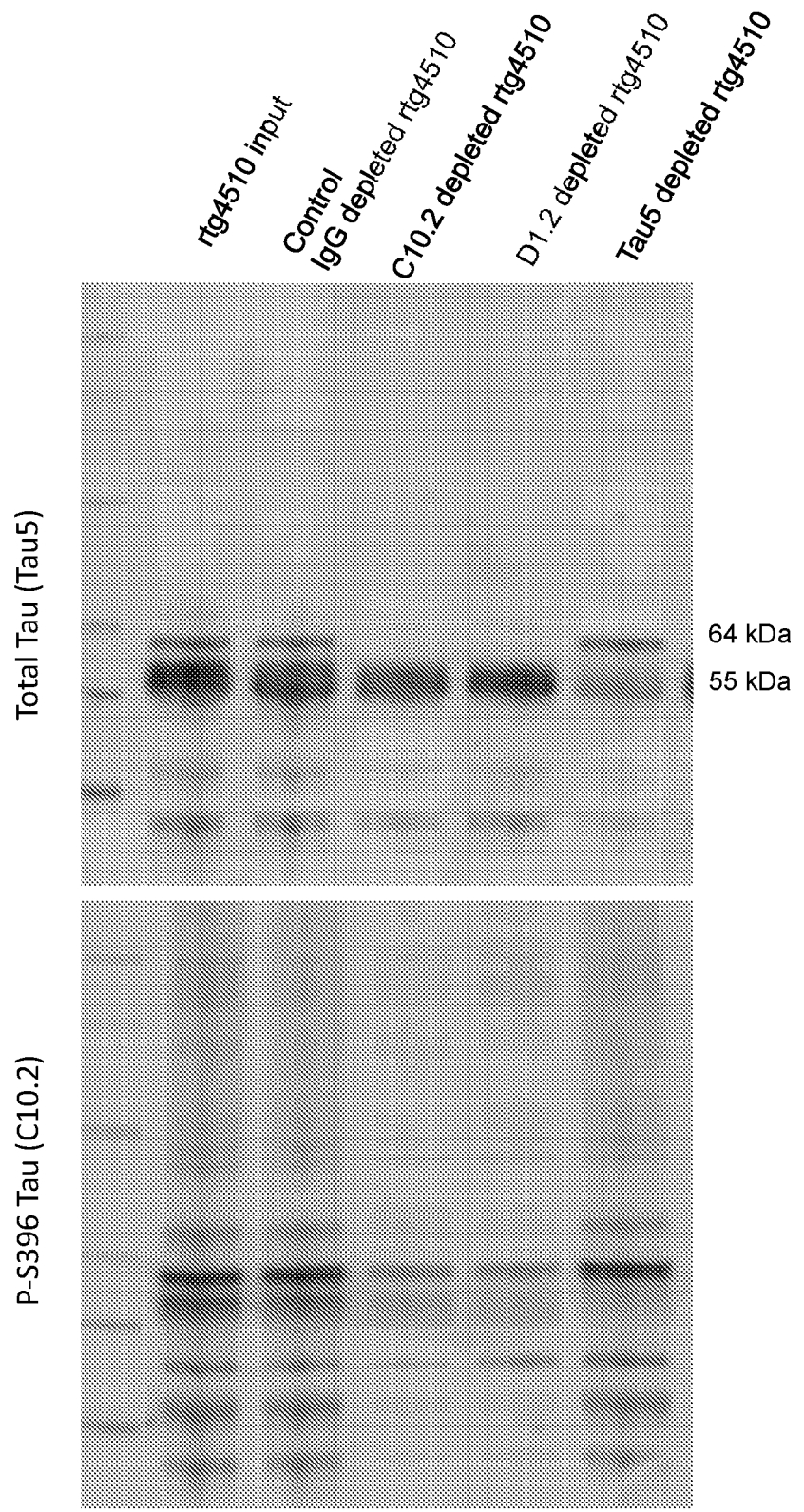
Figure 20B:
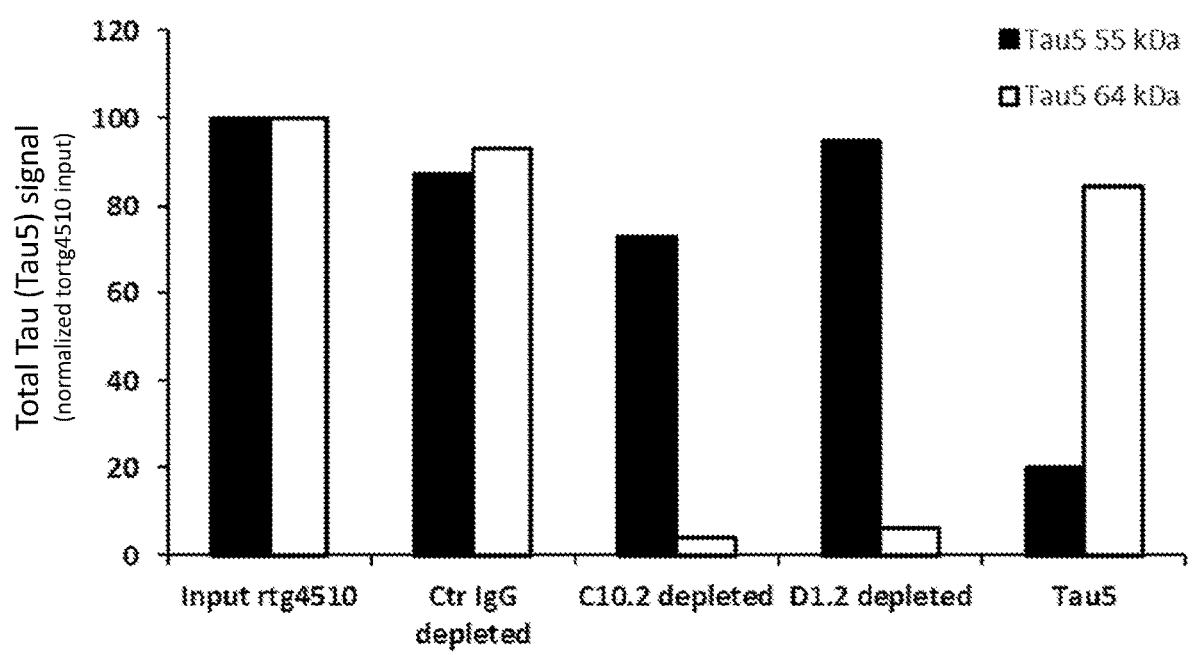

FIGS. 20A-20B: Immunoselectivity of C10-2 and D1.2 for hyperphopsphorylated tau over normal tau.

Immuno depletion rTg4510 material used for in vivo seeding studies: FIG. 20A show Western blot analysis of immuno-depleted rTg4510 brain extracts. FIG. 20B shows that C10-2 and D1.2 specifically reduce the hyperphosphorylated 64 kDa band, phosphorylated at serine 396 over the Tau 55 kDa band, which does not comprise a significant amount of p396. In contrast, Tau5, a commercial total Tau antibody, does reduce normal 55 kDa Tau and is inefficient in binding to the 64 kDa Tau.

Figure 21A:
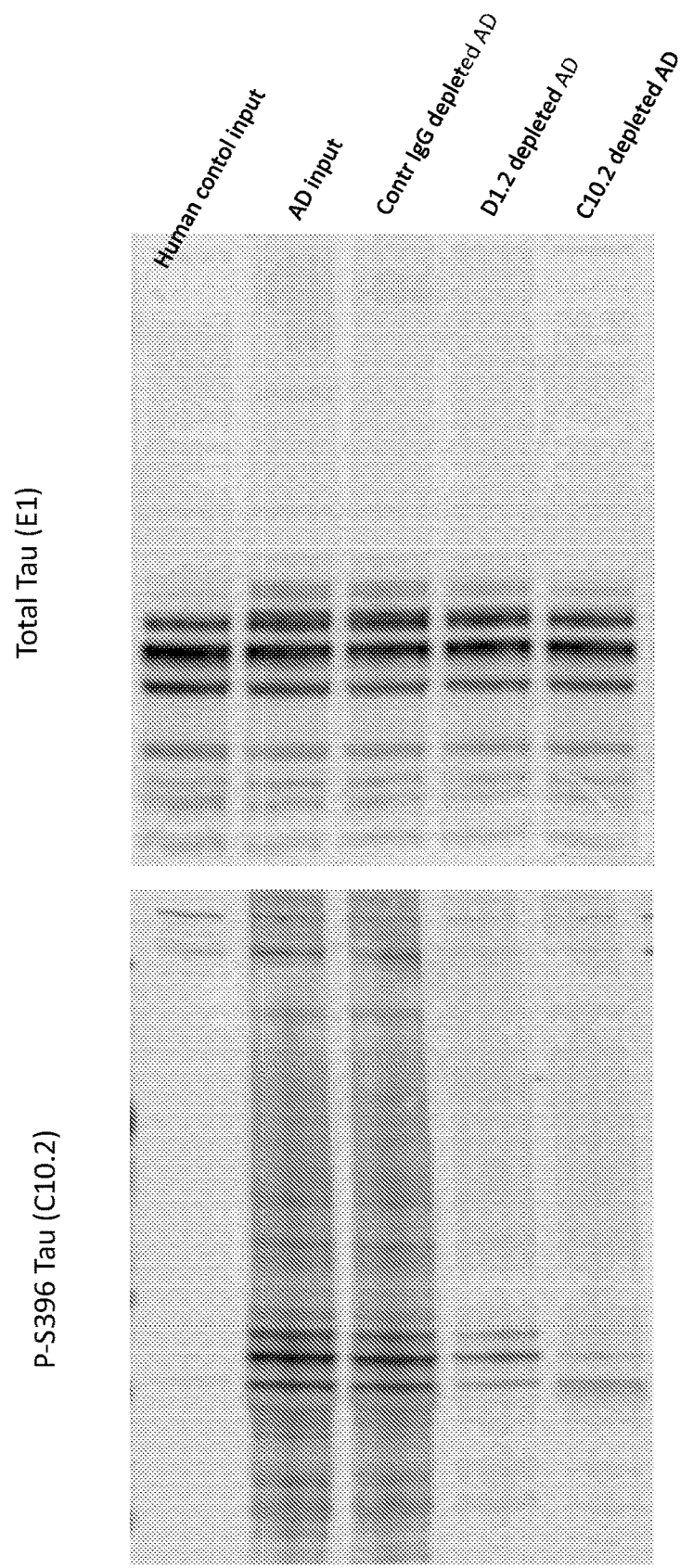
Figure 21B:
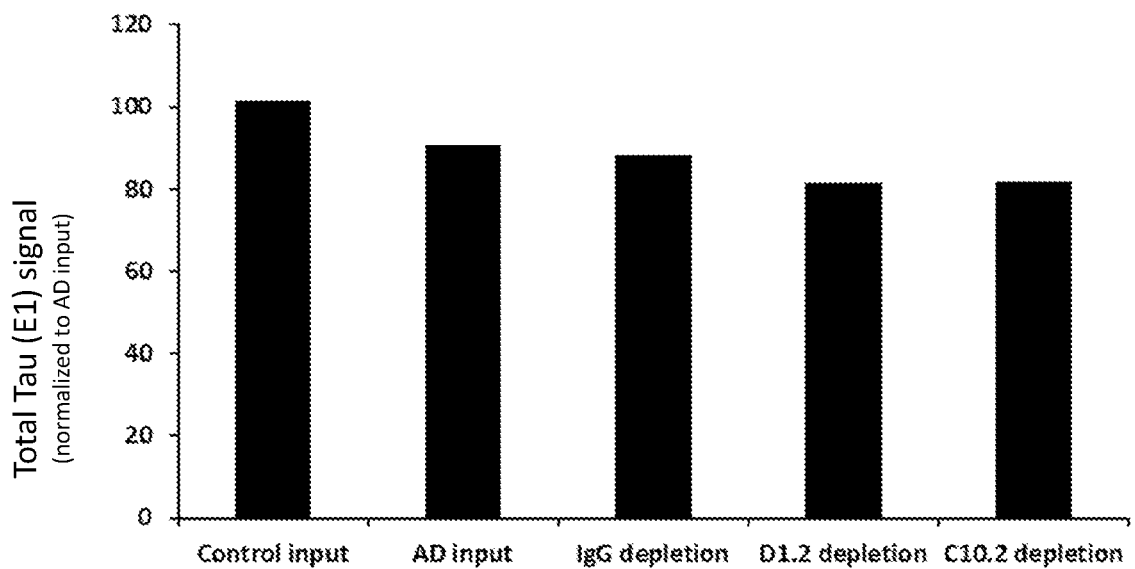
Figure 21C:
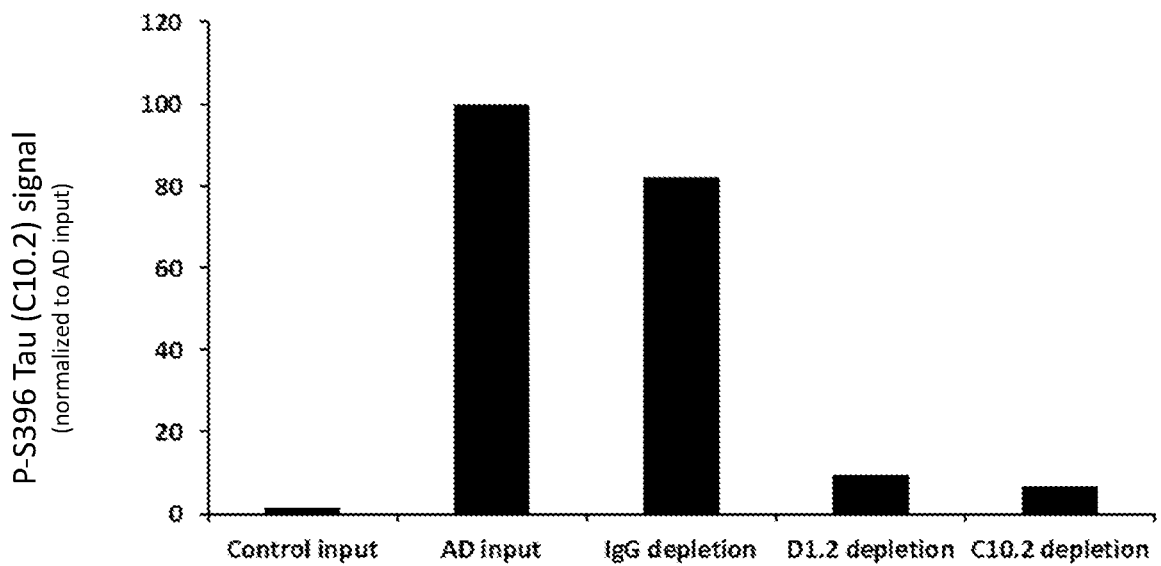

FIGS. 21A-21C: Immunoselectivity of C10-2 and D1.2 for hyperphopsphorylated tau over normal tau.

Immuno depletion AD material (used for in vivo seeding studies: FIG. 21A shows Western blot analysis of immuno-depleted Alzheimer brain extracts. Immuno-depletion using mC10-2 and D1.2 does not reduce the total Tau levels by more than 10% (FIG. 21B), but specifically lower hyperphosphorylated Tau (90% reduction) (FIG. 21C).

Figure 22A:
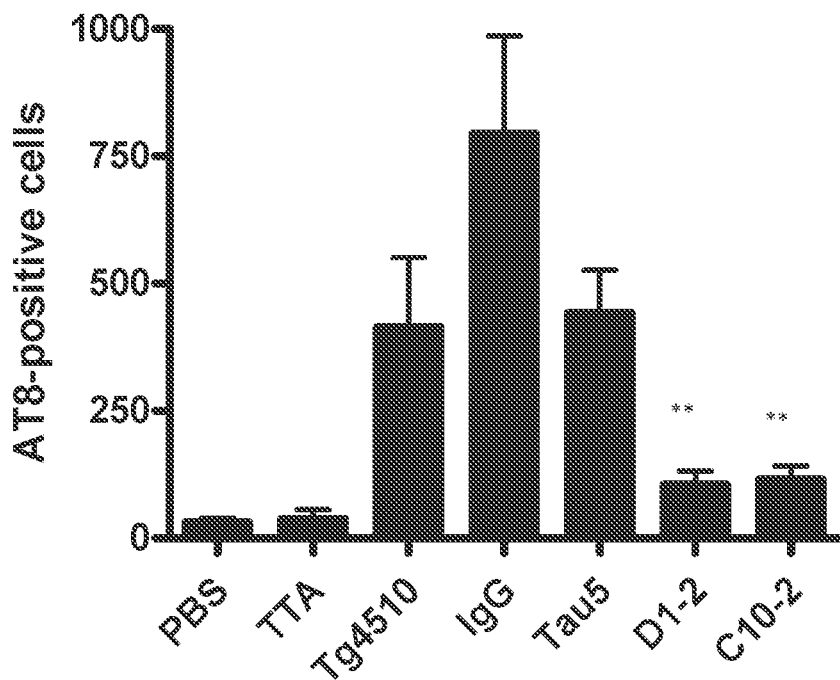
Figure 22B:
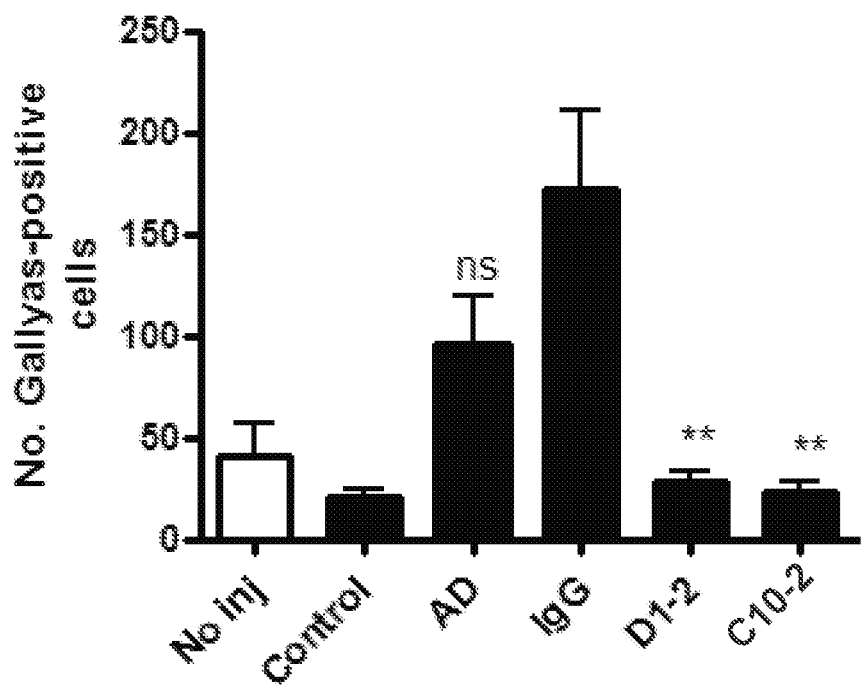

FIGS. 22A-22B: Hippocampal Tau pathology in rTg4510 mice

FIG. 22A shows hippocampal Tau pathology in rTg4510 mice seeded with immuno depleted rTg4510 material. FIG. 22B shows hippocampal tangle pathology in rTg4510 mice seeded with immuno depleted AD material. Quantification of Tau pathology in rTg4510 brains seeded with rTg4510 (A) or AD (B) brain homogenates. Prior to seeding the hyperphosphorylated Tau, but not normal Tau, had been reduced in the homogenates by 90-95% by using antibodies C10-2 or D1.2. By removing hyperphosphorylated tau from the homogenates, the homogenates no longer induce seeding of Tau pathology.

Figure 23:
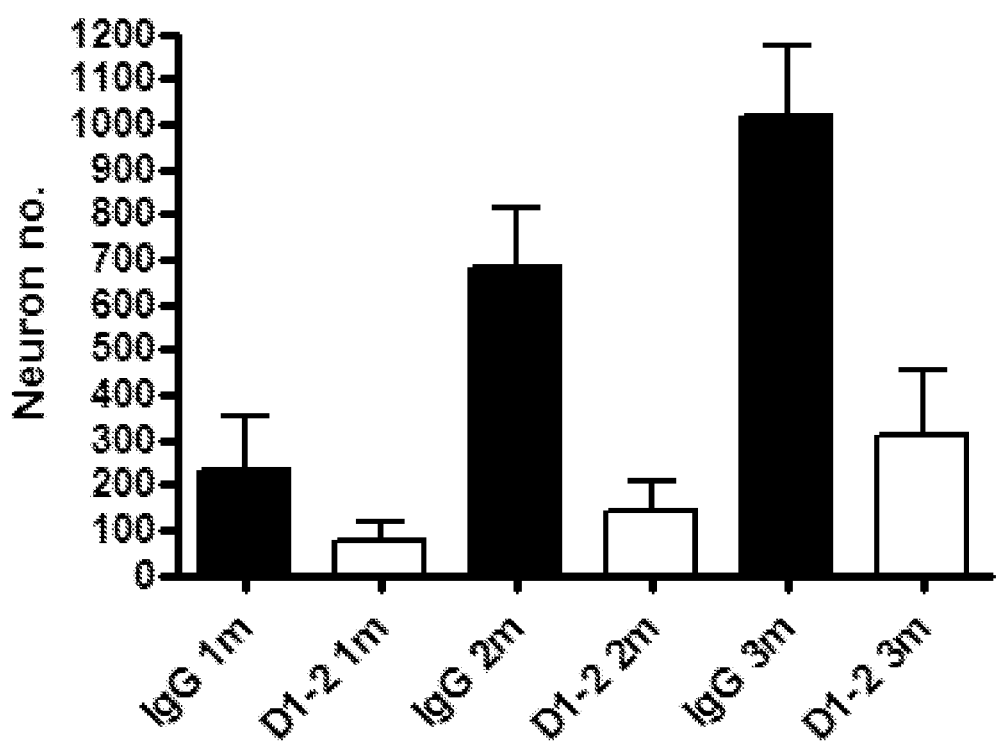

FIG. 23 Hippocampal tangle pathology in seeded rTg4510 mice treated with D1.2

Quantification of tangle bearing neurons in hippocampus of seeded rTg4510 mice. The Figure shows that pathology increases with time and by treating the mice with D1.2, the pathology is significantly lower 2 and 3 months after seeding.

Figure 24:
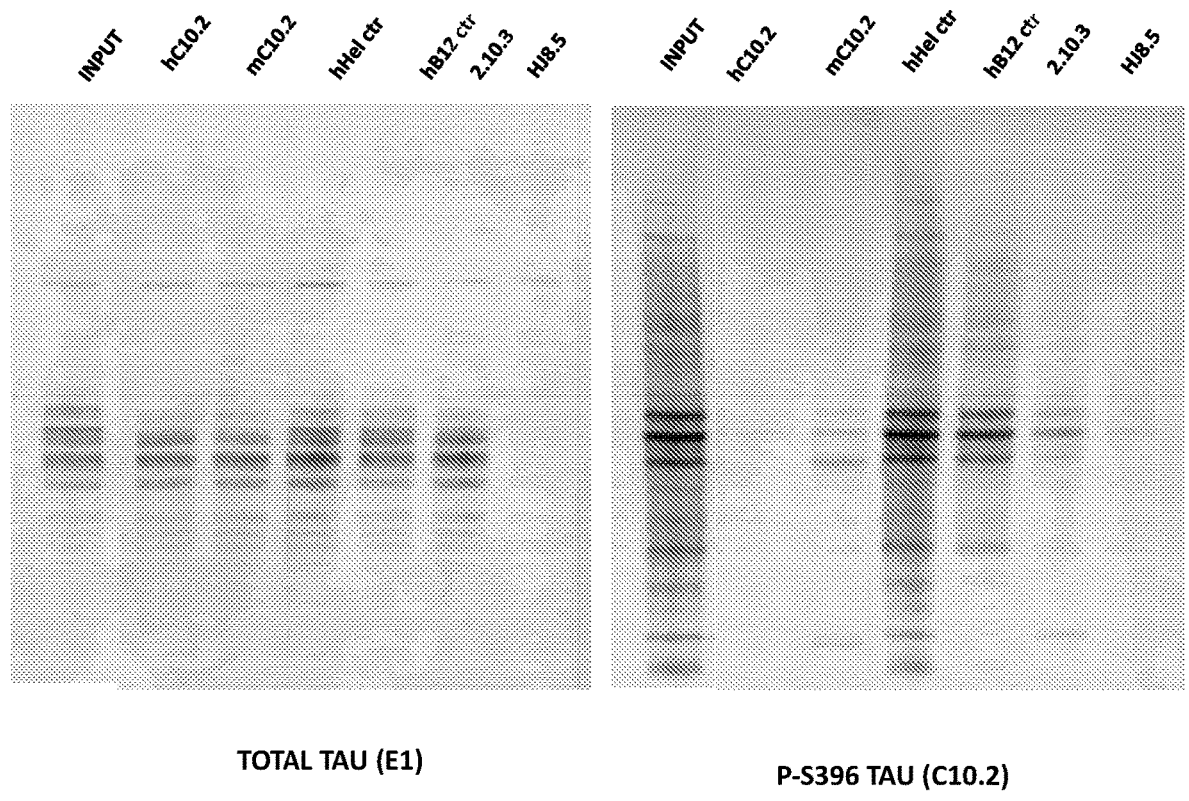

FIG. 24 Western blot analysis of immuno-depleted human AD extracts

The Figure illustrates that humanized version of C10-2 (hC10-2), as well as mC10-2 differ from the 2.10.3 (P-S422) antibody, in that although total tau remaining is not dramatically different (left hand panel) from 2.10.3, C10-2 (hC10-2), as well as mC10-2 remove more of the hyperphosphorylated Tau protein present in Alzheimer brain extracts by immuno depletion methods. This is confirmed in FIG. 25 by quantification.

Figure 25:
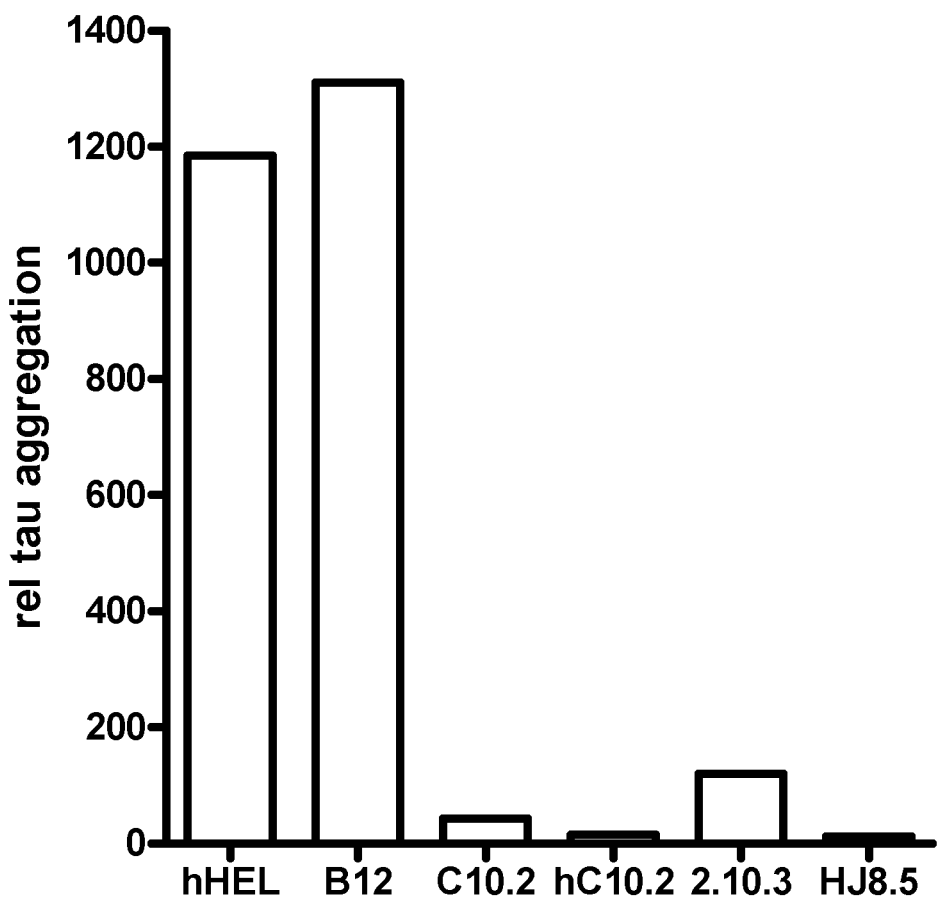

FIG. 25 Quantification of Aggregated Tau after immuno depletion

The hC10-2 and mC10-2 antibodies differ from the 2.10.3 antibody in its ability to removes more of the aggregated Tau protein present in Alzheimer brain extracts by immuno depletion methods.

Figure 26:
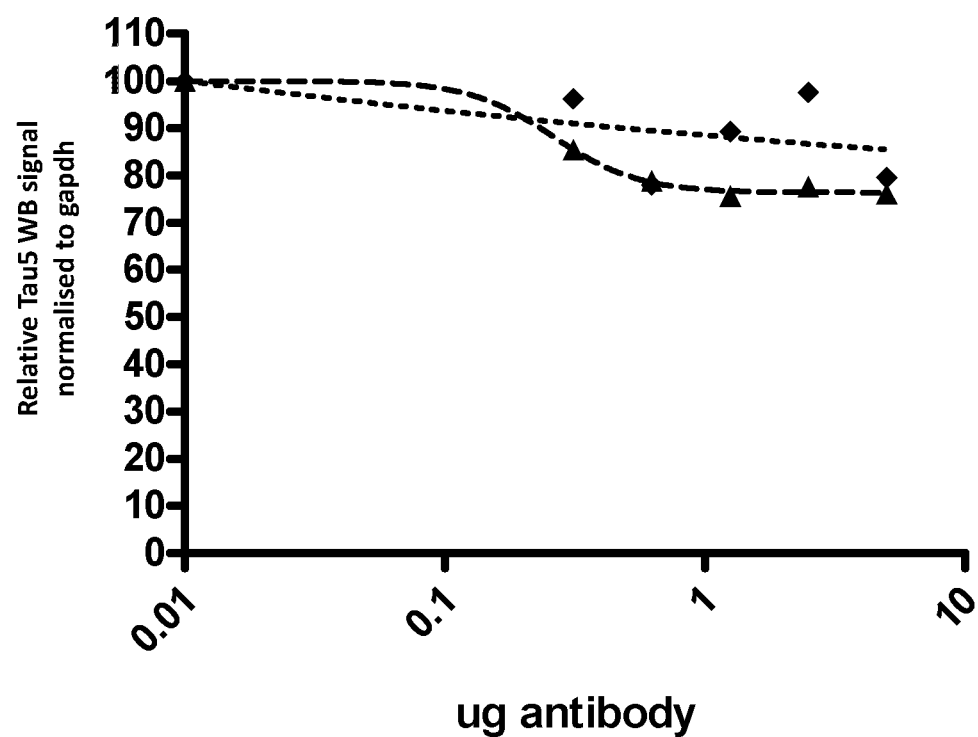

FIG. 26 Total tau remaining after immuno depletion

Quantification of western blot signal after immuno depleting Alzheimer extracts using different amounts of the humanized C10-2 (♦) and 2.10.3 antibody (▲). In FIG. 26, quantification of total tau signal using Tau5 (all tau isoforms were included in the analysis) is shown. Both antibodies remove a small fraction of tau from the Alzheimer brain preparation. 2.10.3, designed to have specificity for P-S422 tau removes up to 24% of the total tau amount, while C10-2 removes up to 15% of the total tau (see FIG. 26).

Figure 27:
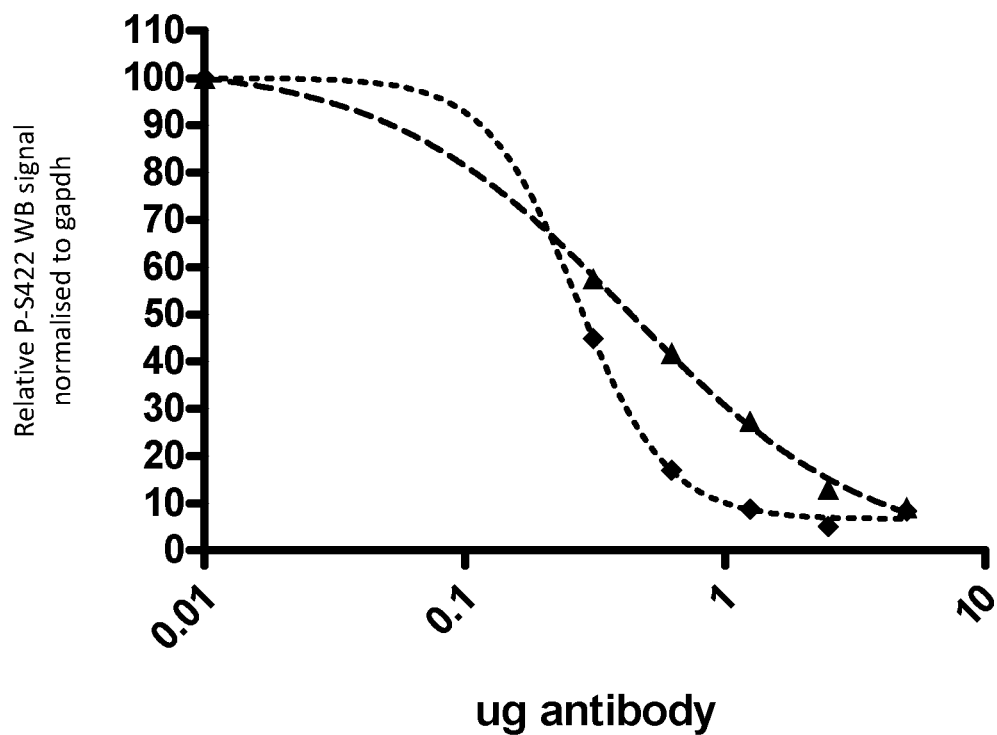

FIG. 27 Total tau remaining after immunodepletion of hyperphosphorylated tau

FIG. 27 illustrates the quantification of the hyperphosphorylated tau, being phosphorylated at serine 422 (all bands and the high molecular weight smear was included in the analysis). 2.10.3 (▲) and C10-2 (♦) both remove more than 90% of the tau phosphorylated at Serine 422. However, the amount of antibody needed to remove 50% of the tau differ: for antibody 2.10.3, 0.42 µg antibody is needed whereas for C10-2, 0.27 µg is needed for the same effect.

Figure 28:
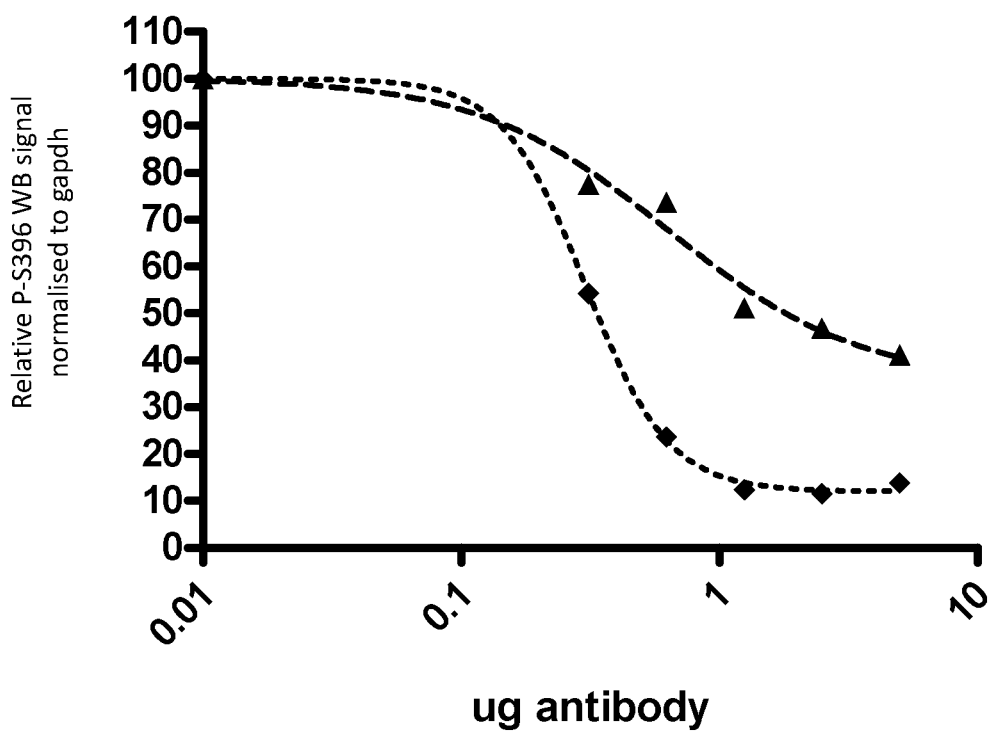

FIG. 28 Total tau remaining after immunodepletion of hyperphosphorylated tau

Quantification of the hyperphosphorylated tau, being phosphorylated at serine 396 (all bands and the high molecular weight smear was included in the analysis). C10-2 (♦) efficiently removes Tau being phosphorylated at serine 396 (Max effect: 88% and half of the effect is reached by using 0.30 µg antibody). 2.10.3 (◊) removes a smaller fraction of tau being phosphorylated at the serine 396 (Max effect: 60% and half of that effect is reached when using 0.63 µg antibody). This indicates that all Tau being phosphorylated at serine 422, also is phosphorylated at serine 396, but that there is a portion of hyperphosphorylated tau being phosphorylated at serine 396 where the phosphorylated serine at position 422 is not present.

Figure 29:
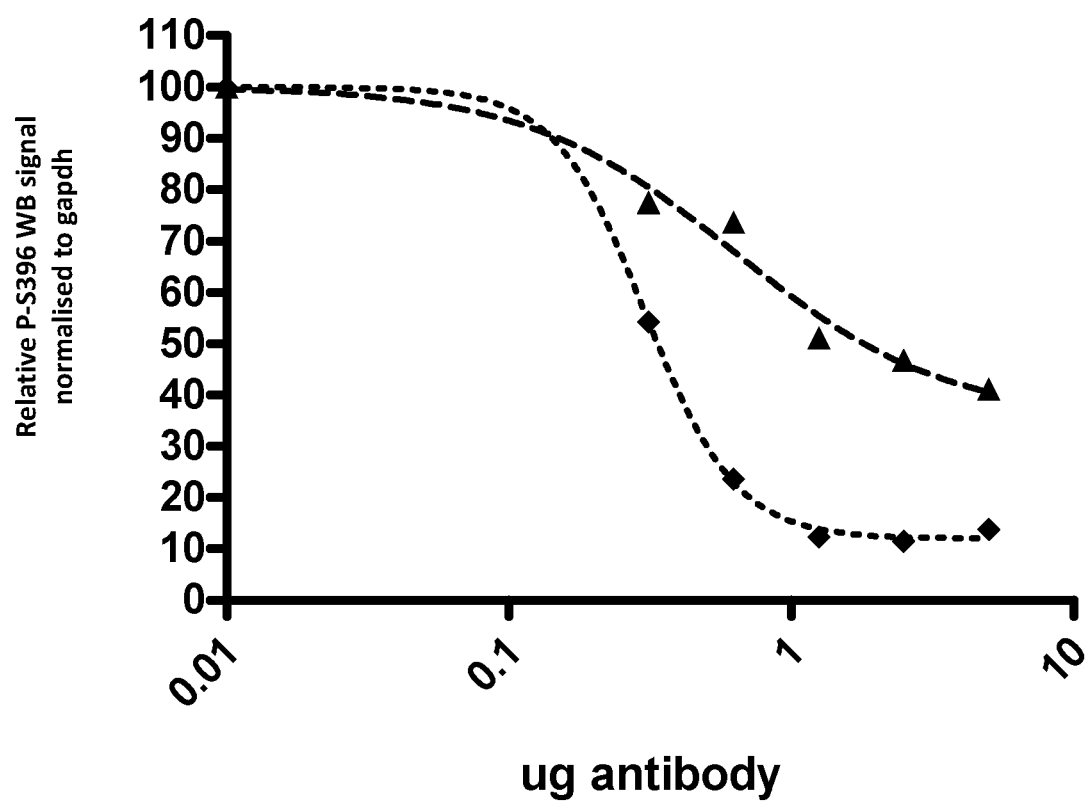

FIG. 29 Total tau remaining after immunodepletion of hyperphosphorylated tau

Quantification of the hyperphosphorylated tau, being phosphorylated at serine 199/202 (all bands and the high molecular weight smear was included in the analysis). A large portion of the tau being removed by C10-2 (♦), is also phosphorylated at Serine 199/202, since 69% of the tau having that phosphporylation is affected by the immunodepletion (50% of the effect when using 0.34 µg antibody). The 2.10.3 (▲) immunodepletion does not give a sigmoidal dose response on the P-S199/202 tau although a drop in signal is seen with increasing amount of antibody (max 52% reduction when using the max amount of antibody (5 µg). This data indicates that the C10-2 antibody targeting the phosphorylated serine 396 binds a larger pool of the hyperphosporylated tau then the 2.10.3 antibody targeting the phosphorylated serine at the 422 position.

Figure 30:
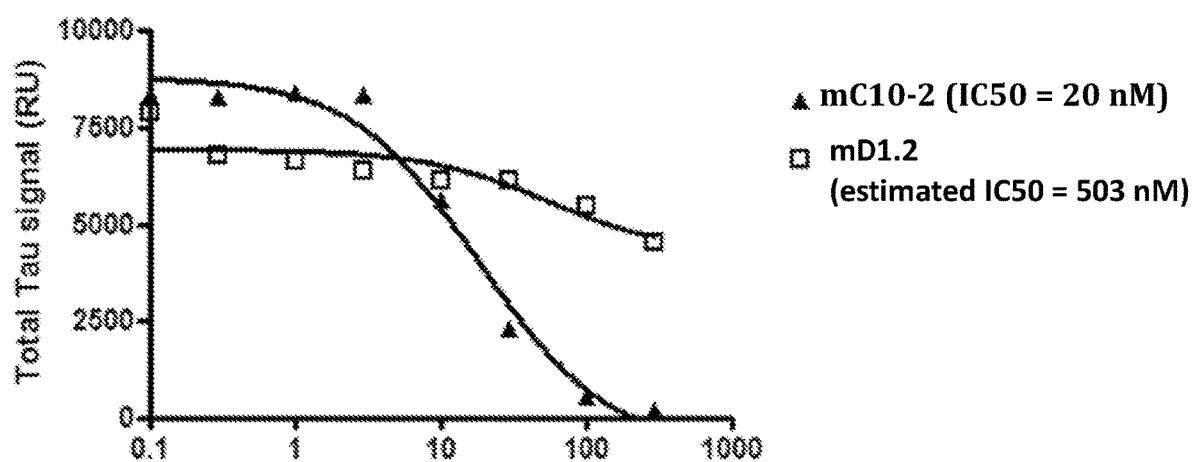

FIG. 30 mD1.2 and mC10-2 inhibition of Tau antigen capture in mC10-2 coated plates In fluid phase ELISA, where a mixture of rTg4510 P3 preparation and variable amounts of C10-2 or D1.2 antibodies is added onto C10-2 coated plates. The more antibodies binding to P3 tau in the solution, less available tau epitopes are able to bind to the plates. The amount of tau binding to the plates is determined by a sulfo-tagged human tau antibody. C10-2 (▲) and D1.2 (□) have a different binding to the tau in solution, wherein C10-2 can compete out all binding to the plates (IC50 20 nM). D1.2, on the other hand, shows a very low level of binding to the tau in solution.

Figure 31:
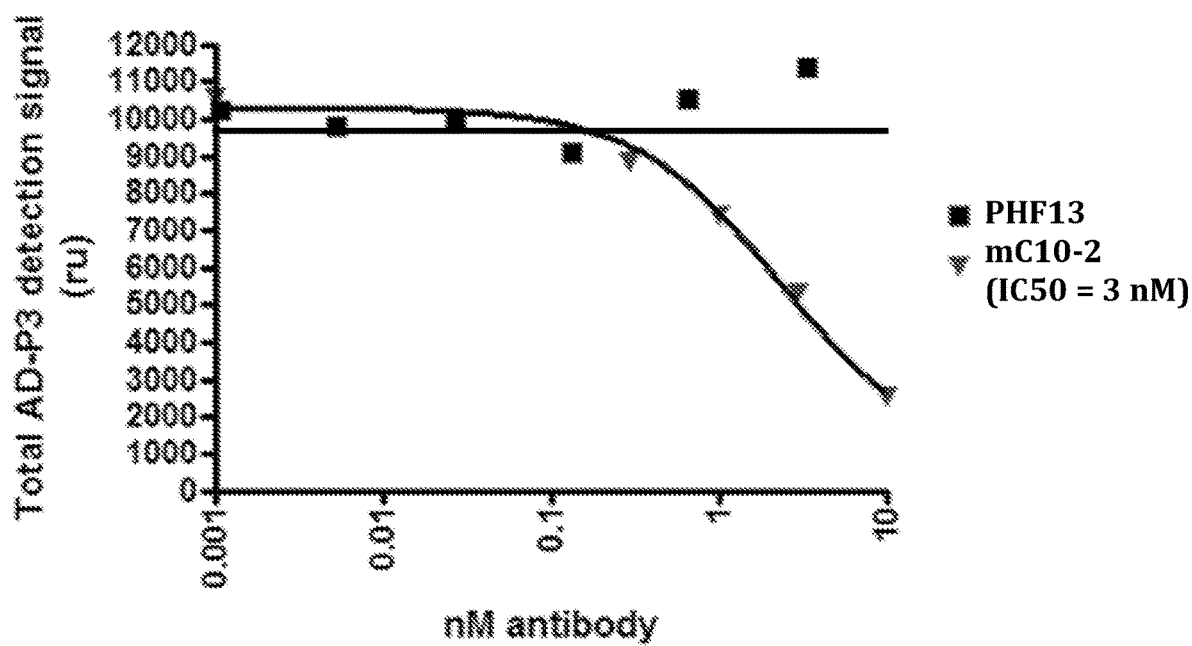

FIG. 31 PHF13 and mC10-2 inhibition of Tau antigen capture in mC10-2 coated plates In fluid phase ELISA, a mixture of AD P3 preparation and variable amounts of C10-2 and PHF13 antibodies were added onto C10-2 coated plates. The more antibodies binding to P3 tau in the solution, the less available tau epitopes are able to bind to the plates. The amount of tau binding to the plates is determined by a sulfo-tagged human tau antibody. C10-2 and PHF13 have a different binding to the tau in solution, wherein C10-2 can compete out all binding to the plates (IC50=3 nM), whereas PHF13 does not.

Figure 32:
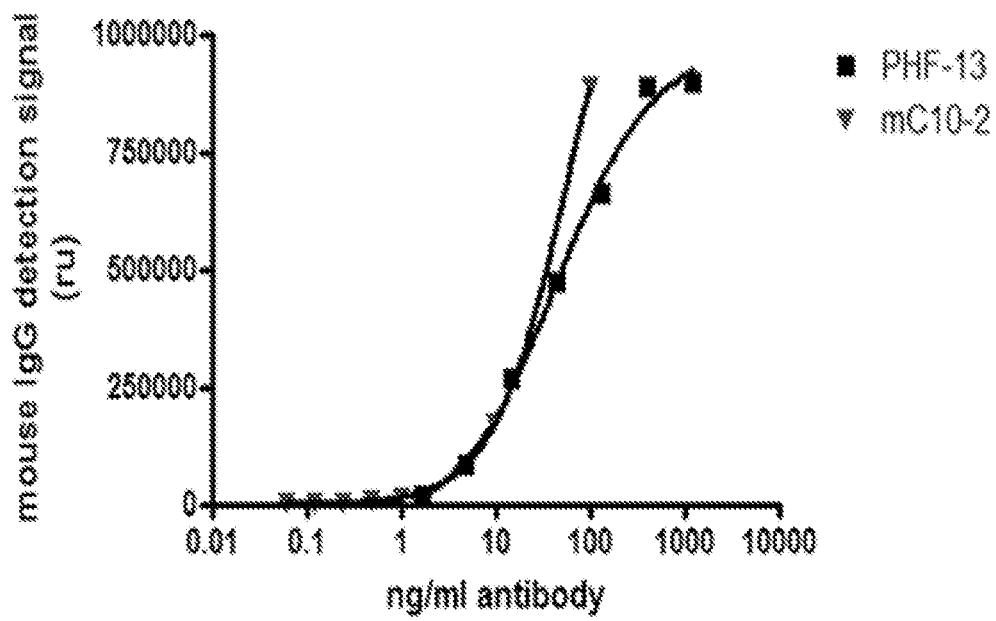

FIG. 32 Both mC10-2 and PFH-13 bind dose dependently to Ptau 386-408 (pS396/pS404)

FIG. 32 shows mC10-2 and PHF-13 bind equally well in MSD plates coated with 100 ng/ml p-tau 386-408 (pS396/pS404). Increasing concentrations of antibodies (indicated on x-axis) was incubated in wells for 2 hrs followed by wash and detection of bound antibodies using sulfo tagged anti-human IgG antibodies. This indicates that the prepared PHF-13 used in subsequent examples is active.

Figure 33:
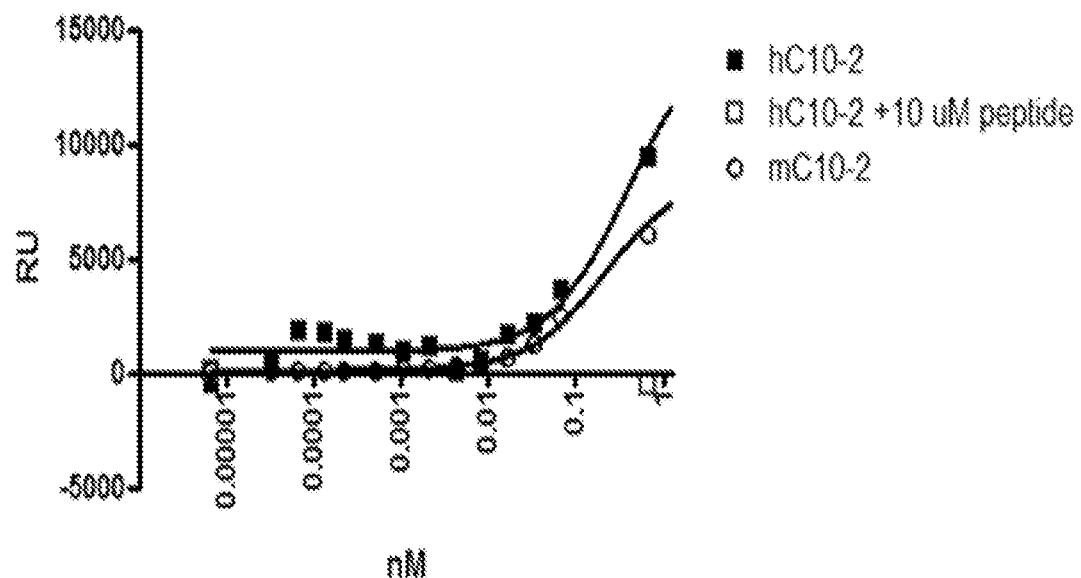

FIG. 33 Comparing mD1.2 and mC10-2 binding to AD-P3

FIG. 33 shows mD1.2 and mC10-2 binds equally well in MSD plates coated with 1 µg/ml AD-P3. Increasing concentrations of antibodies (indicated on x-axis) incubated in the presence and absence of 10 uM p-tau 386-408 (pS396/pS404) peptide for 1 hour at room temp followed by incubation in wells for 2 hours followed prior to detection of bound antibodies using sulfo tagged anti-human IgG antibodies. IC50 values were 320 nM and 11 nM for capture of AD-P3 and AD-S1(p). In contrast mD1.2 showed significantly weaker inhibition of tau antigen capture with IC50 values of 589 and 503 nM—suggesting much lower affinity binding to soluble antigens.

Assay was performed in two steps A: 1 µg/ml AD-P3 and 20 ng/ml AD s1(p), respectively was incubated with increasing concentration of mD1.2 and mC10-2 and incubated 1 hour at room temperature to allow increasing antibody-antigen binding (occupancy). B: The samples were incubated on MSD plates coated with AD-P3 (1 µg/ml) for 2 hours followed by wash and detection of captured Tau antigens using sulfo tagged anti-total TauG antibodies.

Figure 34:
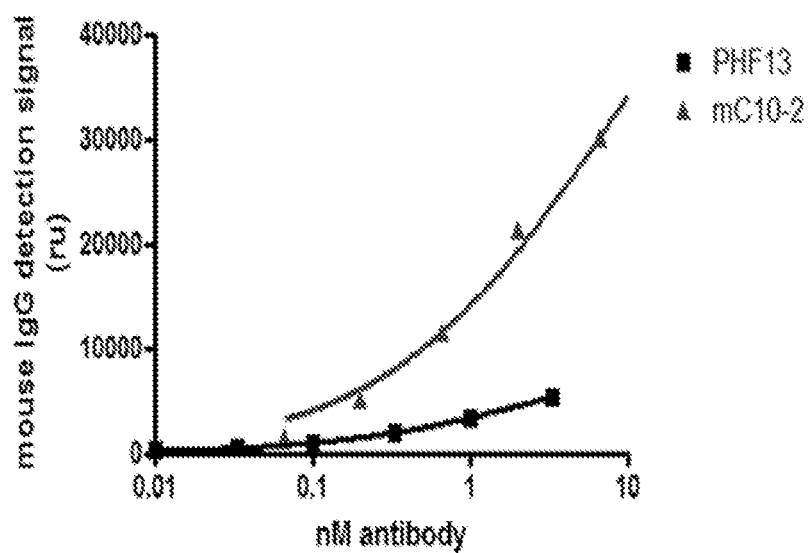

FIG. 34 mC10-2 but not PHF-13 binds efficiently to solid phase displayed AD-P3 antigens Highly specific binding of mC10-2 but not PHF-13: FIG. 34 shows that mC10-2 bind efficiently to AD-P3 antigens coated MSD plates (1 µg/ml). In comparison, the low binding activity of PHF-13 indicates lower affinity to physiological p-tau Antigens. Furthermore PHF-13 demonstrated substantial higher degree of non-specific binding in comparison to mC10-2 (see Table 5). Increasing concentrations of antibodies (indicated on x-axis) incubated for 2 hours followed prior to detection of bound antibodies using sulfo tagged anti-human IgG antibodies. Binding signal was corrected for non-specific binding activity (defined as signals measured in presence of 10 uM p-tau 386-408 (pS396/pS404) peptide. IC50 value were 3 nM for mC10-2 capture of AD-P3. In contrast PHF-13 showed virtually no inhibition.

Assay was performed in two steps. A: 1 µg/ml AD-P3 was incubated with increasing concentration of mC10-2 and PHF-13 and incubated 1 hour at room temperature to allow increasing antibody-antigen binding (occupancy). B: The samples were incubated on MSD plates coated with AD-P3 (1 µg/ml) for 2 hours followed by wash and detection of captured Tau antigens using sulfo tagged anti-total Tau antibodies.

SEQUENCES INCORPORATED BY REFERENCE

SEQ ID NO:1 D1.2 Light Chain CDR1
SEQ ID NO:2 D1.2 Light Chain CDR2
SEQ ID NO:3 D1.2 Light Chain CDR3
SEQ ID NO:4 D1.2 Heavy Chain CDR1
SEQ ID NO:5 D1.2 Heavy Chain CDR2
SEQ ID NO:6 D1.2 Heavy Chain CDR3
SEQ ID NO:7 D1.2 Light Chain
SEQ ID NO:8 D1.2 Heavy Chain
SEQ ID NO:9 C10-2 Light Chain CDR1
SEQ ID NO:10 C10-2 Light Chain CDR2
SEQ ID NO:11 C10-2 Light Chain CDR3
SEQ ID NO:12 C10-2 Heavy Chain CDR1
SEQ ID NO:13 C10-2 Heavy Chain CDR2
SEQ ID NO:14 C10-2 Heavy Chain CDR3
SEQ ID NO:15 C10-2 Light Chain
SEQ ID NO:16 C10-2 Heavy Chain
SEQ ID NO:17 C5.2 Light Chain CDR1
SEQ ID NO:18 C5.2 Light Chain CDR2
SEQ ID NO:19 C5.2 Light Chain CDR3
SEQ ID NO:20 C5.2 Heavy Chain CDR1
SEQ ID NO:21 C5.2 Heavy Chain CDR2
SEQ ID NO:22 C5.2 Heavy Chain CDR3
SEQ ID NO:23 C5.2 Light Chain
SEQ ID NO:24 C5.2 Heavy Chain
SEQ ID NO:25 C8.3 Light Chain CDR1
SEQ ID NO:26 C8.3 Light Chain CDR2
SEQ ID NO:27 C8.3 Light Chain CDR3
SEQ ID NO:28 C8.3 Heavy Chain CDR1
SEQ ID NO:29 C8.3 Heavy Chain CDR2
SEQ ID NO:30 C8.3 Heavy Chain CDR3
SEQ ID NO:31 C8.3 Light Chain
SEQ ID NO:32 C8.3 Heavy Chain
SEQ ID NO:33 Human tau
SEQ ID NO:34 D1.2* Light Chain
SEQ ID NO:35 humanized C10-2 Heavy Chain
SEQ ID NO:36 humanized C10-2 Light Chain
SEQ ID NO:37 tau residues 386-408 (pS396, pS404)

DETAILED DESCRIPTION OF THE INVENTION

As used herein, the term "tau" is synonymous with "the tau protein" and refers to any of the tau protein isoforms (identified in, for example, UniProt as P10636, 1-9). The amino acid numbering of tau that is used herein is given with respect to isoform 2 (SEQ ID NO:33) as shown below, with methionine (M) being amino acid residue 1:

```
SEQ ID NO: 33:
MAEPRQEFEV MEDHAGTYGL GDRKDQGGYT MHQDQEGDTD
AGLKESPLQT PTEDGSEEPG SETSDAKSTP TAEDVTAPLV
DEGAPGKQAA AQPHTEIPEG TTAEEAGIGD TPSLEDEAAG
HVTQARMVSK SKDGTGSDDK KAKGADGKTK IATPRGAAPP
GQKGQANATR IPAKTPPAPK TPPSSGEPPK SGDRSGYSSP
GSPGTPGSRS RTPSLPTPPT REPKKVAVVR TPPKSPSSAK
SRLQTAPVPM PDLKNVKSKI GSTENLKHQP GGGKVQIINK
KLDLSNVQSK CGSKDNIKHV PGGGSVQIVY KPVDLSKVTS
KCGSLGNIHH KPGGGQVEVK SEKLDFKDRV QSKIGSLDNI
THVPGGGNKK IETHKLTFRE NAKAKTDHGA EIVYKSPVVS
GDTSPRHLSN VSSTGSIDMV DSPQLATLAD EVSASLAKQG L
```

The present invention relates to antibodies and epitope-binding fragments thereof that are capable of specifically binding to tau, and in particular to human tau, and in one embodiment exhibit the ability to specifically bind to the phosphorylated S396 residue (pS396) of human tau. The antibodies and epitope-binding fragments thereof of the invention, are further characterized by being incapable or substantially incapable of specifically binding to the phosphorylated 404 (pS404) residue on human tau, for example under antibody limited or non-saturating conditions. Furthermore, phosphorylation at pS404 does not interfere with the specific binding to pS396. As used herein, the notations "pS" and "$^{\{p\}}$S" denote the amino acid residue phosphoserine. As used herein, an antibody is "substantially" incapable of binding to an epitope if relative to another epitope such binding is less than 20%, less than 10%, less than 5%, less than 2%, and more preferably, less than 1% of the binding observed with such other epitope.

The term "antibody" (Ab) in the context of the present invention refers to an immunoglobulin molecule or according to some embodiments of the invention, a fragment of an immunoglobulin molecule which has the ability to specifically bind to an epitope of a molecule ("antigen"). Naturally occurring antibodies typically comprise a tetramer which is usually composed of at least two heavy (H) chains and at least two light (L) chains. Each heavy chain is comprised of a heavy chain variable domain (abbreviated herein as VH) and a heavy chain constant domain, usually comprised of three domains (CH1, CH2 and CH3). Heavy chains can be of any isotype, including IgG (IgG1, IgG2, IgG3 and IgG4 subtypes). Each light chain is comprised of a light chain variable domain (abbreviated herein as VL) and a light chain constant domain (CL). Light chains include kappa chains and lambda chains. The heavy and light chain variable domain is typically responsible for antigen recognition, while the heavy and light chain constant domain may mediate the binding of the immunoglobulin to host tissues or factors, including various cells of the immune system (e.g., effector cells) and the first component (C1q) of the classical complement system. The VH and VL domains can be further subdivided into domains of hypervariability, termed "complementarity determining regions," that are interspersed with domains of more conserved sequence, termed "framework regions" (FR). Each VH and VL is composed of three CDR Domains and four FR Domains arranged from amino-terminus to carboxy-terminus in the following order: FR1-CDR1-FR2-CDR2-FR3-CDR3-FR4. The variable domains of the heavy and light chains contain a binding domain that interacts with an antigen. Of particular relevance are antibodies and their epitope-binding fragments that have been "isolated" so as to exist in a physical milieu distinct from that in which it may occur in nature or that have been modified so as to differ from a naturally occurring antibody in amino acid sequence.

The term "epitope" means an antigenic determinant capable of specific binding to an antibody. Epitopes usually consist of surface groupings of molecules such as amino acids or sugar side chains and usually have specific three dimensional structural characteristics, as well as specific charge characteristics. Conformational and linear epitopes are distinguished in that the binding to the former, but not the latter, is always lost in the presence of denaturing solvents. The epitope may comprise amino acid residues directly involved in the binding and other amino acid residues, which are not directly involved in the binding, such as amino acid residues which are effectively blocked by the specifically epitope-binding peptide (in other words, the amino acid residue is within the footprint of the specifically epitope-binding peptide).

As used herein, the term "epitope-binding fragment of an antibody" means a fragment, portion, region or domain of an antibody (regardless of how it is produced (e.g., via cleavage, recombinantly, synthetically, etc.)) that is capable of specifically binding to an epitope. An epitope-binding fragment may contain 1, 2, 3, 4, 5 or all 6 of the CDR Domains of such antibody and, although capable of specifically binding to such epitope, may exhibit a specificity, affinity or selectivity toward such epitope that differs from that of such antibody. Preferably, however, an epitope-binding fragment will contain all 6 of the CDR Domains of such antibody. An epitope-binding fragment of an antibody may be part of, or comprise, a single polypeptide chain (e.g., an scFv), or may be part of, or comprise, two or more polypeptide chains, each having an amino-terminus and a carboxyl terminus (e.g., a diabody, a Fab fragment, a Fab$_2$ fragment, etc.). Fragments of antibodies that exhibit epitope-binding ability can be obtained, for example, by protease cleavage of intact antibodies. More preferably, although the two domains of the Fv fragment, VL and VH, are naturally encoded by separate genes, polynucleotides that encode such gene sequences (e.g., their encoding cDNA) can be joined, using recombinant methods, by a flexible linker that enables them to be made as a single protein chain in which the VL and VH regions associate to form monovalent epitope-binding molecules (known as single-chain Fv (scFv); see e.g., Bird et al., (1988) Science 242:423-426; and Huston et al. (1988) Proc. Natl. Acad. Sci. (U.S.A.) 85:5879-5883). Alternatively, by employing a flexible linker that is too short (e.g., less than about 9 residues) to enable the VL and VH domains of a single polypeptide chain to associate together, one can form a bispecific antibody, diabody, or similar molecule (in which two such polypeptide chains associate together to form a bivalent epitope-binding molecule) (see for instance PNAS USA 90(14), 6444-8 (1993) for a description of diabodies). Examples of epitope-binding fragments encompassed within the present invention include (i) a Fab' or Fab fragment, a monovalent fragment consisting of the VL, VH, CL and CH1 domains, or a monovalent antibody as described in WO2007059782; (ii) F(ab')2 fragments, bivalent fragments comprising two Fab fragments linked by a disulfide bridge at the hinge domain; (iii) an Fd fragment consisting essentially of the VH and CH1 domains; (iv) a Fv fragment consisting essentially of a VL and VH domains, (v) a dAb fragment (Ward et al., Nature 341, 544-546 (1989)), which consists essentially of a VH domain and also called domain antibodies (Holt et al; Trends Biotechnol. 2003 November; 2i(II):484-90); (vi) camelid or nanobodies (Revets et al; Expert Opin Biol Ther. 2005 January; 5_(I): III-24) and (vii) an isolated complementarity determining region (CDR). Furthermore, although the two domains of the Fv fragment, VL and VH, are coded for by separate genes, they may be joined, using recombinant methods, by a synthetic linker that enables them to be made as a single protein chain in which the VL and VH domains pair to form monovalent molecules (known as single chain antibodies or sisngle chain Fv (scFv), see for instance Bird et al., Science 242, 423-426 (1988) and Huston et al., PNAS USA 85, 5879-5883 (1988)). These and other useful antibody fragments in the context of the present invention are discussed further herein. It also should be understood that the term antibody, unless specified otherwise, also includes antibody-like polypeptides, such as chimeric antibodies and humanized antibodies, and antibody fragments retaining the ability to specifically bind to the antigen (epitope-binding fragments) provided by any known technique, such as enzymatic cleavage, peptide synthesis, and recombinant techniques. An antibody as generated can possess any isotype. As used herein, "isotype" refers to the immunoglobulin class (for instance IgG1, IgG2, IgG3 or IgG4) that is encoded by heavy chain constant domain genes. Such antibody fragments are obtained using conventional techniques known to those of skill in the art; suitable fragments capable of binding to a desired epitope may be readily screened for utility in the same manner as an intact antibody.

The term "bispecific antibody" refers to an antibody containing two independent epitope-binding fragments that each target independent targets. These targets can be epitopes present on different proteins or different epitopes present on the same target. Bispecific antibody molecules can be made using compensatory amino acid changes in the constant domains of the HCs of the parent monospecific bivalent antibody molecules. The resulting heterodimeric antibody contains one Fabs contributed from two different parent monospecific antibodies. Amino acid changes in the Fc domain leads to increased stability of the heterodimeric antibody with bispecificity that is stable over time. (Ridgway et al., Protein Engineering 9, 617-621 (1996), Gunasekaran et al., JBC 285, 19637-1(2010), Moore et al., MAbs 3:6 546-557 (2011), Strop et al., JMB 420, 204-219 (2012), Metz et al., Protein Engineering 25:10 571-580 (2012), Labrijn et al., PNAS 110:113, 5145-5150 (2013), Spreter Von Kreudenstein et al., MAbs 5:5 646-654 (2013)). Bispecific antibodies can also include molecules that are generated using ScFv fusions. Two monospecific scfv are then independently joined to Fc domains able to form stable heterodimers to generate a single bispecific molecule (Mabry et al., PEDS 23:3 115-127 (2010). Bispecific molecules have dual binding capabilities.

The term "antibody D1.2" is intended to denote an antibody or an epitope-binding fragment thereof, comprising, or consisting of, an antibody Light Chain Variable domain having:

(a) a Light Chain CDR1 having the amino acid sequence of SEQ ID NO:1;

(b) a Light Chain CDR2 having the amino acid sequence of SEQ ID NO:2; and (c) a Light Chain CDR3 having the amino acid sequence of SEQ ID NO:3;

and an antibody Heavy Chain Variable domain having:
(d) a Heavy Chain CDR1 having the amino acid sequence of SEQ ID NO:4;
(e) a Heavy Chain CDR2 having the amino acid sequence of SEQ ID NO:5; and
(f) a Heavy Chain CDR3 having the amino acid sequence of SEQ ID NO:6.

In one embodiment, the antibody D1.2 or epitope-binding fragment thereof may comprise or consist of the heavy chain of SEQ ID NO:8 and/or the light chain of SEQ ID NO:7.

In a related embodiment, the antibody D1.2* or epitope-binding fragment thereof may comprise or consist of the heavy chain of SEQ ID NO:8 and/or the light chain of SEQ ID NO:34.

The term "antibody C10-2" is intended to denote an antibody or an epitope-binding fragment thereof comprising, or consisting of, an antibody Light Chain Variable domain having:
(a) a Light Chain CDR1 having the amino acid sequence of SEQ ID NO:9;
(b) a Light Chain CDR2 having the amino acid sequence of SEQ ID NO:10; and
(c) a Light Chain CDR3 having the amino acid sequence of SEQ ID NO:11;
and an antibody Heavy Chain Variable domain having:
(d) a Heavy Chain CDR1 having the amino acid sequence of SEQ ID NO:12;
(e) a Heavy Chain CDR2 having the amino acid sequence of SEQ ID NO:13; and
(f) a Heavy Chain CDR3 having the amino acid sequence of SEQ ID NO:14.

In one embodiment, the antibody C10-2 or epitope-binding fragment thereof may comprise or consist of the heavy chain of SEQ ID NO:16 and/or the light chain of SEQ ID NO:15.

In a further embodiment, the humanized the antibody C10-2 or epitope-binding fragment thereof may comprise or consist of the heavy chain of SEQ ID NO:35, the light chain of SEQ ID NO:36., or both. One embodiment of the invention is directed to an antibody or epitope-binding fragment thereof comprising or consisting of the heavy chain of SEQ ID NO:35, the light chain of SEQ ID NO:36.

The term "antibody C5.2" is intended to denote an antibody or epitope-binding fragment thereof comprising, or consisting of, an antibody Light Chain Variable domain having:
(a) a Light Chain CDR1 having the amino acid sequence of SEQ ID NO:17;
(b) a Light Chain CDR2 having the amino acid sequence of SEQ ID NO:18; and
(c) a Light Chain CDR3 having the amino acid sequence of SEQ ID NO:19;
and an antibody Heavy Chain Variable domain having:
(d) a Heavy Chain CDR1 having the amino acid sequence of SEQ ID NO:20;
(e) a Heavy Chain CDR2 having the amino acid sequence of SEQ ID NO:21; and
(f) a Heavy Chain CDR3 having the amino acid sequence of SEQ ID NO:22.

In one embodiment, the antibody C5.2 or epitope-binding fragment thereof may comprise or consist of the heavy chain of SEQ ID NO 24 and/or the light chain of SEQ ID NO:23.

The term "antibody C8.3" is intended to denote an antibody or an epitope-binding fragment thereof fragment thereof comprising, or consisting of, an antibody Light Chain Variable domain having:
(a) a Light Chain CDR1 having the amino acid sequence of SEQ ID NO:25;
(b) a Light Chain CDR2 having the amino acid sequence of SEQ ID NO:26; and
(c) a Light Chain CDR3 having the amino acid sequence of SEQ ID NO:27;
and an antibody Heavy Chain Variable domain having:
(d) a Heavy Chain CDR1 having the amino acid sequence of SEQ ID NO:28;
(e) a Heavy Chain CDR2 having the amino acid sequence of SEQ ID NO:29; and
(f) a Heavy Chain CDR3 having the amino acid sequence of SEQ ID NO:30.

In one embodiment, the antibody C8.3 or epitope-binding fragment thereof may comprise or consist of the heavy chain of SEQ ID NO 32 and/or the light chain of SEQ ID NO:31.

An "anti-tau antibody" is an antibody or an epitope-binding fragment thereof, which binds specifically to tau or a tau fragment.

The terms "monoclonal antibody" or "monoclonal antibody composition" as used herein refer to a preparation of antibody molecules of single molecular composition. A conventional monoclonal antibody composition displays a single binding specificity and affinity for a particular epitope. In certain embodiments a monoclonal antibody can be composed of more than one Fab domain thereby increasing the specificity to more than one target. The terms "monoclonal antibody" or "monoclonal antibody composition" are not intended to be limited by any particular method of production (e.g., recombinant, transgenic, hybridoma, etc.).

The antibodies of the present invention and epitope-binding fragments thereof will preferably be "humanized," particularly if employed for therapeutic purposes. The term "humanized" refer to a molecule, generally prepared using recombinant techniques, having an epitope-binding site derived from an immunoglobulin from a non-human species and a remaining immunoglobulin structure based upon the structure and/or sequence of a human immunoglobulin. The epitope-binding site may comprise either complete non-human antibody variable domains fused to human constant domains, or only the complementarity determining regions (CDRs) of such variable domains grafted to appropriate human framework regions of human variable domains. The framework residues of such humanized molecules may be wild type (e.g., fully human) or they may be modified to contain one or more amino acid substitutions not found in the human antibody whose sequence has served as the basis for humanization. Humanization lessens or eliminates the likelihood that a constant domain of the molecule will act as an immunogen in human individuals, but the possibility of an immune response to the foreign variable domain remains (LoBuglio, A. F. et al. (1989) "*Mouse/Human Chimeric Monoclonal Antibody In Man: Kinetics And Immune Response*," Proc. Natl. Acad. Sci. (U.S.A.) 86:4220-4224). Another approach focuses not only on providing human-derived constant domains, but modifying the variable domains as well so as to reshape them as closely as possible to human form. It is known that the variable domains of both heavy and light chains contain three complementarity-determining regions (CDRs) which vary in response to the antigens in question and determine binding capability, flanked by four framework regions (FRs) which are relatively conserved in a given species and which putatively provide a scaffolding for the CDRs. When nonhuman antibodies are prepared with respect to a particular antigen, the variable domains can be "reshaped" or "humanized" by grafting CDRs derived from nonhuman antibody on the FRs present in the human antibody to be modified. Application of this approach to various antibodies has been reported by Sato, K. et al. (1993) Cancer Res 53:851-856. Riechmann, L. et al. (1988) "Reshaping Human Antibodies for Therapy," Nature 332:323-327; Verhoeyen, M. et al. (1988) "*Reshaping Human Antibodies: Grafting An Antilysozyme Activity*," Science 239:1534-1536; Kettleborough, C. A. et al. (1991) "*Humanization Of A Mouse Monoclonal Antibody By CDR-Grafting: The Importance Of Framework Residues On Loop Conformation*," Protein Engineering 4:773-3783; Maeda, H. et al. (1991) "*Construction Of Reshaped Human Antibodies With HIV-Neutralizing Activity*," Human Antibodies Hybridoma 2:124-134; Gorman, S. D. et al. (1991) "*Reshaping A Therapeutic CD4 Antibody*," Proc. Natl. Acad. Sci. (U.S.A.) 88:4181-4185; Tempest, P. R. et al. (1991) "*Reshaping A Human Monoclonal Antibody To Inhibit Human Respiratory Syncytial Virus Infection in vivo*," Bio/Technology 9:266-271; Co, M. S. et al. (1991) "*Humanized Antibodies For Antiviral Therapy*," Proc. Natl. Acad. Sci. (U.S.A.) 88:2869-2873; Carter, P. et al. (1992) "*Humanization Of An Anti-p185her2 Antibody For Human Cancer Therapy*," Proc. Natl. Acad. Sci. (U.S.A.) 89:4285-4289; and Co, M. S. et al. (1992) "*Chimeric And Humanized Antibodies With Specificity For The CD33 Antigen*," J. Immunol. 148:1149-1154. In some embodiments, humanized antibodies preserve all CDR sequences (for example, a humanized mouse antibody which contains all six CDRs from the mouse antibodies). In other embodiments, humanized antibodies have one or more CDRs (one, two, three, four, five, six) which are altered with respect to the original antibody, which are also termed one or more CDRs "derived from" one or more CDRs from the original antibody. The ability to humanize an antigen is well known (see, e.g., U.S. Pat. Nos. 5,225,539; 5,530,101; 5,585,089; 5,859,205; 6,407,213; 6,881,557).

The term "antibody "XX" is intended to denote an antibody or epitope-binding fragment thereof (for example antibody "C10-2"), comprising or consisting of the Light Chain, the Light Chain Variable domain, or the Light Chain Variable domain CDR1-3, as defined by its respective SEQ ID NO, and the Heavy Chain, Heavy Chain Variable Domain, or Heavy Chain Variable Domain CDR1-3 as defined by its respective SEQ ID NO. In certain embodiments the antibody or epitope-binding fragment thereof are defined by their entire Heavy Chain Variable Domain comprising as defined by their SEQ ID NO and their Light Chain Variable Domain as defined by their SEQ ID NO.

Unless otherwise specified herein, numbering of amino acid residues in the Fc region or constant domain of an antibody is according to the EU numbering system, also called the EU index, as described in Kabat et al., Sequences of Proteins of Immunological Interest, 5th Ed. Public Health Service, National Institutes of Health, Bethesda, Md., 1991.

As used herein, an antibody or an epitope-binding fragment thereof is said to "specifically" bind a region of another molecule (i.e., an epitope) if it reacts or associates more frequently, more rapidly, with greater duration and/or with greater affinity or avidity with that epitope relative to alternative epitopes. It is also understood by reading this definition that, for example, an antibody or epitope-binding fragment thereof that specifically binds to a first target may or may not specifically or preferentially bind to a second target. As used herein, the term "binding" in the context of the binding of an antibody to a predetermined antigen typically refers to binding with an affinity corresponding to a KD of about $10^{-7}$ M or less, such as about $10^{-8}$ M or less, such as about $10^{-9}$ M or less when determined by for instance surface plasmon resonance (SPR) technology in a BIAcore® 3000 instrument using the antigen as the ligand and the antibody as the analyte, and binds to the predetermined antigen with an affinity corresponding to a KD that is at least ten-fold lower, such as at least 100 fold lower, for instance at least 1,000 fold lower, such as at least 10,000 fold lower, for instance at least 100,000 fold lower than its affinity for binding to a non-specific antigen (e.g., BSA, casein) other than the predetermined antigen or a closely-related antigen. The amount with which the affinity is lower is dependent on the KD of the antibody, so that when the KD of the antibody is very low (that is, the antibody is highly specific), then the amount with which the affinity for the antigen is lower than the affinity for a non-specific antigen may be at least 10,000 fold.

The term "kd" (sec−1 or 1/s), as used herein, refers to the dissociation rate constant of a particular antibody-antigen interaction. Said value is also referred to as the koff value.

The term "ka" (M−1× sec−1 or 1/Msec), as used herein, refers to the association rate constant of a particular antibody-antigen interaction.

The term "KD" (M), as used herein, refers to the dissociation equilibrium constant of a particular antibody-antigen interaction and is obtained by dividing the kd by the ka.

The term "KA" (M−1 or 1/M), as used herein, refers to the association equilibrium constant of a particular antibody-antigen interaction and is obtained by dividing the ka by the kd.

In one embodiment, the invention relates to an anti-tau antibody, or epitope-binding fragment thereof, which exhibits one or more of the following properties:
   (i) a substantial inability to bind to non-phosphorylated tau;
   (ii) a substantial inability to bind to tau that is phosphorylated at S404 and not phosphorylated at S396;
   (iii) the ability to bind to tau phosphorylated at S396;
   (iv) the ability to bind to tau phosphorylated at both S396 and at S404;
   (v) the ability to selectively discriminate between phosphorylated tau residues S396 and S404 such that it is substantially unable to bind the phosphorylated 404 residue (pS404);
   (vi) the ability to bind hyper-phosphorylated tau from human Alzheimer's disease brains;
   (vii) the ability to discriminate between pathological and non-pathological human tau protein; and/or
   (viii) the capability, when used as described herein with immune-depleted rTg4510 extracts from transgenic mice, to specifically reduce the hyperphosphorylated tau 64 kDa and 70 kDa bands by at least 90%, while not reducing the 55 kDa tau band by more than 10%; or the capability, when used as described herein with extracts from human AD post-mortem brains to specifically reduce the S396 phosphorylated hyperphosphorylated tau bands by at least 90%, while not reducing the non-hyperphosphorylated tau bands by more than 10%.

A further embodiment of the invention relates to an antibody generated by a method for generating high specificity, high affinity antibodies that are immunospecific for pathogenic hyperphosphorylated tau comprising residue a phosphorylated S396, wherein said method comprises the steps of:
   (A) injecting an immunogen into a mammal, said immunogen comprising the bi-phosphorylated peptide comprising 18-40, such as at 18-30, such as 20-30 amino consecutive acid residues comprising TDHGAEIVYK$^{\{p\}}$SPVVSGDT$^{\{p\}}$SPRHL (SEQ ID NO:37) covering residues 386-410 of 2N4R tau., to thereby immunize said mammal;

(B) repeating said immunization of said mammal two or more times;

(C) screening a serum sample from said repeatedly immunized mammal for the presence of high specificity, high affinity antibodies capable of binding pathogenic hyperphosphorylated tau comprising residue a phosphorylated S396, but substantially less capable of binding non-pathogenic tau; and (D) recovering said high specificity, high affinity antibodies.

As used herein, a "substantial inability" to bind a tau molecule denotes more than a 20% difference, more than a 40% difference, more than a 60% difference, more than an 80% difference, more than a 100% difference, more than a 150% difference, more than a 2-fold difference, more than a 4-fold difference, more than a 5-fold difference, or more than a 10-fold difference in functionality, relative to the detectable binding mediated by a reference antibody.

The term "selective" and "immunoselective" when referring to the binding capabilities of an anti-tau antibody with respect to two epitopes is intended to denote that the observed binding under saturating conditions exhibits at least an 80% difference, at least a 95% difference, and most preferably a 100% difference (i.e., no detectable binding to one epitope). The term "selective" and "immunoselective" when referring to a tau antibody is further intended to mean the antibody binds hyper-phosphorylated tau from human Alzheimer's disease brains and is able to discriminate between pathological and non-pathological human tau protein.

The terms TBS-extractable (S1), high salt/sarkosyl-extractable (S3), and sarkosyl-insoluble (P3) fractions are fractions as obtained by the Tau biochemical fractionation described herein.

In some antibodies, only part of a CDR, namely the subset of CDR residues required for binding, termed the SDRs, are needed to retain binding in a humanized antibody. CDR residues not contacting the relevant epitope and not in the SDRs can be identified based on previous studies (for example residues H60-H65 in CDR H2 are often not required), from regions of Kabat CDRs lying outside Chothia hypervariable loops (see, Kabat et al. (1992) SEQUENCES OF PROTEINS OF IMMUNOLOGICAL INTEREST, National Institutes of Health Publication No. 91-3242; Chothia, C. et al. (1987) "*Canonical Structures For The Hypervariable Regions Of Immunoglobulins*," J. Mol. Biol. 196:901-917), by molecular modeling and/or empirically, or as described in Gonzales, N. R. et al. (2004) "*SDR Grafting Of A Murine Antibody Using Multiple Human Germline Templates To Minimize Its Immunogenicity*," Mol. Immunol. 41:863-872. In such humanized antibodies at positions in which one or more donor CDR residues is absent or in which an entire donor CDR is omitted, the amino acid occupying the position can be an amino acid occupying the corresponding position (by Kabat numbering) in the acceptor antibody sequence. The number of such substitutions of acceptor for donor amino acids in the CDRs to include reflects a balance of competing considerations. Such substitutions are potentially advantageous in decreasing the number of mouse amino acids in a humanized antibody and consequently decreasing potential immunogenicity. However, substitutions can also cause changes of affinity, and significant reductions in affinity are preferably avoided. Positions for substitution within CDRs and amino acids to substitute can also be selected empirically.

The fact that a single amino acid alteration of a CDR residue can result in loss of functional binding (Rudikoff, S. etc. (1982) "*Single Amino Acid Substitution Altering Antigen-Binding Specificity*," Proc. Natl. Acad. Sci. (USA) 79(6):1979-1983) provides a means for systematically identifying alternative functional CDR sequences. In one preferred method for obtaining such variant CDRs, a polynucleotide encoding the CDR is mutagenized (for example via random mutagenesis or by a site-directed method (e.g., polymerase chain-mediated amplification with primers that encode the mutated locus)) to produce a CDR having a substituted amino acid residue. By comparing the identity of the relevant residue in the original (functional) CDR sequence to the identity of the substituted (non-functional) variant CDR sequence, the BLOSUM62.iij substitution score for that substitution can be identified. The BLOSUM system provides a matrix of amino acid substitutions created by analyzing a database of sequences for trusted alignments (Eddy, S. R. (2004) "*Where Did The BLOSUM62 Alignment Score Matrix Come From?*," Nature Biotech. 22(8):1035-1036; Henikoff, J. G. (1992) "Amino acid substitution matrices from protein blocks," Proc. Natl. Acad. Sci. (USA) 89:10915-10919; Karlin, S. et al. (1990) "*Methods For Assessing The Statistical Significance Of Molecular Sequence Features By Using General Scoring Schemes*," Proc. Natl. Acad. Sci. (USA) 87:2264-2268; Altschul, S. F. (1991) "*Amino Acid Substitution Matrices From An Information Theoretic Perspective*," J. Mol. Biol. 219, 555-565. Currently, the most advanced BLOSUM database is the BLOSUM62 database (BLOSUM62.iij). FIG. 35 presents the BLOSUM62.iij substitution scores (the higher the score the more conservative the substitution and thus the more likely the substitution will not affect function). If an epitope-binding fragment comprising the resultant CDR fails to bind to tau, for example, then the BLOSUM62.iij substitution score is deemed to be insufficiently conservative, and a new candidate substitution is selected and produced having a higher substitution score. Thus, for example, if the original residue was glutamate (E), and the non-functional substitute residue was histidine (H), then the BLOSUM62.iij substitution score will be 0, and more conservative changes (such as to aspartate, asparagine, glutamine, or lysine) are preferred.

The invention thus contemplates the use of random mutagenesis to identify improved CDRs. In the context of the present invention, conservative substitutions may be defined by substitutions within the classes of amino acids reflected in one or more of Tables 1, 2, or 3:

Amino Acid Residue Classes For Conservative Substitutions:

TABLE 1

| | |
|---|---|
| Acidic Residues | Asp (D) and Glu (E) |
| Basic Residues | Lys (K), Arg (R), and His (H) |
| Hydrophilic Uncharged Residues | Ser (S), Thr (T), Asn (N), and Gln (Q) |
| Aliphatic Uncharged Residues | Cly (G), Ala (A), Val (V), Leu (L), and Ile (I) |
| Non-polar Uncharged Residues | Cys (C), Met (M), and Pro (P) |
| Aromatic Residues | Phe (F), Tyr (Y), and Trp (W) |

Alternative Conservative Amino Acid Residue Substitution Classes:

TABLE 2

| 1 | A | S | T |
|---|---|---|---|
| 2 | D | E |   |
| 3 | N | Q |   |
| 4 | R | K |   |
| 5 | I | L | M |
| 6 | F | Y | W |

Alternative Physical and Functional Classifications of Amino Acid Residues:

TABLE 3

| Alcohol Group-Containing Residues | S and T |
|---|---|
| Aliphatic Residues | I, L, V and M |
| Cycloalkenyl-Associated Residues | F, H, W and Y |
| Hydrophobic Residues | A, C, F, G, H, I, L, M, R, T, V, W and Y |
| Negatively Charged Residues | D and E |
| Polar Residues | C, D, E, H, K, N, Q, R, S and T |
| Positively Charged Residues | H, K and R |
| Small Residues | A, C, D, G, N, P, S, T and V |
| Very Small Residues | A, G and S |
| Residues Involved In Turn Formation | A, C, D, E, G, H, K, N, Q, R, S, P and T |
| Flexible Residues | Q, T, K, S, G, P, D, E and R |

More conservative substitutions groupings include: valine-leucine-isoleucine, phenylalanine-tyrosine, lysine-arginine, alanine-valine, and asparagine-glutamine.

Additional groups of amino acids may also be formulated using the principles described in, e.g., Creighton (1984) Proteins: Structure and Molecular Properties (2d Ed. 1993), W. H. Freeman and Company.

Phage display technology can alternatively be used to increase (or decrease) CDR affinity. This technology, referred to as affinity maturation, employs mutagenesis or "CDR walking" and re-selection uses the target antigen or an antigenic epitope-binding fragment thereof to identify antibodies having CDRs that bind with higher (or lower) affinity to the antigen when compared with the initial or parental antibody (See, e.g. Glaser et al. (1992) J. Immunology 149:3903). Mutagenizing entire codons rather than single nucleotides results in a semi-randomized repertoire of amino acid mutations. Libraries can be constructed consisting of a pool of variant clones each of which differs by a single amino acid alteration in a single CDR and which contain variants representing each possible amino acid substitution for each CDR residue. Mutants with increased (or decreased) binding affinity for the antigen can be screened by contacting the immobilized mutants with labeled antigen. Any screening method known in the art can be used to identify mutant antibodies with increased or decreased affinity to the antigen (e.g., ELISA) (See Wu et al. 1998, Proc. Natl. Acad. Sci. (U.S.A.) 95:6037; Yelton et al., 1995, J. Immunology 155:1994). CDR walking which randomizes the Light Chain may be used possible (see, Schier et al., 1996, J. Mol. Bio. 263:551).

Methods for accomplishing such affinity maturation are described for example in: Krause, J. C. et al. (2011) "*An Insertion Mutation That Distorts Antibody Binding Site Architecture Enhances Function Of A Human Antibody,*" MBio. 2(1) pii: e00345-10. doi: 10.1128/mBio.00345-10; Kuan, C. T. et al. (2010) "*Affinity-Matured Anti-Glycoprotein NMB Recombinant Immunotoxins Targeting Malignant Gliomas And Melanomas,*" Int. J. Cancer 10.1002/ijc.25645; Hackel, B. J. et al. (2010) "*Stability And CDR Composition Biases Enrich Binder Functionality Landscapes,*" J. Mol. Biol. 401(1):84-96; Montgomery, D. L. et al. (2009) "*Affinity Maturation And Characterization Of A Human Monoclonal Antibody Against HIV-1 gp41,*" MAbs 1(5):462-474; Gustchina, E. et al. (2009) "*Affinity Maturation By Targeted Diversification Of The CDR-H2 Loop Of A Monoclonal Fab Derived From A Synthetic Naïve Human Antibody Library And Directed Against The Internal Trimeric Coiled-Coil Of Gp41 Yields A Set Of Fabs With Improved HIV-1 Neutralization Potency And Breadth,*" Virology 393(1):112-119; Finlay, W. J. et al. (2009) "*Affinity Maturation Of A Humanized Rat Antibody For Anti-RAGE Therapy: Comprehensive Mutagenesis Reveals A High Level Of Mutational Plasticity Both Inside And Outside The Complementarity-Determining Regions,*" J. Mol. Biol. 388(3):541-558; Bostrom, J. et al. (2009) "*Improving Antibody Binding Affinity And Specificity For Therapeutic Development,*" Methods Mol. Biol. 525: 353-376; Steidl, S. et al. (2008) "*In Vitro Affinity Maturation Of Human GM-CSF Antibodies By Targeted CDR-Diversification,*" Mol. Immunol. 46(1):135-144; and Barderas, R. et al. (2008) "*Affinity Maturation Of Antibodies Assisted By In Silico Modeling,*" Proc. Natl. Acad. Sci. (USA) 105(26): 9029-9034.

Thus, the sequence of CDR variants of encompassed antibodies or their epitope-binding fragments may differ from the sequence of the CDR of the parent antibody, D1.2, C10-2, C5.2 or C8.3, through substitutions; for instance substituted 4 amino acid residue, 3 amino acid residue, 2 amino acid residue or 1 of the amino acid residues. According to an embodiment of the invention it is furthermore envisaged that the amino acids in the CDR regions may be substituted with conservative substitutions, as defined in the 3 tables above. For example, the acidic residue Asp can be substituted with Glu without substantially affecting the binding characteristic of the antibody.

The term "normal tau" refers to normal brain tau containing 2-3 moles of phosphate per mole of the protein.

The term "hyperphosphorylated tau" refers to a polyphosphorylated species of tau consistent with poly-anionic species induced mobility shift in Western Blot or to a tau species which has more than five, six or seven Serine, Threonine or Tyrosine sites phosphorylated.

The term "tau having residue 396 phosphorylated" relates hyperphosphorylated tau wherein residue 396 is phosphorylated and residue 404 is or is not phosphorylated.

The term "transgenic non-human animal" refers to a non-human animal having a genome comprising one or more human heavy and/or light chain transgenes or trans-chromosomes (either integrated or non-integrated into the animal's natural genomic DNA) and which is capable of expressing fully humanized antibodies. For example, a transgenic mouse can have a humanized light chain transgene and either a humanized heavy chain transgene or humanized heavy chain trans-chromosome, such that the mouse produces humanized anti-tau antibody when immunized with tau antigen and/or cells expressing tau. The humanized heavy chain transgene may be integrated into the chromosomal DNA of the mouse, as is the case for transgenic mice, for instance HuMAb mice, such as HCo7 or HCo12 mice, or the humanized heavy chain transgene may be maintained extra-chromosomally, as is the case for trans-chromosomal KM mice as described in WO02/43478. Such transgenic and trans-chromosomal mice (collectively referred to herein as "transgenic mice") are capable of producing multiple isotypes of humanized monoclonal antibodies to a given antigen (such as IgG, IgA, IgM, IgD and/or IgE) by undergoing V-D-J recombination and isotype switching.

Transgenic, nonhuman animal can also be used for production of antibodies against a specific antigen by introducing genes encoding such specific antibody, for example by operatively linking the genes to a gene which is expressed in the milk of the animal.

The term "treatment" or "treating" as used herein means ameliorating, slowing, attenuating, or reversing the progress or severity of a disease or disorder, or ameliorating, slowing, attenuating, or reversing one or more symptoms or side effects of such disease or disorder. For purposes of this invention, "treatment" or "treating" further means an approach for obtaining beneficial or desired clinical results, where "beneficial or desired clinical results" include, without limitation, alleviation of a symptom, diminishment of the extent of a disorder or disease, stabilized (i.e., not worsening) disease or disorder state, delay or slowing of the progression a disease or disorder state, amelioration or palliation of a disease or disorder state, and remission of a disease or disorder, whether partial or total, detectable or undetectable.

An "effective amount," when applied to an antibody or epitope-binding fragment thereof of the invention, refers to an amount sufficient, at dosages and for periods of time necessary, to achieve an intended biological effect or a desired therapeutic result including, without limitation, clinical results. The phrase "therapeutically effective amount," when applied to an antibody or an epitope-binding fragment thereof of the invention, is intended to denote an amount of the antibody, or epitope-binding fragment thereof, that is sufficient to ameliorate, palliate, stabilize, reverse, slow, attenuate or delay the progression of a disorder or disease state, or of a symptom of the disorder or disease. In an embodiment, the method of the present invention provides for administration of the antibody, or epitope-binding fragment thereof, in combinations with other compounds. In such instances, the "effective amount" is the amount of the combination sufficient to cause the intended biological effect.

A therapeutically effective amount of an anti-tau antibody or epitope-binding fragment thereof of the invention may vary according to factors such as the disease state, age, sex, and weight of the individual, and the ability of the anti-tau antibody, or epitope-binding fragment thereof, to elicit a desired response in the individual. A therapeutically effective amount is also one in which any toxic or detrimental effects of the antibody or antibody portion are outweighed by the therapeutically beneficial effects.

As indicated above, the present invention particularly relates to monoclonal antibodies, or epitope-binding fragments thereof, and to a completely new method for producing such molecules (and thus of such epitope-binding fragments thereof). This method is outlined in FIG. 9. This ability of the new method to isolate monoclonal antibodies is exemplified herein by its use to isolate monoclonal antibodies that are capable of specifically binding to the phosphorylated residue serine 396 ($^{\{p\}}$S396) of human tau (SEQ ID NO:33). These antibodies are further characterized by their ability to discriminate between phosphorylated residues serine 396 and serine 404 (pS404) such that they do not bind to tau protein with phosphorylated serine 404 unless the tau is also phosphorylated at residue 396.

The antibodies of the present invention, or epitope-binding fragment thereof, have been generated and isolated by use of a novel a method (FIG. 9) which favors the selection of $^{\{p\}}$S396 specific antibodies (FIG. 9). Furthermore, by applying this very strict antibody clone selection procedure, antibodies have been obtained that are not only highly specific towards S396, but also highly selective towards the phosphorylated $^{\{p\}}$S396 epitope. These antibodies uniquely recognize tau from Alzheimer's disease brains. We also demonstrate that the screening procedure outlined in FIG. 9 ensures the identification of antibodies which possess a functional and therapeutic utility.

Antibodies were raised against the bi-phosphorylated peptide: TDHGAEIVYK$^{\{p\}}$SPVVSGDT$^{\{p\}}$SPRHL (SEQ ID NO:37) covering residues 386-408 of 2N4R tau (Example 1). Mice were immunized with the phospho-peptide. Once sufficient antibody titres had been obtained, the mice were sacrificed and hybridomas were generated (Example 2). The hybridomas were screened using dot-blot (Example 3) and MSD ELISA with immobilized human pathological and non-pathological tau (Example 4). The ability to discriminate between pathological and non-pathological human tau protein in dot-blot and Western blot was used for the selection of hybridomas. Sixteen clones were selected, of which four hybridoma clones were recovered that produced antibodies which exhibited extraordinary capabilities for binding to human pathological tau material.

Specific binding to pathological and non-pathological tau was also determined by isolation of tau from diseased and non-diseased human AD brains and immobilization of this material on MSD ELISA plates (Example 4).

A further aspect of the invention relates to monoclonal antibody or an epitope-binding fragment thereof elicited against the bi-phosphorylated peptide comprising at least 18, such as at least 20 amino consecutive acid residues within TDHGAEIVYK$^{\{p\}}$SPVVSGDT$^{\{p\}}$SPRHL (SEQ ID NO:37) covering residues 386-410 of 2N4R tau. In this aspect of the invention, the monoclonal antibody or an epitope-binding fragment thereof is typically elicited against the bi-phosphorylated peptide comprising 18-40, such as at 18-30, such as 20-30 amino consecutive acid residues comprising TDHGAEIVYK$^{\{p\}}$SPVVSPVVSGDT$^{\{p\}}$SPRHL (SEQ ID NO:37) covering residues 386-410 of 2N4R tau.

A further aspect of the invention is directed to the monoclonal antibody or an epitope-binding fragment thereof of the invention, having a specificity for phosphoTau (pTau) from AD-diseased patients over age-matched healthy controls, such that said monoclonal antibody or an epitope-binding fragment thereof has a specificity difference for phosphoTau (pTau) from AD-diseased patients over tau from age-healthy matched controls of more than 50-fold, such as more than 100-fold increase in specificity for AD disease material compared to healthy control material in an ELISA based assay detect phosphoTau (pTau) in brain homogenates from AD and from healthy control subjects, using a phospho- and multimer-specific Setup 1 ELISA as described herein.

A related aspect of the invention is directed to the monoclonal antibody or an epitope-binding fragment thereof of the invention, having a specificity for AD-diseased Tau such that said monoclonal antibody or an epitope-binding fragment thereof has a specificity difference for AD over age-healthy matched controls of more than 50-fold, such as more than 100-fold increase in specificity for AD disease material compared to healthy control material in an ELISA based assay detect phosphoTau (pTau) in brain homogenates from AD and from healthy control subjects, using a phospho- and multimer-specific Setup 1 ELISA.

Setup 1 ELISA method comprises the steps A) a capture of pathological human Tau antigens from AD brains using C10-2 coated plates; B) incubation of Tau antigens with increasing concentrations of pS396 specific antibodies; and C) detection of the Tau antigen capture and antibody mediated inhibition using sulfo-tagged anti human (total) Tau antibodies from MSD.

The invention further relates to an antibody generated by a method for generating high specificity, high affinity antibodies that are immunospecific for pathogenic hyperphosphorylated tau comprising residue a phosphorylated S396, wherein said method comprises the steps of:

(A) injecting an immunogen into a mammal, said immunogen comprising the bi-phosphorylated peptide comprising 18-40, such as at 18-30, such as 20-30 amino consecutive acid residues comprising TDHGAEIV-YK{p}SPVVSGDT{p}SPRHL (SEQ ID NO:37) covering residues 386-410 of 2N4R tau, to thereby immunize said mammal;

(B) repeating said immunization of said mammal two or more times;

(C) screening a serum sample from said repeatedly immunized mammal for the presence of high specificity, high affinity antibodies capable of binding pathogenic hyperphosphorylated tau comprising residue a phosphorylated S396, but substantially less capable of binding non-pathogenic tau; and (D) recovering said high specificity, high affinity antibodies.

More specifically, step A comprises: coating of MSD plates (typically overnight at 4 C) with C10-2 antibody, typically 0.5 µg/ml (capture antibody) in coating buffer, blocking (typically 1 hour at room temperature) and washing, typically 3 times. Step B comprises: mixing of samples of P3 lysate (typically 1:1000=2-4 µg/ml total protein) and/or S1(p) (typically 1:300=20-40 ng/ml total protein) from AD (pooled from 3 patients) with graded concentrations of pS396 peptide epitope specific antibody and incubating (typically 1 hour at room temperature). The reactions are subsequently incubated for 2 hours on plates prepared in step A. Step C comprises detecting C10-2 captured Tau was using sulfo-tagged human tau. Tau antibody (typically 1:50) from MSD following manufacturer instructions. Plates are analyzed on MSD SECTOR® S600. AD P3 and AD S1(p) are tested in a similar setup.

A further embodiment is directed to an antibody, or antigen-binding fragment thereof, capable of immunospecifically binding to the phosphorylated residue 396 of human tau (SEQ ID NO:33), which has been produced or manufactured in a cell line such as a human cell line, a mammal non-human cell line, an insect, yeast or bacterial cell line.

The antibody, or antigen binding fragment thereof, capable of immunospecifically binding to the phosphorylated residue 396 of human tau (SEQ ID NO:33), produced in a CHO cell line, HEK cell line, BHK-21 cell line, murine cell line (such as a myeloma cell line), fibrosarcoma cell line, PER.C6 cell line, HKB-11 cell line, CAP cell line and HuH-7 human cell line.

Specific affinities and binding properties of D1.2 and C10-2 have been characterized using tau 386-410 (2R4N) peptides which are either phosphorylated or un-phosphorylated at position 396 or 404 (SEQ ID NOs:29-32). Using the specific immunization and screening protocol (FIG. 9) outlined in this application will produce highly phosphor-serine-396 (pS396) specific antibodies as demonstrated in FIG. 4.

In order to demonstrate that the antibodies are specific towards pathological tau, D1.2 and C10-2 antibodies have also been characterized by immune-histochemical analysis (Example 6). The antibodies exhibit highly specific binding to neurofibrillary tangles in Alzheimer's disease brains and in sections from Tg4510 tau transgenic mice expressing human (P301L) mutant tau (FIG. 5). No binding is observed to tissue from human control brains and from non-transgenic mouse brains, demonstrating that the antibodies specifically bind human tau and in particular tau associated with Alzheimer's pathology.

The unique capability of these antibodies to recognize tau associated with disease pathology is demonstrated here in Example 7. We compare the binding of pathological vs. non-pathological tau in the assay described in Example 3. The comparison is to five published tau antibodies: hACI-2B6, IPN002, HJ8.5, 2.10.3, and 4E4. FIG. 6 illustrates the binding of each of the reference antibodies towards tau from healthy and diseased brains, and binding to P301L human mutant tau isolated from 10 month old Tg4510 tau transgenic mice. This demonstrates that the isolated antibodies exhibit an exceptionally high degree of specificity and selectivity towards human pathological tau. This selectivity is superior to any of the comparator antibodies as shown in Table 4.

TABLE 4

| mAb Tested | AD/ctrl | TG/wt |
|---|---|---|
| hACI-2B6 | 3 | 1 |
| IPN002 | 3 | 37 |
| HJ8.5 | 3 | 51 |
| 4E4 | no binding | 1 |
| 2.10.3 | 5 | 2 |
| C5-2_C10-2 | >100 | 118 |

At saturation binding antibodies D1.2 and C10-2 exhibit more than 100-fold selectivity towards P3 tau isolated from human AD brains.

Figure 7A:
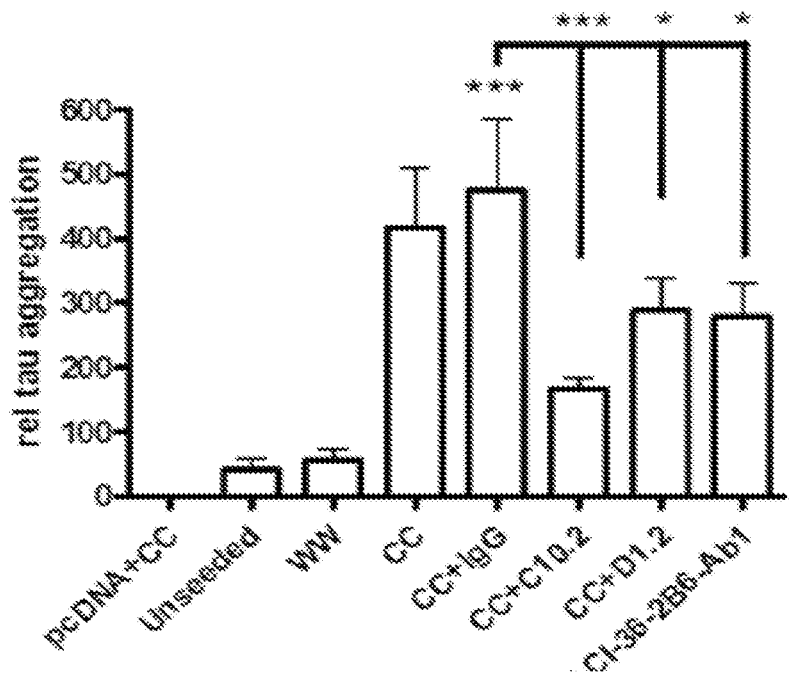
FIGS. 7A-7C: Prevention of seeding in HEK293 cells and in-vitro
Figure 7B:
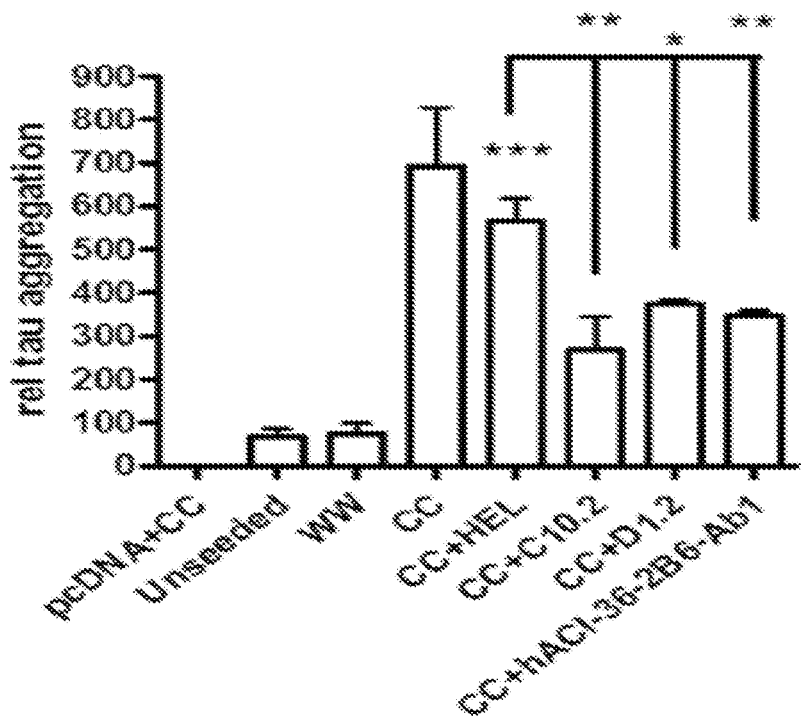
Figure 7C:
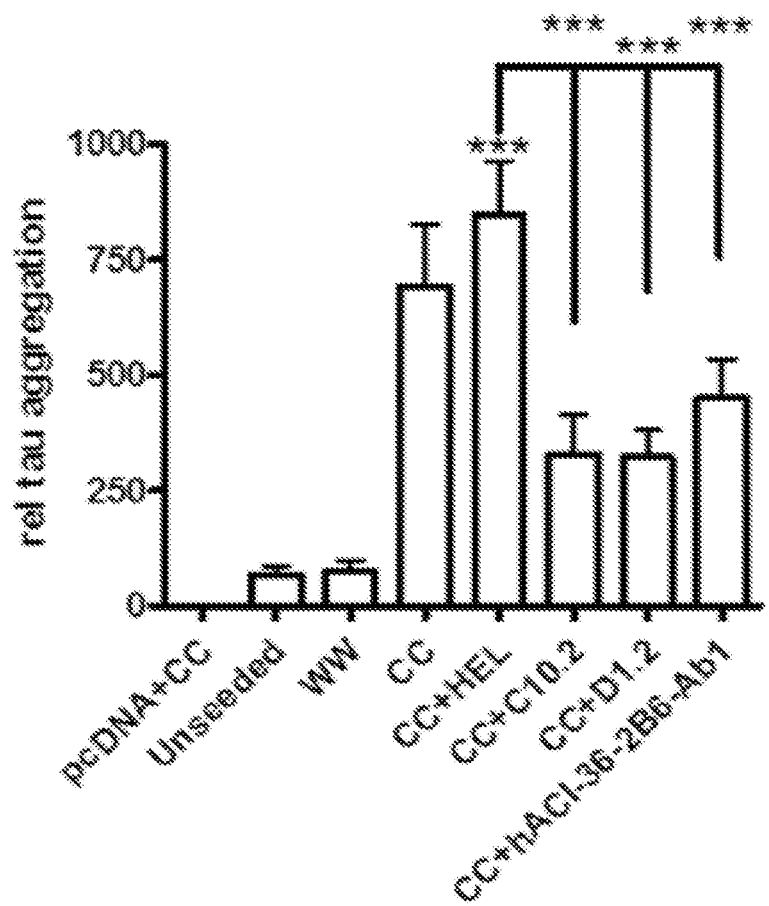

To demonstrate that the selected antibodies have functional and therapeutic utility, antibodies were tested in in-vitro and in-cell tau-aggregation assays (Example 8). These assays are functional assays which demonstrate that the antibodies are able to interfere with the pathological aggregation process of tau. HEK293 cells are transiently transfected with human tau-P301L-FLAG (4R0N). Subsequently the cells are exposed to tau extracts from human AD brains or from transgenic Tg4510 brains. This exposure to pathological tau promotes tau uptake into cells and intracellular aggregation. Both immuno-depletion of tau-preparations using antibodies D1.2 and C10-2, and direct treatment of cells with these antibodies is able to reduce the formation of tau aggregates dramatically (FIG. 7).

Therapeutic utility of antibodies D1.2 and C10-2 has also been evaluated in the human tau/PS1 mouse (Example 9). This mouse model is a more AD disease relevant animal model which only generates AD pathology late in life (12-18 month of age). However, the mice do exhibit tau hyper phosphorylation before the occurrence of solid tangle pathology. Mice were injected chronically for 13 weeks, twice weekly with 15 mg/kg dose. Antibody treated mice exhibit a dramatic reduction in phosphorylated tau as demonstrated in FIG. 9, indicating that chronic treatment with antibodies D1.2 and C10-2 will reduce tangle pathology and thus subsequent neurodegeneration in vivo.

The antibodies of the invention specifically remove hyperphosphorylated Tau from rTg4510 mouse brain extracts by immunodepletion methods. Moreover, the antibodies of the invention do not remove the normal Tau from the homogenates, whereas the commercially available tau5 antibody does. In contrast to commercial antibodies which bind to tau proteins wherein phosphorylation at residue 404 or at both residues 404 and 396, the antibodies of the invention specifically remove the hyperphosphorylated tau by 95%, that is phosphorylated on serine 396. Experiments (Example 12) demonstrate that the antibody of the invention, despite only removing a very small fraction of the total tau in the brain homogenate (8%), the antibodies do however specifically remove the hyperphosphorylated tau (by 90%). Accordingly, one aspect of the invention is directed to a monoclonal antibody, or an epitope-binding fragment thereof, capable of immunospecifically binding to the pathogenic hyperphosphorylated tau. Furthermore, in experiments wherein hyperphosphorylated Tau was removed using an antibody of the invention, the seeding activity is abolished. By removing hyperphosphorylated tau from the homogenates, the homogenates no longer induce seeding of Tau pathology. It has been proposed that reduction of seeding reduces the development of tangle formation and the progression of tauopathies, including Alzheimer's disease. Accordingly, a further aspect of the invention is directed to an antibody of the invention for use in the reduction of the progression of AD or in the symptoms of AD.

More specifically, as detailed above, the invention relates to any one of four monoclonal antibodies selected from the group comprising:

Antibody D1.2
(a) a Light Chain CDR1 having the amino acid sequence of SEQ ID NO:1;
(b) a Light Chain CDR2 having the amino acid sequence of SEQ ID NO:2;
(c) a Light Chain CDR3 having the amino acid sequence of SEQ ID NO:3;
(d) a Heavy Chain CDR1 having the amino acid sequence of SEQ ID NO:4;
(e) a Heavy Chain CDR2 having the amino acid sequence of SEQ ID NO:5; and
(f) a Heavy Chain CDR3 having the amino acid sequence of SEQ ID NO:6.

The antibody or epitope-binding fragment thereof may comprise or consist of the heavy chain variable domain of SEQ ID NO:8 and/or the light chain variable domain of SEQ ID NO:7.

In a related embodiment, the antibody D1.2 or epitope-binding fragment thereof may comprise or consist of the heavy chain of SEQ ID NO 8 and/or the light chain of SEQ ID NO:34.

Antibody C10-2
(a) a Light Chain CDR1 having the amino acid sequence of SEQ ID NO:9;
(b) a Light Chain CDR2 having the amino acid sequence of SEQ ID NO:10;
(c) a Light Chain CDR3 having the amino acid sequence of SEQ ID NO:11;
(d) a Heavy Chain CDR1 having the amino acid sequence of SEQ ID NO:12;
(e) a Heavy Chain CDR2 having the amino acid sequence of SEQ ID NO:13; and
(f) a Heavy Chain CDR3 having the amino acid sequence of SEQ ID NO:14.

The antibody or epitope-binding fragment thereof may comprise or consist of the heavy chain variable domain of SEQ ID NO:15 and/or the light chain variable domain of SEQ ID NO:16.

The amino acid sequence of the heavy chain of humanized C10-2 antibody is shown in SEQ ID NO:35. The amino acid sequence of the light chain of humanized C10-2 antibody is shown in SEQ ID NO:36.

Altogether, the Examples show that the antibodies of the invention, including C10-2, bind efficiently to AD-P3 antigens coated MSD plates. In comparison, commercial antibodies such as PHF-13, have low binding activity. Furthermore PHF-13 demonstrated substantial higher degree of non-specific binding in comparison to the antibodies of the invention (see Table 5 A-Table 5D). Table 5 shows that mC10-2 fluid phase inhibition of Ptau antigen capture in C10-2 coated plate is effective (IC50=10-20 nM) whereas mD1.2 is ineffective (IC50=500-1000 nM). mC10-2 fluid phase inhibition of p-tau antigen capture in mC10-2 coated plate is effective with an of IC50=10-20 nM) whereas PHF-13 is ineffective (IC50=500-1000 nM).

One aspect of the invention is directed to an antibody comprising
(a) a Light Chain CDR1 having the amino acid sequence of SEQ ID NO:9;
(b) a Light Chain CDR2 having the amino acid sequence of SEQ ID NO:10;
(c) a Light Chain CDR3 having the amino acid sequence of SEQ ID NO:11.

A further aspect of the invention is directed to an antibody comprising
(d) a Heavy Chain CDR1 having the amino acid sequence of SEQ ID NO:12;
(e) a Heavy Chain CDR2 having the amino acid sequence of SEQ ID NO:13; and
(f) a Heavy Chain CDR3 having the amino acid sequence of SEQ ID NO:14.

A further aspect of the invention is directed to an antibody comprising
(d) a Heavy Chain CDR1 having the amino acid sequence of SEQ ID NO:12;
(e) a Heavy Chain CDR2 having the amino acid sequence of SEQ ID NO:13; and
(f) a Heavy Chain CDR3 having the amino acid sequence of SEQ ID NO:14 and one, two or three of
(a) a Light Chain CDR1 having the amino acid sequence of SEQ ID NO:9;
(b) a Light Chain CDR2 having the amino acid sequence of SEQ ID NO:10; and
(c) a Light Chain CDR3 having the amino acid sequence of SEQ ID NO:11.

Antibody C5.2
(a) a Light Chain CDR1 having the amino acid sequence of SEQ ID NO:17;
(b) a Light Chain CDR2 having the amino acid sequence of SEQ ID NO:18;
(c) a Light Chain CDR3 having the amino acid sequence of SEQ ID NO:19;
(d) a Heavy Chain CDR1 having the amino acid sequence of SEQ ID NO:20;
(e) a Heavy Chain CDR2 having the amino acid sequence of SEQ ID NO:21; and
(f) a Heavy Chain CDR3 having the amino acid sequence of SEQ ID NO:22.

The antibody or epitope-binding fragment thereof may comprise or consist of the heavy chain variable domain of SEQ ID NO:23 and/or the light chain variable domain of SEQ ID NO:24.

As can be seen from the crystal structure of FIG. 10, the epitope is bound across the heavy chain and light chains of C5.2. Accordingly, in a related embodiment, the antibody of the invention or epitope-binding fragment thereof comprises (a) a Light Chain CDR1 having the amino acid sequence of SEQ ID NO:17; or
(b) a Light Chain CDR2 having the amino acid sequence of SEQ ID NO:18; or
(c) a Light Chain CDR3 having the amino acid sequence of SEQ ID NO:19; and
(d) a Heavy Chain CDR1 having the amino acid sequence of SEQ ID NO:20; or
(e) a Heavy Chain CDR2 having the amino acid sequence of SEQ ID NO:21; or
(f) a Heavy Chain CDR3 having the amino acid sequence of SEQ ID NO:22.

Antibody C8.3
(a) a Light Chain CDR1 having the amino acid sequence of SEQ ID NO:25;
(b) a Light Chain CDR2 having the amino acid sequence of SEQ ID NO:26
(c) a Light Chain CDR3 having the amino acid sequence of SEQ ID NO:27;
(d) a Heavy Chain CDR1 having the amino acid sequence of SEQ ID NO:28;
(e) a Heavy Chain CDR2 having the amino acid sequence of SEQ ID NO:29; and
(f) a Heavy Chain CDR3 having the amino acid sequence of SEQ ID NO:30.

The antibody or epitope-binding fragment thereof may comprise or consist of the heavy chain variable domain of SEQ ID NO:31 and/or the light chain variable domain of SEQ ID NO:32.

The antibody or epitope-binding fragment thereof is preferably a human or humanized antibody.

The antibodies and epitope-binding fragment thereof mentioned above may, according to one embodiment, further comprise a variant of such light and/or heavy chain CDR1, CDR2 or CDR3 (with no more than 4 amino acid differences, or no more than 3 amino acid differences, or no more than 2 amino acid differences, or no more than 1 amino acid difference.

As can be seen from FIG. 11, HC CDR1, HC CDR2, HC CDR3 and LC CDR3 are, in at least one embodiment, important, for the binding to the 392-398 region of Tau. In one embodiment of the invention, the antibody of the invention, or epitope-binding fragment thereof comprises:
 a) a Heavy Chain CDR1 comprising the amino acid sequence selected from the group consisting of SEQ ID NO:4, SEQ ID NO:12, SEQ ID NO:20, and SEQ ID NO:28;
 b) a Heavy Chain CDR2 comprising the amino acid sequence selected from the group consisting of SEQ ID NO:5, SEQ ID NO:13, SEQ ID NO:21, and SEQ ID NO:29; and
 c) a Heavy Chain CDR3 comprising the amino acid sequence selected from the group consisting of SEQ ID NO:6, SEQ ID NO:14, SEQ ID NO:22, and SEQ ID NO:30; and
 d) a Light Chain CDR3 comprising the amino acid sequence selected from the group consisting of SEQ ID NO:3, SEQ ID NO:11, SEQ ID NO:19, and SEQ ID NO:27.

The antibody of the invention, or epitope-binding fragment thereof may comprise
 a) a Heavy Chain CDR1 comprising the amino acid sequence of SEQ ID NO:20;
 b) a Heavy Chain CDR2 comprising the amino acid sequence of SEQ ID NO:21;
 c) a Heavy Chain CDR3 comprising the amino acid sequence of SEQ ID NO:22; and
 d) a Light Chain CDR3 comprising the amino acid sequence of SEQ ID NO:19.

In one aspect of the invention, the invention is directed to an antibody or epitope-binding fragments thereof, that forms a hydrophobic pocket formed by L3:H3, L3:F8*, H1:H13, H2:Y1, H2:Y3 with Y394 of the tau peptide. In an embodiment, the invention is directed to an antibody that competes with an antibody further described herein for forming a hydrogen bonding network between solvated ${}^{\{p\}}$S396 and L3:T4, H1:R10, H11T11, H3:R1, H3:T3; (*) L3:F8 is the C-terminal flanking framework residue of CDR L3 (see FIG. 11).

As can be seen from the x-ray crystal structure, the antibody of the invention binds with two levels of selectivity. The first level of selectivity is selectivity for hyperphosphorylated pathological, tau and the second level of selectivity is selectivity for a phosphorylated serine residue wherein the phosphate of said phosphorylated serine is hydrogen bonded to the side chain of a tyrosine residue two residues removed from said phosphorylated serine. Accordingly, an interesting aspect of the invention is directed to an antibody or epitope-binding fragment thereof selective for an amino acid motif of hyperphosphorylated tau comprising of a phosphorylated serine two residues removed from a tyrosine residue. Typically, the amino acid motif has the sequence:

Y-X-S(phosphorylated)-P- wherein Y is tyrosine, X is a naturally occurring amino acid, P is proline and S(phosphorylated) is serine with a phosphorylated hydroxyl side chain.

Similarly, an interesting aspect of the invention is directed to an antibody or epitope-binding fragment thereof which binds to phosphorylated tau, preferably hyperphosphorylated tau, wherein said antibody or epitope-binding fragment thereof is selective for the amino acid residue motif IA, wherein R is a side chain of a naturally occurring amino acid.

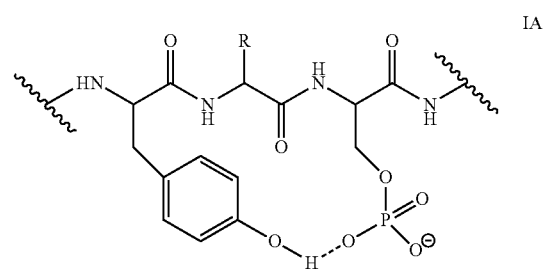

IA

Without being bound to a particular theory, it is believed that the antibody of the invention is selective for amino acid motif IA when said motif is in a conformation adopted by pathological tau. Accordingly, the amino acid motif IA is typically the sequence selectively recognized by the antibody of the invention. Accordingly, an interesting aspect of the invention is directed to an antibody or epitope-binding fragment thereof which binds to phosphorylated tau, preferably hyperphosphorylated tau, wherein said antibody or epitope-binding fragment thereof is selective for the amino acid residue motif IB, wherein R is a side chain of a naturally occurring amino acid.

In a typical embodiment of this aspect of the invention, the invention is directed to an antibody or epitope-binding fragment thereof which binds to phosphorylated tau, preferably hyperphosphorylated tau, wherein said antibody or epitope-binding fragment thereof is selective for the amino acid residue motif IB, wherein R is a side chain of a naturally occurring amino acid such as, but not limited to IC or ID.

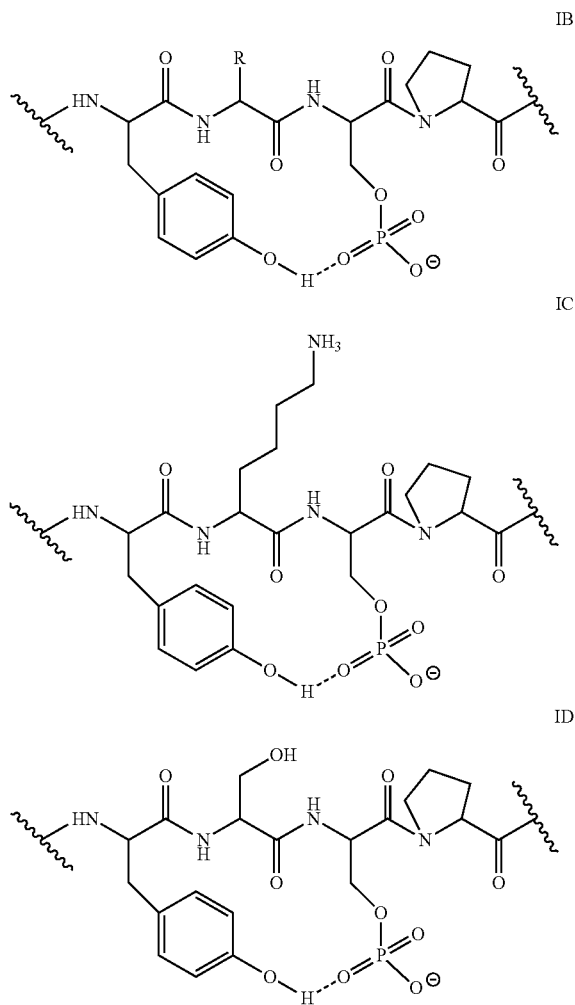

The present invention also provides a method of reducing tau tangle formation in a patient, comprising administering to the patient in need of such treatment, a therapeutically effective amount of an antibody of the invention, or epitope-binding fragments thereof.

One aspect of the invention is directed to a method of treating a taupathy using an antibody of the invention, or epitope-binding fragments thereof. Typically, the taupathy is selected from the group consisting of Alzheimer's disease, Argyrophilic Grain Disease (AGD), Psychosis, particularly Psychosis due to AD or Psychosis in patients with AD, psychiatric symptoms of patients with Lewy body dementia, Progressive Supranuclear Palsy (PSP), Frontotemporal dementia (FTD or variants thereof), TBI (traumatic brain injury, acute or chronic), Corticobasal Degeneration (CBD), Picks Disease, Primary age-related tauopathy (PART), Neurofibrillary tangle-predominant senile dementia, Dementia pugilistica, Chronic traumatic encephalopathy, stroke, stroke recovery, neurodegeneration in relation to Parkinson's disease, Parkinsonism linked to chromosome, Lytico-Bodig disease (Parkinson-dementia complex of Guam), Ganglioglioma and gangliocytoma, Meningioangiomatosis, Postencephalitic parkinsonism, Subacute sclerosing panencephalitis, Huntington's disease, lead encephalopathy, tuberous sclerosis, Hallervorden-Spatz disease and lipofuscinosis. More typically, the taupathy is selected from the group consisting of Alzheimer's disease, Argyrophilic Grain Disease (AGD), Psychosis, particularly Psychosis due to AD or Psychosis in patients with AD, psychiatric symptoms of patients with Lewy body dementia, Progressive Supranuclear Palsy (PSP), Frontotemporal dementia (FTD or variants thereof), TBI (traumatic brain injury, acute or chronic), Corticobasal Degeneration (CBD), and Picks Disease. In particular, the tauopathies may be selected from Alzheimer's disease, Argyrophilic Grain Disease (AGD), Psychosis due to AD or Psychosis in patients with AD, and psychiatric symptoms of patients with Lewy body dementia.

Accordingly, a further aspect of the invention is directed to an antibody of the invention or epitope-binding fragments thereof, for use in the treatment of a taupathy. Typically, the taupathy is selected from the group consisting of Alzheimer's disease, Argyrophilic Grain Disease (AGD), Psychosis, particularly Psychosis due to AD or Psychosis in patients with AD, psychiatric symptoms of patients with Lewy body dementia, Progressive Supranuclear Palsy (PSP), Frontotemporal dementia (FTD or variants thereof), TBI (traumatic brain injury, acute or chronic), Corticobasal Degeneration (CBD), Picks Disease, Primary age-related tauopathy (PART), Neurofibrillary tangle-predominant senile dementia, Dementia pugilistica, Chronic traumatic encephalopathy, stroke, stroke recovery, neurodegeneration in relation to Parkinson's disease, Parkinsonism linked to chromosome, Lytico-Bodig disease (Parkinson-dementia complex of Guam), Ganglioglioma and gangliocytoma, Meningioangiomatosis, Postencephalitic parkinsonism, Subacute sclerosing panencephalitis, Huntington's disease, lead encephalopathy, tuberous sclerosis, Hallervorden-Spatz disease and lipofuscinosis. More typically, the taupathy is selected from the group consisting of Alzheimer's disease, Argyrophilic Grain Disease (AGD), Psychosis, particularly Psychosis due to AD or Psychosis in patients with AD, psychiatric symptoms of patients with Lewy body dementia, Progressive Supranuclear Palsy (PSP), Frontotemporal dementia (FTD or variants thereof), TBI (traumatic brain injury, acute or chronic), Corticobasal Degeneration (CBD), and Picks Disease. In particular, the tauopathies may be selected from Alzheimer's disease, Argyrophilic Grain Disease (AGD), Psychosis due to AD or Psychosis in patients with AD, and psychiatric symptoms of patients with Lewy body dementia.

A further aspect of the invention is directed to an antibody of the invention or epitope-binding fragments thereof, in a composition together with a pharmaceutically acceptable carrier, diluent, adjuvant and/or stabilizer. The antibodies of the invention, or epitope-binding fragments thereof, may be used in therapy for the treatment of a taupathy. Typically, the taupathy is selected from the group consisting of Alzheimer's disease, Argyrophilic Grain Disease (AGD), Psychosis, particularly Psychosis due to AD or Psychosis in patients with AD, psychiatric symptoms of patients with Lewy body dementia, Progressive Supranuclear Palsy (PSP), Frontotemporal dementia (FTD or variants thereof), TBI (traumatic brain injury, acute or chronic), Corticobasal Degeneration (CBD), Picks Disease, Primary age-related tauopathy (PART), Neurofibrillary tangle-predominant senile dementia, Dementia pugilistica, Chronic traumatic encephalopathy, stroke, stroke recovery, neurodegeneration in relation to Parkinson's disease, Parkinsonism linked to chromosome, Lytico-Bodig disease (Parkinson-dementia complex of Guam), Ganglioglioma and gangliocytoma, Meningioangiomatosis, Postencephalitic parkinsonism, Subacute sclerosing panencephalitis, Huntington's disease, lead encephalopathy, tuberous sclerosis, Hallervorden-Spatz disease and lipofuscinosis. More typically, the taupathy is selected from the group consisting of Alzheimer's disease, Argyrophilic Grain Disease (AGD), Psychosis, particularly Psychosis due to AD or Psychosis in patients with AD, psychiatric symptoms of patients with Lewy body dementia, Progressive Supranuclear Palsy (PSP), Frontotemporal dementia (FTD or variants thereof), TBI (traumatic brain injury, acute or chronic), Corticobasal Degeneration (CBD), and Picks Disease. In particular, the tauopathies may be selected from Alzheimer's disease, Argyrophilic Grain Disease (AGD), Psychosis due to AD or Psychosis in patients with AD, and psychiatric symptoms of patients with Lewy body dementia.

The treatment envisioned by the present invention may be chronic and the patient may be treated at least 2 weeks, such as at least for 1 month, 6, months, 1 year or more.

The antibodies of the present invention may, for example, be monoclonal antibodies produced by the hybridoma method first described by Kohler et al., Nature 256, 495 (1975), or may be monoclonal antibodies produced by recombinant DNA or other methods, or more preferably may be produced by the novel method disclosed herein (FIG. 9). Monoclonal antibodies may also be isolated from phage antibody libraries using the techniques described in, for example, Clackson et al., Nature 352, 624-628 (1991) and Marks et al., J. Mol. Biol. 222, 581-597 (1991). Monoclonal antibodies may be obtained from any suitable source. Thus, for example, monoclonal antibodies may be obtained from hybridomas prepared from murine splenic B lymphocyte cells obtained from mice immunized with an antigen of interest, for instance, in the form of cells expressing the antigen on the surface, or a nucleic acid encoding an antigen of interest. Monoclonal antibodies may also be obtained from hybridomas derived from antibody-expressing cells of immunized humans or from non-human mammals such as rats, rabbits, dogs, sheep, goats, primates, etc.

In one embodiment, the antibody of the invention is a humanized antibody. Humanized monoclonal antibodies directed against tau may be generated using transgenic or trans-chromosomal mice carrying parts of the human immune system rather than the mouse system. Such transgenic and transchromosomic mice include mice referred to herein as HuMAb (Humanized monoclonal antibody) mice and KM mice, respectively, and are collectively referred to herein as "transgenic mice".

The HuMAb mouse contains a human immunoglobulin gene mini-locus that encodes un-rearranged human heavy variable and constant (p and Y) and light variable and constant (K) chain immunoglobulin sequences, together with targeted mutations that inactivate the endogenous p and K chain loci (Lonberg, N. et al., Nature 368, 856-859 (1994)). Accordingly, the mice exhibit reduced expression of mouse IgM or K and in response to immunization, the introduced human heavy and light chain transgenes, undergo class switching and somatic mutation to generate high affinity human IgG, K monoclonal antibodies (Lonberg, N. et al. (1994), supra; reviewed in Lonberg, N., Handbook of Experimental Pharmacology 113, 49-101 (1994), Lonberg, N. and Huszar, D., Intern. Rev. Immunol. Vol. 13 65-93 (1995) and Harding, F. and Lonberg, N., Ann. N. Y. Acad. Sci 764 536-546 (1995)). The preparation of HuMAb mice is described in detail in Taylor, L. et al., Nucleic Acids Research 20, 6287-6295 (1992), Chen, J. et al., International Immunology 5, 647-656 (1993), Tuaillon et al., J. Immunol. 152, 2912-2920 (1994), Taylor, L. et al., International Immunology 6, 579-591 (1994), Fishwild, D. et al., Nature Biotechnology 14, 845-851 (1996). See also U.S. Pat. Nos. 5,545,806, 5,569,825, U.S. Pat. Nos. 5,625,126, 5,633,425, 5,789,650, 5,877,397, 5,661,016, 5,814,318, 5,874,299, 5,770,429, 5,545,807, WO 98/24884, WO 94/25585, WO 93/1227, WO 92/22645, WO 92/03918 and WO 01/09187.

The HCo7, HCo12, HCo17 and HCo20 mice have a JKD disruption in their endogenous light chain (kappa) genes (as described in Chen et al., EMBO J. 12, 811-820 (1993)), a CMD disruption in their endogenous heavy chain genes (as described in Example 1 of WO 01/14424), and a KCo5 human kappa light chain transgene (as described in Fishwild et al., Nature Biotechnology 14, 845-851 (1996)). Additionally, the HCo7 mice have a HCo7 human heavy chain transgene (as described in U.S. Pat. No. 5,770,429), the HCo12 mice have a HCo12 human heavy chain transgene (as described in Example 2 of WO 01/14424), the HCo17 mice have a HCo17 human heavy chain transgene (as described in Example 2 of WO 01/09187) and the HCo20 mice have a HCo20 human heavy chain transgene. The resulting mice express human immunoglobulin heavy and kappa light chain transgenes in a background homozygous for disruption of the endogenous mouse heavy and kappa light chain loci.

In the KM mouse strain, the endogenous mouse kappa light chain gene has been homozygously disrupted as described in Chen et al., EMBO J. 12, 811-820 (1993) and the endogenous mouse heavy chain gene has been homozygously disrupted as described in Example 1 of WO 01/09187. This mouse strain carries a human kappa light chain transgene, KCo5, as described in Fishwild et al., Nature Biotechnology 14, 845-851 (1996). This mouse strain also carries a human heavy chain transchromosome composed of chromosome 14 fragment hCF (SC20) as described in WO 02/43478. HCo12-Balb/c, HCo17-Balb/c and HCo20-Balb/c mice can be generated by crossing HCo12, HCo17 and HCo20 to KCo5[J/K](Balb) as described in WO 09/097006.

The rTg4510 mouse is a known tauopathy model providing temporal and spatial control over mutant tau transgene expression. In the KM mouse strain, the endogenous mouse kappa light chain gene has been homozygously disrupted as described in Chen et al., EMBO J. 12, 811-820 (1993) and the endogenous mouse heavy chain gene has been homozygously disrupted as described in Example 1 of WO 01/09187. This mouse strain carries a human kappa light chain transgene, KCo5, as described in Fishwild et al., Nature Biotechnology 14, 845-851 (1996). This mouse strain also carries a human heavy chain trans-chromosome composed of chromosome 14 epitope-binding fragment hCF (SC20) as described in WO 02/43478.

Splenocytes from these transgenic mice may be used to generate hybridomas that secrete humanized monoclonal antibodies according to well-known techniques. Humanized monoclonal or polyclonal antibodies of the present invention, or antibodies, of the present invention originating from other species may also be generated transgenically through the generation of another non-human mammal or plant that is transgenic for the immunoglobulin heavy and light chain sequences of interest and production of the antibody in a recoverable form therefrom. In connection with the transgenic production in mammals, antibodies may be produced in, and recovered from, the milk of goats, cows, or other mammals. See for instance U.S. Pat. Nos. 5,827,690; 5,756, 687; 5,750,172 and 5,741,957.

The antibody of the invention may be of any isotype. The choice of isotype typically will be guided by the desired effector functions, such as ADCC induction. Exemplary isotypes are IgG1, IgG2, IgG3, and IgG4. Either of the human light chain constant domains, kappa or lambda, may be used. If desired, the class of an anti-tau antibody of the present invention may be switched by known methods. For example, an antibody of the present invention that was originally IgM may be class switched to an IgG antibody of the present invention. Further, class switching techniques may be used to convert one IgG subclass to another, for instance from IgG1 to IgG2. Thus, the effector function of the antibodies of the present invention may be changed by isotype switching to, e.g., an IgG1, IgG2, IgG3, IgG4, IgD, IgA, IgE, or IgM antibody for various therapeutic uses. In one embodiment an antibody of the present invention is an IgG1 antibody, for instance an IgG1, κ. An antibody is said to be of a particular isotype if its amino acid sequence is most homologous to that isotype, relative to other isotypes.

In one embodiment, the antibody of the invention is a full-length antibody, preferably an IgG antibody, in particular an IgG1, κ antibody. In another embodiment, the antibody of the invention is an antibody epitope-binding fragment or a single-chain antibody.

Antibodies and epitope-binding fragments thereof may e.g. be obtained by epitope-binding fragmentation using conventional techniques, and epitope-binding fragments screened for utility in the same manner as described herein for whole antibodies. For example, F(ab')$_2$ epitope-binding fragments may be generated by treating antibody with pepsin. The resulting F(ab')$_2$ epitope-binding fragment may be treated to reduce disulfide bridges to produce Fab' epitope-binding fragments. Fab epitope-binding fragments may be obtained by treating an IgG antibody with papain; Fab' epitope-binding fragments may be obtained with pepsin digestion of IgG antibody. An F(ab') epitope-binding fragment may also be produced by binding Fab'-described below via a thioether bond or a disulfide bond. A Fab' epitope-binding fragment is an antibody epitope-binding fragment obtained by cutting a disulfide bond of the hinge domain of the F(ab')$_2$. A Fab'-epitope-binding fragment may be obtained by treating an F(ab')$_2$ epitope-binding fragment with a reducing agent, such as dithiothreitol. Antibody epitope-binding fragment may also be generated by expression of nucleic acids encoding such epitope-binding fragments in recombinant cells (see for instance Evans et al., J. Immunol. Meth. 184, 123-38 (1995)). For example, a chimeric gene encoding a portion of an F(ab')2 epitope-binding fragment could include DNA sequences encoding the CH1 domain and hinge domain of the H chain, followed by a translational stop codon to yield such a truncated antibody epitope-binding fragment molecule.

In one embodiment, the anti-tau antibody is a monovalent antibody, preferably a monovalent antibody as described in WO2007059782 (which is incorporated herein by reference in its entirety) having a deletion of the hinge region. Accordingly, in one embodiment, the antibody is a monovalent antibody, wherein said anti-tau antibody is constructed by a method comprising: i) providing a nucleic acid construct encoding the light chain of said monovalent antibody, said construct comprising a nucleotide sequence encoding the VL region of a selected antigen specific anti-tau antibody and a nucleotide sequence encoding the constant CL region of an Ig, wherein said nucleotide sequence encoding the VL region of a selected antigen specific antibody and said nucleotide sequence encoding the CL region of an Ig are operably linked together, and wherein, in case of an IgG1 subtype, the nucleotide sequence encoding the CL region has been modified such that the CL region does not contain any amino acids capable of forming disulfide bonds or covalent bonds with other peptides comprising an identical amino acid sequence of the CL region in the presence of polyclonal human IgG or when administered to an animal or human being; ii) providing a nucleic acid construct encoding the heavy chain of said monovalent antibody, said construct comprising a nucleotide sequence encoding the VH region of a selected antigen specific antibody and a nucleotide sequence encoding a constant CH region of a human Ig, wherein the nucleotide sequence encoding the CH region has been modified such that the region corresponding to the hinge region and, as required by the Ig subtype, other regions of the CH region, such as the CH3 region, does not comprise any amino acid residues which participate in the formation of disulphide bonds or covalent or stable non-covalent inter-heavy chain bonds with other peptides comprising an identical amino acid sequence of the CH region of the human Ig in the presence of polyclonal human IgG or when administered to an animal human being, wherein said nucleotide sequence encoding the VH region of a selected antigen specific antibody and said nucleotide sequence encoding the CH region of said Ig are operably linked together; iii) providing a cell expression system for producing said monovalent antibody; iv) producing said monovalent antibody by co-expressing the nucleic acid constructs of (i) and (ii) in cells of the cell expression system of (iii).

Similarly, in one embodiment, the anti-tau antibody of the invention is a monovalent antibody, which comprises:
(i) a variable domain of an antibody of the invention as described herein or an epitope-binding part of the said domain, and
(ii) a CH domain of an immunoglobulin or a domain thereof comprising the CH2 and CH3 domains, wherein the CH domain or domain thereof has been modified such that the domain corresponding to the hinge domain and, if the immunoglobulin is not an IgG4 subtype, other domains of the CH domain, such as the CH3 domain, do not comprise any amino acid residues, which are capable of forming disulfide bonds with an identical CH domain or other covalent or stable non-covalent inter-heavy chain bonds with an identical CH domain in the presence of polyclonal human IgG.

In a further embodiment, the heavy chain of the monovalent antibody of the invention has been modified such that the entire hinge region has been deleted.

In another further embodiment, the sequence of the monovalent antibody has been modified so that it does not comprise any acceptor sites for N-linked glycosylation.

The invention also includes "Bispecific Antibodies," wherein an anti-tau binding region (e.g., a tau-binding region of an anti-tau monoclonal antibody) is part of a bivalent or polyvalent bispecific scaffold that targets more than one epitope, (for example a second epitope could comprise an epitope of an active transport receptor, such that the Bispecific Antibody would exhibit improved transcytosis across a biological barrier, such as the Blood Brain Barrier). Thus, in another further embodiment, the monovalent Fab of an anti-tau antibody may be joined to an additional Fab or scfv that targets a different protein to generate a bispecific antibody. A bispecific antibody can have a dual function, for example a therapeutic function imparted by an anti-tau binding domain and a transport function that can bind to a receptor molecule to enhance transfer cross a biological barrier, such as the blood brain barrier.

Antibodies and epitope-binding fragments thereof of the invention, also include single chain antibodies. Single chain antibodies are peptides in which the heavy and light chain Fv domains are connected. In one embodiment, the present invention provides a single-chain Fv (scFv) wherein the heavy and light chains in the Fv of an anti-tau antibody of the present invention are joined with a flexible peptide linker (typically of about 10, 12, 15 or more amino acid residues) in a single peptide chain. Methods of producing such antibodies are described in for instance U.S. Pat. No. 4,946,778, Pluckthun in The Pharmacology of Monoclonal Antibodies, vol. 113, Rosenburg and Moore eds. Springer-Verlag, New York, pp. 269-315 (1994), Bird et al., Science 242, 423-426 (1988), Huston et al., PNAS USA 85, 5879-5883 (1988) and McCafferty et al., Nature 348, 552-554 (1990). The single chain antibody may be monovalent, if only a single VH and VL are used, bivalent, if two VH and VL are used, or polyvalent, if more than two VH and VL are used.

The antibodies and epitope-binding fragments thereof described herein may be modified by inclusion may be modified by inclusion of any suitable number of modified amino acids and/or associations with such conjugated substituents. Suitability in this context is generally determined by the ability to at least substantially retain the tau selectivity and/or the tau specificity associated with the non-derivatized parent anti-tau antibody. The inclusion of one or more modified amino acids may be advantageous in, for example, increasing polypeptide serum half-life, reducing polypeptide antigenicity, or increasing polypeptide storage stability. Amino acid(s) are modified, for example, co-translationally or post-translationally during recombinant production (e.g., N-linked glycosylation at N-X-S/T motifs during expression in mammalian cells) or modified by synthetic means. Non-limiting examples of a modified amino acid include a glycosylated amino acid, a sulfated amino acid, a prenylated (e.g., farnesylated, geranyl-geranylated) amino acid, an acetylated amino acid, an acylated amino acid, a PEGylated amino acid, a biotinylated amino acid, a carboxylated amino acid, a phosphorylated amino acid, and the like. References adequate to guide one of skill in the modification of amino acids are replete throughout the literature. Example protocols are found in Walker (1998) Protein Protocols On CD-Rom, Humana Press, Totowa, N.J. The modified amino acid may, for instance, be selected from a glycosylated amino acid, a PEGylated amino acid, a farnesylated amino acid, an acetylated amino acid, a biotinylated amino acid, an amino acid conjugated to a lipid moiety, or an amino acid conjugated to an organic derivatizing agent.

The antibodies and epitope-binding fragments thereof of the invention, may also be chemically modified by covalent conjugation to a polymer to for instance increase their circulating half-life. Exemplary polymers, and methods to attach them to peptides, are illustrated in for instance U.S. Pat. Nos. 4,766,106; 4,179,337; 4,495,285 and 4,609,546. Additional illustrative polymers include polyoxyethylated polyols and polyethylene glycol (PEG) (e.g., a PEG with a molecular weight of between about 1,000 and about 40,000, such as between about 2,000 and about 20,000, e.g., about 3,000-12,000 g/mol).

The antibodies and epitope-binding fragments thereof of the present invention may further be used in a diagnostic method or as a diagnostic imaging ligand.

In one embodiment, antibodies and epitope-binding fragments thereof of the invention comprising one or more radiolabeled amino acids are provided. A radiolabeled anti-tau antibody may be used for both diagnostic and therapeutic purposes (conjugation to radiolabeled molecules is another possible feature). Non-limiting examples of such labels include, but are not limited to bismuth ($^{213}$Bi), carbon ($^{11}$C, $^{13}$C, $^{14}$C), chromium ($^{51}$Cr), cobalt ($^{57}$Co, $^{60}$Co), copper ($^{64}$Cu), dysprosium ($^{165}$Dy), erbium ($^{169}$Er), fluorine ($^{18}$F), gadolinium ($^{153}$Gd, $^{159}$Gd), gallium ($^{68}$Ga, $^{67}$Ga), germanium ($^{68}$Ge), gold ($^{198}$Au), holmium ($^{166}$Ho), hydrogen ($^{3}$H), indium ($^{111}$In, $^{112}$In, $^{113}$In, $^{115}$In), iodine ($^{121}$I, $^{123}$I, $^{125}$I, $^{131}$I), iridium ($^{192}$Ir), iron ($^{59}$Fe), krypton ($^{81m}$Kr), lanthanium ($^{140}$La), lutelium ($^{177}$Lu), manganese ($^{54}$Mn), molybdenum ($^{99}$Mo), nitrogen ($^{13}$N, $^{15}$N), oxygen ($^{15}$O), palladium ($^{103}$Pd), phosphorus ($^{32}$P), potassium ($^{42}$K), praseodymium ($^{142}$Pr), promethium ($^{149}$Pm), rhenium ($^{188}$Re, $^{188}$Re), rhodium ($^{105}$Rh), rubidium ($^{81}$Rb, $^{82}$Rb), ruthenium ($^{82}$Ru, $^{97}$Ru), samarium ($^{153}$Sm), scandium ($^{47}$Sc), selenium ($^{75}$Se), sodium ($^{24}$Na), strontium ($^{85}$Sr, $^{89}$Sr, $^{92}$Sr), sulfur ($^{35}$S), technetium ($^{99}$Tc), thallium ($^{201}$Tl), tin ($^{113}$Sn, $^{117}$Sn), xenon ($^{133}$Xe), ytterbium ($^{169}$Yb, $^{175}$Yb, $^{177}$Yb), yttrium ($^{90}$Y), zinc ($^{65}$Zn) and zirconium ($^{89}$Zr). Zirconium ($^{89}$Zr) is particularly interesting. Methods for preparing radiolabeled amino acids and related peptide derivatives are known in the art (see for instance Junghans et al., in Cancer Chemotherapy and Biotherapy 655-686 (2nd edition, Chafner and Longo, eds., Lippincott Raven (1996)) and U.S. Pat. Nos. 4,681,581; 4,735,210; 5,101,827; 5,102,990 (U.S. RE35, 500), U.S. Pat. Nos. 5,648,471 and 5,697,902. For example, a radioisotope may be conjugated by a chloramine T method (Lindegren, S. et al. (1998) "*Chloramine-T In High-Specific-Activity Radioiodination Of Antibodies Using N-Succinimidyl-3-(Trimethylstannyl)Benzoate As An Intermediate,*" Nucl. Med. Biol. 25(7):659-665; Kurth, M. et al. (1993) "*Site-Specific Conjugation Of A Radioiodinated Phenethylamine Derivative To A Monoclonal Antibody Results In Increased Radioactivity Localization In Tumor,*" J. Med. Chem. 36(9):1255-1261; Rea, D. W. et al. (1990) "Site-specifically radioiodinated antibody for targeting tumors," Cancer Res. 50(3 Suppl):857s-861s).

The invention also provides anti-tau antibodies and epitope-binding fragments thereof that are detectably labeled using a fluorescent label (such as a rare earth chelate (e.g., a europium chelate)), a fluorescein-type label (e.g., fluorescein, fluorescein isothiocyanate, 5-carboxyfluorescein, 6-carboxy fluorescein, dichlorotriazinylamine fluorescein), a rhodamine-type label (e.g., ALEXA FLUOR® 568 (Invitrogen), TAMRA® or dansyl chloride), VIVOTAG 680 XL FLUOROCHROME™ (Perkin Elmer), phycoerythrin; umbelliferone, Lissamine; a cyanine; a phycoerythrin, Texas Red, BODIPY FL-SE® (Invitrogen) or an analogue thereof, all of which are suitable for optical detection. Chemiluminescent labels may be employed (e.g., luminol, luciferase, luciferin, and aequorin). Such diagnosis and detection can also be accomplished by coupling the diagnostic molecule of the present invention to detectable substances including, but not limited to, various enzymes, enzymes including, but not limited to, horseradish peroxidase, alkaline phosphatase, beta-galactosidase, or acetylcholinesterase, or to prosthetic group complexes such as, but not limited to, streptavidin/biotin and avidin/biotin.

Chemiluminescent labels may be employed (e.g., luminol, luciferase, luciferin, and aequorin). Such diagnosis and detection can also be accomplished by coupling the diagnostic molecule of the present invention to detectable substances including, but not limited to, various enzymes, enzymes including, but not limited to, horseradish peroxidase, alkaline phosphatase, beta-galactosidase, or acetylcholinesterase, or to prosthetic group complexes such as, but not limited to, streptavidin/biotin and avidin/biotin. Paramagnetic labels can also be employed, and are preferably detected using Positron Emission Tomography (PET) or Single-Photon Emission Computed Tomography (SPECT). Such paramagnetic labels include, but are not limited to compounds containing paramagnetic ions of Aluminum (Al), Barium (Ba), Calcium (Ca), Cerium (Ce), Dysprosium (Dy), Erbium (Er), Europium (Eu), Gandolinium (Gd), Holmium (Ho), Iridium (Ir), Lithium (Li), Magnesium (Mg), Manganese (Mn), Molybdenum (M), Neodymium (Nd), Osmium (Os), Oxygen (O), Palladium (Pd), Platinum (Pt), Rhodium (Rh), Ruthenium (Ru), Samarium (Sm), Sodium (Na), Strontium (Sr), Terbium (Tb), Thulium (Tm), Tin (Sn), Titanium (Ti), Tungsten (W), and Zirconium (Zi), and particularly, $Co^{+2}$, $CR^{+2}$, $Cr^{+3}$, $Cu^{+2}$, $Fe^{+2}$, $Fe^{+3}$, $Ga^{+3}$, $Mn^{+3}$, $Ni^{+2}$, $Ti^{+3}$, $V^{+3}$, and $V^{+4}$, positron emitting metals using various positron emission tomographies, and non-radioactive paramagnetic metal ions.

Thus in one embodiment the anti-tau antibody or tau-binding fragment thereof of the invention may be labelled with a fluorescent label, a chemiluminescent label, a paramagnetic label, a radioisotopic label or an enzyme label. The labelled antibody of fragment may be used in detecting or measuring the presence or amount of said tau in the brain of a subject. This method may comprise the detection or measurement of in vivo imaging of anti-tau antibody or tau-binding fragment bound to said tau and may comprises ex vivo imaging of said anti-tau antibody or tau-binding fragment bound to such tau.

In a further aspect, the invention relates to an expression vector encoding one or more polypeptide chains of an antibody of the invention or a tau-binding fragment thereof. Such expression vectors may be used for recombinant production of antibodies or epitope-binding fragments thereof of the invention.

An expression vector in the context of the present invention may be any suitable DNA or RNA vector, including chromosomal, non-chromosomal, and synthetic nucleic acid vectors (a nucleic acid sequence comprising a suitable set of expression control elements). Examples of such vectors include derivatives of SV40, bacterial plasmids, phage DNA, baculovirus, yeast plasmids, vectors derived from combinations of plasmids and phage DNA, and viral nucleic acid (RNA or DNA) vectors. In one embodiment, an anti-tau antibody-encoding nucleic acid is comprised in a naked DNA or RNA vector, including, for example, a linear expression element (as described in, for instance, Sykes and Johnston, Nat Biotech 12, 355-59 (1997)), a compacted nucleic acid vector (as described in for instance U.S. Pat. No. 6,077,835 and/or WO 00/70087), a plasmid vector such as pBR322, pUC 19/18, or pUC 118/119, a "midge" minimally-sized nucleic acid vector (as described in, for instance, Schakowski et al., Mol Ther 3, 793-800 (2001)), or as a precipitated nucleic acid vector construct, such as a CaPO4-precipitated construct (as described in, for instance, WO 00/46147, Benvenisty and Reshef, PNAS USA 83, 9551-55 (1986), Wigler et al., Cell 14, 725 (1978), and Coraro and Pearson, Somatic Cell Genetics 2, 603 (1981)). Such nucleic acid vectors and the usage thereof are well known in the art (see for instance U.S. Pat. Nos. 5,589,466 and 5,973,972).

In one embodiment, the vector is suitable for expression of anti-tau antibodies or epitope-binding fragments thereof of the invention in a bacterial cell. Examples of such vectors include expression vectors such as BlueScript (Stratagene), pIN vectors (Van Heeke & Schuster, J. Biol. Chem. 264, 5503-5509 (1989), pET vectors (Novagen, Madison, Wis.), and the like.

An expression vector may also or alternatively be a vector suitable for expression in a yeast system. Any vector suitable for expression in a yeast system may be employed. Suitable vectors include, for example, vectors comprising constitutive or inducible promoters such as alpha factor, alcohol oxidase and PGH (reviewed in: F. Ausubel et al., ed. Current Protocols in Molecular Biology, Greene Publishing and Wiley InterScience New York (1987), Grant et al., Methods in Enzymol 153, 516-544 (1987), Mattanovich, D. et al. Methods Mol. Biol. 824, 329-358 (2012), Celik, E. et al. Biotechnol. Adv. 30(5), 1108-1118 (2012), Li, P. et al. Appl. Biochem. Biotechnol. 142(2), 105-124 (2007), BOer, E. et al. Appl. Microbiol. Biotechnol. 77(3), 513-523 (2007), van der Vaart, J. M. Methods Mol. Biol. 178, 359-366 (2002), and Holliger, P. Methods Mol. Biol. 178, 349-357 (2002)).

In an expression vector of the invention, anti-tau antibody-encoding nucleic acids may comprise or be associated with any suitable promoter, enhancer, and other expression-facilitating elements. Examples of such elements include strong expression promoters (e.g., human CMV IE promoter/enhancer as well as RSV, SV40, SL3-3, MMTV, and HIV LTR promoters), effective poly (A) termination sequences, an origin of replication for plasmid product in E. coli, an antibiotic resistance gene as selectable marker, and/or a convenient cloning site (e.g., a polylinker). Nucleic acids may also comprise an inducible promoter as opposed to a constitutive promoter such as CMV IE (the skilled artisan will recognize that such terms are actually descriptors of a degree of gene expression under certain conditions).

In an even further aspect, the invention relates to a recombinant eukaryotic or prokaryotic host cell, such as a transfectoma, which produces an antibody or epitope-binding fragment thereof of the invention as defined herein or a bispecific molecule of the invention as defined herein. Examples of host cells include yeast, bacteria, and mammalian cells, such as CHO or HEK cells. For example, in one embodiment, the present invention provides a cell comprising a nucleic acid stably integrated into the cellular genome that comprises a sequence coding for expression of an anti-tau antibody of the present invention or an epitope-binding fragment thereof. In another embodiment, the present invention provides a cell comprising a non-integrated nucleic acid, such as a plasmid, cosmid, phagemid, or linear expression element, which comprises a sequence coding for expression of an anti-tau antibody or epitope-binding fragment thereof of the invention.

In a further aspect, the invention relates to a method for producing an anti-tau antibody of the invention, said method comprising the steps of a) culturing a hybridoma or a host cell of the invention as described herein above, and b) purifying the antibody of the invention from the culture media.

In one embodiment, the invention relates to a preparation that, as such term is used herein, comprises an anti-tau antibody as defined herein, and that is substantially free of naturally-arising antibodies that are either not capable of binding to tau or that do not materially alter the anti-tau functionality of the preparation. Thus, such a preparation does not encompass naturally-arising serum, or a purified derivative of such serum, that comprises a mixture of an anti-tau antibody and another antibody that does not alter the functionality of the anti-tau antibody of the preparation, wherein such functionality is:

(i) a substantial inability to bind to non-phosphorylated tau;
(ii) a substantial inability to bind to tau that is phosphorylated at S404 and not phosphorylated at S396;
(iii) the ability to bind to tau phosphorylated at S396;
(iv) the ability to bind to tau phosphorylated at both S396 and at S404;

(v) the ability to selectively discriminate between phosphorylated tau residues S396 and S404 such that it is substantially unable to bind the phosphorylated 404 residue;
(vi) the ability to bind hyper-phosphorylated tau from human Alzheimer's disease brains;
(vii) the ability to discriminate between pathological and non-pathological human tau protein; and/or
(viii) the capability, when used as described herein with immune-depleted rTg4510 extracts from transgenic mice, to specifically reduce the hyperphosphorylated tau 64 kDa and 70 kDa bands by at least 90%, while not reducing the 55 kDa tau band by more than 10% or the capability, when used as described herein with extracts from human AD post-mortem brains, to specifically reduce the S396 phosphorylated hyperphosphorylated tau bands by at least 90%, while not reducing the non-hyperphosphorylated tau bands by more than 10%.

The invention particularly relates to preparations of such an anti-tau antibody having a structural change in its amino acid sequence (in any of its CDRs, variable domains, framework residues and/or constant domains) relative to the structure of a naturally-occurring anti-tau antibody, wherein said structural change causes the anti-tau antibody to exhibit a markedly altered functionality (i.e., more than a 20% difference, more than a 40% difference, more than a 60% difference, more than an 80% difference, more than a 100% difference, more than a 150% difference, more than a 2-fold difference, more than a 4-fold difference, more than a 5-fold difference, or more than a 10-fold difference in functionality) relative to the functionality exhibited by said naturally-occurring anti-tau antibody; wherein such functionality is:
(i) a substantial inability to bind to non-phosphorylated tau;
(ii) a substantial inability to bind to tau that is phosphorylated at S404 and not phosphorylated at S396;
(iii) the ability to bind to tau phosphorylated at S396;
(iv) the ability to bind to tau phosphorylated at both S396 and at S404;
(v) the ability to selectively discriminate between phosphorylated tau residues S396 and S404 such that it is substantially unable to bind the phosphorylated 404 residue;
(vi) the ability to bind hyper-phosphorylated tau from human Alzheimer's disease brains;
(vii) the ability to discriminate between pathological and non-pathological human tau protein; and/or
(viii) the capability, when used as described herein with immune-depleted rTg4510 extracts from transgenic mice, to specifically reduce the hyperphosphorylated tau 64 kDa and 70 kDa bands by at least 90%, while not reducing the 55 kDa tau band by more than 10%; or the capability, when used as described herein with extracts from human AD post-mortem brains to specifically reduce the S396 phosphorylated hyperphosphorylated tau bands by at least 90%, while not reducing the non-hyperphosphorylated tau bands by more than 10%.

The term "substantially free" of naturally-arising antibodies refers to the complete absence of such naturally-arising antibodies in such preparations, or of the inclusion of a concentration of such naturally-arising antibodies in such preparations that does not materially affect the tau-binding properties of the preparations. An antibody is said to be "isolated" if it has no naturally-arising counterpart or has been separated or purified from components which naturally accompany it.

The term "naturally-arising antibodies," as it relates to such preparations, refers to antibodies (including naturally-arising autoantibodies) elicited within living humans or other animals, as a natural consequence to the functioning of their immune systems.

Thus, the preparations of the present invention do not exclude, and indeed explicitly encompass, such preparations that contain an anti-tau antibody and a deliberately added additional antibody capable of binding to an epitope that is not possessed by tau. Such preparations particularly include embodiments thereof wherein the preparation exhibits enhanced efficacy in treating Alzheimer's disease (AD), Argyrophilic Grain Disease (AGD), Progressive Supranuclear Palsy (PSP), and Corticobasal Degeneration (CBD). Furthermore, the present invention is directed to preparations that contain an anti-tau antibody antibodies, or epitope-binding fragments thereof, intended for use in the treatment of Psychosis, particularly Psychosis due to AD or Psychosis in patients with AD, and psychiatric symptoms of patients with Lewy body dementia. Furthermore, the preparations of the present invention contain an anti-tau antibody antibodies, or epitope-binding fragments thereof, that may be used in the treatment of stroke, stroke recovery, neurodegeneration in relation to Parkinson's disease.

In an even further aspect, the invention relates to a pharmaceutical composition comprising:
(i) a tau antibody, or epitope-binding fragment thereof, both as defined herein, or a preparation, as such term is defined herein, that comprises such an anti-tau antibody or epitope-binding fragment thereof; and
(ii) a pharmaceutically-acceptable carrier.

The pharmaceutical compositions may be formulated with pharmaceutically acceptable carriers or diluents as well as any other known adjuvants and excipients in accordance with conventional techniques such as those disclosed in Remington: The Science and Practice of Pharmacy, 22nd Edition, Gennaro, Ed., Mack Publishing Co., Easton, Pa., 2013.

The pharmaceutically acceptable carriers or diluents as well as any other known adjuvants and excipients should be suitable for the chosen compound of the present invention and the chosen mode of administration. Suitability for carriers and other components of pharmaceutical compositions is determined based on the lack of significant negative impact on the desired biological properties of the chosen compound or pharmaceutical composition of the present invention (e.g., less than a substantial impact (10% or less relative inhibition, 5% or less relative inhibition, etc.)) on epitope binding.

A pharmaceutical composition of the present invention may also include diluents, fillers, salts, buffers, detergents (e.g., a nonionic detergent, such as Tween-20 or Tween-80), stabilizers (e.g., sugars or protein-free amino acids), preservatives, tissue fixatives, solubilizers, and/or other materials suitable for inclusion in a pharmaceutical composition. The diluent is selected to not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, or non-toxic, nontherapeutic, non-immunogenic stabilizers and the like. The compositions may also include large, slowly metabolized macromolecules, such as proteins, polysaccharides like chitosan, polylactic acids, polyglycolic acids and copolymers (e.g., latex functionalized sepharose, agarose, cellulose, and the like), polymeric amino acids, amino acid copolymers, and lipid aggregates (e.g., oil droplets or liposomes).

The actual dosage levels of the active ingredients in the pharmaceutical compositions of the present invention may be varied so as to obtain an amount of the active ingredient which is effective to achieve the desired therapeutic response for a particular patient, composition, and mode of administration. The selected dosage level will depend upon a variety of pharmacokinetic factors including the activity of the particular compositions of the present invention employed, or the amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The pharmaceutical composition may be administered by any suitable route and mode, including: parenteral, topical, oral or intranasal means for prophylactic and/or therapeutic treatment. In one embodiment, a pharmaceutical composition of the present invention is administered parenterally. The phrases "parenteral administration" and "administered parenterally" as used herein means modes of administration other than enteral and topical administration, usually by injection, and include epidermal, intravenous, intramuscular, intraarterial, intrathecal, intracapsular, intraorbital, intracardiac, intradermal, intraperitoneal, intratendinous, transtracheal, subcutaneous, subcuticular, intraarticular, subcapsular, subarachnoid, intraspinal, intracranial, intrathoracic, epidural and intrasternal injection and infusion.

Additional suitable routes of administering a compound of the present invention in vivo and in vitro are well known in the art and may be selected by those of ordinary skill in the art.

In one embodiment that pharmaceutical composition is administered by intravenous or subcutaneous injection or infusion.

Pharmaceutically acceptable carriers include any and all suitable solvents, dispersion media, coatings, antibacterial and antifungal agents, isotonicity agents, antioxidants and absorption delaying agents, and the like that are physiologically compatible with a compound of the present invention.

Examples of suitable aqueous and nonaqueous carriers which may be employed in the pharmaceutical compositions of the present invention include water, saline, phosphate buffered saline, ethanol, dextrose, polyols (such as glycerol, propylene glycol, polyethylene glycol, and the like), and suitable mixtures thereof, vegetable oils, such as olive oil, corn oil, peanut oil, cottonseed oil, and sesame oil, carboxymethyl cellulose colloidal solutions, tragacanth gum and injectable organic esters, such as ethyl oleate, and/or various buffers.

Other carriers are well known in the pharmaceutical arts.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the present invention is contemplated.

Proper fluidity may be maintained, for example, by the use of coating materials, such as lecithin, by the maintenance of the required particle size in the case of dispersions, and by the use of surfactants.

Pharmaceutical compositions of the present invention may also comprise pharmaceutically acceptable antioxidants for instance (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Pharmaceutical compositions of the present invention may also comprise isotonicity agents, such as sugars, polyalcohols, such as mannitol, sorbitol, glycerol or sodium chloride in the compositions.

The pharmaceutical compositions of the present invention may also contain one or more adjuvants appropriate for the chosen route of administration such as preservatives, wetting agents, emulsifying agents, dispersing agents, preservatives or buffers, which may enhance the shelf life or effectiveness of the pharmaceutical composition. The compounds of the present invention may be prepared with carriers that will protect the compound against rapid release, such as a controlled release formulation, including implants, transdermal patches, and microencapsulated delivery systems. Such carriers may include gelatin, glyceryl monostearate, glyceryl distearate, biodegradable, biocompatible polymers such as ethylene vinyl acetate, polyanhydrides, polyglycolic acid, collagen, polyorthoesters, and polylactic acid alone or with a wax, or other materials well known in the art. Methods for the preparation of such formulations are generally known to those skilled in the art. See, e.g., Sustained and Controlled Release Drug Delivery Systems, J. R. Robinson, ed., Marcel Dekker, Inc., New York, 1978.

In one embodiment, the compounds of the present invention may be formulated to ensure proper distribution in vivo. Pharmaceutically acceptable carriers for parenteral administration include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the present invention is contemplated. Supplementary active compounds may also be incorporated into the compositions.

Pharmaceutical compositions for injection must typically be sterile and stable under the conditions of manufacture and storage. The composition may be formulated as a solution, micro-emulsion, liposome, or other ordered structure suitable to high drug concentration. The carrier may be an aqueous or non-aqueous solvent or dispersion medium containing for instance water, ethanol, polyols (such as glycerol, propylene glycol, polyethylene glycol, and the like), and suitable mixtures thereof, vegetable oils, such as olive oil, and injectable organic esters, such as ethyl oleate. The proper fluidity may be maintained, for example, by the use of a coating such as lecithin, by the maintenance of the required particle size in the case of dispersion and by the use of surfactants. In many cases, it will be preferable to include isotonic agents, for example, sugars, polyalcohols such as glycerol, mannitol, sorbitol, or sodium chloride in the composition. Prolonged absorption of the injectable compositions may be brought about by including in the composition an agent that delays antibody absorption, for example, monostearate salts and gelatin. Sterile injectable solutions may be prepared by incorporating the active compound in the required amount in an appropriate solvent with one or a combination of ingredients e.g. as enumerated above, as required, followed by sterilization microfiltration. Generally, dispersions are prepared by incorporating the active compound into a sterile vehicle that contains a basic dispersion medium and the required other ingredients e.g. from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

Sterile injectable solutions may be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

Dosage regimens in the above methods of treatment and uses described herein are adjusted to provide the optimum desired response (e.g., a therapeutic response). For example, a single bolus may be administered, several divided doses may be administered over time or the dose may be proportionally reduced or increased as indicated by the exigencies of the therapeutic situation. Parenteral compositions may be formulated in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the present invention are dictated by and directly dependent on (a) the unique characteristics of the active compound and the particular therapeutic effect to be achieved, and (b) the limitations inherent in the art of compounding such an active compound for the treatment of sensitivity in individuals.

The effective dosages and the dosage regimens for the antibodies or epitope-binding fragments thereof of the invention, depend on the disease or condition to be treated and may be determined by persons skilled in the art. On any given day that a dosage is given, the dosage may range from about 0.0001 to about 100 mg/kg, and more usually from about 0.01 to about 5 mg/kg, of the host body weight. For example, dosages can be 1 mg/kg body weight or 10 mg/kg body weight or within the range of 1-10 mg/kg body weight. Exemplary dosages thus include: from about 0.1 to about 10 mg/kg/body weight, from about 0.1 to about 5 mg/kg/body weight, from about 0.1 to about 2 mg/kg/body weight, from about 0.1 to about 1 mg/kg/body weight, for instance about 0.15 mg/kg/body weight, about 0.2 mg/kg/body weight, about 0.5 mg/kg/body weight, about 1 mg/kg/body weight, about 1.5 mg/kg/body weight, about 2 mg/kg/body weight, about 5 mg/kg/body weight, or about 10 mg/kg/body weight.

A physician having ordinary skill in the art may readily determine and prescribe the effective amount of the pharmaceutical composition required. For example, the physician could start doses of an antibody or epitope-binding fragment thereof of the invention employed in the pharmaceutical composition at levels lower than that required in order to achieve the desired therapeutic effect and gradually increase the dosage until the desired effect is achieved. In general, a suitable daily dose of a composition of the present invention will be that amount of the compound which is the lowest dose effective to produce a therapeutic effect. Such an effective dose will generally depend upon the factors described above. Administration may e.g. be intravenous, intramuscular, intraperitoneal, or subcutaneous. If desired, the effective daily dose of a pharmaceutical composition may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical composition as described above.

The labeled antibodies or epitope-binding fragments thereof of the invention can be used for diagnostic purposes to detect, diagnose, or monitor diseases or disorders. The invention provides for the detection or diagnosis of a neurodegenerative or cognitive disease or disorder, including but not limited to Alzheimer's disease, Argyrophilic Grain Disease (AGD), Progressive Supranuclear Palsy (PSP), and Corticobasal Degeneration (CBD), comprising: (a) assaying the existence of pyroglutamated Aβ fragments in cells or tissue samples of a subject using one or more antibodies that specifically bind to tau; and (b) comparing the level of the antigen with a control level, e.g. levels in normal tissue samples, whereby an increase in the assayed level of antigen compared to the control level of antigen is indicative of the disease or disorder, or indicative of the severity of the disease or disorder.

The antibodies or epitope-binding fragments thereof of the invention can be used to assay tau or fragments of tau in a biological sample using immunohistochemical methods well-known in the art. Other antibody-based methods useful for detecting protein include immunoassays such as the enzyme linked immunoassay (ELISA) and the radioimmunoassay assay (RIA) and mesoscale discovery platform based assays (MSD). Suitable antibody labels may be used in such kits and methods, and labels known in the art include enzyme labels, such as alkaline phosphatase and glucose oxidase; radioisotope labels, such as iodine ($^{125}$I, $^{131}$I), carbon ($^{14}$C), sulfur ($^{35}$S), tritium ($^{3}$H), indium ($^{121}$In), and technetium ($^{99m}$Tc); and luminescent labels, such as luminol and luciferase; and fluorescent labels, such as fluorescein and rhodamine.

The presence of labeled anti-tau antibodies or their tau-binding fragments may be detected in vivo for diagnostic purposes. In one embodiment, diagnosis comprises: a) administering to a subject an effective amount of such labeled molecule; b) waiting for a time interval following administration to allow the labeled molecule to concentrate at sites (if any) of Aβ deposition and to allow for unbound labeled molecule to be cleared to background level; c) determining a background level; and d) detecting the labeled molecule in the subject, such that detection of labeled molecule above the background level is indicative that the subject has the disease or disorder, or is indicative of the severity of the disease or disorder. In accordance with such embodiment, the molecule is labeled with an imaging moiety suitable for detection using a particular imaging system known to those skilled in the art. Background levels may be determined by various methods known in the art, including comparing the amount of labeled antibody detected to a standard value previously determined for a particular imaging system. Methods and systems that may be used in the diagnostic methods of the invention include, but are not limited to, computed tomography (CT), whole body scan such as positron emission tomography (PET), magnetic resonance imaging (MRI), and sonography.

In a further aspect, the invention provides a monoclonal antibody, or an epitope-binding fragment thereof, as defined herein for use in therapy.

In a further aspect, the invention provides a monoclonal antibody, or an epitope-binding fragment thereof, as defined herein for use in treating, diagnosing or imaging of tauopathies.

In a further aspect, the invention provides a monoclonal antibody, or an epitope-binding fragment thereof, as defined herein for use in treating Alzheimer's disease, Argyrophilic Grain Disease (AGD), Progressive Supranuclear Palsy (PSP), and Corticobasal Degeneration (CBD).

In a further aspect, the invention provides a monoclonal antibody, or an epitope-binding fragment thereof, as defined herein for use in the manufacture of a medicament for treating, diagnosing or imaging tauopathies.

Preferably, the medicament is for treating Alzheimer's disease (AD), Argyrophilic Grain Disease (AGD), Progressive Supranuclear Palsy (PSP), and Corticobasal Degeneration (CBD) most preferably Alzheimer's disease (AD). The medicament is also preferably for the treatment of Psychosis, particularly Psychosis due to AD or Psychosis in patients with AD, and psychiatric symptoms of patients with Lewy body dementia.

In a further aspect, the invention provides a method of treating, diagnosing or imaging Alzheimer's disease or other tauopathies in a subject, said method comprising administering the medicament monoclonal antibody or epitope-binding fragment thereof as defined herein, to said subject in an effective amount.

In a preferred embodiment, the treatment is chronic, preferably for at least 2 weeks, such as at least for 1 month, 6, months, 1 year or more.

In a further aspect, the invention provides a kit comprising the antibody, or fragment thereof, as defined herein for use in therapy.

Embodiments

1. A monoclonal antibody, or an epitope-binding fragment thereof, capable of immunospecifically binding to the phosphorylated residue 396 of human tau, such as phosphorylated residue 396 of SEQ ID NO:33.
2. The antibody according to embodiment 1 consisting of an intact antibody.
3. The antibody or epitope-binding fragment thereof according to embodiment 1 or 2 comprising or consisting of an epitope-binding fragment selected from the group consisting of: an Fv fragment (e.g. single chain Fv and disulphide-bonded Fv); a Fab-like fragment (e.g. Fab fragment, Fab' fragment and F(ab)2 fragment); a minibody (Fv)2-CH3 domain, and a domain antibody (e.g. a single VH variable domain or VL variable domain).
4. The antibody or epitope-binding fragment thereof according to any preceding embodiment, wherein the antibody is selected from the group consisting of antibodies of subtype IgG1, IgG2, IgG3, or IgG4.
5. The monoclonal antibody or epitope-binding fragment thereof according to any of the previous embodiments which is human or humanized.
6. The monoclonal antibody, or epitope-binding fragment thereof, according to any one of the preceding embodiments wherein the antibody or epitope-binding fragment exhibits one or more of the following properties
   (a) selectivity and specificity for human pathological tau;
   (b) a binding affinity (KD) for p-Tau 386-408 (pS396/pS404) (SEQ ID NO:33) between 0.5-10 nM, such as 1-5 nM or 1-2 nM
7. The monoclonal antibody, or epitope-binding fragment thereof, according to any one of the preceding embodiments, wherein said antibody does not substantially bind the phosphorylated 404 residue on tau (SEQ ID NO:33).
8. A monoclonal antibody, or an epitope-binding fragment thereof comprising:
   (a) a Light Chain CDR1 having the amino acid sequence of SEQ ID NO:1 or an amino acid sequence having no more than 4 amino acid differences, or no more than 3 amino acid differences, or no more than 2 amino acid differences, or no more than 1 amino acid difference;
   (b) a Light Chain CDR2 having the amino acid sequence of SEQ ID NO:2 or an amino acid sequence having no more than 4 amino acid differences, or no more than 3 amino acid differences, or no more than 2 amino acid differences, or no more than 1 amino acid difference;
   (c) a Light Chain CDR3 having the amino acid sequence of SEQ ID NO:3 or an amino acid sequence having no more than 4 amino acid differences, or no more than 3 amino acid differences, or no more than 2 amino acid differences, or no more than 1 amino acid difference;
   (d) a Heavy Chain CDR1 having the amino acid sequence of SEQ ID NO:4 or an amino acid sequence having no more than 4 amino acid differences, or no more than 3 amino acid differences, or no more than 2 amino acid differences, or no more than 1 amino acid difference;
   (e) a Heavy Chain CDR2 having the amino acid sequence of SEQ ID NO:5 or an amino acid sequence having no more than 4 amino acid differences, or no more than 3 amino acid differences, or no more than 2 amino acid differences, or no more than 1 amino acid difference; and
   (f) a Heavy Chain CDR3 having the amino acid sequence of SEQ ID NO:6 or an amino acid sequence having no more than 4 amino acid differences, or no more than 3 amino acid differences, or no more than 2 amino acid differences, or no more than 1 amino acid difference.
9. The monoclonal antibody according to embodiment 8, comprising the heavy chain variable domain of SEQ ID NO:8 or an amino acid sequence having no more than 4 amino acid differences, or no more than 3 amino acid differences, or no more than 2 amino acid differences, or no more than 1 amino acid difference and/or the light chain variable domain of SEQ ID NO:7, having no more than 4 amino acid differences, or no more than 3 amino acid differences, or no more than 2 amino acid differences, or no more than 1 amino acid difference.
10. A monoclonal antibody, or an epitope-binding fragment thereof, comprising:
    (a) a Light Chain CDR1 having the amino acid sequence of SEQ ID NO:9 or an amino acid sequence having no more than 4 amino acid differences, or no more than 3 amino acid differences, or no more than 2 amino acid differences, or no more than 1 amino acid difference;
    (b) a Light Chain CDR2 having the amino acid sequence of SEQ ID NO:10 or an amino acid sequence having no more than 4 amino acid differences, or no more than 3 amino acid differences, or no more than 2 amino acid differences, or no more than 1 amino acid difference;
    (c) a Light Chain CDR3 having the amino acid sequence of SEQ ID NO:11 or an amino acid sequence having no (d) a Heavy Chain CDR1 having the amino acid sequence of SEQ ID NO:12 or an amino acid sequence having no more than 4 amino acid differences, or no more than 3 amino acid differences, or no more than 2 amino acid differences, or no more than 1 amino acid difference;

(e) a Heavy Chain CDR2 having the amino acid sequence of SEQ ID NO:13 or an amino acid sequence having no more than 4 amino acid differences, or no more than 3 amino acid differences, or no more than 2 amino acid differences, or no more than 1 amino acid difference; and (f) a Heavy Chain CDR3 having the amino acid sequence of SEQ ID NO:14 or an amino acid sequence having no more than 4 amino acid differences, or no more than 3 amino acid differences, or no more than 2 amino acid differences, or no more than 1 amino acid difference.

11. The monoclonal antibody according to embodiment 10, comprising the heavy chain variable domain of SEQ ID NO:16 or an amino acid sequence having no more than 4 amino acid differences, or no more than 3 amino acid differences, or no more than 2 amino acid differences, or no more than 1 amino acid difference and or the light chain variable domain of SEQ ID NO:15 or an amino acid sequence having no more than 4 amino acid differences, or no more than 3 amino acid differences, or no more than 2 amino acid differences, or no more than 1 amino acid difference.

12. A monoclonal antibody, wherein the epitope-binding fragment comprises:
   (a) a Light Chain CDR1 having the amino acid sequence of SEQ ID NO:17 or an amino acid sequence having no more than 4 amino acid differences, or no more than 3 amino acid differences, or no more than 2 amino acid differences, or no more than 1 amino acid difference;
   (b) a Light Chain CDR2 having the amino acid sequence of SEQ ID NO:18 or an amino acid sequence having no more than 4 amino acid differences, or no more than 3 amino acid differences, or no more than 2 amino acid differences, or no more than 1 amino acid difference;
   (c) a Light Chain CDR3 having the amino acid sequence of SEQ ID NO:19 or an amino acid sequence having no more than 4 amino acid differences, or no more than 3 amino acid differences, or no more than 2 amino acid differences, or no more than 1 amino acid difference;
   (d) a Heavy Chain CDR1 having the amino acid sequence of SEQ ID NO:20 or an amino acid sequence having no more than 4 amino acid differences, or no more than 3 amino acid differences, or no more than 2 amino acid differences, or no more than 1 amino acid difference;
   (e) a Heavy Chain CDR2 having the amino acid sequence of SEQ ID NO:21 or an amino acid sequence having no more than 4 amino acid differences, or no more than 3 amino acid differences, or no more than 2 amino acid differences, or no more than 1 amino acid difference; and
   (f) a Heavy Chain CDR3 having the amino acid sequence of SEQ ID NO:22 or an amino acid sequence having no more than 4 amino acid differences, or no more than 3 amino acid differences, or no more than 2 amino acid differences, or no more than 1 amino acid difference.

13. The monoclonal antibody according to embodiment 12, comprising the heavy chain variable domain of SEQ ID NO:24 or an amino acid sequence having no more than 4 amino acid differences, or no more than 3 amino acid differences, or no more than 2 amino acid differences, or no more than 1 amino acid difference and or the light chain variable domain of SEQ ID NO:23 or an amino acid sequence having no more than 4 amino acid differences, or no more than 3 amino acid differences, or no more than 2 amino acid differences, or no more than 1 amino acid difference.

14. A monoclonal antibody, or an epitope-binding fragment thereof comprising:
   (a) a Light Chain CDR1 having the amino acid sequence of SEQ ID NO:25 or an amino acid sequence having no more than 4 amino acid differences, or no more than 3 amino acid differences, or no more than 2 amino acid differences, or no more than 1 amino acid difference;
   (b) a Light Chain CDR2 having the amino acid sequence of SEQ ID NO:26 or an amino acid sequence having no more than 4 amino acid differences, or no more than 3 amino acid differences, or no more than 2 amino acid differences, or no more than 1 amino acid difference;
   (c) a Light Chain CDR3 having the amino acid sequence of SEQ ID NO:27 or an amino acid sequence having no more than 4 amino acid differences, or no more than 3 amino acid differences, or no more than 2 amino acid differences, or no more than 1 amino acid difference;
   (d) a Heavy Chain CDR1 having the amino acid sequence of SEQ ID NO:28 or an amino acid sequence having no more than 4 amino acid differences, or no more than 3 amino acid differences, or no more than 2 amino acid differences, or no more than 1 amino acid difference;
   (e) a Heavy Chain CDR2 having the amino acid sequence of SEQ ID NO:29 or an amino acid sequence having no more than 4 amino acid differences, or no more than 3 amino acid differences, or no more than 2 amino acid differences, or no more than 1 amino acid difference; and
   (f) a Heavy Chain CDR3 having the amino acid sequence of SEQ ID NO:30 or an amino acid sequence having no more than 4 amino acid differences, or no more than 3 amino acid differences, or no more than 2 amino acid differences, or no more than 1 amino acid difference.

15. The monoclonal antibody according to embodiment 14, comprising the heavy chain variable domain of SEQ ID NO:32 or an amino acid sequence having no more than 4 amino acid differences, or no more than 3 amino acid differences, or no more than 2 amino acid differences, or no more than 1 amino acid difference and or the light chain variable domain of SEQ ID NO:31 or an amino acid sequence having no more than 4 amino acid differences, or no more than 3 amino acid differences, or no more than 2 amino acid differences, or no more than 1 amino acid difference.

16. The antibody or epitope-binding fragment thereof according to one of embodiments 1 to 7, wherein said antibody or fragment thereof competes with the antibody or epitope-binding fragment thereof defined in Embodiment 8-15 for binding to human tau.

17. The antibody or epitope-binding fragment thereof according to any preceding embodiment comprising an Fc domain.

18. The antibody or epitope-binding fragment thereof according to any preceding embodiment further comprising a moiety for increasing in vivo half-life.

19. The antibody or epitope-binding fragment thereof according to Embodiment 18, wherein the moiety for increasing the in vivo half-life is selected from the group consisting of polyethylene glycol (PEG), human serum albumin, glycosylation groups, fatty acids and dextran.

20. The antibody or epitope-binding fragment thereof according to any preceding embodiment wherein the antibody further comprises a detectable moiety.

21. The antibody or epitope-binding fragment thereof according to Embodiment 20 wherein the detectable moiety is selected from the group consisting of: a fluorescent label; a chemiluminescent label; a paramagnetic label; a radio-isotopic label; or an enzyme label.

22. The antibody or epitope-binding fragment thereof according to Embodiments 20 or 21 wherein the detectable moiety comprises or consists of a radioisotope.

23. The antibody or epitope-binding fragment thereof according to Embodiment 22 wherein the radioisotope is selected from the group consisting of 99mTc, 111In, 67Ga, 68Ga, 72As, 89Zr, 123I and 201Tl.

24. The antibody or epitope-binding fragment thereof according to Embodiment 21 wherein the detectable moiety comprises or consists of a paramagnetic isotope.

25. The antibody or epitope-binding fragment thereof according to Embodiment 24 wherein the paramagnetic isotope is selected from the group consisting of 157Gd, 55Mn, 162Dy, 52Cr and 56Fe.

26. The antibody or epitope-binding fragment thereof according to any of Embodiments 20 to 25 wherein the detectable moiety is detectable by an imaging technique such as SPECT, PET, MRI, optical or ultrasound imaging.

27. The antibody or epitope-binding fragment thereof according to any of Embodiments 20 to 26 wherein the detectable moiety is joined to the antibody or epitope-binding fragment thereof indirectly, via a linking moiety.

28. The antibody or epitope-binding fragment thereof according to Embodiment 27 wherein the linking moiety is selected from the group consisting of derivatives of 1,4,7,10-tetraazacyclododecane-1,4,7,10,tetraacetic acid (DOTA), deferoxamine (DFO), derivatives of diethylen-etriaminepentaacetic avid (DTPA), derivatives of S-2-(4-Isothiocyanatobenzyl)-1,4,7-triazacyclononane-1,4,7-triacetic acid (NOTA) and derivatives of 1,4,8,11-tetraazacyclododecane-1,4,8,11-tetraacetic acid (TETA).

29. The monoclonal antibody, or epitope-binding fragment thereof wherein the Heavy Chain is selected from the group consisting of SEQ ID NO:8, SEQ ID NO:16, SEQ ID NO:24, SEQ ID NO:32, and SEQ ID NO:35, and the Light Chain is selected from the group consisting of SEQ ID NO:7, SEQ ID NO:15, SEQ ID NO:23, and SEQ ID NO:36

30. A monoclonal antibody, or epitope-binding fragment thereof comprising
   (a) a Heavy Chain CDR1 comprising the amino acid sequence selected from the group consisting of SEQ ID NO:4, SEQ ID NO:12, SEQ ID NO:20, and SEQ ID NO:28;
   (b) a Heavy Chain CDR2 comprising the amino acid sequence selected from the group consisting of SEQ ID NO:5, SEQ ID NO:13, SEQ ID NO:21, and SEQ ID NO:29; and
   (c) a Heavy Chain CDR3 comprising the amino acid sequence selected from the group consisting of SEQ ID NO:6, SEQ ID NO:14, SEQ ID NO:22, and SEQ ID NO:30; and
   (d) a Light Chain CDR3 comprising the amino acid sequence selected from the group consisting of SEQ ID NO:3, SEQ ID NO:11, SEQ ID NO:19, and SEQ ID NO:27.

31. The antibody of the invention, or epitope-binding fragment thereof according to any one of Embodiments 1 to 7 comprising
   (a) a Heavy Chain CDR1 comprising the amino acid sequence of SEQ ID NO:20;
   (b) a Heavy Chain CDR2 comprising the amino acid sequence of SEQ ID NO:21;
   (c) a Heavy Chain CDR3 comprising the amino acid sequence of SEQ ID NO:22; and
   (d) a Light Chain CDR3 comprising the amino acid sequence of SEQ ID NO:19.

32. An isolated nucleic acid molecule encoding an antibody or epitope-binding fragment thereof as defined in any of Embodiments 1 to 31.

33. A nucleic acid molecule according to Embodiment 32 wherein the molecule is a cDNA molecule.

34. A vector comprising a nucleic acid molecule as defined in Embodiment 32 or 33.

35. A recombinant host cell comprising a nucleic acid molecule as defined in any of Embodiments 32 to 34.

36. A method for producing an antibody or epitope-binding fragment as defined in any of Embodiments 1 to 31, the method comprising culturing a host cell as defined in Embodiment 35 under conditions which permit expression of the encoded antibody or epitope-binding fragment thereof.

37. A preparation comprising the antibody or epitope-binding fragment thereof according to any one of the previous claims, wherein said preparation is substantially free of naturally-arising antibodies that are either not capable of binding to tau or that do not materially alter an anti-tau functionality of the preparation, wherein said functionality is selected from the group consisting of:
   (i) a substantial inability to bind to non-phosphorylated tau;
   (ii) a substantial inability to bind to tau that is phosphorylated at S404 and not phosphorylated at S396;
   (iii) the ability to bind to tau phosphorylated at S396;
   (iv) the ability to bind to tau phosphorylated at both S396 and at S404;
   (v) the ability to selectively discriminate between phosphorylated tau residues S396 and S404 such that it is substantially unable to bind the phosphorylated 404 residue;
   (vi) the ability to bind hyper-phosphorylated tau from human Alzheimer's disease brains;
   (vii) the ability to discriminate between pathological and non-pathological human tau protein; and/or
   (viii) the capability, when used as described herein with immune-depleted rTg4510 extracts from transgenic mice, to specifically reduce the hyperphosphorylated tau 64 kDa and 70 kDa bands by at least 90%, while not reducing the 55 kDa tau band by more than 10% %; or the capability, when used as described herein with extracts from human AD post-mortem brains, to specifically reduce the S396 phosphorylated hyperphosphorylated tau bands by at least 90%, while not reducing the non-hyperphosphorylated tau bands by more than 10%.

38. A preparation comprising the antibody or epitope-binding fragment thereof according to any one of the previous claims, wherein said antibody or said epitope-binding fragment thereof possesses a structural change in its amino acid sequence, relative to the structure of a naturally-occurring anti-tau antibody, wherein said structural change causes said antibody or said fragment to exhibit an altered functionality relative to the functionality exhibited by said naturally-occurring anti-tau antibody, wherein said functionality is selected from the group consisting of:

(i) a substantial inability to bind to non-phosphorylated tau;
(ii) a substantial inability to bind to tau that is phosphorylated at S404 and not phosphorylated at S396;
(iii) the ability to bind to tau phosphorylated at S396;
(iv) the ability to bind to tau phosphorylated at both S396 and at S404;
(v) the ability to selectively discriminate between phosphorylated tau residues S396 and S404 such that it is substantially unable to bind the phosphorylated 404 residue;
(vi) the ability to bind hyper-phosphorylated tau from human Alzheimer's disease brains;
(vii) the ability to discriminate between pathological and non-pathological human tau protein; and/or
(viii) the capability, when used as described herein with immune-depleted rTg4510 extracts from transgenic mice, to specifically reduce the hyperphosphorylated tau 64 kDa and 70 kDa bands by at least 90%, while not reducing the 55 kDa tau band by more than 10%; or the capability, when used as described herein with extracts from human AD post-mortem brains, to specifically reduce the S396 phosphorylated hyperphosphorylated tau bands by at least 90%, while not reducing the non-hyperphosphorylated tau bands by more than 10%.

39. A pharmaceutical composition comprising the monoclonal antibody or epitope-binding fragment thereof as defined in any of embodiments 1 to 31, or the preparation as defined in any of embodiments 37-38; and a pharmaceutical acceptable carrier.

40. The monoclonal antibody, or fragment thereof, of any of embodiments 1-31, the preparation of any of embodiments 37-38, or the pharmaceutical composition of embodiment 39, for use in medicine.

41. The monoclonal antibody, or fragment thereof, of any of embodiments 1-31, the preparation of any of embodiments 37-38, or the pharmaceutical composition of embodiment 39, for use in treating a tauopathy.

42. The monoclonal antibody, or fragment thereof, the preparation, or the pharmaceutical composition, according to embodiment 41 wherein the tauopathy is selected from the group consisting of Alzheimer's disease, Argyrophilic Grain Disease (AGD), Progressive Supranuclear Palsy (PSP), Corticobasal Degeneration (CBD), Psychosis, particularly Psychosis due to AD or Psychosis in patients with AD, and psychiatric symptoms of patients with Lewy body dementia.

43. Use of the monoclonal antibody, or fragment thereof, of any of embodiments 1-31, the preparation of any of embodiments 37-38, or the pharmaceutical composition of embodiment 39 in the manufacturing of a medicament for treating a tauopathy.

44. The use of the monoclonal antibody, or fragment thereof, the preparation, or the pharmaceutical composition according to embodiment 43 wherein the tauopathy is selected from the group consisting of Alzheimer's disease, Argyrophilic Grain Disease (AGD), Progressive Supranuclear Palsy (PSP), Corticobasal Degeneration (CBD, Psychosis due to AD or Psychosis in patients with AD, and psychiatric symptoms of patients with Lewy body dementia.

45. A method of treating Alzheimer's disease or other tauopathies in a subject, said method comprising administering the monoclonal antibody, or fragment thereof, of any of embodiments 1-31, the preparation of any of embodiments 37-38, or the pharmaceutical composition of embodiment 39 to said subject in an effective amount.

46. The method according to embodiment 45, wherein the treatment is chronic.

47. The method according to embodiment 46, wherein the chronic treatment is for at least 2 weeks, such as at least for 1 month, 6, months, 1 year or more.

48. The method according to any one of embodiments 45 to 47, wherein the subject is human.

49. A kit comprising the monoclonal antibody, or fragment thereof, of any of embodiments 1-31, the preparation of any of embodiments 37-38, or the pharmaceutical composition of embodiment 39 for use in medicine.

50. The monoclonal antibody, or fragment thereof, of any of embodiments 1-31, the preparation of any of embodiments 37-38, or the pharmaceutical composition of embodiment 39 for use in detecting or measuring the presence or amount of said tau in the brain of a subject.

51. The monoclonal antibody, or fragment thereof, the preparation or the pharmaceutical composition of embodiment 50, wherein said detection or measurement comprises in vivo imaging of said anti-tau antibody bound to said tau.

52. The monoclonal antibody, or fragment thereof, the preparation or the pharmaceutical composition of embodiment 50, wherein said detection or measurement comprises ex vivo imaging of said anti-tau antibody or said fragment thereof, bound to said tau.

53. A monoclonal antibody, or an epitope-binding fragment thereof, capable of immunospecifically binding to the phosphorylated residue 396 of human tau (SEQ ID NO:33) in the presence of human tau phosphorylated at residue 404 but not phosphorylated at residue 396.

54. A monoclonal antibody or an epitope-binding fragment thereof that exhibits immunospecifically binding to human tau comprising a phosphorylated residue 396 according to the test criteria: i) the antibody does not substantially bind to non-phosphorylated tau; ii) the antibody does not substantially bind to tau phosphorylated at 404 when 396 is not phosphorylated; iii) the antibody does bind to tau phosphorylated at 396; and iv) the antibody does bind to tau when both 396 and 404 are phosphorylated.

55. A monoclonal antibody, raised against the bi-phosphorylated peptide: TDHGAEIVYK$^{\{p\}}$SPVVSGDT$^{\{p\}}$SPRHL (SEQ ID NO:37) covering residues 386-410 of 2N4R tau, or an epitope-binding fragment thereof, capable of immunospecifically binding to the phosphorylated residue 396 of human tau (SEQ ID NO:33).

56. The monoclonal antibody according to embodiment 55, wherein hybridomas are screened with human pathological and non-pathological tau to isolate clones that both i) were immunospecific towards the either of the phospho-epitopes S396 and ii) specifically recognize hyper-phosphorylated tau from human Alzheimer's disease brains, wherein said antibodies are able to discriminate between pathological and non-pathological human tau protein.

57. A method of removing hyperphosphorylated Tau from a tangle said tangle comprising hyperphosphorylated Tau said method comprising contacting hyperphosphorylated Tau with an antibody, said antibody selective for Tau having residue 396 phosphorylated, so as to result the tangle being depleted of 90% of hyperphosphorylated tau.

58. A method of delaying the progression of Alzheimer's Disease in a patient said method comprising reducing or attenuating the accumulation of pathological tau protein in said patient, said method comprising administering an antibody which removes a tau protein with a phosphorylated 396 residue.

59. A method of delaying the progression of Alzheimer's Disease in a patient said method comprising removing the tau proteins that seed for pathological tau proteins, wherein tau proteins having residue 396 phosphorylated are removed.

60. A method of treating a patient with Alzheimer's Disease comprising removing hyperphosphorylated Tau from a tangle said tangle comprising hyperphosphorylated Tau and normal Tau by contacting hyperphosphorylated Tau with an antibody selective for Tau having residue 396 phosphorylated.

61. A method according to any of embodiments 57 to 59 comprising the use of an antibody as defined in any one of embodiments 1 to 31, 40-42 or 50 to 56.

62. An isolated monoclonal antibody, or an isolated epitope-binding fragment thereof, capable of immunospecifically binding to the phosphorylated residue 396 of human tau (SEQ ID NO:33).

63. A recombinant human or recombinant humanized monoclonal antibody, or an isolated epitope-binding fragment thereof, capable of immunospecifically binding to the phosphorylated residue 396 of human tau (SEQ ID NO:33).

64. A recombinant monoclonal antibody, or an epitope-binding fragment thereof, raised against the bi-phosphorylated peptide: TDHGAEIVYK{p}SPVVSGDT{p}SPRHL (SEQ ID NO:37) covering residues 386-410 of 2N4R tau, wherein said recombinant monoclonal antibody, or an epitope-binding fragment thereof, is capable of immunospecifically binding to the phosphorylated residue 396 of human tau (SEQ ID NO:33).

65. A pharmaceutical composition comprising an isolated monoclonal antibody, or an isolated epitope-binding fragment thereof, wherein said isolated monoclonal antibody, or an isolated epitope-binding fragment thereof is as defined in any one of the above embodiments.

66. A chimeric monoclonal antibody or an isolated epitope-binding fragment thereof, capable of immunospecifically binding to the phosphorylated residue 396 of human tau (SEQ ID NO:33).

67. An antibody, or antigen-binding fragment thereof, as defined in any of embodiments 1-31 and 51-56 which has been produced or manufactured in a cell line such as a human cell line, a mammal non-human cell line, an insect, yeast or bacterial cell line.

68. The antibody, or antigen binding fragment thereof, according to embodiment 67 produced in a CHO cell line, HEK cell line, BHK-21 cell line, murine cell line (such as a myeloma cell line), fibrosarcoma cell line, PER.C6 cell line, HKB-11 cell line, CAP cell line and HuH-7 human cell line.

EXAMPLES

Example 1: Immunisation of Mice with Phospho-Peptides 396/404

C56/BL6 and FVB mice were immunised with 10 μg P30 conjugated phosphorylated tau 386-408 (pS396/pS404) (SEQ ID NO:37) formulated in TiterMax adjuvant.

Mice (C56/BL6 and FVB strains, female and male. 2- to 3-month-old mice were immunized with peptide epitope P30 conjugated phosphorylated tau 386-408.

Immunogenic P30 conjugated phosphorylated tau 386-408 (pS396/pS404) peptide was formulated in TiterMax (400 μg/ml peptide mixed 1:1 vol:vol) following the TiterMax/vendor protocol and mice were injected subcutaneously with 20 μg peptide (100 μl) of antigen. Control mice were injected with adjuvant only. All peptide-immunised mice were boosted with 0.5 μg peptide/Titermax (10 μg/ml peptide formulated as described above and injected) at monthly intervals. The mice were finally boosted with P30 conjugated phosphorylated tau 386-408 (pS396/pS404) without Titermax 3 days prior to fusion of splenocytes with SP-2 cells. Hybridomas were selected for re-cloning cycles after exhibiting positive binding to ELISA plates that had been coated with 1 μg/ml phosphorylated tau 386-408 (pS396/pS404), and exhibiting preferential binding activity to S1 and P3 antigens from AD and TG4510 brain lysate (described below in Example 3). Such binding was compared with the binding activity of such antibodies to brain lysate from controls, using dot blots and brain lysate coated ELISA or MSD plates.

Example 2: Hybridoma Generation

The mice were boosted with P30 conjugated phosphorylated tau 386-408 (pS396/pS404) without Titermax 3 days prior to fusion of splenocytes with SP-2 cells. Hybridomas were selected for re-cloning cycles after positive binding in ELISA plates coated with 1 μg/ml phosphorylated tau 386-408 (pS396/pS404), and preferential binding activity to S1 and P3 antigens from AD and TG4510 brain lysate in comparison to brain lysate from controls using dot blots and brain lysate coated ELISA or MSD plates.

Example 3 Western Blot and Dot-Blot Analysis of Specific Antibodies

Tau Biochemical Fractionation

Brain tissues from humans or rTg4510 mice overexpressing the human tau mutation P301L were homogenized in 10 volumes of Tris-buffered saline containing protease and phosphatase inhibitors as follows: 50 mM Tris/HCl (pH 7.4); 274 mM NaCl; 5 mM KCl; 1% protease inhibitor mixture (Roche); 1% phosphatase inhibitor cocktail I & II (Sigma); and 1 mM phenylmethylsulfonyl fluoride (PMSF; Sigma). The homogenates were centrifuged at 27,000×g for 20 min at 4° C. to obtain supernatant (S1) and pellet fractions. Pellets were re-homogenized in 5 volumes of high salt/sucrose buffer (0.8 M NaCl, 10% sucrose, 10 mM Tris/HCl, [pH 7.4], 1 mM EGTA, 1 mM PMSF) and centrifuged as above. The supernatants were collected and incubated with sarkosyl (1% final concentration; Sigma) for one hour at 37° C., followed by centrifugation at 150,000×g for one hour at 4° C. to obtain sarkosyl-insoluble pellets, referred to as P3 fraction. The P3 pellet was resuspended in TE buffer (10 mM Tris/HCl [pH 8.0], 1 mM EDTA) to a volume equivalent to half of the original volume used for the brain homogenates.

Western and Dot Blots

Figure 1A:
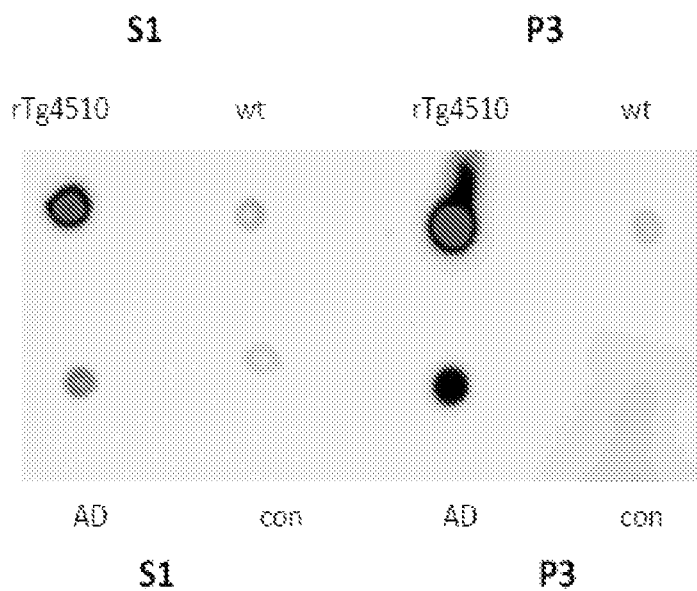
FIGS. 1A-1B: Binding to pathological material dot-blot
Figure 1B:
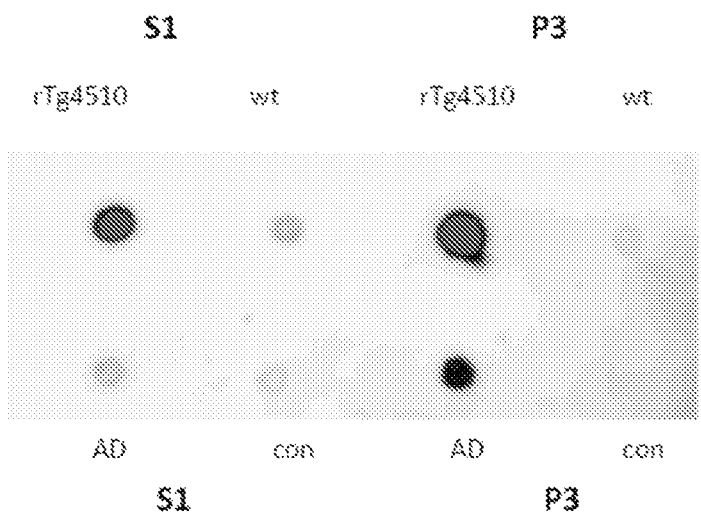
Figure 2A:
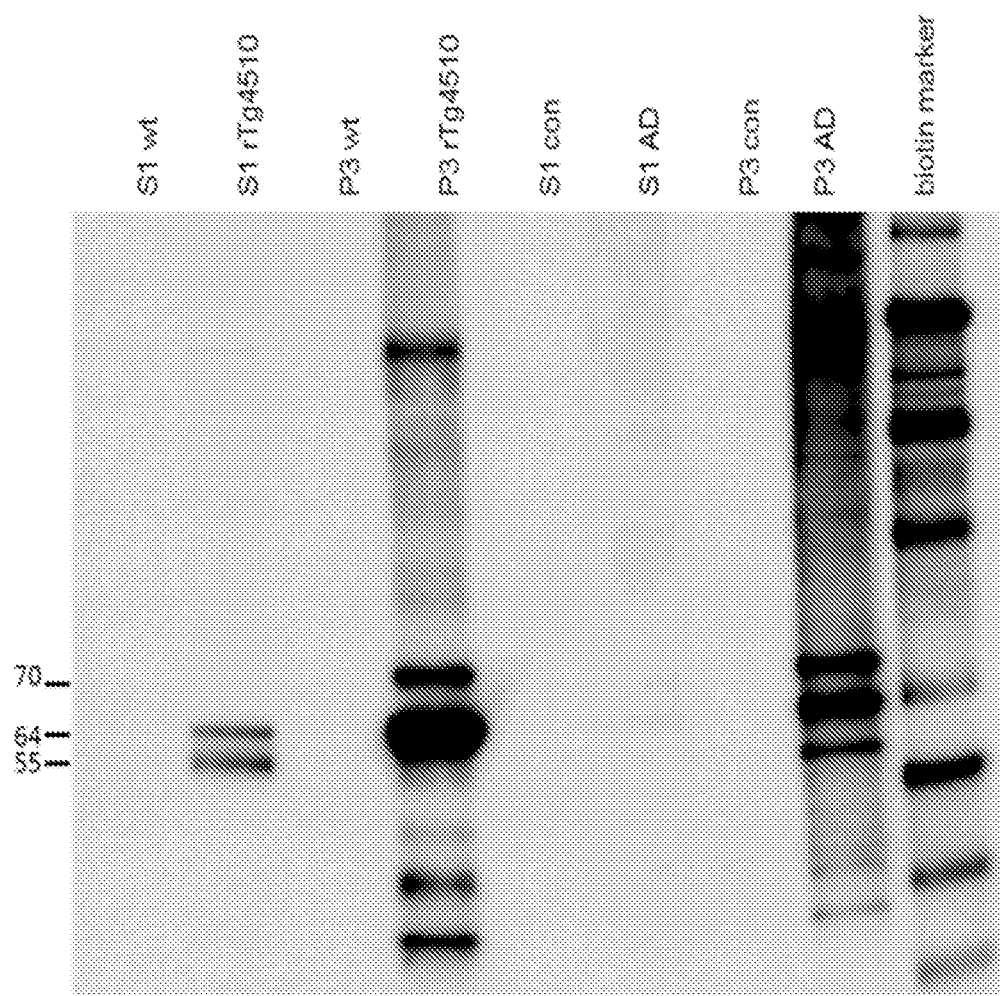
FIGS. 2A-2B: Western blot analysis of D1.2 and C10-2 antibodies
Figure 2B:
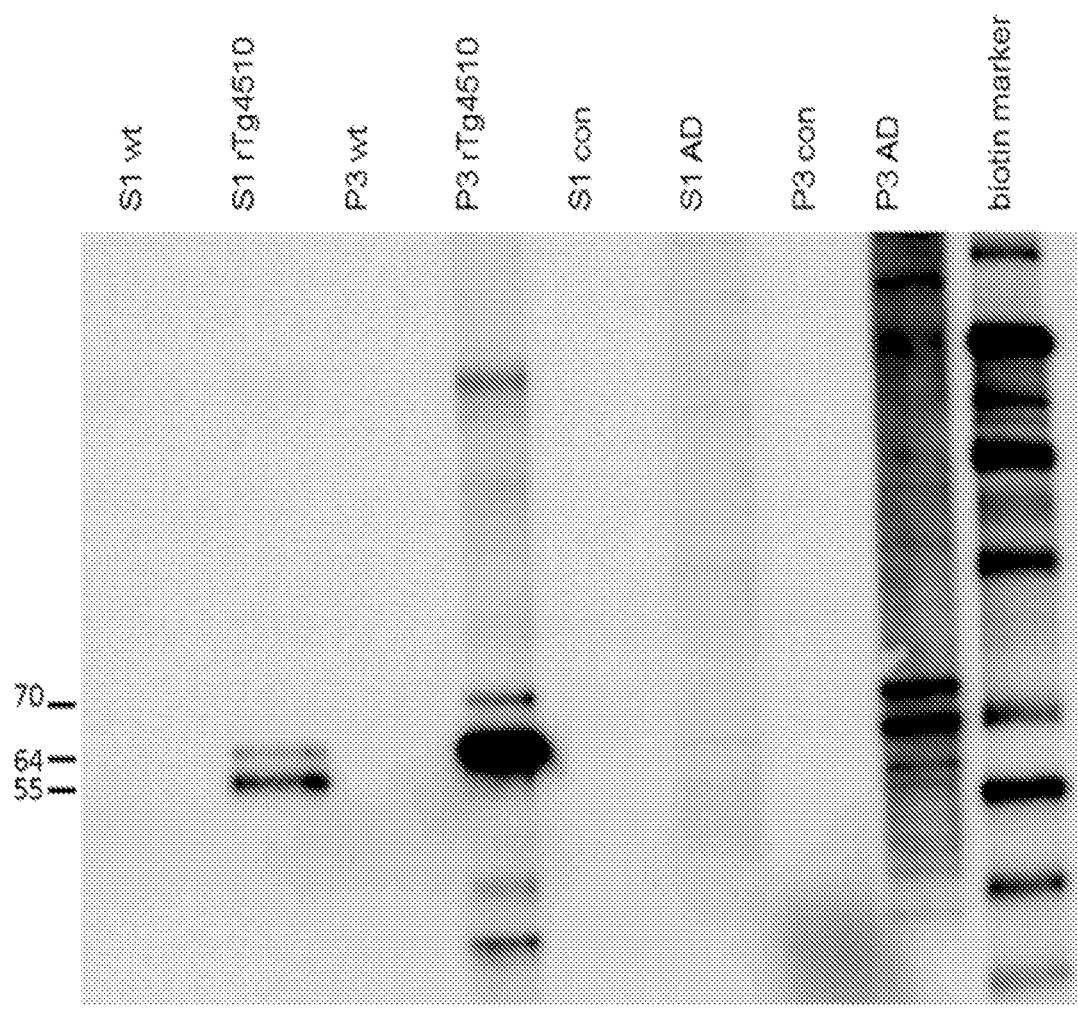
Figure 3A:
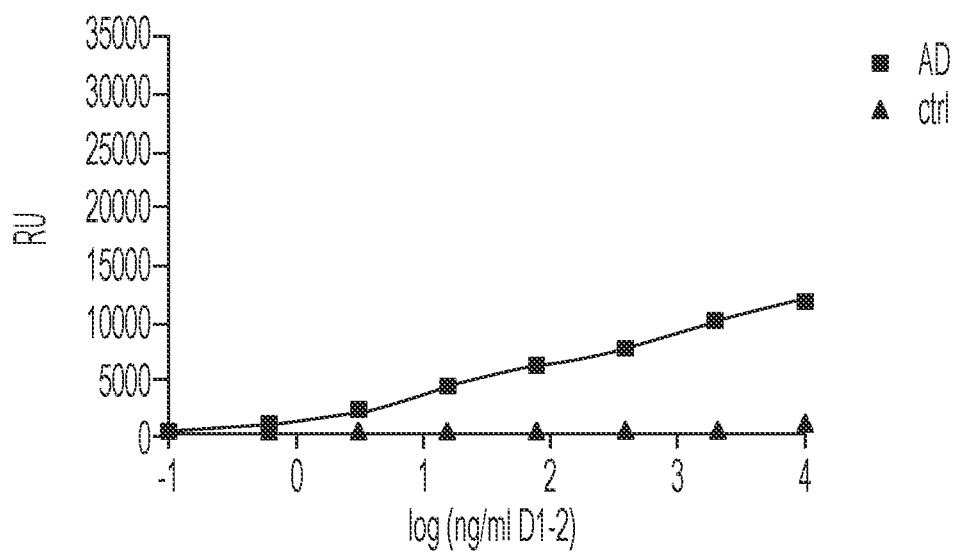
FIGS. 3A-3D: Binding to pathological P3 material in MSD
Figure 3B:
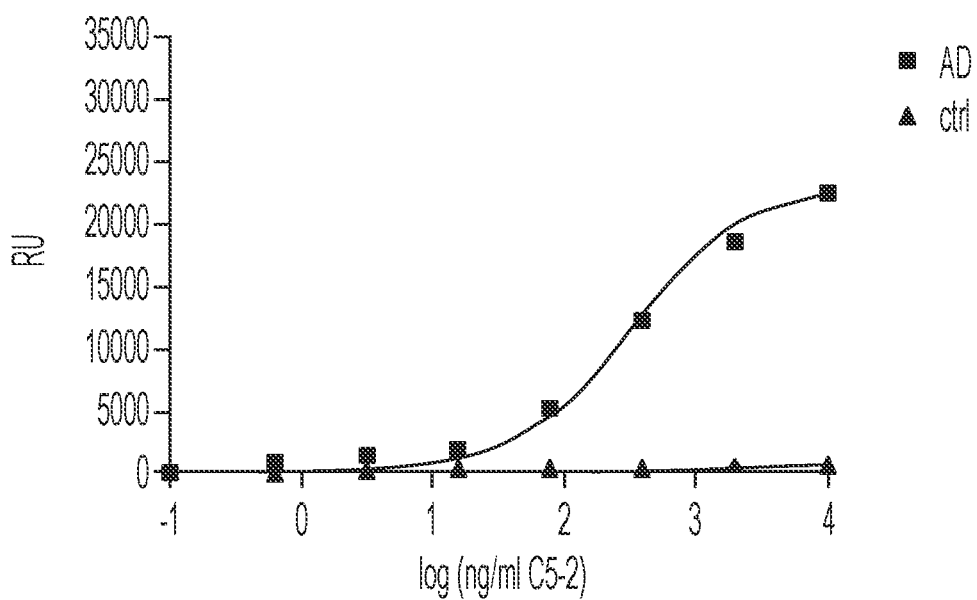
Figure 3C:
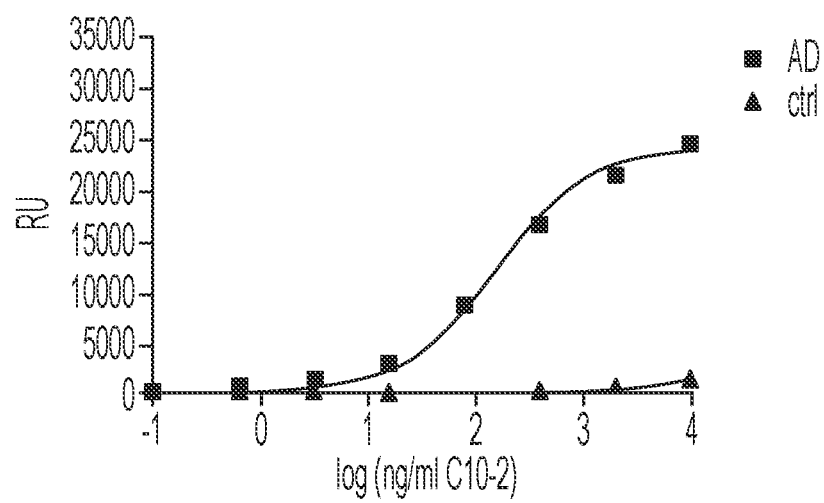
Figure 3D:
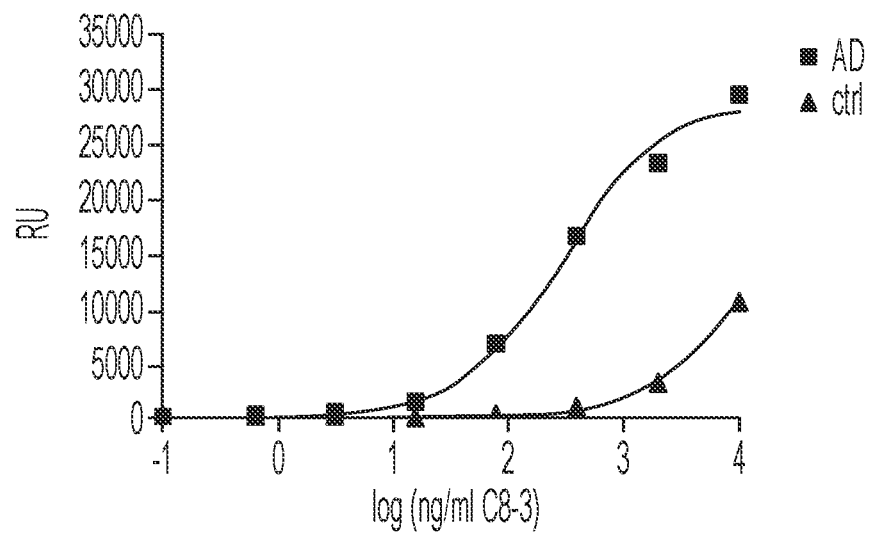
Figure 4A:
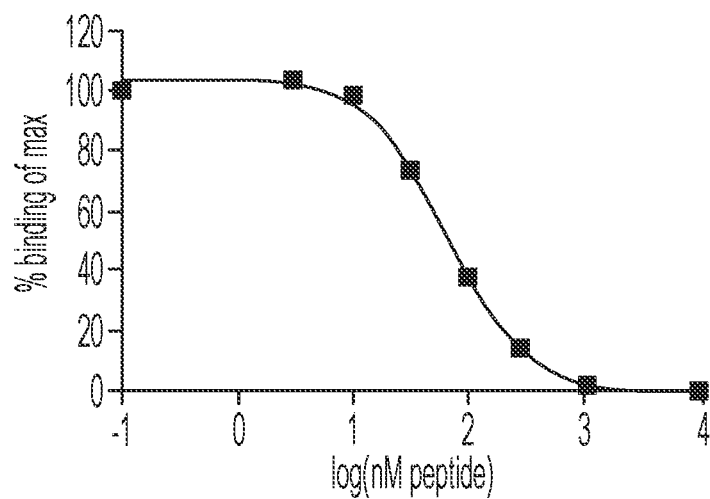
FIGS. 4A-4D: Peptide affinity and pS396 selectivity (peptide binding)
Figure 4B:
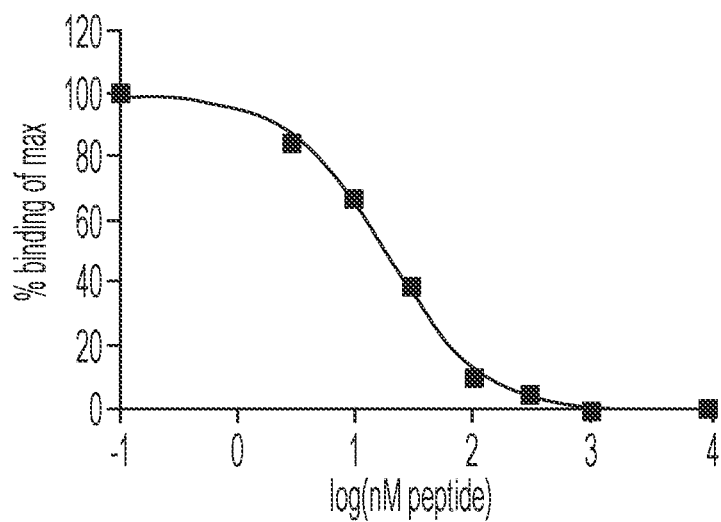
Figure 4C:
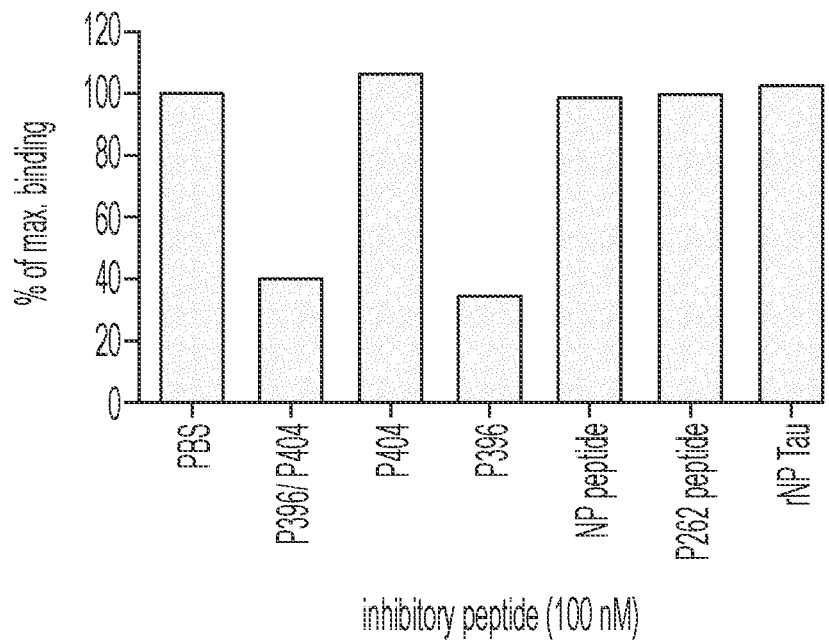
Figure 4D:
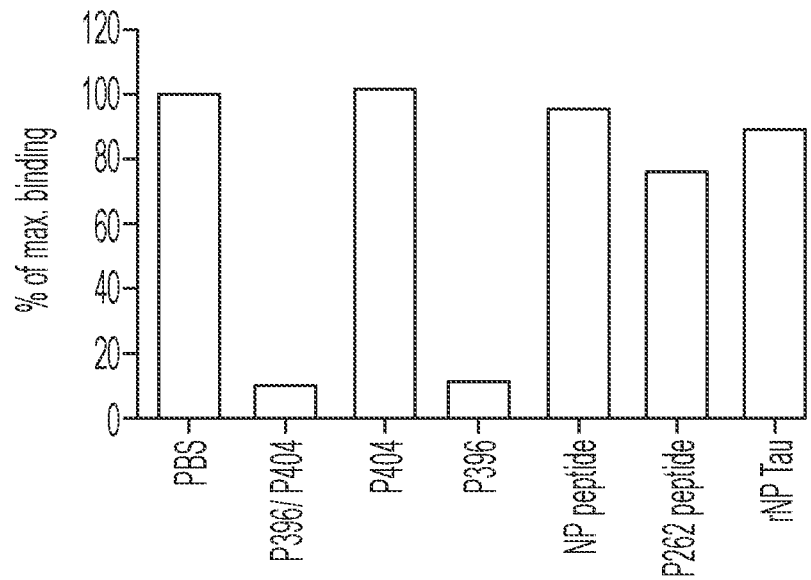
Figure 5A:
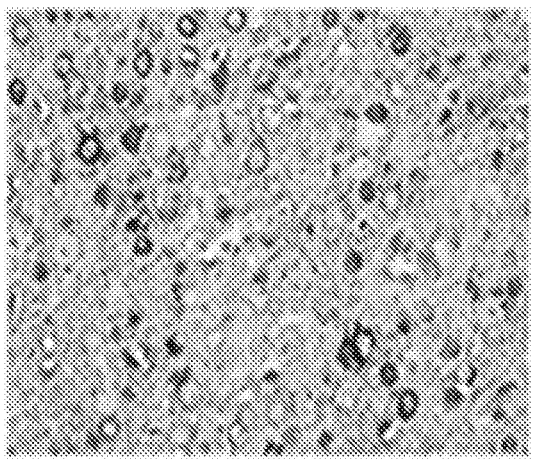
FIGS. 5A-5B: Histological characterisation of pathology specific antibodies
Figure 5A:
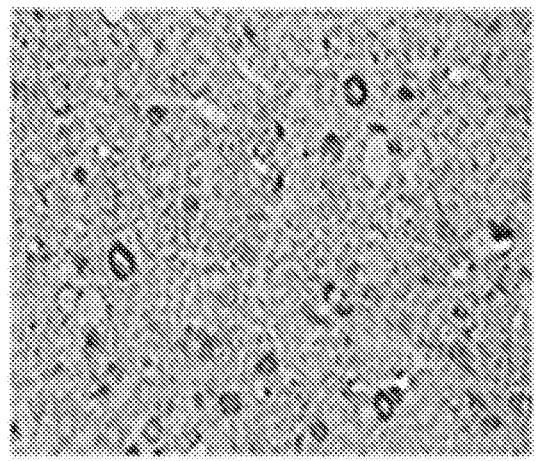
Figure 5A:
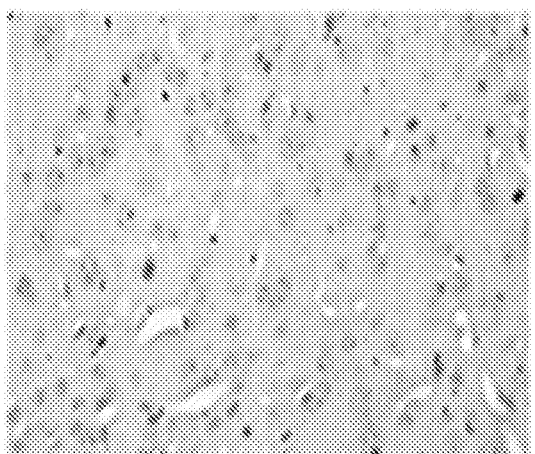
Figure 5A:
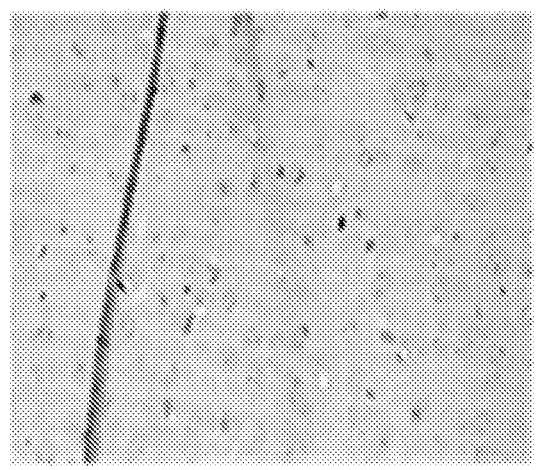
Figure 5B:
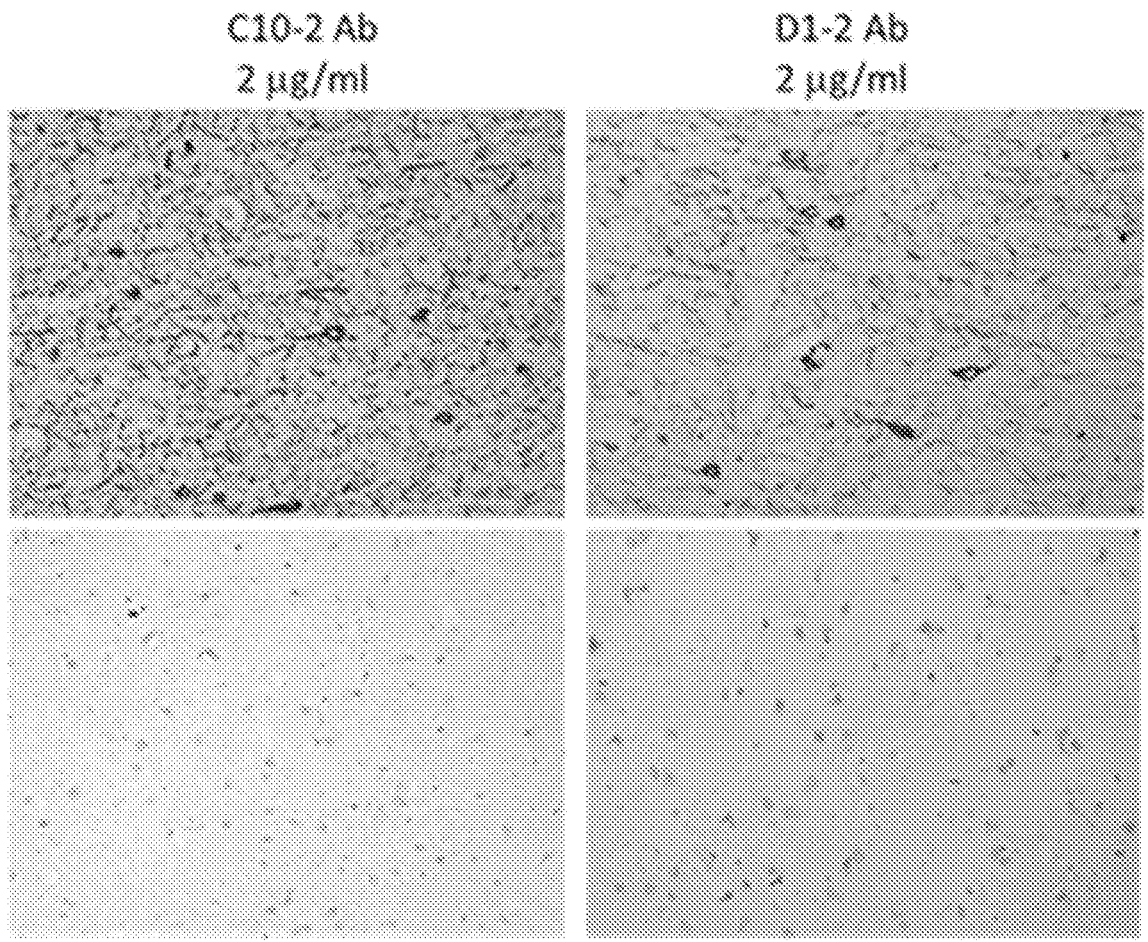
Figure 6A:
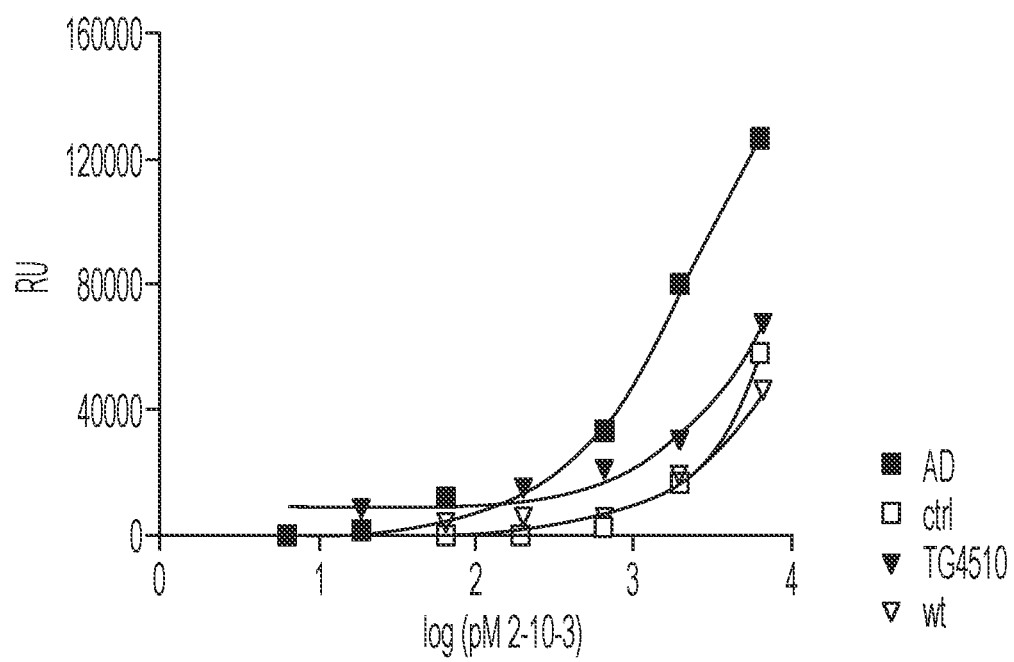
Figure 6C:
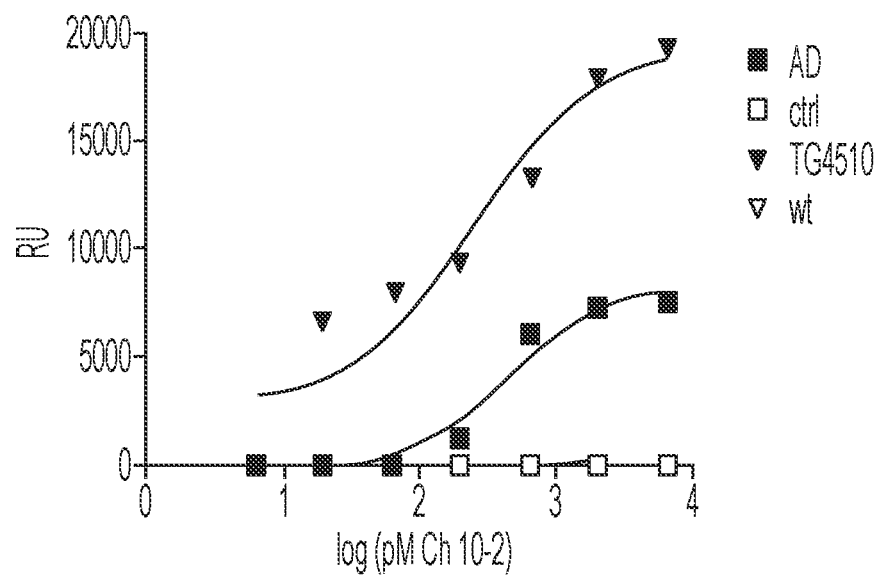
Figure 6D:
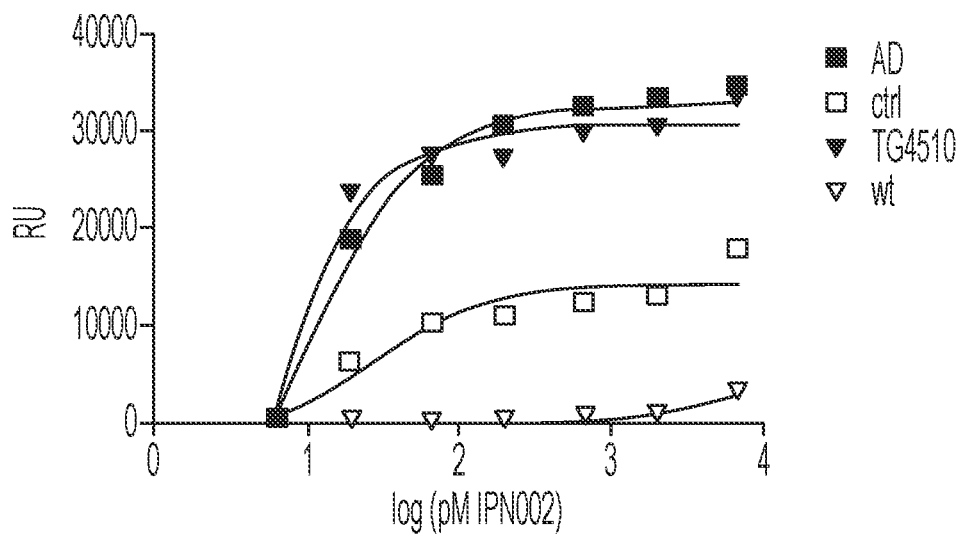
Figure 6E:
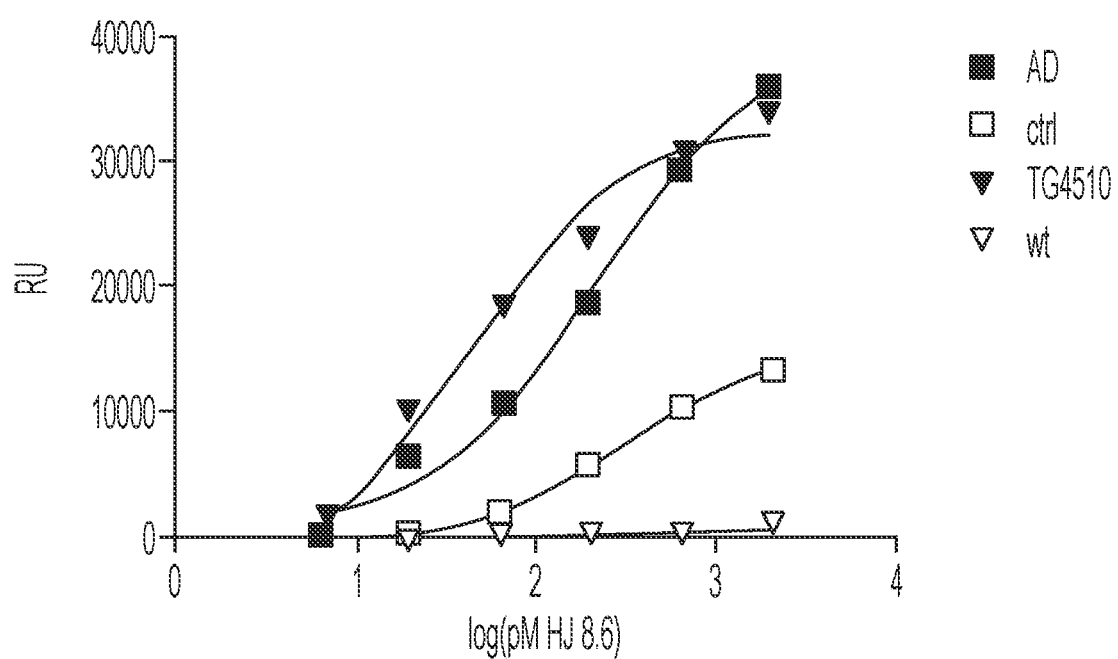

Fractionated tissue extracts S1 and P3 were dissolved in SDS-sample buffer containing 0.1 M DTT. The heat-treated samples (95° C. for 10 min) were separated by gel electrophoresis on 4-12% Bis-Tris SDS-PAGE gels (Invitrogen) and transferred onto PVDF membranes (BioRad Laboratories, Hercules, Calif.). Dot blot samples were spotted directly onto nitrocellulose membranes (Amersham, Pittsburgh, Pa.) at known concentrations across samples. Both Western and dot blot membranes were blocked in 5% non-fat dry milk in TBS-Tween (0.5%) pH 7.4, followed by incubation in 1 µg/ml D1.2 or C10-2 overnight at 4° C. Membranes were washed and incubated with peroxidase-conjugated anti-mouse IgG (1:5000; Jackson ImmunoResearch, West Grove, Pa.). Bound antibodies were detected using an enhanced chemiluminescence system (ECL PLUS kit; PerkinElmer). Quantitation and visual analysis of Western and dot blot immunoreactivity was performed with a computer-linked LAS-4000 BioImaging Analyzer System (Fujifilm, Tokyo, Japan) and Multi Gauge v3.1 software (Fujifilm). Protein loading was adjusted by the volume of original fractions and can be converted to original tissue wet weight. Results are shown in FIG. 1 and FIG. 2.

Example 4 Screening and Selection of 396/404 Antibodies Using Immobilized Human Pathological Material Hybridoma supernatants were screened for antibody binding in nunc plates coated with 1 µg/ml peptide phosphorylated tau 386-408 (pS396/pS404) using 0.1 M carbonate buffer pH 9.

Positive supernatants were subsequently diluted 1:50-1:800 in PBS, 0.1% BSA and 0.1 NP40 for binding in ELISA or MSD plates coated with brain (P3 pellet, see Example 3) lysate antigens from AD and healthy controls (HC), respectively. Brain lysate antigens were diluted 1500 fold in 0.1 M Carbonate buffer pH9 prior to incubation/coating of ELISA or MSD plates. Wells were subsequently blocked 2 hrs at room temperature (PBS, 3 mg/ml BSA, 0.1% NP-40) and antibody binding activity detected with HRP (DAKO) and sulfotag (MSD, product #) conjugated anti-mouse IgG following vendor protocol. Selections of antibodies (D1-2, C5-2, C8-3 and C10-2) diluted in PBS with 0.1% BSA were characterised by dose response and showed sub-nanomolar-nanomolar binding activity to AD-P3 antigen coated plates were furthermore characterised for binding-activity to selection of specific and control peptides. Results are shown in FIG. 3.

Example 5: Peptide Specificity and Binding Affinity

Antibodies positive for binding to pathological tau were further characterised for apparent affinity (IC50) and selectivity/specificity to a range of phospho-peptide (p) epitopes. MSD plates were coated with 100 ng/ml phosphorylated tau 386-408 (pS396/pS404) as described above. Antibodies against phosphorylated tau were analysed in dose response assays to identify antibody concentrations providing appropriate analytical signal level (typical 5,000-20,000 RU in MSD corresponding to 0.5-2% of maximal instrumental signal or OD signals of 1.0-1.5 at 450 nm in ELISA. A selection of antibodies was incubated with graded concentrations (0-1000 nM) of phosphorylated tau 386-408 (pS396/404) for 2 hrs/room temperature. The reactions were subsequently applied to peptide coated MSD plates coated with 100 ng/ml peptide phosphorylated tau 386-408 (pS396/pS404) as described above and binding activity measured. IC50 values from the inhibition assays correspond to apparent affinities (KD) between 10-100 nM.

Specificity and phospho-selectivity: An appropriate concentration of monoclonal antibody was incubated with 100 nM double phosphorylated (pS396/pS404) non-phosphorylated or monophosphorylated (pS396 or pS404) phosphorylated tau 386-408 and analysed for binding activity (inhibition assays). Control phosphorylated tau peptides (phosphorylated tau 260-270 (pS262) or phosphorylated tau 240-270 (pS262) and recombinant non-phosphorylated tau protein was analysed for comparison. All AD-P3 antigen positive antibodies showed strong preference for phosphorylated peptide tau 386-408 (pS396/pS404) and monophosphorylated peptide phosphorylated tau 386-408 (pS396) and no binding activity for mono-phosphorylated peptide phosphorylated tau 386-408 (pS404) and non-phosphorylated peptide tau 386-408. Control phosphor-peptides tau 240-270 and phosphorylated tau. Results are shown in FIG. 4 and FIG. 32.

Example 6: Histological Characterization of Antibodies by Immunohistochemistry

Mouse brain tissues were collected from 8 months old rTg4510 mice (overexpressing human P301L-tau under the CamKII promoter) and non-transgenic littermate (non-Tg), fixed in 4% paraformaldehyde and embedded in paraffin. Paraffin-embedded human brain samples of frontal cortex were acquired from Tissue Solutions (Glasgow, UK). Tissue from donors with diagnosed end stage Alzheimer's disease was compared to age-matched non-demented control donors. Four um thick sections were deparaffinized and subjected to antigen retrieval by microwaving the sections in 10 mM Citrate buffer, pH 6, for 10 minutes. Endogenous peroxidases were blocked with 1% hydrogen peroxidase followed by 5% normal swine serum in PBS/1% BSA/0.3% Triton X-100 (PBS-BT). Sections were incubated overnight at 4° C. with D1.2 and C10-2 antibodies diluted in PBS-BT at a range of concentrations. The sections were washed in PBS, 0.25% BSA, 0.1% Triton X-100, before being incubated with a biotinylated secondary swine anti-mouse antibody (E0464; DAKO, Glostrup, Denmark) at 1:500 for 1 hour. Following additional washing, StreptAvidin-Biotin Complex kit (Vector Laboratories, Burlingame, Calif.) was applied and immunoreactivity was visualized with diaminobenzidine. Sections were counterstained with hematoxylin. Results are shown in FIG. 5.

Example 7: Selectivity of Antibodies Towards Pathological Tau

MSD plates were coated with solubilized P3 antigens from AD brain (diluted 1:1500) or TG4510 brain (diluted 1:3000). Results are shown in FIG. 6.

Detection is performed as described in Example 4 above.

Example 8: HEK Cell Seeding Assay

HEK293 cells were transiently transfected with human tau-P301L-FLAG in 6-well plates 24 h after plating, followed 24 h later by incubation with brain homogenate for 24 h, followed by splitting and replating cells and harvesting after an additional 24 h. Cells were lysed and sonicated in PBS, supplemented with 1% triton X, Phos-stop and complete phosphatase and protease inhibitors (Roche) buffer and ultracentrifugated at 100,000×g for 30 min. The pellet was resuspended in SDS, sonicated and ultracentrifugated for 30 min at 100,000×g. Supernatants were analyzed by western blotting. Cells expressing human tau-P301L showed insoluble (SDS fraction, E1/FLAG detection), hyperphosphorylated {D1.2}pS396 detection) tau upon seeding with total brain homogenates from rTg4510 tau transgenic mice. Cells treated with control brain homogenate from mice showed an absence of aggregated hyperphosphorylated human tau. Additionally, total cell lysates of HEK293 cells were analyzed using the tau aggregation assay from Cisbio.

This assay is based on time-resolved fluorescence using the same antibody for both donor (Tb3$_+$ conjugated) and acceptor (d2 conjugated) antibody in FRET. A 10 µl sample was mixed with 10 µl antibody mix and incubated for 20 h. The plate was read on the Pherastar plate reader to assess time-resolved fluorescence (FRET signal measured/integrated after switching of the excitation light). The assay measures aggregated tau both in human autopsy material, rTg4510 mice and in seeded HEK cells with high specificity and sensitivity. Results are shown in FIG. 7 and show that the seeding effect was not affected by treatment with HEL, but was partially reversed by treatment with tau antibodies (C10-2>D1.2>hACI36-2B6-Ab1).

Example 9: Reversal of Functional (Electrophysiology (Elphys)) Response in-Vivo for D1.2 and C10-2

In vivo electrophysiological assessment of synaptic transmission and plasticity in the CA1 area of the hippocampus in 4.5 to 5.5 months old rTg4510 and tTA control mice showed that i) basal synaptic transmission is significantly impaired in rTg4510 compared to tTA mice, and ii) paired-pulse facilitation is significantly reduced rTg4510 compared to tTA mice.

All experiments were carried out in accordance with the European Communities Council Directive (86/609/EEC) for the care and use of laboratory animals and the Danish legislation regulating animal experiments.

rTg4510 and tTA male mice (Taconic Europe A/S) aged 5 to 5.5 months were used in the present study at the time of the recordings. Mice were grouped-housed in controlled temperature (22±1.5° C.) and humidity conditions (55-65%) and kept in a 12:12 hour light/dark cycle (lights on at 06:00 h). Food and water were available ad libitum.

Animals were anesthetized with an intraperitoneal (i.p.) injection of urethane (1.2 g/kg). Mice were then mounted in a stereotaxic frame, their temperature adjusted to 37.5° C. via a heating pad, and the skull was exposed. A platinum wire was placed in the frontal bone to act as a reference, and an additional hole was drilled for insertion of the recording and stimulating electrodes in the hippocampus, at the following coordinates according to the atlas of Paxinos and Franklin (Paxinos and Franklin, 2001): recording, 1.5-1.7 mm posterior to Bregma, 1.0-1.2 mm lateral to the midline, 1.4-1.7 mm below the surface of the brain; stimulation, 1.8-2.0 mm posterior to Bregma, 1.5-1.7 mm lateral to the midline, 1.3-1.7 mm below the surface of the brain. Animals were left in the stereotaxic frame throughout the whole duration of the recordings and their level of anesthesia was regularly checked.

Field potentials (fEPSP) were evoked in the CA1 by electrical stimulation of the Schaffer collateral every 30 s, and the depth of the recording electrode was adjusted until a negative fEPSP was recorded in response to a unipolar square pulse. The slope of the evoked fEPSP was typically measured between 30 and 70% of the maximum amplitude of the fEPSP.

Once an optimal fEPSP was induced, basal synaptic transmission was assessed by the relationship between stimulation intensity and slope of the evoked fEPSP (input-output relationship). The different intensities of stimulation were 0, 25, 50, 75, 100, 150, 200, 300, 400, and 500 pA, and were applied successively in increasing order, with 2 to 3 repeats at each intensity. Basal synaptic transmission was found to be significantly impaired in rTg4510 compared to tTA mice.

Paired-pulse facilitation, a short-term synaptic plasticity believed to rely on presynaptic mechanisms, was further measured in rTg4510 and tTA mice. Briefly, a pair of stimuli with an inter-stimulus interval (ISI) varying from 25 to 1000 ms was applied to the Schaffer collateral, and the slope of the second fEPSP was compared to the slope of the first fEPSP. Facilitation was observed at all ISIs, with a maximum facilitation at ISIs of 50 and 75 ms. Interestingly, a significantly lower PPF was observed in rTg4510 mice when compared tTA mice.

The identified impairments in basal synaptic transmission and paired-pulse facilitation in rTg4510 mice were further used as readout to test antibody efficacy.

Recordings were performed in all experiments 2 to 4 days following administration of 4 doses of antibody twice per week for 2 weeks, i.p.). Basal synaptic transmission and paired-pulse facilitation were recorded in both hippocampi in each animal when possible, and further used as individual experiments. Results are shown in FIG. 8 and show antibody reversal of paired pulse facilitation and basal synaptic transmission deficits in CA1 evoked field potentials.

Example 10: Immunodepletion of Tau from rTg4510 Brain Extracts

60 µg mouse and humanized C10-2 antibody was immobilized to 300 µl of Magnetic dynabead suspension (Immunoprecipitation Kit Dynabeads Protein G Novex, Cat no 10007D). After thorough washing the beads were mixed with 60 µl rTg4510 brain extract and incubated at room temperature for 10 minutes. The magnetic beads were separated from the extract and the extracts were analysed by western blot. Depletion with mC10-2 and hC10-2 removed tau aggregates 99 and 99.5% respectively. Results are shown in FIG. 12.

Example 11: HEK Cell Seeding Assay Using Immunodepleted Extracts

HEK293 cells were transiently transfected with human tau-P301L-FLAG in 6-well plates. 24 h later cells were incubated with brain homogenate that had been immunodepleted using humanized or mouse C10-2. After 24 h cells were re-plated and harvested after an additional 24 h. Cells were lysed and sonicated in TBS, supplemented with 1% triton X, phosphatase and protease inhibitors (Roche) and ultracentrifugated at 100,000×g for 30 min. The pellet was resuspended in 1% SDS, sonicated and ultracentrifugated for 30 min at 100,000×g. Supernatants were analyzed by western blotting. Cells expressing human tau-P301L showed insoluble (SDS fraction, E1/FLAG detection), hyperphosphorylated tau (D1.2/pS396 Tau, running at a higher molecular weight) upon seeding with total brain homogenates from rTg4510 tau transgenic mice. Cells treated with control brain homogenate from tTA mice showed an absence of aggregated hyperphosphorylated human tau. Additionally, total cell lysates of HEK293 cells were analyzed using the tau aggregation assay from Cisbio. Depletion with HEL and hHEL antibodies did not affect seeding, whereas depletion with mC10-2 and hC10-2 prevented tau aggregation 88 and 96% and insoluble tau 97 and 100% respectively. Results are shown in FIG. 13.

Example 11: Immunodepletion of Tau from rTg4510 Brain Extracts

100 µg mouse C10-2, D1.2 and Tau5 (Invitrogen) antibody was immobilized to 500 µl of Magnetic dynabead suspension (Immunoprecipitation Kit Dynabeads Protein G Novex, Cat no 10007D). After thorough washing the beads were mixed with 100 µl rTg4510 brain extract and incubated at room temperature for 10 minutes. The magnetic beads were separated from the extract and the extracts were analysed by western blot. C10-2 and D1.2 do not remove the normal Tau from the homogenates, as the commercially available Tau5 antibody does. In contrast, two antibodies of the invention specifically remove the hyperphosphorylated tau (64 kDa) by 95%, that is tau phosphorylated on serine 396. Results are shown in FIG. 14.

Example 12: Immunodepletion of Tau from Alzheimer's Brain Extracts

100 µg mouse C10-2 and D1 antibody was immobilized to 500 µl of Magnetic dynabead suspension (Immunoprecipitation Kit Dynabeads Protein G Novex, Cat no 10007D). After thorough washing the beads were mixed with 100 µl Alzheimer brain extract and incubated at room temperature for 10 minutes. The magnetic beads were separated from the extract and the extracts were analysed by western blot. D1.2 and C10-2 does only remove a very small fraction of the total tau in the brain homogenate (8%). The antibodies do however specifically remove the hyperphosphorylated tau (90%), specific for AD patients. Results are shown in FIG. 15.

Example 13: Seeding in rTg4510 Mice Using Immunodepleted Extracts

Transgenic mice expressing human mutated Tau (P301L ON4R) under a tet-off responsive element in CamK2 positive neurons (rTg4510) was used. This model normally starts developing Tau pathology at 3 months of age, but by feeding the mothers with doxycycline during pregnancy and for the first 3 weeks of the pup's life, the pathology develops at a later stage (starting after 6 months of age). The doxycycline pre-treated mice used in the studies were 2.5 months old at the time-point of injection. Mice were anesthetized by isoflouran inhalation fixed in a stereotactic frame. The scull was exposed and adjusted until bregma and lambda was in level. A hole was drilled in the scull 2 mm lateral (right) and 2.4 mm posterior of the bregma. A 10 µl syringe beveled tip (SGE) was used to inject the seeding material 1.4 mm ventral to the brain surface at the at the above mentioned co-ordinates. 2 µl of the immunodepleted extracts, described in Examples 11 and 12, was slowly infused at the site (1 µl/minute) and the syringe was left for 5 minutes before removing it. The wound was closed by stiches and mice were heated while waking up. The mice were housed for 3 months and then sacrificed and perfusion fixed with 4% PFA.

Immunohistochemistry: Fixed brains were cut into 35 µm coronal sections at NSA and every 6$^{th}$ section was stained for Tau tangles (Gallyas silver stain) and for hyperphosphorylated Tau (AT8). Positively stained neurons (soma) were counted in ipsi- and contralateral sides of hippocampi of all brains. All sub-regions of hippocampus were included. Eight sections were counted per brain. Results reflect the sum of positive neurons from the 8 sections. The background signal was determined in 2 non-injected mice. By removing hyperphosphorylated tau from the homogenates, the homogenates do no longer induce seeding of Tau pathology. Results are shown in FIG. 16. Quantification of Tau pathology in rTg4510 brains seeded with rTg4510 (A) or AD (B) brain homogenates. Prior to seeding the hyperphosphorylated Tau, but not normal Tau, had been reduced in the homogenates by 90-95% by using C10-2 or D1.2. By removing hyperphosphorylated tau from the homogenates, the homogenates no longer induce seeding of Tau pathology.

Homogenates from rTg4510 or Alzheimer brains can seed Tau pathology in rTg4510 mice at a stage when endogenous Tau pathology has not developed. By removing the hyperphosphorylated Tau from the homogenates by using D1.2 or C10-2, as described in Examples 11 and 12. the seeding activity is abolished.

Example 14: Antibody Treatment in Seeded rTg4510 Mice

Doxycyclin treated rTg4510 mice (as described in Example 13) were chronically treated with mouse D1.2 or control antibody, 15 mg/kg/week starting at 2 months of age. At 2.5 months rTg4510 brain extract was infused into the hippocampus (as described in Example 13). Mice were sacrificed 1, 2 and 3 months after the brain infusion and immunohistochemistry and the following analysis was performed as described in Example 13. D1.2 treatment significantly reduced Tau pathology 2 and 3 months after seeding had been initiated. Results are shown in FIG. 17.

Quantification of tangle bearing neurons in hippocampus of seeded rTg4510 mice. The pathology increase with time and by treating the mice with D1.2 the pathology is significantly lower 2 and 3 months after seeding. Quantification of tangle bearing neurons in hippocampus of seeded rTg4510 mice. The pathology increase with time and by treating the mice with D1.2 the pathology is significantly lower 2 and 3 months after seeding.

Homogenates from rTg4510 or Alzheimer brains can seed Tau pathology in rTg4510 mice at a stage when endogenous Tau pathology has not developed. By systemically treating the mice with D1.2 the development of tau pathology can be significantly reduced.

Example 15: Immunodepletion of Tau from Alzheimer's Brain Extracts Using Humanized Tau Antibodies 100 µg mouse and humanized C10-2 as well as prior art antibodies 2.10.3 and HJ8.5 antibody (source) was immobilized to 500 µl of Magnetic dynabead suspension (Immunoprecipitation Kit Dynabeads Protein G Novex, Cat no 10007D). After thorough washing the beads were mixed with 100 µl Alzheimer brain extract and incubated at room temperature for 10 minutes. The magnetic beads were separated from the extract and the extracts were analysed by western blot and the CisBio assay. The mouse and humanized C10-2 efficiently removed 93 and 97% of the pS396 phosphorylated Tau, but only 22 and 17% of the total Tau compared to the hHeI control antibody. The 2.10.3 antibody removed 91% of Serine 396 phosphorylated tau and 10% of total tau. It seems like the 2.10.3 is less efficient in removing one of the hyper phosphorylated bands in comparison to the C10-2 antibodies (the middle 64 kDa band). The HJ8.5 antibody has a completely different profile then both the C10-2 and 2.10.3 antibodies, by removing the majority of tau, 89% of total tau and 88% of pS396 Tau. Results are shown in FIGS. 23-24.

Example 16: Immunodepletion of Aggregated Tau from Alzheimer's Brain Extracts Using Humanized Tau Antibodies The immunodepleted AD extracts described in Example 13 was also analysed by using the Tau aggregation assay described in example 10. The C10-2 and HJ8.5 antibodies are more efficiently removing aggregated Tau from the AD material then the 2.10.3 antibody. In order of efficiency: HJ8.5 (99%), hC10-2 (98%), mC10-2 (96%) and 2.10.3 (90%) all in comparison to hHeI antibody. Results are shown in FIG. 25.

Example 17: Immunodepletion of Tau

25 µg antibody (humanized C10-2 or 2.10.3) was immobilized to 125 µl of Magnetic dynabead suspension (Immunoprecipitation Kit Dynabeads Protein G Novex, Cat no 10007D). After thorough washing the coated beads were mixed with variable amounts of non-coated, washed beads. Starting from 100% Ab coated beads, corresponding to 5 µg antibody, down to 100% non-coated beads. The total amount of beads was the same in all samples. The beads were mixed with 20 µl AD extract and incubated at room temperature for 10 minutes. The magnetic beads were separated from the extract and the extracts were aliquoted, snap frozen and kept at −80 C until use.

Analysis of Depletion Using Western Blot

Samples were boiled in 1×LDS loading buffer and 100 mM DTT. A volume corresponding to 3 µl of extracts were loaded on a 4-12% Bis-Tris NuPAGE Gel (LifeTech Novex). After electrophoresis, the proteins were blotted over to a Immobilon-FL PVDF membrane (0.45 µm, IPFL10100, Millipore). The membrane was blocked with SEA blocking buffer (Prod #37527, Thermo). Tau and P-tau levels were assessed in the samples using Tau5 (Abcam ab80579, 1:2000) mouse C10-2 (1 µg/ml), P-S199/202 (Invitrogen 44768 G, 1:1000), P-S422 (Abcam ab79415, 1:750), human IPN (1 µg/ml). Gapdh and actin were used as a loading controls (Abcam ab9484, 1:2000, Sigma A5441, 1:20000). Secondary fluorophore conjugated IgG antibodies was used (IRDye 800CW Goat anti-Human, IRDye 800CW, Goat anti-rabbit, IRDye 680 Goat anti-mouse, LI-COR biosciences) and the signal was quantified using Odyssey CLx and Image studio software (LI-COR biosciences).

Quantification of individual bands as well as signal in whole lanes was done and from this sigmoidal dose-response curves were plotted and when possible max effect and EC50 values were estimated.

Results

Both antibodies remove a small fraction of tau from the Alzheimer brain preparation. 2.10.3, designed to have specificity for P-S422 tau removes up to 24% of the total tau amount, while C10-2 removes up to 15% of the total tau (see FIG. 26).

2.10.3 and C10-2 both remove more than 90% of the tau phosphorylated at Serine 422 although the amount of antibody needed to remove 50% of the P-S422 tau differ, for 2.10.3, 0.42 µg antibody is needed and for C10-2, 0.27 µg is needed for the same effect (see FIG. 27).

C10-2 efficiently remove Tau being phosphorylated at serine 396 (Max effect: 88% and half of the effect is reached by using 0.30 mg antibody). 2.10.3 removes a smaller fraction of tau being phosphorylated at the serine 396 (Max effect: 60% and half of that effect is reached when using 0.63 µg antibody)(see FIG. 28). This indicates that all Tau being phosphorylated at serine 422, also is phosphorylated at serine 396, but that there is a portion of hyperphosphorylated tau being phosphorylated at serine 396 where the phosphorylated serine at position 422 is not present.

A large portion of the tau, being removed by C10-2, is also phosphorylated at Serine 199/202, since 69% of the tau having that phosphporylation is affected by the immunodepletion (50% of the effect when using 0.34 µg antibody) (see FIG. 29). The 2.10.3 immunodepletion does not give a sigmoidal dose response on the P-S199/202 tau although a drop in signal is seen with increasing amount of antibody (max 52% reduction when using the max amount of antibody (5 µg)(see FIG. 29).

This data indicates that the C10-2 antibody targeting the phosphorylated serine 396 binds a larger pool of the hyperphosphorylated tau then the 2.10.3 antibody targeting the phosphorylated serine at the 422 position.

Example 18: Antibody Mediated Inhibition of mC10-2 Specific Capture of Pathological Tau Antigens in AD Brain Lysates Materials and Methods Material Coating buffer: Carbonate buffer pH 8.5, 150 mM NaCL. Blocking buffer: 3% BSA (fraction V), 0.1% NP40 in PBS pH7.4. Washing buffer: 0.1% BSA (fraction V), 0.1% NP40 in PBS, pH 7.4. Sulfotag goat total humanized Tau antibody (MSD D221LA-1, 50 µg/ml)

Method aim to measure capture of pathological human Tau antigens from AD brains using C10-2 coated plates (step A) after incubation of Tau antigens with increasing concentrations of pS396 specific antibodies (step B). The Tau antigen capture and antibody mediated inhibition was detected using sulfo-tagged anti human (total) Tau antibodies from MSD A: MSD plates were coated (o/n at 4C) with 0.5 µg/ml mC10-2 (capture antibody) in coating buffer and subsequently blocked for 1 hour at room temperature) and washed 3 times. (FIG. 30)

B: Samples P3 lysate (1:1000=2-4 µg/ml total protein) and/or S1(p) (1:300=20-40 ng/ml total protein) from AD (pool from 3 patient) were mixed with graded concentrations of pS396 peptide epitope specific antibody and incubated for 1 hour at room temperature. The reactions were subsequently incubated 2 hours on plates prepared in step A. (FIG. 31)

C: C10-2 captured Tau was detected using sulfo-tagged human tau. Tau antibody (1:50) from MSD following manufacture instruction. Plates were analyzed on MSD SECTOR® S 600. AD P3 and AD S1(p) was tested in similar setup. (FIG. 33/34)

TABLE 5A

| mouse C10-2, + tau peptide, 10 µM | mean Signal | signal | signal |
|---|---|---|---|
| PBS/0.1% BSA | 388 | 403 | 373 |
| C10-2 3 ng/ml | 366 | 384 | 348 |
| C10-2 10 ng/ml | 383 | 398 | 367 |
| C10-2 30 ng/ml | 345 | 384 | 306 |
| C10-2 100 ng/ml | 357 | 401 | 313 |
| C10-2 300 ng/ml | 407 | 434 | 379 |
| C10-2 1000 ng/ml | 451 | 462 | 439 |
| C10-2 10000 ng/ml | 870 | 920 | 820 |

TABLE 5B

| mouse C10-2, + PBS/0.1% BSA | mean Signal | signal | signal |
|---|---|---|---|
| PBS/0.1% BSA + PBS | 303 | 293 | 312 |
| C10-2 3 ng/ml + PBS | 1881 | 1890 | 1871 |
| C10-2 10 ng/ml + PBS | 5721 | 5863 | 5579 |

TABLE 5B-continued

| mouse C10-2, + PBS/0.1% BSA | mean Signal | signal | signal |
|---|---|---|---|
| C10-2 30 ng/ml + PBS | 11922 | 12044 | 11799 |
| C10-2 100 ng/ml + PBS | 21833 | 21925 | 21741 |
| C10-2 300 ng/ml + PBS | 30410 | 30311 | 30508 |
| C10-2 1000 ng/ml + PBS | 38524 | 38233 | 38814 |
| C10-2 10000 ng/ml + PBS | 51171 | 51253 | 51089 |

TABLE 5C

| mouse clone PHF 13, + tau peptide, 10 μM | mean Signal | signal | signal |
|---|---|---|---|
| PBS/0.1% BSA | 287 | 286 | 287 |
| PHF 13 1000000 | 280 | 284 | 276 |
| PHF 13 300000 | 299 | 305 | 292 |
| PHF 13 100000 | 355 | 370 | 340 |
| PHF 13 30000 | 481 | 472 | 490 |
| PHF 13 10000M | 953 | 1019 | 886 |

TABLE 5C-continued

| mouse clone PHF 13, + tau peptide, 10 μM | mean Signal | signal | signal |
|---|---|---|---|
| PHF 13 3000 | 2182 | 2279 | 2084 |
| PHF 13 1000 | 6896 | 7542 | 6249 |

TABLE 5D

| mouse clone PHF 13, ± PBS/0.1% BSA | mean Signal | signal | signal |
|---|---|---|---|
| PBS/0.1% BSA + PBS | 281 | 282 | 280 |
| PHF 13 1000000 + PBS | 335 | 358 | 312 |
| PHF 13 300000 + PBS | 560 | 568 | 551 |
| PHF 13 100000 + PBS | 852 | 856 | 847 |
| PHF 13 30000 + PBS | 1579 | 1661 | 1496 |
| PHF 13 10000 + PBS | 2882 | 2899 | 2864 |
| PHF 13 3000 + PBS | 5792 | 6126 | 5458 |
| PHF 13 1000 + PBS | 12639 | 13654 | 11624 |

Table 5A-5D:Tau Antigen Capture Inhibition

The invention claimed is:

1. An immunoglobulin molecule comprising
   (a) a Light Chain CDR1 having the amino acid sequence of SEQ ID NO:17;
   (b) a Light Chain CDR2 having the amino acid sequence of SEQ ID NO:18;
   (c) a Light Chain CDR3 having the amino acid sequence of SEQ ID NO:19;
   (d) a Heavy Chain CDR1 having the amino acid sequence of SEQ ID NO:20;
   (e) a Heavy Chain CDR2 having the amino acid sequence of SEQ ID NO:21; and
   (f) a Heavy Chain CDR3 having the amino acid sequence of SEQ ID NO:22.

2. The immunoglobulin molecule according to claim 1, wherein said immunoglobulin molecule is a monoclonal antibody or a bispecific antibody having an Fc domain.

3. The immunoglobulin molecule according to claim 1, wherein said immunoglobulin molecule is an epitope-binding fragment of a monoclonal antibody that is selected from the group consisting of: an Fv fragment, an Fv fragment fused to an Fc domain, a Fab fragment, a Fab' fragment, a F(ab)$_2$ fragment, a single $V_H$ variable domain and a single $V_L$ variable domain.

4. The immunoglobulin molecule according to claim 1, wherein said immunoglobulin molecule is a humanized antibody.

5. The immunoglobulin molecule according to claim 1, comprising the heavy chain of SEQ ID NO:24 and/or the light chain of SEQ ID NO:23.

6. A pharmaceutical composition comprising immunoglobulin molecule according to claim 1, and a pharmaceutical acceptable carrier.

7. A nucleic acid encoding the immunoglobulin molecule according to claim 1.

8. A method of treating Alzheimer's disease or other tauopathy in a subject in need thereof, said method comprising administering to said subject an effective amount of the immunoglobulin molecule of claim 1.

9. A method of diagnosing or imaging Alzheimer's disease or other tauopathy in a subject in need thereof, wherein said method comprises administering to said subject an amount of the immunoglobulin molecule of claim 1 sufficient to detect or measure the presence or amount of said hyperphosphorylated variant of human tau in the brain of said subject.

10. A method of treating Alzheimer's Disease in a subject in need thereof, wherein said method comprises administering to said subject an amount of the immunoglobulin molecule of claim 1 sufficient to reduce or attenuate the accumulation of pathological tau protein in said patient.

11. The immunoglobulin molecule of claim 1, wherein the immunoglobulin molecule is capable of immunospecifically binding to the phosphorylated residue 396 of human tau (SEQ ID NO:33).

* * * * *

```
                          SEQUENCE LISTING

<160> NUMBER OF SEQ ID NOS: 37

<210> SEQ ID NO 1
<211> LENGTH: 16
<212> TYPE: PRT
<213> ORGANISM: Artificial
<220> FEATURE:
<223> OTHER INFORMATION: D1.2 CDR 1 Light Chain

<400> SEQUENCE: 1

Arg Ser Ser Gln Ser Leu Val His Ser Asn Gly Asn Thr Tyr Leu His
1               5                   10                  15

<210> SEQ ID NO 2
<211> LENGTH: 7
<212> TYPE: PRT
<213> ORGANISM: Artificial
<220> FEATURE:
<223> OTHER INFORMATION: D1.2 CDR 2 Light Chain

<400> SEQUENCE: 2

Lys Val Ser Asn Arg Phe Ser
1               5

<210> SEQ ID NO 3
<211> LENGTH: 7
<212> TYPE: PRT
<213> ORGANISM: Artificial
<220> FEATURE:
<223> OTHER INFORMATION: D1.2 CDR 3 Light Chain

<400> SEQUENCE: 3

Ser Gln Ser Thr His Val Pro
1               5

<210> SEQ ID NO 4
<211> LENGTH: 13
<212> TYPE: PRT
<213> ORGANISM: Artificial
<220> FEATURE:
<223> OTHER INFORMATION: D1.2 CDR 1 Heavy Chaiin

<400> SEQUENCE: 4
```

```
Lys Ala Ser Gly Asn Thr Phe Thr Asp Tyr Glu Ile His
 1               5                  10
```

<210> SEQ ID NO 5
<211> LENGTH: 17
<212> TYPE: PRT
<213> ORGANISM: Artificial
<220> FEATURE:
<223> OTHER INFORMATION: D1.2 CDR 2 Heavy Chain

<400> SEQUENCE: 5

```
Ala Ile Asp Pro Glu Thr Gly Asn Thr Ala Tyr Asn Gln Lys Phe Lys
 1               5                  10                  15
Gly
```

<210> SEQ ID NO 6
<211> LENGTH: 6
<212> TYPE: PRT
<213> ORGANISM: Artificial
<220> FEATURE:
<223> OTHER INFORMATION: D1.2 CDR 3 Heavy Chain

<400> SEQUENCE: 6

```
Ser Arg Gly Phe Asp Tyr
 1               5
```

<210> SEQ ID NO 7
<211> LENGTH: 219
<212> TYPE: PRT
<213> ORGANISM: Artificial
<220> FEATURE:
<223> OTHER INFORMATION: D1.2 Light Chain

<400> SEQUENCE: 7

```
Asp Val Met Met Thr Gln Thr Pro Leu Ser Leu Pro Val Ser Leu Gly
 1               5                  10                  15

Asp Gln Ala Ser Ile Ser Cys Arg Ser Ser Gln Ser Leu Val His Ser
                20                  25                  30

Asn Gly Asn Thr Tyr Leu His Trp His Leu Gln Lys Pro Gly Gln Ser
            35                  40                  45

Pro Lys Phe Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Phe Thr Phe Gly Ser Gly Thr Lys Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205
```

```
Pro Ile Val Lys Ser Phe Asn Arg Asn Glu Cys
    210                 215
```

<210> SEQ ID NO 8
<211> LENGTH: 451
<212> TYPE: PRT
<213> ORGANISM: Artificial
<220> FEATURE:
<223> OTHER INFORMATION: D1.2 Heavy Chain

<400> SEQUENCE: 8

```
Gln Val Gln Leu Gln Gln Ser Gly Ala Glu Leu Val Arg Pro Gly Ala
1               5                   10                  15

Ser Val Thr Leu Ser Cys Lys Ala Ser Gly Asn Thr Phe Thr Asp Tyr
            20                  25                  30

Glu Ile His Trp Val Lys Gln Thr Pro Val His Gly Leu Glu Trp Ile
        35                  40                  45

Gly Ala Ile Asp Pro Glu Thr Gly Asn Thr Ala Tyr Asn Gln Lys Phe
    50                  55                  60

Lys Gly Lys Ala Arg Leu Thr Ala Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Arg Ser Arg Gly Phe Asp Tyr Trp Gly Gln Gly Thr Thr Leu Thr
            100                 105                 110

Val Ser Ser Ala Lys Thr Thr Pro Pro Ser Val Tyr Pro Leu Ala Pro
        115                 120                 125

Gly Cys Gly Asp Thr Thr Gly Ser Ser Val Thr Leu Gly Cys Leu Val
    130                 135                 140

Lys Gly Tyr Phe Pro Glu Ser Val Thr Val Thr Trp Asn Ser Gly Ser
145                 150                 155                 160

Leu Ser Ser Ser Val His Thr Phe Pro Ala Leu Leu Gln Ser Gly Leu
                165                 170                 175

Tyr Thr Met Ser Ser Ser Val Thr Val Pro Ser Ser Thr Trp Pro Ser
            180                 185                 190

Gln Thr Val Thr Cys Ser Val Ala His Pro Ala Ser Ser Thr Thr Val
        195                 200                 205

Asp Lys Lys Leu Glu Pro Ser Gly Pro Ile Ser Thr Ile Asn Pro Cys
    210                 215                 220

Pro Pro Cys Lys Glu Cys His Lys Cys Pro Ala Pro Asn Leu Glu Gly
225                 230                 235                 240

Gly Pro Ser Val Phe Ile Phe Pro Pro Asn Ile Lys Asp Val Leu Met
                245                 250                 255

Ile Ser Leu Thr Pro Lys Val Thr Cys Val Val Val Asp Val Ser Glu
            260                 265                 270

Asp Asp Pro Asp Val Arg Ile Ser Trp Phe Val Asn Asn Val Glu Val
        275                 280                 285

His Thr Ala Gln Thr Gln Thr His Arg Glu Asp Tyr Asn Ser Thr Ile
    290                 295                 300

Arg Val Val Ser Ala Leu Pro Ile Gln His Gln Asp Trp Met Ser Gly
305                 310                 315                 320

Lys Glu Phe Lys Cys Lys Val Asn Asn Lys Asp Leu Pro Ser Pro Ile
                325                 330                 335

Glu Arg Thr Ile Ser Lys Ile Lys Gly Leu Val Arg Ala Pro Gln Val
            340                 345                 350
```

```
Tyr Ile Leu Pro Pro Ala Glu Gln Leu Ser Arg Lys Asp Val Ser
        355                 360                 365

Leu Thr Cys Leu Val Val Gly Phe Asn Pro Gly Asp Ile Ser Val Glu
    370                 375                 380

Trp Thr Ser Asn Gly His Thr Glu Glu Asn Tyr Lys Asp Thr Ala Pro
385                 390                 395                 400

Val Leu Asp Ser Asp Gly Ser Tyr Phe Ile Tyr Ser Lys Leu Asp Ile
                405                 410                 415

Lys Thr Ser Lys Trp Glu Lys Thr Asp Ser Phe Ser Cys Asn Val Arg
                420                 425                 430

His Glu Gly Leu Lys Asn Tyr Tyr Leu Lys Lys Thr Ile Ser Arg Ser
            435                 440                 445

Pro Gly Lys
        450

<210> SEQ ID NO 9
<211> LENGTH: 11
<212> TYPE: PRT
<213> ORGANISM: Artificial
<220> FEATURE:
<223> OTHER INFORMATION: C10.2 CDR 1 Light Chain

<400> SEQUENCE: 9

Gln Ala Ser Gln Gly Thr Ser Ile Asn Leu Asn
1               5                   10

<210> SEQ ID NO 10
<211> LENGTH: 7
<212> TYPE: PRT
<213> ORGANISM: Artificial
<220> FEATURE:
<223> OTHER INFORMATION: C10.2 CDR 2 Light Chain

<400> SEQUENCE: 10

Gly Ala Ser Asn Leu Glu Asp
1               5

<210> SEQ ID NO 11
<211> LENGTH: 7
<212> TYPE: PRT
<213> ORGANISM: Artificial
<220> FEATURE:
<223> OTHER INFORMATION: C10.2 CDR 3 Light Chain

<400> SEQUENCE: 11

Leu Gln His Thr Tyr Leu Pro
1               5

<210> SEQ ID NO 12
<211> LENGTH: 13
<212> TYPE: PRT
<213> ORGANISM: Artificial
<220> FEATURE:
<223> OTHER INFORMATION: C10.2 CDR 1 Heavy Chain

<400> SEQUENCE: 12

Lys Ala Ser Gly Tyr Thr Phe Thr Asp Arg Thr Ile His
1               5                   10

<210> SEQ ID NO 13
<211> LENGTH: 17
<212> TYPE: PRT
<213> ORGANISM: Artificial
```

```
<220> FEATURE:
<223> OTHER INFORMATION: C10.2 CDR 2 Heavy Chain

<400> SEQUENCE: 13

Tyr Ile Tyr Pro Gly Asp Gly Ser Thr Lys Tyr Asn Glu Asn Phe Lys
1               5                   10                  15
Gly

<210> SEQ ID NO 14
<211> LENGTH: 6
<212> TYPE: PRT
<213> ORGANISM: Artificial
<220> FEATURE:
<223> OTHER INFORMATION: C10.2 CDR 3 Heavy Chain

<400> SEQUENCE: 14

Arg Gly Ala Met Asp Tyr
1               5

<210> SEQ ID NO 15
<211> LENGTH: 214
<212> TYPE: PRT
<213> ORGANISM: Artificial
<220> FEATURE:
<223> OTHER INFORMATION: C10.2 Light Chain

<400> SEQUENCE: 15

Asp Val Gln Met Ile Gln Ser Pro Ser Ser Leu Ser Ala Ser Leu Gly
1               5                   10                  15

Asp Ile Val Thr Met Thr Cys Gln Ala Ser Gln Gly Thr Ser Ile Asn
            20                  25                  30

Leu Asn Trp Phe Gln Gln Lys Pro Gly Lys Ala Pro Lys Leu Leu Ile
        35                  40                  45

Tyr Gly Ala Ser Asn Leu Glu Asp Gly Val Pro Ser Arg Phe Ser Gly
    50                  55                  60

Ser Arg Tyr Gly Thr Asp Phe Thr Leu Thr Ile Ser Ser Leu Glu Asp
65                  70                  75                  80

Glu Asp Met Ala Thr Tyr Phe Cys Leu Gln His Thr Tyr Leu Pro Phe
                85                  90                  95

Thr Phe Gly Ser Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 16
<211> LENGTH: 439
<212> TYPE: PRT
```

-continued

<213> ORGANISM: Artificial
<220> FEATURE:
<223> OTHER INFORMATION: C10.2 Heavy Chain

<400> SEQUENCE: 16

```
Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp Arg
            20                  25                  30

Thr Ile His Trp Val Lys Gln Arg Pro Glu Gln Gly Leu Glu Trp Ile
        35                  40                  45

Gly Tyr Ile Tyr Pro Gly Asp Gly Ser Thr Lys Tyr Asn Glu Asn Phe
    50                  55                  60

Lys Gly Lys Ala Thr Leu Thr Ala Asp Lys Ser Ser Ser Thr Ala Tyr
65                  70                  75                  80

Met Gln Leu Asn Ser Leu Thr Ser Glu Asp Ser Ala Val Tyr Phe Cys
                85                  90                  95

Ala Arg Arg Gly Ala Met Asp Tyr Trp Gly Gln Gly Thr Ser Val Thr
            100                 105                 110

Val Ser Ser Ala Lys Thr Thr Pro Pro Ser Val Tyr Pro Leu Ala Pro
        115                 120                 125

Gly Ser Ala Ala Gln Thr Asn Ser Met Val Thr Leu Gly Cys Leu Val
    130                 135                 140

Lys Gly Tyr Phe Pro Glu Pro Val Thr Val Thr Trp Asn Ser Gly Ser
145                 150                 155                 160

Leu Ser Ser Gly Val His Thr Phe Pro Ala Val Leu Gln Ser Asp Leu
                165                 170                 175

Tyr Thr Leu Ser Ser Ser Val Thr Val Pro Ser Ser Thr Trp Pro Ser
            180                 185                 190

Glu Thr Val Thr Cys Asn Val Ala His Pro Ala Ser Ser Thr Lys Val
        195                 200                 205

Asp Lys Lys Ile Val Pro Arg Asp Cys Gly Cys Lys Pro Cys Ile Cys
    210                 215                 220

Thr Val Pro Glu Val Ser Ser Val Phe Ile Phe Pro Pro Lys Pro Lys
225                 230                 235                 240

Asp Val Leu Thr Ile Thr Leu Thr Pro Lys Val Thr Cys Val Val Val
                245                 250                 255

Asp Ile Ser Lys Asp Asp Pro Glu Val Gln Phe Ser Trp Phe Val Asp
            260                 265                 270

Asp Val Glu Val His Thr Ala Gln Thr Gln Pro Arg Glu Glu Gln Phe
        275                 280                 285

Asn Ser Thr Phe Arg Ser Val Ser Glu Leu Pro Ile Met His Gln Asp
    290                 295                 300

Trp Leu Asn Gly Lys Glu Phe Lys Cys Arg Val Asn Ser Ala Ala Phe
305                 310                 315                 320

Pro Ala Pro Ile Glu Lys Thr Ile Ser Lys Thr Lys Gly Arg Pro Lys
                325                 330                 335

Ala Pro Gln Val Tyr Thr Ile Pro Pro Pro Lys Glu Gln Met Ala Lys
            340                 345                 350

Asp Lys Val Ser Leu Thr Cys Met Ile Thr Asp Phe Phe Pro Glu Asp
        355                 360                 365

Ile Thr Val Glu Trp Gln Trp Asn Gly Gln Pro Ala Glu Asn Tyr Lys
    370                 375                 380

Asn Thr Gln Pro Ile Met Asp Thr Asp Gly Ser Tyr Phe Val Tyr Ser
```

```
                385                 390                 395                 400
Lys Leu Asn Val Gln Lys Ser Asn Trp Glu Ala Gly Asn Thr Phe Thr
                405                 410                 415

Cys Ser Val Leu His Glu Gly Leu His Asn His His Thr Glu Lys Ser
                420                 425                 430

Leu Ser His Ser Pro Gly Lys
                435

<210> SEQ ID NO 17
<211> LENGTH: 11
<212> TYPE: PRT
<213> ORGANISM: Artificial
<220> FEATURE:
<223> OTHER INFORMATION: C5.2 CDR 1 Light Chain

<400> SEQUENCE: 17

Gln Ala Ser Gln Asp Thr Ser Ile Asn Leu Asn
1               5                   10

<210> SEQ ID NO 18
<211> LENGTH: 7
<212> TYPE: PRT
<213> ORGANISM: Artificial
<220> FEATURE:
<223> OTHER INFORMATION: C5.2 CDR 2 Light Chain

<400> SEQUENCE: 18

Gly Ala Ser Asn Leu Glu Asp
1               5

<210> SEQ ID NO 19
<211> LENGTH: 7
<212> TYPE: PRT
<213> ORGANISM: Artificial
<220> FEATURE:
<223> OTHER INFORMATION: C5.2 CDR 3 Light Chain

<400> SEQUENCE: 19

Leu Gln His Thr Tyr Leu Pro
1               5

<210> SEQ ID NO 20
<211> LENGTH: 13
<212> TYPE: PRT
<213> ORGANISM: Artificial
<220> FEATURE:
<223> OTHER INFORMATION: C5.2 CDR 1 Heavy Chain

<400> SEQUENCE: 20

Lys Ala Ser Gly Tyr Thr Phe Thr Asp Arg Thr Ile His
1               5                   10

<210> SEQ ID NO 21
<211> LENGTH: 17
<212> TYPE: PRT
<213> ORGANISM: Artificial
<220> FEATURE:
<223> OTHER INFORMATION: C5.2 CDR 2 Heavy Chain

<400> SEQUENCE: 21

Tyr Ile Tyr Pro Gly Asp Asp Ser Thr Lys Tyr Asn Asp Asn Phe Lys
1               5                   10                  15

Gly
```

-continued

```
<210> SEQ ID NO 22
<211> LENGTH: 6
<212> TYPE: PRT
<213> ORGANISM: Artificial
<220> FEATURE:
<223> OTHER INFORMATION: C5.2 CDR 3 Heavy Chain

<400> SEQUENCE: 22

Arg Gly Thr Met Asp Tyr
1               5

<210> SEQ ID NO 23
<211> LENGTH: 214
<212> TYPE: PRT
<213> ORGANISM: Artificial
<220> FEATURE:
<223> OTHER INFORMATION: C5.2 Light Chain

<400> SEQUENCE: 23

Asp Val Gln Met Ile Gln Ser Pro Ser Ser Leu Ser Ala Ser Leu Gly
1               5                  10                  15

Asp Ile Val Thr Met Thr Cys Gln Ala Ser Gln Asp Thr Ser Ile Asn
            20                  25                  30

Leu Asn Trp Phe Gln Gln Lys Pro Gly Lys Ala Pro Lys Leu Leu Ile
        35                  40                  45

Tyr Gly Ala Ser Asn Leu Glu Asp Gly Val Pro Ser Arg Phe Ser Gly
    50                  55                  60

Ser Arg Tyr Gly Thr Asp Phe Thr Leu Thr Ile Ser Ser Leu Glu Asp
65                  70                  75                  80

Glu Asp Met Ala Thr Tyr Phe Cys Leu Gln His Thr Tyr Leu Pro Phe
                85                  90                  95

Thr Phe Gly Ser Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 24
<211> LENGTH: 439
<212> TYPE: PRT
<213> ORGANISM: Artificial
<220> FEATURE:
<223> OTHER INFORMATION: C5.2 Heavy Chain

<400> SEQUENCE: 24

Gln Val Gln Leu Gln Gln Ser Asp Ala Glu Leu Val Lys Pro Gly Ala
1               5                  10                  15

Ser Val Lys Ile Ser Cys Lys Ala Ser Gly Tyr Thr Phe Thr Asp Arg
            20                  25                  30
```

```
Thr Ile His Trp Val Lys Gln Arg Pro Glu Gln Gly Leu Glu Trp Ile
        35                  40                  45

Gly Tyr Ile Tyr Pro Gly Asp Asp Ser Thr Lys Tyr Asn Asp Met Phe
 50                  55                  60

Lys Ala Lys Ala Thr Leu Thr Ala Asp Lys Ser Ser Asn Thr Ala Tyr
 65                  70                  75                  80

Met Gln Leu Asn Ser Leu Thr Ser Asp Ser Ala Val Tyr Phe Cys
                 85                  90                  95

Ala Arg Arg Gly Thr Met Asp Tyr Trp Gly Gln Gly Thr Ser Val Thr
            100                 105                 110

Val Ser Ser Ala Lys Thr Thr Pro Pro Ser Val Tyr Pro Leu Ala Pro
            115                 120                 125

Gly Ser Ala Ala Gln Thr Asn Ser Met Val Thr Leu Gly Cys Leu Val
130                 135                 140

Lys Gly Tyr Phe Pro Glu Pro Val Thr Val Thr Trp Asn Ser Gly Ser
145                 150                 155                 160

Leu Ser Ser Gly Val His Thr Phe Pro Ala Val Leu Gln Ser Asp Leu
                165                 170                 175

Tyr Thr Leu Ser Ser Ser Val Thr Val Pro Ser Ser Thr Trp Pro Ser
            180                 185                 190

Glu Thr Val Thr Cys Asn Val Ala His Pro Ala Ser Ser Thr Lys Val
            195                 200                 205

Asp Lys Lys Ile Val Pro Arg Asp Cys Gly Cys Lys Pro Cys Ile Cys
210                 215                 220

Thr Val Pro Glu Val Ser Ser Val Phe Ile Phe Pro Pro Lys Pro Lys
225                 230                 235                 240

Asp Val Leu Thr Ile Thr Leu Thr Pro Lys Val Thr Cys Val Val Val
                245                 250                 255

Asp Ile Ser Lys Asp Asp Pro Glu Val Gln Phe Ser Trp Phe Val Asp
            260                 265                 270

Asp Val Glu Val His Thr Ala Gln Thr Gln Pro Arg Glu Glu Gln Phe
            275                 280                 285

Asn Ser Thr Phe Arg Ser Val Ser Glu Leu Pro Ile Met His Gln Asp
            290                 295                 300

Trp Leu Asn Gly Lys Glu Phe Lys Cys Arg Val Asn Ser Ala Ala Phe
305                 310                 315                 320

Pro Ala Pro Ile Glu Lys Thr Ile Ser Lys Thr Lys Gly Arg Pro Lys
                325                 330                 335

Ala Pro Gln Val Tyr Thr Ile Pro Pro Pro Lys Glu Gln Met Ala Lys
            340                 345                 350

Asp Lys Val Ser Leu Thr Cys Met Ile Thr Asp Phe Phe Pro Glu Asp
            355                 360                 365

Ile Thr Val Glu Trp Gln Trp Asn Gly Gln Pro Ala Glu Asn Tyr Lys
            370                 375                 380

Asn Thr Gln Pro Ile Met Asp Thr Asp Gly Ser Tyr Phe Val Tyr Ser
385                 390                 395                 400

Lys Leu Asn Val Gln Lys Ser Asn Trp Glu Ala Gly Asn Thr Phe Thr
                405                 410                 415

Cys Ser Val Leu His Glu Gly Leu His Asn His His Thr Glu Lys Ser
            420                 425                 430

Leu Ser His Ser Pro Gly Lys
            435
```

```
<210> SEQ ID NO 25
<211> LENGTH: 11
<212> TYPE: PRT
<213> ORGANISM: Artificial
<220> FEATURE:
<223> OTHER INFORMATION: C8.3 CDR 1 Light Chain

<400> SEQUENCE: 25

Gln Ala Ser Gln Gly Thr Ser Ile Asn Leu Asn
1               5                   10

<210> SEQ ID NO 26
<211> LENGTH: 7
<212> TYPE: PRT
<213> ORGANISM: Artificial
<220> FEATURE:
<223> OTHER INFORMATION: C8.3 CDR 2 Light Chain

<400> SEQUENCE: 26

Gly Ser Ser Asn Leu Glu Asp
1               5

<210> SEQ ID NO 27
<211> LENGTH: 7
<212> TYPE: PRT
<213> ORGANISM: Artificial
<220> FEATURE:
<223> OTHER INFORMATION: C8.3 CDR 3 Light Chain

<400> SEQUENCE: 27

Leu Gln His Ser Tyr Leu Pro
1               5

<210> SEQ ID NO 28
<211> LENGTH: 13
<212> TYPE: PRT
<213> ORGANISM: Artificial
<220> FEATURE:
<223> OTHER INFORMATION: C8.3 CDR 1 Heavy Chain

<400> SEQUENCE: 28

Lys Ala Ser Gly Tyr Thr Phe Thr Asp Arg Thr Ile His
1               5                   10

<210> SEQ ID NO 29
<211> LENGTH: 17
<212> TYPE: PRT
<213> ORGANISM: Artificial
<220> FEATURE:
<223> OTHER INFORMATION: C8.3 CDR 2 Heavy Chain

<400> SEQUENCE: 29

Tyr Ile Tyr Pro Gly Asp Gly Ser Thr Lys Tyr Asn Glu Asn Phe Lys
1               5                   10                  15

Gly

<210> SEQ ID NO 30
<211> LENGTH: 6
<212> TYPE: PRT
<213> ORGANISM: Artificial
<220> FEATURE:
<223> OTHER INFORMATION: C8.3 CDR 3 Heavy Chain

<400> SEQUENCE: 30

Arg Gly Ala Met Asp Tyr
1               5
```

```
<210> SEQ ID NO 31
<211> LENGTH: 214
<212> TYPE: PRT
<213> ORGANISM: Artificial
<220> FEATURE:
<223> OTHER INFORMATION: C8.3 Light Chain

<400> SEQUENCE: 31
```

Asp Val Gln Met Ile Gln Ser Pro Ser Ser Leu Ser Ala Ser Leu Gly
1               5                   10                  15

Asp Ile Val Thr Met Thr Cys Gln Ala Ser Gln Gly Thr Ser Ile Asn
            20                  25                  30

Leu Asn Trp Phe Gln Gln Lys Pro Gly Lys Ala Pro Lys Leu Leu Ile
        35                  40                  45

Tyr Gly Ser Ser Asn Leu Glu Asp Gly Val Pro Ser Arg Phe Ser Gly
    50                  55                  60

Ser Arg Tyr Gly Thr Asp Phe Thr Leu Thr Ile Ser Ser Leu Glu Asp
65                  70                  75                  80

Glu Asp Met Ala Thr Tyr Phe Cys Leu Gln His Ser Tyr Leu Pro Phe
                85                  90                  95

Thr Phe Gly Ser Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

```
<210> SEQ ID NO 32
<211> LENGTH: 439
<212> TYPE: PRT
<213> ORGANISM: Artificial
<220> FEATURE:
<223> OTHER INFORMATION: C8.3 Heavy Chain

<400> SEQUENCE: 32
```

Gln Val Gln Leu Gln Gln Ser Asp Ala Glu Leu Val Asn Pro Gly Ala
1               5                   10                  15

Ser Val Lys Ile Ser Cys Lys Ala Ser Gly Tyr Thr Phe Thr Asp Arg
            20                  25                  30

Thr Ile His Trp Val Lys Gln Arg Pro Glu Gln Gly Leu Glu Trp Ile
        35                  40                  45

Gly Tyr Ile Tyr Pro Gly Asp Gly Ser Thr Lys Tyr Asn Glu Asn Phe
    50                  55                  60

Lys Gly Lys Ala Thr Leu Thr Ala Asp Lys Ser Ser Ser Thr Ala Tyr
65                  70                  75                  80

Met Gln Leu Asn Ser Leu Ala Ser Glu Asp Ser Ala Val Tyr Phe Cys

```
                    85                  90                  95
Ala Arg Arg Gly Ala Met Asp Tyr Trp Gly Gln Gly Thr Ser Val Thr
                100                 105                 110

Val Ser Ser Ala Lys Thr Thr Pro Pro Ser Val Tyr Pro Leu Ala Pro
                115                 120                 125

Gly Ser Ala Ala Gln Thr Asn Ser Met Val Thr Leu Gly Cys Leu Val
            130                 135                 140

Lys Gly Tyr Phe Pro Glu Pro Val Thr Val Thr Trp Asn Ser Gly Ser
145                 150                 155                 160

Leu Ser Ser Gly Val His Thr Phe Pro Ala Val Leu Gln Ser Asp Leu
                165                 170                 175

Tyr Thr Leu Ser Ser Ser Val Thr Val Pro Ser Ser Thr Trp Pro Ser
                180                 185                 190

Glu Thr Val Thr Cys Asn Val Ala His Pro Ala Ser Ser Thr Lys Val
                195                 200                 205

Asp Lys Lys Ile Val Pro Arg Asp Cys Gly Cys Lys Pro Cys Ile Cys
            210                 215                 220

Thr Val Pro Glu Val Ser Ser Val Phe Ile Phe Pro Pro Lys Pro Lys
225                 230                 235                 240

Asp Val Leu Thr Ile Thr Leu Thr Pro Lys Val Thr Cys Val Val Val
                245                 250                 255

Asp Ile Ser Lys Asp Asp Pro Glu Val Gln Phe Ser Trp Phe Val Asp
                260                 265                 270

Asp Val Glu Val His Thr Ala Gln Thr Gln Pro Arg Glu Glu Gln Phe
            275                 280                 285

Asn Ser Thr Phe Arg Ser Val Ser Glu Leu Pro Ile Met His Gln Asp
290                 295                 300

Trp Leu Asn Gly Lys Glu Phe Lys Cys Arg Val Asn Ser Ala Ala Phe
305                 310                 315                 320

Pro Ala Pro Ile Glu Lys Thr Ile Ser Lys Thr Lys Gly Arg Pro Lys
                325                 330                 335

Ala Pro Gln Val Tyr Thr Ile Pro Pro Lys Glu Gln Met Ala Lys
                340                 345                 350

Asp Lys Val Ser Leu Thr Cys Met Ile Thr Asp Phe Phe Pro Glu Asp
            355                 360                 365

Ile Thr Val Glu Trp Gln Trp Asn Gly Gln Pro Ala Glu Asn Tyr Lys
370                 375                 380

Asn Thr Gln Pro Ile Met Asp Thr Asp Gly Ser Tyr Phe Val Tyr Ser
385                 390                 395                 400

Lys Leu Asn Val Gln Lys Ser Asn Trp Glu Ala Gly Asn Thr Phe Thr
                405                 410                 415

Cys Ser Val Leu His Glu Gly Leu His Asn His His Thr Glu Lys Ser
            420                 425                 430

Leu Ser His Ser Pro Gly Lys
            435

<210> SEQ ID NO 33
<211> LENGTH: 441
<212> TYPE: PRT
<213> ORGANISM: Artificial
<220> FEATURE:
<223> OTHER INFORMATION: No 33 Human Tau

<400> SEQUENCE: 33

Met Ala Glu Pro Arg Gln Glu Phe Glu Val Met Glu Asp His Ala Gly
```

-continued

```
1               5                   10                  15
Thr Tyr Gly Leu Gly Asp Arg Lys Asp Gln Gly Gly Tyr Thr Met His
                20                  25                  30
Gln Asp Gln Glu Gly Asp Thr Asp Ala Gly Leu Lys Glu Ser Pro Leu
                35                  40                  45
Gln Thr Pro Thr Glu Asp Gly Ser Glu Glu Pro Gly Ser Glu Thr Ser
        50                  55                  60
Asp Ala Lys Ser Thr Pro Thr Ala Glu Asp Val Thr Ala Pro Leu Val
65                  70                  75                  80
Asp Glu Gly Ala Pro Gly Lys Gln Ala Ala Gln Pro His Thr Glu
                        85                  90                  95
Ile Pro Glu Gly Thr Thr Ala Glu Glu Ala Gly Ile Gly Asp Thr Pro
                100                 105                 110
Ser Leu Glu Asp Glu Ala Ala Gly His Val Thr Gln Ala Arg Met Val
                115                 120                 125
Ser Lys Ser Lys Asp Gly Thr Gly Ser Asp Asp Lys Lys Ala Lys Gly
                130                 135                 140
Ala Asp Gly Lys Thr Lys Ile Ala Thr Pro Arg Gly Ala Ala Pro Pro
145                 150                 155                 160
Gly Gln Lys Gly Gln Ala Asn Ala Thr Arg Ile Pro Ala Lys Thr Pro
                165                 170                 175
Pro Ala Pro Lys Thr Pro Pro Ser Ser Gly Glu Pro Pro Lys Ser Gly
                180                 185                 190
Asp Arg Ser Gly Tyr Ser Ser Pro Gly Ser Pro Gly Thr Pro Gly Ser
                195                 200                 205
Arg Ser Arg Thr Pro Ser Leu Pro Thr Pro Pro Thr Arg Glu Pro Lys
                210                 215                 220
Lys Val Ala Val Val Arg Thr Pro Pro Lys Ser Pro Ser Ser Ala Lys
225                 230                 235                 240
Ser Arg Leu Gln Thr Ala Pro Val Pro Met Pro Asp Leu Lys Asn Val
                245                 250                 255
Lys Ser Lys Ile Gly Ser Thr Glu Asn Leu Lys His Gln Pro Gly Gly
                260                 265                 270
Gly Lys Val Gln Ile Ile Asn Lys Lys Leu Asp Leu Ser Asn Val Gln
                275                 280                 285
Ser Lys Cys Gly Ser Lys Asp Asn Ile Lys His Val Pro Gly Gly Gly
                290                 295                 300
Ser Val Gln Ile Val Tyr Lys Pro Val Asp Leu Ser Lys Val Thr Ser
305                 310                 315                 320
Lys Cys Gly Ser Leu Gly Asn Ile His His Lys Pro Gly Gly Gly Gln
                325                 330                 335
Val Glu Val Lys Ser Glu Lys Leu Asp Phe Lys Asp Arg Val Gln Ser
                340                 345                 350
Lys Ile Gly Ser Leu Asp Asn Ile Thr His Val Pro Gly Gly Gly Asn
                355                 360                 365
Lys Lys Ile Glu Thr His Lys Leu Thr Phe Arg Glu Asn Ala Lys Ala
                370                 375                 380
Lys Thr Asp His Gly Ala Glu Ile Val Tyr Lys Ser Pro Val Val Ser
385                 390                 395                 400
Gly Asp Thr Ser Pro Arg His Leu Ser Asn Val Ser Ser Thr Gly Ser
                405                 410                 415
Ile Asp Met Val Asp Ser Pro Gln Leu Ala Thr Leu Ala Asp Glu Val
                420                 425                 430
```

Ser Ala Ser Leu Ala Lys Gln Gly Leu
        435                 440

<210> SEQ ID NO 34
<211> LENGTH: 219
<212> TYPE: PRT
<213> ORGANISM: Artificial
<220> FEATURE:
<223> OTHER INFORMATION: D1.2* Light Chain

<400> SEQUENCE: 34

Asp Val Val Met Thr Gln Thr Pro Leu Ser Leu Pro Val Ser Leu Gly
1               5                   10                  15

Asp Gln Ala Ser Ile Ser Cys Arg Ser Gln Ser Leu Val His Ser
            20                  25                  30

Asn Gly Asn Thr Tyr Leu His Trp His Leu Gln Lys Pro Gly Gln Ser
        35                  40                  45

Pro Lys Phe Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Phe Thr Phe Gly Ser Gly Thr Lys Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215

<210> SEQ ID NO 35
<211> LENGTH: 444
<212> TYPE: PRT
<213> ORGANISM: Artificial
<220> FEATURE:
<223> OTHER INFORMATION: hC10.2 Heavy Chain

<400> SEQUENCE: 35

Gln Val Gln Leu Val Gln Ser Gly Ala Glu Val Lys Pro Gly Ala
1               5                   10                  15

Ser Val Lys Ile Ser Cys Lys Ala Ser Gly Tyr Thr Phe Thr Asp Arg
            20                  25                  30

Thr Ile His Trp Val Arg Gln Ala Pro Gly Gln Gly Leu Glu Trp Ile
        35                  40                  45

Gly Tyr Ile Tyr Pro Gly Asp Gly Ser Thr Lys Tyr Ser Gln Lys Phe
    50                  55                  60

Gln Gly Arg Ala Thr Leu Thr Ala Asp Thr Ser Ala Ser Thr Ala Tyr

```
            65                  70                  75                  80
Met Glu Leu Ser Ser Leu Arg Ser Glu Asp Thr Ala Val Tyr Tyr Cys
                    85                  90                  95

Ala Arg Arg Gly Ala Met Asp Tyr Trp Gly Gln Gly Thr Ser Val Thr
                100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
        290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440

<210> SEQ ID NO 36
<211> LENGTH: 214
<212> TYPE: PRT
<213> ORGANISM: Artificial
<220> FEATURE:
<223> OTHER INFORMATION: hC10.2 LC
```

```
<400> SEQUENCE: 36

Asp Val Gln Met Thr Gln Ser Pro Ser Ser Leu Ser Ala Ser Val Gly
1               5                   10                  15

Asp Arg Val Thr Met Thr Cys Gln Ala Ser Gln Asp Thr Ser Ile Asn
                20                  25                  30

Leu Asn Trp Phe Gln Gln Lys Pro Gly Lys Ala Pro Lys Leu Leu Ile
            35                  40                  45

Tyr Gly Ala Ser Asn Leu Glu Thr Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Met Ala Thr Tyr Tyr Cys Leu Gln His Thr Tyr Leu Pro Phe
                85                  90                  95

Thr Phe Gly Ser Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 37
<211> LENGTH: 23
<212> TYPE: PRT
<213> ORGANISM: Artificial
<220> FEATURE:
<223> OTHER INFORMATION: 386-408 Tau with Phosphorylated S396 and S404

<400> SEQUENCE: 37

Thr Asp His Gly Ala Glu Ile Val Tyr Lys Ser Pro Val Val Ser Gly
1               5                   10                  15

Asp Thr Ser Pro Arg His Leu
            20
```